(12) United States Patent
Strum

(10) Patent No.: US 10,981,887 B2
(45) Date of Patent: Apr. 20, 2021

(54) BENZOTHIOPHENE ESTROGEN RECEPTOR MODULATORS

(71) Applicant: G1 Therapeutics, Inc., Research Triangle Park, NC (US)

(72) Inventor: Jay Copeland Strum, Hillsborough, NC (US)

(73) Assignee: G1 Therapeutics, Inc., Research Triangle Park, NC (US)

( * ) Notice: Subject to any disclaimer, the term of this patent is extended or adjusted under 35 U.S.C. 154(b) by 0 days.

(21) Appl. No.: 16/824,290

(22) Filed: Mar. 19, 2020

(65) Prior Publication Data

US 2020/0216406 A1    Jul. 9, 2020

Related U.S. Application Data

(63) Continuation of application No. 16/221,201, filed on Dec. 14, 2018, now Pat. No. 10,633,362, which is a continuation of application No. 15/893,295, filed on Feb. 9, 2018, now Pat. No. 10,208,011.

(60) Provisional application No. 62/614,279, filed on Jan. 5, 2018, provisional application No. 62/460,358, filed on Feb. 17, 2017, provisional application No. 62/457,643, filed on Feb. 10, 2017.

(51) Int. Cl.
| | |
|---|---|
| *C07D 333/64* | (2006.01) |
| *C07D 409/10* | (2006.01) |
| *C07D 409/12* | (2006.01) |
| *A61K 31/381* | (2006.01) |
| *A61K 31/397* | (2006.01) |
| *A61K 31/4025* | (2006.01) |
| *A61K 31/499* | (2006.01) |
| *A61K 31/55* | (2006.01) |
| *A61P 35/00* | (2006.01) |
| *A61K 31/4535* | (2006.01) |

(52) U.S. Cl.
CPC .......... *C07D 333/64* (2013.01); *A61K 31/381* (2013.01); *A61K 31/397* (2013.01); *A61K 31/4025* (2013.01); *A61K 31/4535* (2013.01); *A61K 31/499* (2013.01); *A61K 31/55* (2013.01); *A61P 35/00* (2018.01); *C07D 409/12* (2013.01)

(58) Field of Classification Search
CPC .. C07D 333/64; C07D 409/10; C07D 409/12; A61K 31/381; A61K 31/397; A61K 31/4025; A61K 31/499; A61K 31/55; A61P 35/00
See application file for complete search history.

(56) References Cited

U.S. PATENT DOCUMENTS

| | | |
|---|---|---|
| 4,075,227 A | 2/1978 | Jones |
| 4,133,814 A | 1/1979 | Jones et al. |
| 4,418,068 A | 11/1983 | Jones |
| 5,393,763 A | 2/1995 | Black et al. |
| 5,457,117 A | 10/1995 | Black et al. |
| 5,478,847 A | 12/1995 | Draper |
| 5,998,402 A | 12/1999 | Miller et al. |
| 6,326,392 B1 | 12/2001 | Gast et al. |
| 6,403,614 B1 | 6/2002 | Dodge et al. |
| 6,797,719 B2 | 9/2004 | Arbuthnot et al. |
| 8,030,330 B2 | 10/2011 | Arbuthnot et al. |
| 9,475,798 B2 | 10/2016 | Govek et al. |
| 9,714,221 B1 | 7/2017 | Bouaboula et al. |
| 2001/0056099 A1 | 12/2001 | Day et al. |
| 2004/0044059 A1 | 3/2004 | Pinney et al. |
| 2007/0066680 A1 | 3/2007 | Moinet et al. |
| 2014/0378422 A1 | 12/2014 | Alejandro et al. |
| 2015/0005286 A1 | 1/2015 | Smith et al. |
| 2015/0080438 A1 | 3/2015 | Wintermantel |
| 2015/0284357 A1 | 10/2015 | Thatcher et al. |
| 2015/0291552 A1 | 10/2015 | Thatcher et al. |
| 2016/0090377 A1 | 3/2016 | Govek et al. |
| 2016/0090378 A1 | 3/2016 | Kahraman et al. |
| 2016/0175284 A1 | 6/2016 | Labadie et al. |
| 2016/0175289 A1 | 6/2016 | Labadie et al. |
| 2016/0304450 A1 | 10/2016 | Liang et al. |
| 2016/0347742 A1 | 12/2016 | Labadie et al. |
| 2017/0166550 A1 | 6/2017 | Thatcher et al. |
| 2017/0166551 A1 | 6/2017 | Thatcher et al. |

FOREIGN PATENT DOCUMENTS

| | | |
|---|---|---|
| EP | 0146243 A1 | 6/1985 |
| EP | 0752421 A1 | 1/1997 |
| EP | 0802184 B1 | 6/2002 |
| EP | 1947085 A1 | 7/2008 |
| GB | 2483736 A | 3/2012 |
| WO | WO 1999/024027 A2 | 5/1999 |
| WO | WO 2002/003975 A2 | 1/2002 |
| WO | WO 2002/003976 A2 | 1/2002 |
| WO | WO 2002/003977 A2 | 1/2002 |
| WO | WO 2002/003986 A2 | 1/2002 |
| WO | WO 2002/003988 A2 | 1/2002 |

(Continued)

OTHER PUBLICATIONS

Abdelhamid et al. "Benzothiophene Selective Estrogen Receptor Modulators Provide Neuroprotection by a Novel GPR30-Dependent Mechanism" ACS Chem. Neuro., Mar. 15, 2011; 2: 256-268.

(Continued)

*Primary Examiner* — Bruck Kifle

(74) *Attorney, Agent, or Firm* — Knowles Intellectual Property Strategies, LLC

(57) ABSTRACT

This invention is a benzothiophene estrogen receptor modulator or its pharmaceutically acceptable salt or a pharmaceutically acceptable composition thereof to treat an estrogen-related medical disorder.

19 Claims, 15 Drawing Sheets

(56) References Cited

FOREIGN PATENT DOCUMENTS

| | | |
|---|---|---|
| WO | WO 2002/003989 A2 | 1/2002 |
| WO | WO 2002/003990 A2 | 1/2002 |
| WO | WO 2002/003991 A2 | 1/2002 |
| WO | WO 2002/003992 A2 | 1/2002 |
| WO | WO 2002/004418 A2 | 1/2002 |
| WO | WO 2002/013802 A2 | 2/2002 |
| WO | WO 2005/016929 A1 | 2/2005 |
| WO | WO 2006/078834 A1 | 7/2006 |
| WO | WO 2006/084338 A1 | 8/2006 |
| WO | WO 2007/087684 A1 | 8/2007 |
| WO | WO 2008/002490 A2 | 1/2008 |
| WO | WO 2009/013195 A1 | 1/2009 |
| WO | WO 2010/093578 A1 | 8/2010 |
| WO | WO 2010/127452 A1 | 11/2010 |
| WO | WO 2011/156518 A2 | 12/2011 |
| WO | WO 2012/037410 A2 | 3/2012 |
| WO | WO 2012/037411 A2 | 3/2012 |
| WO | WO 2012/084711 A1 | 6/2012 |
| WO | WO 2013/090829 A1 | 6/2013 |
| WO | WO 2013/090836 A1 | 6/2013 |
| WO | WO 2013/090921 A1 | 6/2013 |
| WO | WO 2013/142266 A1 | 9/2013 |
| WO | WO 2014/066692 A1 | 5/2014 |
| WO | WO 2014/066695 A1 | 5/2014 |
| WO | WO 2014/130310 A1 | 8/2014 |
| WO | WO 2014/151899 A1 | 9/2014 |
| WO | WO 2014/191726 A1 | 12/2014 |
| WO | WO 2014/203129 A1 | 12/2014 |
| WO | WO 2014/203132 A1 | 12/2014 |
| WO | WO 2014/205136 A1 | 12/2014 |
| WO | WO 2014/205138 A1 | 12/2014 |
| WO | WO 2015/000867 A1 | 1/2015 |
| WO | WO 2015/028409 A1 | 3/2015 |
| WO | WO 2015/092634 A1 | 6/2015 |
| WO | WO 2015/136016 A2 | 9/2015 |
| WO | WO 2015/136017 A1 | 9/2015 |
| WO | WO 2015/149045 A1 | 10/2015 |
| WO | WO 2016/097071 A1 | 6/2016 |
| WO | WO 2016/097072 A1 | 6/2016 |
| WO | WO 2016/097073 A1 | 6/2016 |
| WO | WO 2016/189011 A1 | 12/2016 |
| WO | WO 2017/056115 A1 | 4/2017 |
| WO | WO 2017/059139 A1 | 4/2017 |
| WO | WO 2017/060326 A1 | 4/2017 |
| WO | WO 2017/072792 A1 | 5/2017 |

OTHER PUBLICATIONS

Bolton et al. "Potential Mechanisms of Estrogen Quinone Carcinogenesis" Chem. Res. Toxicol., Dec. 2007 ; 21: 93-101.
Dowers, et al. Bioactivation of Selective Estrogen Receptor Modulators (SERMs) Chem. Res. Toxicol. 2006; 19: 1125-1137.
Gherezghiher et al. "The Naphthol Selective Estrogen Receptor Modulator (SERM), LY2066948, is Oxidized to an o-quinone Analogous to the Naphthol Equine Estrogen, Equilenin" Chemico-Biological Interactions 196 (2012); 1-10.
Gutgesell et al. "Estrogen receptor ligands and their responses in de novo and tamoxifen resistant cell models" Poster Presented at AACR, Apr. 16-20, 2016; New Orleans, LA.
Gutgesell et al. "Combination therapy of targeted anticancer pathways and estrogen receptor ligands and their responses in de novo and tamoxifen resistant cell models" Poster Presented at San Antonio Breast Cancer Symposium, Dec. 8, 2016.
Hemachandra et al."SERMs Attenuate Estrogen-Induced Malignant Transformation of Human Mammary Epithelial Cells by Upregulating Detoxification of Oxidative Metabolites" Published OnlineFirst Mar. 5, 2014; DOI: 10.1158/1940-6207. CAPR-13-0296+O91:O95.
Kastrati et al. "Raloxifene and Desmethylarzoxifene Block Estrogen-Induced Malignant Transformation of Human Breast Epithelial Cells" PLOS-One, 2011.
Liu et al. "Bioactivation of the Selective Estrogen Receptor Modulator Desmethylated Arzoxifene to Quinoids: 4'-Fluoro Substitution Prevents Quinoid Formation" Chem. Res. Toxicol. 2005, 18: 162-173.
Liu et al. "Bioactivation of the Selective Estrogen Receptor Modulator Desmethylated Arzoxifene to Quinoids: 4'-Fluoro Substitution Prevents Quinoid Formation" Chem. Res. Toxicol. 2005, 18: 174-182.
Liu et al. "Analysis of Protein Covalent Modification by Xenobiotics Using a Covert Oxidatively Activated Tag: Raloxifene Proof-of-Principle Study" Chem. Res. Toxicol. 2005, 18: 1485-1496.
Liu et al. "Chemical Modification Modulates Estrogenic Activity, Oxidative Reactivity, and Metabolic Stability in 4'F-DMA, a New Benzothiophene Selective Estrogen Receptor Modulator" Chem. Res. Toxicol. 2006, 19: 779-787.
Liu et al. "Uterine Peroxidase-Catalyzed Formation of Diquinone Methides from the Selective Estrogen Receptor Modulators Raloxifene and Desmethylated Arzoxifene" Chem. Res. Toxicol. 207, 20: 1676-1684.
Michalsen et al. "Selective Estrogen Receptor Modulator (SERM) Lasofoxifene Forms Reactive Quinones Similar to Estradiol" Chem. Res. Toxicol. 2012, 25: 1472-1483.
Molloy et al. "Novel Selective Estrogen Mimics for the Treatment of Tamoxifen-Resistant Breast Cancer" Published OnlineFirst Sep. 9, 2014: DOI: 10.1158/1535-7163.MCT-14-0319.
Overk et al. "Structure-Activity Relationships for a Family of Benzothiophene Selective Estrogen Receptor Modulators Including Raloxifene and Arzoxifene" ChemMedChem 2007, 2: 1520-1526.
Patel et al. "A Chimeric SERM-Histone Deacetylase Inhibitor Approach to Breast Cancer Therapy" ChemMedChem 2014, 9: 602-613.
Peng et al. "Selective Estrogen Receptor Modulator Delivery of Quinone Warheads to DNA Triggering Apoptosis in Breast Cancer Cells" ACS Chemical Biology, 2009 vol. 4 No. 12, 1039-1049.
Peng et al. "Unexpected Hormonal Activity of a Catechol Equine Estrogen Metabolite Reveals Reversible Glutathione Conjugation" Chem. Res. Toxicol. 2010, 23: 1374-1383.
Qin et al. "Structural Modulation of Oxidative Metabolism in Design of Improved Benzothiophene Selective Estrogen Receptor Modulators" Drug Metabolism and Disposition; 2009, vol. 37, No. 1.
Qin et al. "Benzothiophene Selective Estrogen Receptor Modulators with Modulated Oxidative Activity and Receptor Affinity" J. Med. Chem. 2007, 50: 2682-2692.
Romagnoli et al. "Synthesis and Biological Evaluation of 2- and 3-Aminobenzo[b]thiophene Derivatives as Antimitotic Agents and Inhibitors of Tubulin Polymerization", J. Med. Chem. 2007, vol. 50, pp. 2273-2277.
Romagnoli et al. "Synthesis and biological evaluation of 2-(3', 4', 5"-trimethoxybenzoyl)-3-aryl/arylaminobenzo[b]thiophene derivatives as novel class of antiproliferative agents", Eur J Med Chem. 2010. vol. 45(12), pp. 5781-5791.
Thatcher et al. "Endocrine-independent ER+ breast cancer therapy: Benzothiophene SERMs, SERDs, MERDs, SEMs, and ShERPAs" PowerPoint presented at 252nd ACS National Meeting, Aug. 21, 2016.
Toader et al. "Nitrosation, Nitration, and Autoxidation of the Selective Estrogen Receptor Modulator Raloxifene by Nitric Oxide, Peroxynitrite, and Reactive Nitrogen/Oxygen Species" Chem. Res. Toxicol. 2003, 16: 1264-1276.
Weir et al. "AZD9496: An Oral Estrogen Receptor Inhibitor That Blocks the Growth of ER-Positive and ESR1-Mutant Breast Tumors in Preclinical Models" Published OnlineFirst Mar. 28, 2016: DOI: 10.1158/0008-5472.Can-15-2357.
Xiong et al. "1. Novel Selective Estrogen Receptor Downregulators (SERDs) Developed against Treatment-Resistant Breast Cancer" Journal of Medicinal Chemistry 2017, 60(4): 1325-1342.
Xiong et al. "Novel Selective Estrogen Receptor Downregulators Developed Using Endocrine-Independent Breast Cancer Cell Lines" Poster Presented at AACR, Apr. 14, 2016.
Xiong et al. "Novel Selective Estrogen Receptor Downregulators Developed Using Endocrine-Independent Breast Cancer Cell Lines" Poster Presented at Yaoyuan Symposium, Mar. 25, 2016.

(56) References Cited

OTHER PUBLICATIONS

Xiong et al. "Selective Human Estrogen Receptor Partial Agonists (ShERPAs) for Tamoxifen-Resistant Breast Cancer" J. Med. Chem. 2015, 59: 219-237.
Yu et al. "Comparative Methods for Analysis of Protein Covalent Modification by Electrophilic Quinoids Formed from Xenobiotics" Bioconjugate Chem. 2009, 20: 728-741.
Yu et al. "Structural Modulation of Reactivity/Activity in Design of Improved Benzothiophene Selective Estrogen Receptor Modulators: Induction of Chemopreventive Mechanisms" Mol. Cancer, Ther. 2007, 6(9), Sep. 2007.
International Search Report and Written Opinion for PCT/US2018/017668 dated May 24, 2018.

BENZOTHIOPHENE ESTROGEN RECEPTOR MODULATORS

CROSS REFERENCE TO RELATED APPLICATIONS

This application is a continuation of U.S. application Ser. No. 16/221,201, filed on Dec. 14, 2018, which is a continuation of U.S. application Ser. No. 15/893,295, filed on Feb. 9, 2018; which claims the benefit of U.S. Provisional Application 62/457,643, filed on Feb. 10, 2017; U.S. Provisional Application 62/460,358, filed on Feb. 17, 2017; and U.S. Provisional Application 62/614,279, filed on Jan. 5, 2018; the entirety of each of which is hereby incorporated by reference for all purposes.

FIELD OF THE INVENTION

This invention is directed to benzothiophene compounds with basic substituents and their compositions to treat estrogen related disorders.

BACKGROUND

Estrogens modulate a range of metabolic processes in humans, notably, reproduction, cardiovascular health, bone integrity, cognition and behavior. Estrogen also plays a central role in a wide range of human diseases, including various types of cancer (for example, breast, ovarian, colorectal, prostate, kidney and endometrial), osteoporosis, neurodegenerative diseases, cardiovascular disease, insulin resistance, lupus erythematosus, endometriosis, and obesity. In many of these disorders, estrogen mediates the disease through the estrogen receptor. Deroo, et al., Estrogen Receptors and Human Disease, *J. Clin. Invest.* 2006 Mar. 1, 116(3):561-570.

Estrogen receptors orchestrate both transcriptional and non-genomic functions in response to estrogens. These pleotropic and tissue-specific effects are thought to occur because of the differential expression of different subtypes of the estrogen receptor (ERα and ERβ) and their co-regulators. Moggs, et al., Estrogen receptors: Orchestrators of pleiotropic cellular responses, *EMBO Report*, 2001 Sep. 15; 2(9): 775-781. There is intricate complexity to the dynamics of ER-mediated transcription. Id. In addition, estrogen receptors also appear to have a direct effect on cytosolic signaling under some circumstances. Id.

An extensive amount of pharmaceutical research has been directed to identifying compounds that block the estrogen receptor and shut down undesired actions of the receptor while sometimes trying to maintain the beneficial effects of the receptor. Other efforts have been directed to trying to completely shut down all estrogen receptor activity, to treat potentially life-threatening diseases where it is more important to block all activity than preserve certain beneficial effects.

In June 2011, Aragon Pharmaceuticals disclosed benzopyran derivatives and acolbifene analogs for treatment of tamoxifen-resistant breast cancer (see WO2011/156518, U.S. Pat. Nos. 8,455,534 and 8,299,112). Aragon became Seragon in 2013, and was purchased by Genentech in 2014. See also U.S. Pat. Nos. 9,078,871; 8,853,423; 8,703,810 and US 2015/0005286.

Genentech disclosed a series of tetrahydro-pyrido[3,4-b]indol-1-yl compounds with estrogen receptor modulation activity in US2016/0175289 and US2015/0258080. Genentech is now developing Brilanstrant (GDC-0810) for the treatment of locally advanced or metastatic estrogenic receptor positive breast cancer.

Genentech, Inc. also disclosed a series of compounds with a moiety described as a SERMF (selective estrogen receptor modulator fragment) in US 2016/0304450 for the treatment of ER-related diseases.

In US 2016/0347742, Genentech disclosed chromene-, thiochromene-, dihydroquinoline-, and naphthalene-based compounds and their pharmaceutical compositions for the treatment of estrogen-mediated diseases, including but not limited to breast cancer, uterine cancer, and endometrial cancer. Genentech described chromene-based compounds with azetidine functionality in US 2016/0090377 and US 2016/0367526, claiming priority from WO2014/205136. These compounds, with a fluorine substituent on the azetidine ring, were active in breast cancer, ovarian cancer, and uterine cancer cell lines. Genentech disclosed additional compounds with fluorine-substituted azetidine moieties on chromene rings in US 2016/0090378 and US 2016/0175284.

GlaxoSmithKline PLC disclosed a series of benzothiophene analogs, some of which are substituted with short polyethylene glycol basic chains, for the treatment of estrogen receptor-mediated conditions in US 2016/0368911.

Eli Lilly and Company disclosed benzothiophene compounds and their pharmaceutical compositions in U.S. Pat. No. 6,403,614 for the treatment of postmenopausal syndrome and related estrogen-mediated diseases including cancer. Novartis International AG also disclosed benzothiophene derivatives as SERDs (selective estrogen receptor degraders) for the treatment of diseases indicated by estrogen dysfunction in WO 2014/130310.

Fulvestrant, a complete estrogen receptor antagonist with no agonist activity, was disclosed by Imperial Chemical Industries (ICI) in U.S. Pat. No. 4,659,516 and is sold by Astra Zeneca under the name Faslodex. It is indicated for the treatment of hormone receptor positive metastatic breast cancer in post-menopausal women with disease progression following anti-estrogen therapy. Fulvestrant has limited water solubility and requires monthly intramuscular (IM) injections. Fulvestrant's aqueous insolubility creates a challenge to achieve and maintain efficacious serum concentrations.

An example of a selective estrogen receptor modulator (SERMs) which act as antagonists or agonists in a gene-specific and tissue-specific fashion is tamoxifen, initially sold by AstraZeneca under the name Nolvadex. Tamoxifen was also disclosed by ICI in U.S. Pat. No. 4,659,516, (see also U.S. Pat. Nos. 6,774,122 and 7,456,160). AstraZeneca is currently developing AZD9496, a novel, oral selective estrogen receptor downregulator in patients with estrogen receptor positive breast cancer (WO 2014/191726).

Aromatase inhibitors which block the production of estrogen and therefore block ER-dependent growth include letrozole, anastrozole, and exemestane.

A number of SERDs, SERMs, and aromatase inhibitors have been disclosed. The SERM raloxifene was disclosed by Eli Lilly in 1981 (U.S. Pat. Nos. 4,418,068; 5,478,847; 5,393,763; and 5,457,117) for prevention of breast cancer and treatment of osteoporosis.

Additional anti-estrogenic compounds are disclosed in WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S.

Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497 and 5,880,137.

Additional estrogen receptor inhibitors were published by Xiong, et. al., "Novel Selective Estrogen Receptor Downregulators (SERDs) Developed Against Treatment-Resistant Breast Cancer (*J. Med. Chem*, Jan. 24, 2017 web release). Examples of such selective estrogen receptor downregulators and their biological activities were provided at the Apr. 16, 2016 American Associate for Cancer Research (AARC) Conference in a poster presentation by Lauren M. Gutgesell et. al. titled "Estrogen receptor ligands and their responses in de novo and tamoxifen resistant cell models." Additional examples in the series of SERDs were described in the oral presentation and power-point presented by Dr. Thatcher at the 252nd ACS National Meeting in Philadelphia, Pa. on Aug. 21, 2016.

In light of the role estrogen receptors play in a range of human disease, including breast tumors and breast cancer, it would be useful to have additional compounds that are useful to treat these disorders.

SUMMARY OF THE INVENTION

It has been discovered that a compound of Formula I, Formula II, Formula III, or Formula IV or a pharmaceutically acceptable salt thereof is useful to treat an estrogen-related disorder when administered in an effective amount to treat a host, typically a human, optionally in a pharmaceutically acceptable carrier.

In one aspect of the present invention, a compound of Formula I is provided:

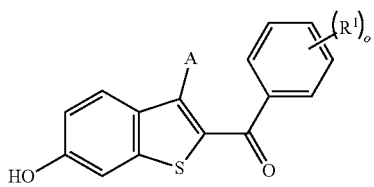

(I)

or a pharmaceutically acceptable salt, N-oxide, isotopic derivative, or prodrug, optionally in a pharmaceutically acceptable carrier to form a pharmaceutically acceptable composition thereof;
wherein A is:

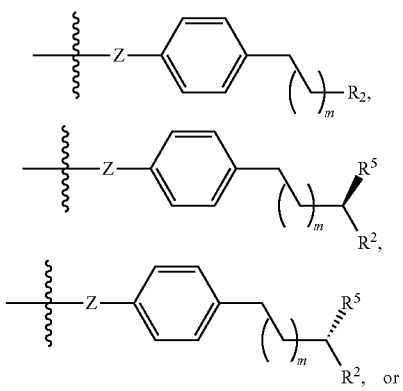

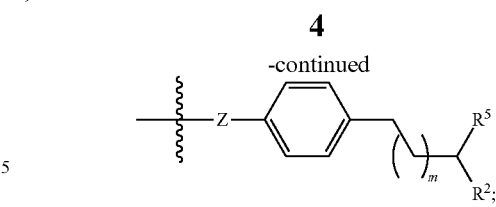

m is 0, 1, or 2;
o is 0, 1, 2, 3, 4, or 5 (and typically 1, 2, or 3);
Z is selected from —O—, —C($R^3$)$_2$—, —CHR$^3$—, —CH$_2$—, —CHF—, —CF$_2$—, and —S—;
each $R^1$ is independently selected from $C_1$-$C_3$alkyl (for example methyl), halogen (for example F), and $C_1$-$C_3$haloalkyl;
$R^2$ is selected from 4-6 membered heterocycle, optionally substituted with one, two, or three groups (and typically one group) independently selected from $R^4$;
or $R^2$ is selected from —NH$_2$, —NH($C_1$-$C_3$alkyl or $C_2$-$C_3$haloalkyl), and —N((independently)$C_1$-$C_3$alkyl or $C_2$-$C_3$haloalkyl)$_2$;
$R^3$ is independently selected from —H, —F, —Cl, —Br, —CH$_3$, —CH$_2$F, —CHF$_2$, and —CF$_3$;
$R^4$ and $R^5$ are independently selected from hydrogen, halogen, $C_1$-$C_3$alkyl, and $C_1$-$C_3$haloalkyl;
or $R^4$ is selected from hydrogen, halogen (for example F), $C_1$-$C_3$alkyl, $C_1$-$C_3$haloalkyl, —COOH, —COO$C_1$-$C_{12}$alkyl, —CONH$_2$, —CON(H)alkyl, and —CON(alkyl)$_2$.

In an alternative embodiment of Formula I, $R^2$ is selected from monocyclic 7-8 membered heterocycle optionally substituted with one, two, or three groups (and typically one group) independently selected from $R^4$.

In another alternative embodiment of Formula I, $R^2$ is selected from 6-12 membered bicyclic or bridged heterocycle optionally substituted with one, two, or three groups (and typically one group) independently selected from $R^4$.

In another alternative embodiment of Formula I, $R^2$ is hydroxyl, alkoxy, —NH—(CH$_2$)$_{n1}$—NH$_2$, —NH—(CH$_2$)$_{n1}$—NH($C_1$-$C_{12}$alkyl or $C_2$-$C_{12}$haloalkyl), —NH—(CH$_2$)$_{n1}$—N((independently)$C_1$-$C_{12}$alkyl or $C_2$-$C_{12}$haloalkyl), —NHC$_4$-$C_{12}$alkyl, or N($C_1$-$C_{12}$alkyl)$_2$, wherein n1 is 2, 3, 4, 5, or 6.

In another alternative embodiment of Formula I, two $R^4$ groups on the same carbon atom are optionally combined together to form a

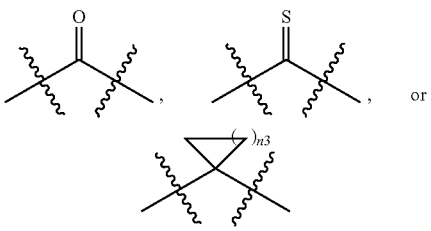

group, wherein n3 is 1, 2, 3, 4, or 5. In one embodiment the

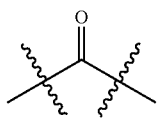 [SMILES: *C(*)=O]

is next to a nitrogen atom and $R^2$ is an amide or lactam.

In one embodiment $C_1$-$C_3$alkyl is cycloalkyl.
In one embodiment $C_4$-$C_{12}$alkyl is $C_4$-$C_{10}$alkyl.
In one embodiment $C_4$-$C_{12}$alkyl is $C_4$-$C_8$alkyl.
In one embodiment $C_4$-$C_{12}$alkyl is $C_4$-$C_6$alkyl.
In one embodiment $C_4$-$C_{12}$alkyl is $C_6$-$C_{10}$alkyl.
In one embodiment $C_4$-$C_{12}$alkyl is $C_6$-$C_8$alkyl.
In one embodiment $C_4$-$C_{12}$alkyl is a 4, 5, 6, 7, 8, 9, 10, 11, or 12 carbon alkyl.
In one embodiment $C_1$-$C_{12}$alkyl is $C_4$-$C_{10}$alkyl.
In one embodiment $C_1$-$C_{12}$alkyl is $C_4$-$C_8$alkyl.
In one embodiment $C_1$-$C_{12}$alkyl is $C_4$-$C_6$alkyl.
In one embodiment $C_1$-$C_{12}$alkyl is $C_6$-$C_{10}$alkyl.
In one embodiment $C_1$-$C_{12}$alkyl is $C_6$-$C_8$alkyl.
In one embodiment $C_1$-$C_{12}$alkyl is a 1, 2, 3, 4, 5, 6, 7, 8, 9, 10, 11, or 12 carbon alkyl.
In one embodiment n1 is 2.
In one embodiment n1 is 3.
In one embodiment n1 is 4.
In one embodiment n1 is 5.
In one embodiment n1 is 6.
In one aspect of the present invention, a compound of Formula II is provided:

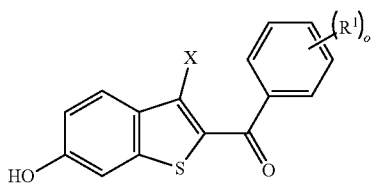

(II)

or a pharmaceutically acceptable salt, N-oxide, isotopic derivative, or prodrug, optionally in a pharmaceutically acceptable carrier to form a pharmaceutically acceptable composition thereof;
wherein
X is

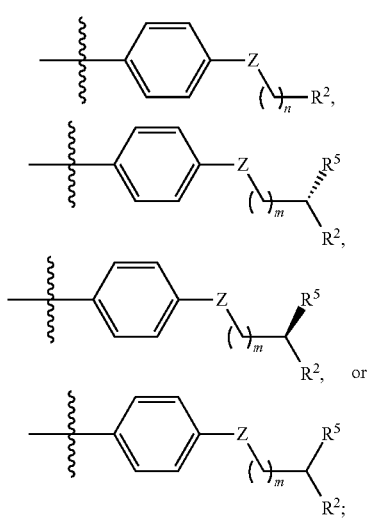

m is 0, 1, or 2;
n is 1, 2, or 3;
o is 0, 1, 2, 3, 4, or 5 (and typically 1, 2 or 3);
Z is selected from —O—, —C($R^3$)$_2$—, —CH$R^3$—, —CH$_2$—, —CHF—, —CF$_2$—, and —S—;

each $R^1$ is independently selected from $C_1$-$C_3$alkyl (for example methyl), halogen (for example F), and $C_1$-$C_3$haloalkyl (for example F substituted alkyl);

$R^2$ is selected from 4-6 membered heterocycle optionally substituted with one, two, or three groups (and typically one group) independently selected from $R^4$;

or $R^2$ is selected from —NH$_2$, —NH($C_1$-$C_3$alkyl or $C_2$-$C_3$haloalkyl), and —N((independently)$C_1$-$C_3$alkyl or $C_2$-$C_3$haloalkyl)$_2$;

$R^3$ is independently selected from —F, —Cl, —Br, —CH$_3$, —CH$_2$F, —CHF$_2$, and —CF$_3$;

$R^4$ and $R^5$ are independently selected from hydrogen, halogen (for example F), $C_1$-$C_3$alkyl, and $C_1$-$C_3$haloalkyl;

or $R^4$ is selected from hydrogen, halogen (for example F), $C_1$-$C_3$alkyl, $C_1$-$C_3$haloalkyl, —COOH, —COO$C_1$-$C_{12}$alkyl, —CONH$_2$, —CON(H)alkyl, and —CON(alkyl)$_2$.

In an alternative embodiment of Formula II, $R^2$ is selected from monocyclic 7-8 membered heterocycle optionally substituted with one, two, or three groups (and typically one group) independently selected from $R^4$.

In another alternative embodiment of Formula II, $R^2$ is selected from 6-12 membered bicyclic or bridged heterocycle optionally substituted with one, two, or three groups (and typically one group) independently selected from $R^4$.

In another alternative embodiment of Formula II, $R^2$ is hydroxyl, alkoxy, —NH—(CH$_2$)$_{n1}$—NH$_2$, —NH—(CH$_2$)$_{n1}$—NH($C_1$-$C_{12}$alkyl or $C_2$-$C_{12}$haloalkyl), —NH—(CH$_2$)$_{n1}$—N((independently)$C_1$-$C_{12}$alkyl or $C_2$-$C_{12}$haloalkyl)$_2$, —NH$C_4$-$C_{12}$alkyl, or —N($C_1$-$C_{12}$alkyl)$_2$, wherein n1 is 2, 3, 4, 5, or 6.

In another alternative embodiment of Formula II, two $R^4$ groups on the same carbon atom are optionally combined together to form a

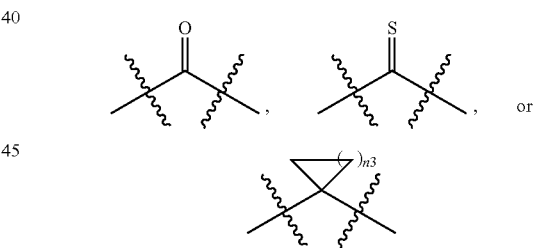

group, wherein n3 is 1, 2, 3, 4, or 5. In one embodiment the

is next to a nitrogen atom and $R^2$ is an amide or lactam.
In one embodiment n is 1.
In one embodiment n is 2.
In one embodiment n is 3.

In one aspect of the present invention, a compound of Formula III is provided:

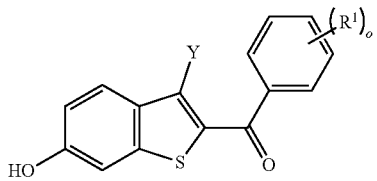

(III)

or a pharmaceutically acceptable salt, N-oxide, isotopic derivative, or prodrug, optionally in a pharmaceutically acceptable carrier to form a pharmaceutically acceptable composition thereof;
wherein:
m is 0, 1, or 2;
n is 1, 2, or 3;
o is 0, 1, 2, 3, 4, or 5;
Y is

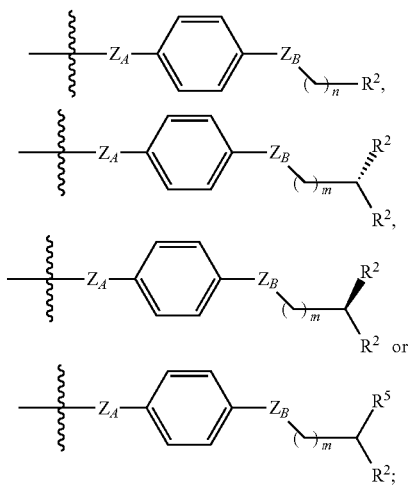

$Z_A$ and $Z_B$ are independently selected from —O—, —C(R$^3$)$_2$—, —CHR$^3$—, —CH$_2$—, —CHF—, —CF$_2$—, and —S—;

each R$^1$ is independently selected from C$_1$-C$_3$alkyl, halogen (for example F), and C$_1$-C$_3$haloalkyl (for example F substituted alkyl);

R$^2$ is selected from 4-6 membered heterocycle optionally substituted with one, two, or three groups (and typically one group) independently selected from R$^4$;

or R$^2$ is selected from —NH$_2$, —NH(C$_1$-C$_3$alkyl or C$_2$-C$_3$haloalkyl), and —N((independently)C$_1$-C$_3$alkyl or C$_2$-C$_3$haloalkyl)$_2$;

R$^3$ is independently selected from —F, —Cl, —Br, —CH$_3$, —CH$_2$F, —CHF$_2$, and —CF$_3$; and R$^4$ and R$^5$ are independently selected from hydrogen, halogen (for example F), C$_1$-C$_3$alkyl, and C$_1$-C$_3$haloalkyl;

or R$^4$ is selected from hydrogen, halogen (for example F), C$_1$-C$_3$alkyl, C$_1$-C$_3$haloalkyl, —COOH, —COOC$_1$-C$_{12}$alkyl, —CONH$_2$, —CON(H)alkyl, and —CON(alkyl)$_2$.

In an alternative embodiment of Formula III, R$^2$ is selected from monocyclic 7-8 membered heterocycle optionally substituted with one, two, or three groups (and typically one group) independently selected from R$^4$.

In another alternative embodiment of Formula III, R$^2$ is selected from 6-12 membered bicyclic or bridged heterocycle optionally substituted with one, two, or three groups (and typically one group) independently selected from R$^4$.

In another alternative embodiment of Formula III, R$^2$ is hydroxyl, alkoxy, —NH—(CH$_2$)$_{n1}$—NH$_2$, —NH—(CH$_2$)$_{n1}$—NH(C$_1$-C$_{12}$alkyl or C$_2$-C$_{12}$haloalkyl), —NH—(CH$_2$)$_{n1}$—N((independently)C$_1$-C$_{12}$alkyl or C$_2$-C$_{12}$haloalkyl)$_2$, —NHC$_4$-C$_{12}$alkyl, or —N(C$_1$-C$_{12}$alkyl)$_2$, wherein n1 is 2, 3, 4, 5, or 6.

In another alternative embodiment of Formula III, two R$^4$ groups on the same carbon atom are optionally combined together to form a

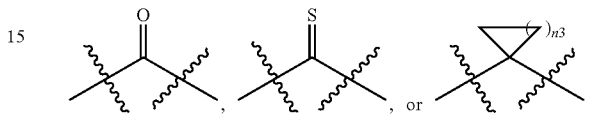

group, wherein n3 is 12, 3, 4, or 5. In one embodiment the

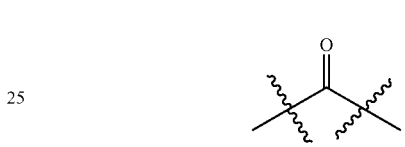

is next to a nitrogen atom and R$^2$ is an amide or lactam.

In one aspect of the present invention, a compound of Formula IV is provided:

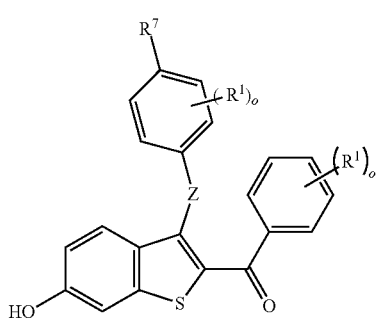

(IV)

or a pharmaceutically acceptable salt, N-oxide, isotopic derivative, or prodrug, optionally in a pharmaceutically acceptable carrier to form a pharmaceutically acceptable composition thereof; wherein:

R$^7$ is a 4, 5, 6, 7, 8, 9, or 10 membered heterocycle;
o is independently 0, 1, 2, 3, 4, or 5;
Z is selected from the group consisting of —O—, —C(R$^3$)$_2$—, —CHR$^3$—, —CH$_2$—, —CHF—, —CF$_2$—, and —S—;

each R$^1$ is independently selected from the group consisting of C$_1$-C$_3$alkyl, halogen, and C$_1$-C$_3$haloalkyl; and R$^3$ is independently selected from the group consisting of —F, —Cl, —Br, —CH$_3$, —CH$_2$F, —CHF$_2$, and —CF$_3$.

In one optional embodiment R$^7$ is substituted with oxo.

In another optional embodiment R$^7$ is substituted with 1, 2, or 3 groups selected from R$^4$, wherein, two R$^4$ groups on the same carbon atom are optionally combined together to form a

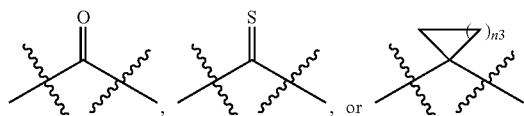

group, wherein n3 is 1, 2, 3, 4, or 5. In one embodiment the

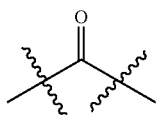 [SMILES: *C(*)=O]

is next to a nitrogen atom and $R^7$ is an amide or lactam.

In one embodiment, the compound of Formula IV is selected from:

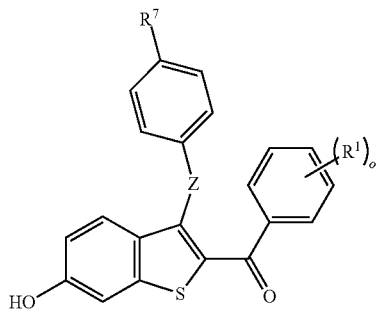

or a pharmaceutically acceptable salt, N-oxide, isotopic derivative, or prodrug, optionally in a pharmaceutically acceptable carrier to form a pharmaceutically acceptable composition thereof.

In certain embodiments, the estrogen-related disorder (for example, a tumor or cancer) is selected from breast, ovarian, endometrial, kidney, and uterine cancer. In another embodiment the disorder is metastatic endocrine therapy resistant breast cancer. In some embodiments, the compound is used following chemotherapy or radiation treatment to avoid recurrence, or instead of chemotherapy or radiation as a primary treatment.

In one aspect, a compound of Formula I, II, III, or IV or its pharmaceutically acceptable salt or prodrug, can be used to treat a hormone-related cancer or tumor that has metastasized to the brain, bone or other organ. In one embodiment of this aspect, the hormone-related cancer is estrogen mediated. In another embodiment, the estrogen mediated cancer is selected from breast, uterine, ovarian and endometrial. In other embodiments, a compound of the present invention or its pharmaceutically acceptable salt or prodrug, can be used to prevent a hormone-related cancer or tumor from metastasizing to the brain, bone or other organ, including a hormone-related cancer that is estrogen mediated, for example, breast, uterine, ovarian or endometrial.

In one aspect of the present invention the compound of Formula I, Formula II, Formula III, or Formula IV is administered in combination with a compound of Formula V. The compound of Formula V is selected from:

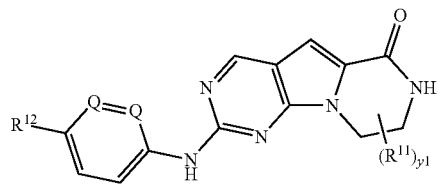

or a pharmaceutically acceptable salt, N-oxide, isotopic derivative, or prodrug, optionally in a pharmaceutically acceptable carrier to form a pharmaceutically acceptable composition thereof; wherein:

each Q is independently CH or N;

each $R^{11}$ is independently aryl, alkyl, or cycloalkyl, wherein two $R^{11}$ groups on adjacent ring atoms or on the same ring atom together with the ring atom(s) to which they are attached optionally form a 3-8-membered cycle;

y1 is 0, 1, 2, or 3;

$R^{12}$ is -(alkylene)$_{m1}$-heterocycle, -(alkylene)$_{m1}$-heteroaryl, -(alkylene)$_{m1}$-NR$^{13}$R$^{14}$, -(alkylene)$_{m1}$-C(O)—NR$^{13}$R$^{14}$, -(alkylene)$_{m1}$-C(O)—O-alkyl, -(alkylene)$_{m1}$-O—R$^{15}$, -(alkylene)$_{m1}$-S(O)$_{n2}$—R$^{15}$, or -(alkylene)$_{m1}$-S(O)$_{n2}$—NR$^{13}$R$^{14}$ any of which may be optionally independently substituted with one or more $R^x$ groups as allowed by valence;

m1 is 0 or 1;

n2 is 1 or 2;

$R^{13}$ and $R^{14}$ at each occurrence are independently:

(i) hydrogen or (ii) alkyl, cycloalkyl, heterocycle, aryl, heteroaryl, cycloalkylalkyl, alkyl-heterocycle, arylalkyl, or heteroarylalkyl, or $R^{13}$ and $R^{14}$ together with the nitrogen atom to which they are attached may combine to form a heterocycle ring;

$R^{15}$ is:

(i) hydrogen or (ii) alkyl, alkenyl, alkynyl, cycloalkyl, heterocycle, aryl, heteroaryl, cycloalkylalkyl, alkyl-heterocycle, arylalkyl, or heteroarylalkyl; and $R^x$ at each occurrence is independently halo, cyano, nitro, alkyl, haloalkyl, alkenyl, alkynyl, cycloalkyl, cycloalkenyl, heterocycle, aryl, heteroaryl, arylalkyl, heteroarylalkyl, cycloalkylalkyl, or alkyl-heterocycle.

In one embodiment the compound of Formula V is selected from:

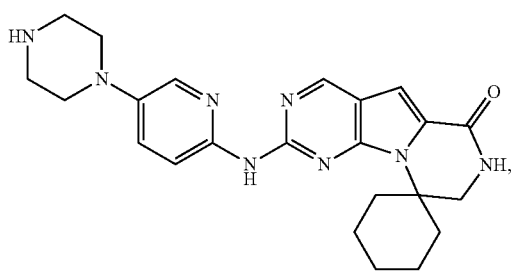

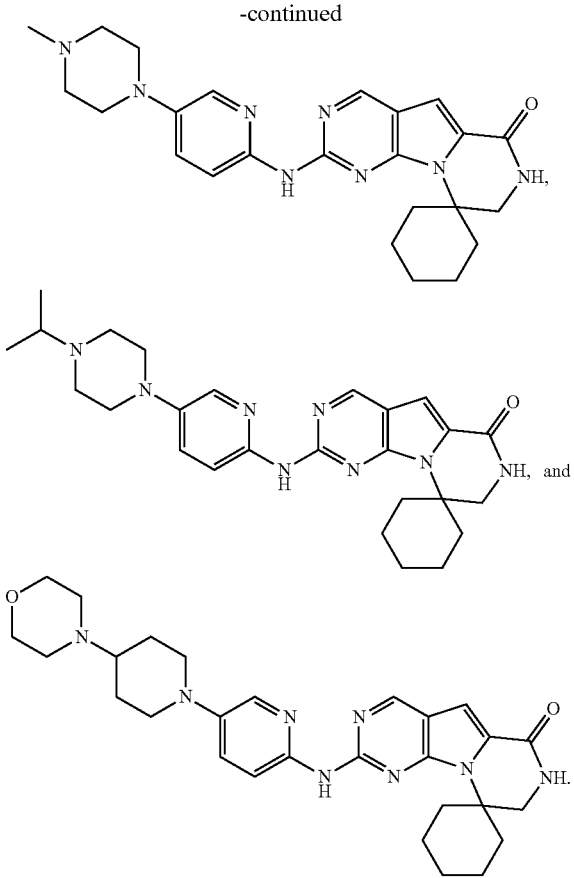

The above compounds and several other compounds of Formula V are disclosed in U.S. Pat. Nos. 8,598,197; 8,598,186; 8,691,830; 8,829,012; 8,822,683; 9,102,682; 9,499,564; 9,527,857; and 9,481,691.

The present invention thus includes at least the following features:

(a) a compound of Formula I, II, III, or IV as described herein, or a pharmaceutically acceptable salt or prodrug thereof;

(b) a compound of Formula I, II, III, or IV as described herein, or a pharmaceutically acceptable salt or prodrug thereof that is useful in the treatment or prevention of an estrogen-related disorder, including without limitation a tumor or cancer;

(c) use of a compound of Formula I, II, III, or IV as described herein, or a pharmaceutically acceptable salt or prodrug thereof in the manufacture of a medicament for the treatment or prevention of an estrogen-related disorder, including but not limited to a tumor or cancer;

(d) a method for manufacturing a medicament for the therapeutic use to treat or prevent a disorder of abnormal cellular proliferation including but not limited to a tumor or cancer, characterized in that a compound of Formula I, II, III, or IV or its salt or prodrug as described herein is used in the manufacture;

(e) a method for manufacturing a medicament for the therapeutic use to treat or prevent an estrogen-related disorder, including but not limited to a tumor or cancer, characterized in that a compound of Formula I, II, III, or IV or its salt or prodrug as described herein is used in the manufacture;

(f) a method of treating or preventing an estrogen-related disorder, including but not limited to a tumor or cancer, comprising administering to a subject in need thereof a therapeutically effective amount of a compound selected from Formula I, II, III, or IV or its pharmaceutically acceptable salt or prodrug thereof, optionally in a pharmaceutically acceptable carrier; (g) a compound of Formula I, II, III, or IV as described herein or its pharmaceutically acceptable salt or prodrug for use in the treatment or prevention of breast, kidney, uterine, ovarian or endometrial cancer;

(h) use of a compound of Formula I, II, III, or IV as described herein or a pharmaceutically acceptable salt or prodrug thereof in the manufacture of a medicament for the treatment or prevention of breast, kidney, uterine, ovarian or endometrial cancer;

(i) a method for manufacturing a medicament for the therapeutic use in treating or preventing breast, kidney, uterine, ovarian or endometrial cancer, characterized in that a compound of Formula I, II, III, or IV as described herein or its pharmaceutically acceptable salt or prodrug is used in the manufacture;

(j) a method of treating or preventing breast, kidney, uterine, ovarian or endometrial cancer, comprising administering to a subject in need thereof a therapeutically effective amount of a compound selected from Formula I, II, III, or IV or its pharmaceutically acceptable salt or prodrug thereof, optionally in a pharmaceutically acceptable carrier;

(k) a compound of Formula I, II, III, or IV as described herein or a pharmaceutically acceptable salt or prodrug thereof for use in the treatment or prevention of hormone receptor positive metastatic breast cancer;

(l) use of a compound of Formula I, II, III, or IV as described herein or a pharmaceutically acceptable salt or prodrug thereof in the manufacture of a medicament for the treatment or prevention of a hormone receptor positive metastatic breast cancer tumor;

(m) a method for manufacturing a medicament for treatment or prevention of a hormone receptor positive metastatic breast cancer, characterized in that a compound of Formula I, II, III, or IV as described herein or its pharmaceutically acceptable salt or prodrug is used in the manufacture;

(n) a method of treating or preventing hormone receptor positive metastatic breast cancer, comprising administering to a subject in need thereof a therapeutically effective amount of a compound selected from Formula I, II, III, or IV or its pharmaceutically acceptable salt or prodrug thereof, optionally in a pharmaceutically acceptable carrier;

(o) a compound of Formula I, II, III, or IV as described herein or a pharmaceutically acceptable salt or prodrug thereof for use to treat or prevent bone loss, including osteoporosis;

(p) use of a compound of Formula I, II, III, or IV as described herein or a pharmaceutically acceptable salt or prodrug thereof in the manufacture of a medicament for the treatment or prevention of bone loss, including osteoporosis;

(q) a method for manufacturing a medicament for use to treat or prevent bone loss, including osteoporosis, characterized in that a compound of Formula I, II, III, or IV as described herein is used in the manufacture;

(r) a method of treating or preventing bone loss, including osteoporosis, comprising administering to a subject in need thereof a therapeutically effective amount of a compound selected from Formula I, II, III, or IV or its pharmaceutically acceptable salt or prodrug thereof, optionally in a pharmaceutically acceptable carrier;

(s) a pharmaceutical formulation comprising an effective treatment or prevention amount of a compound of a compound of Formula I, II, III, or IV as described herein or a pharmaceutically acceptable salt or prodrug thereof together with a pharmaceutically acceptable carrier or diluent;

(t) a compound of Formula I, II, III, or IV as described herein, or its pharmaceutically acceptable salt or prodrug as a mixture of enantiomers or diastereomers (as relevant), including as a racemate;

(u) a compound of Formula I, II, III, or IV of the present invention as described herein in enantiomerically or diastereomerically (as relevant) enriched form, including as an isolated enantiomer or disastereomer (i.e., greater than 85, 90, 95, 97 or 99% pure);

(v) a process for the preparation of a therapeutic product that contain an effective amount of a compound of Formula I, II, III, or IV as described herein, or its pharmaceutically acceptable salt or prodrug;

(w) a compound of Formula I, II, III, or IV as described herein isotopically substituted with deuterium;

(x) an isotopic derivative of a compound of Formula I, II, III, or IV as described herein;

(y) a pharmaceutically acceptable composition as described herein, comprising a compound of Formula I, II, III, or IV, or its pharmaceutically acceptable salt or prodrug thereof, and a compound of Formula V or its pharmaceutically acceptable salt or prodrug thereof;

(z) a pharmaceutically acceptable composition as described herein, comprising a compound of Formula I, II, III, or IV, or its pharmaceutically acceptable salt or prodrug thereof, and a compound of Formula V or its pharmaceutically acceptable salt or prodrug thereof, for use in the treatment or prevention of an estrogen-related disorder, including without limitation a tumor or cancer;

(aa) use of a pharmaceutically acceptable composition as described herein, comprising a compound of Formula I, II, III, or IV, or its pharmaceutically acceptable salt or prodrug thereof, and a compound of Formula V or its pharmaceutically acceptable salt or prodrug thereof, in the manufacture of a medicament for the treatment or prevention of an estrogen-related disorder, including but not limited to a tumor or cancer;

(bb) a method for manufacturing a medicament for the therapeutic use of treating or preventing an estrogen-related disorder, including but not limited to a tumor or cancer, characterized in that a compound of Formula I, II, III, or IV or its pharmaceutically acceptable salt or prodrug thereof and a compound of Formula V or its pharmaceutically acceptable salt or prodrug thereof is used in the manufacture;

(cc) a method of treating or preventing an estrogen-related disorder, including but not limited to a tumor or cancer, comprising administering to a subject in need thereof a therapeutically effective amount of a compound selected from Formula I, II, III, or IV or its pharmaceutically acceptable salt or prodrug thereof and a therapeutically effective amount of a compound of Formula V or its pharmaceutically acceptable salt or prodrug thereof, optionally in a pharmaceutically acceptable carrier;

(dd) a pharmaceutically acceptable composition as described herein, comprising a compound of Formula I, II, III, or IV, or its pharmaceutically acceptable salt or prodrug thereof, and a compound of Formula V or its pharmaceutically acceptable salt or prodrug thereof, for use in the treatment or prevention of breast, kidney, uterine, ovarian, or endometrial cancer;

(ee) use of a pharmaceutically acceptable composition as described herein, comprising a compound of Formula I, II, III, or IV, or its pharmaceutically acceptable salt or prodrug thereof, and a compound of Formula V or its pharmaceutically acceptable salt or prodrug thereof, in the manufacture of a medicament for the treatment or prevention of breast, kidney, uterine, ovarian, or endometrial cancer;

(ff) a method for manufacturing a medicament for the therapeutic use of treating or preventing breast, kidney, uterine, ovarian, or endometrial cancer, characterized in that a compound of Formula I, II, III, or IV or its pharmaceutically acceptable salt or prodrug thereof and a compound of Formula V or its pharmaceutically acceptable salt or prodrug thereof is used in the manufacture;

(gg) a method of treating or preventing breast, kidney, uterine, ovarian, or endometrial cancer, comprising administering to a subject in need thereof a therapeutically effective amount of a compound selected from Formula I, II, III, or IV or its pharmaceutically acceptable salt or prodrug thereof and a therapeutically effective amount of a compound of Formula V or its pharmaceutically acceptable salt or prodrug thereof, optionally in a pharmaceutically acceptable carrier;

(hh) a pharmaceutically acceptable composition as described herein, comprising a compound of Formula I, II, III, or IV, or its pharmaceutically acceptable salt or prodrug thereof, and a compound of Formula V or its pharmaceutically acceptable salt or prodrug thereof, for use in the treatment or prevention of hormone receptor positive metastatic breast cancer;

(ii) use of a pharmaceutically acceptable composition as described herein, comprising a compound of Formula I, II, III, or IV, or its pharmaceutically acceptable salt or prodrug thereof, and a compound of Formula V or its pharmaceutically acceptable salt or prodrug thereof, in the manufacture of a medicament for the treatment or prevention of hormone receptor positive metastatic breast cancer;

(jj) a method for manufacturing a medicament for the therapeutic use of treating or preventing hormone receptor positive metastatic breast cancer, characterized in that a compound of Formula I, II, III, or IV or its pharmaceutically acceptable salt or prodrug thereof and a compound of Formula V or its pharmaceutically acceptable salt or prodrug thereof is used in the manufacture;

(kk) a method of treating or preventing a hormone receptor positive metastatic breast cancer, comprising administering to a subject in need thereof a therapeutically effective amount of a compound selected from Formula I, II, III, or IV or its pharmaceutically acceptable salt or prodrug thereof and a therapeutically effective amount of a compound of Formula V or its pharmaceutically acceptable salt or prodrug thereof, optionally in a pharmaceutically acceptable carrier;

(ll) a pharmaceutically acceptable composition as described herein, comprising a compound of Formula I, II, III, or IV, or its pharmaceutically acceptable salt or prodrug thereof, and a compound of Formula V or its pharmaceutically acceptable salt or prodrug thereof, for use in the treatment or prevention of bone loss, including osteoporosis;

(mm) use of a pharmaceutically acceptable composition as described herein, comprising a compound of Formula I, II, III, or IV, or its pharmaceutically acceptable salt or prodrug thereof, and a compound of Formula V or its pharmaceutically acceptable salt or prodrug thereof, in the manufacture of a medicament for the treatment or prevention of bone loss, including osteoporosis;

(nn) a method for manufacturing a medicament for the therapeutic use of treating or preventing bone loss, including osteoporosis, characterized in that a compound of Formula I, II, III, or IV or its pharmaceutically acceptable salt or prodrug thereof and a compound of Formula V or its pharmaceutically acceptable salt or prodrug thereof is used in the manufacture;

(oo) a method of treating or preventing bone loss, including osteoporosis, comprising administering to a subject in need thereof a therapeutically effective amount of a compound selected from Formula I, II, III, or IV or its pharmaceutically acceptable salt or prodrug thereof and a therapeutically effective amount of a compound of Formula V or its pharmaceutically acceptable salt or prodrug thereof, optionally in a pharmaceutically acceptable carrier;

(pp) a pharmaceutically acceptable composition as described herein, comprising a compound of Formula I, II, III, or IV, or its pharmaceutically acceptable salt or prodrug thereof, and a compound of Formula V or its pharmaceutically acceptable salt or prodrug thereof, for use in the treatment or prevention of bone loss, including osteoporosis;

(qq) use of a pharmaceutically acceptable composition as described herein, comprising a compound of Formula I, II, III, or IV, or its pharmaceutically acceptable salt or prodrug thereof, and a compound of Formula V or its pharmaceutically acceptable salt or prodrug thereof, in the manufacture of a medicament for the treatment or prevention of bone loss, including osteoporosis;

(rr) a method for manufacturing a medicament for the therapeutic use of treating or preventing bone loss, including osteoporosis, characterized in that a compound of Formula I, II, III, or IV or its pharmaceutically acceptable salt or prodrug thereof and a compound of Formula V or its pharmaceutically acceptable salt or prodrug thereof is used in the manufacture;

(ss) a method of treating or preventing bone loss, including osteoporosis, comprising administering to a subject in need thereof a therapeutically effective amount of a compound selected from Formula I, II, III, or IV or its pharmaceutically acceptable salt or prodrug thereof and a therapeutically effective amount of a compound of Formula V or its pharmaceutically acceptable salt or prodrug thereof, optionally in a pharmaceutically acceptable carrier; and (tt) a process for the preparation of a therapeutic product that contains an effective amount of a compound of Formula I, II, III, or IV or its pharmaceutically acceptable salt or prodrug thereof and an effective amount of a compound of Formula V or its pharmaceutically acceptable salt or prodrug thereof.

BRIEF DESCRIPTION OF THE DRAWINGS

In FIG. 15 m is 0, 1, or 2; n is 1, 2, or 3; and each R$^1$ is independently selected from C$_1$-C$_3$alkyl, halogen, and C$_1$-C$_3$haloalkyl.

DETAILED DESCRIPTION OF THE INVENTION

Definitions

Figure 1:
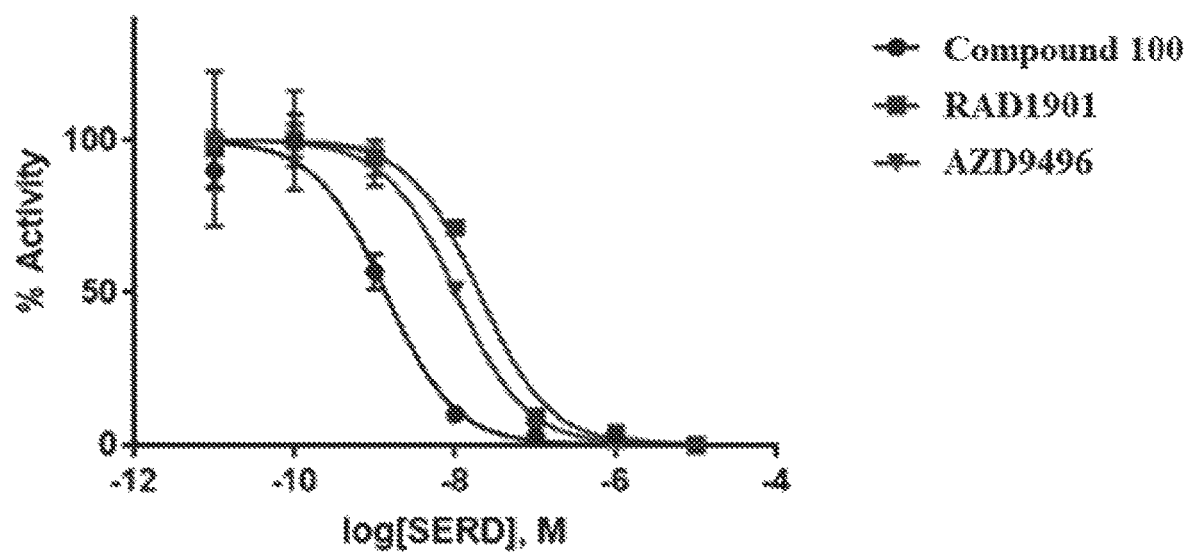
FIG. 1 is a graph of estrogen receptor activity measured in the Human Estrogen Receptor alpha Reporter Assay described in Example 3. The y-axis is estrogen receptor activity measured by percent. The x-axis is concentration of the SERD measured in Molar units and presented on logarithmic scale. The three compounds tested were Compound 100, RAD1901, and AZD9496.

Compounds are described using standard nomenclature. Unless defined otherwise, all technical and scientific terms used herein have the same meaning as is commonly understood by one of skill in the art to which this invention belongs.

The compounds of Formula I, II, III, and IV as described herein may be provided in the form of a racemate, enantiomer, mixture of enantiomers, diastereomer, mixtures of diastereomers, tautomer, N-oxide, an isomer such as a rotamer, as if each is specifically described, unless otherwise drawn or a designation is clear from the context herein.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The term "C$_1$-C$_3$ alkyl" independently refers to methyl, ethyl, propyl, isopropyl, and cyclopropyl as if each were independently recited.

The term "C$_1$-C$_3$ haloalkyl" is C$_1$-C$_3$ alkyl wherein any hydrogen can be replaced independently with fluorine, chlorine, or bromine. The term "C$_1$-C$_3$ haloalkyl" includes —CH$_2$F, —CHF$_2$, —CF$_3$, —CH$_2$CH$_2$F, —CH$_2$CHF$_2$, —CH$_2$CF$_3$, —CHFCF$_3$, —CF$_2$CF$_3$, —CH$_2$CH$_2$CH$_2$F, —CH$_2$CH$_2$CHF$_2$, —CH$_2$CH$_2$CF$_3$, —CH$_2$CHFCF$_3$, —CH$_2$CF$_2$CF$_3$, —CHFCF$_2$CF$_3$, —CF$_2$CF$_2$CF$_3$, CHFCH$_2$F, —CHFCHF$_2$, —CHFCF$_3$, —CHFCH$_2$F, —CHFCH$_2$CHF$_2$, —CHFCH$_2$CF$_3$, —CHFCHFCF$_3$, —CHFCF$_2$CF$_3$, —CF$_2$CH$_2$CH$_2$F, —CF$_2$CH$_2$CHF$_2$, —CF$_2$CH$_2$CF$_3$, —CF$_2$CHFCF$_3$, —CH$_2$CF$_2$CHF$_2$, —CH$_2$CF$_2$CH$_2$F, —CHFCHFCHF$_2$, —CHFCHFCH$_2$F, as if each were independently recited. As clear to one of skill in the art, a number of these embodiments have chiral carbons and thus can exist as enantiomers or diastereomers. This disclosure covers all possible stereoisomers either as mixtures or in enantiomerically enriched form (e.g., at least 80, 85, 90, 95, or 98% free of the other isomers).

The term "alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is C$_1$-C$_2$, C$_1$-C$_3$, C$_1$-C$_4$, C$_1$-C$_5$, or C$_1$-C$_6$. The specified ranges as used herein indicate an alkyl group having each member of the range described as an independent species. For example, the term C$_1$-C$_6$ alkyl as used herein indicates a straight or branched alkyl group having from 1, 2, 3, 4, 5, or 6 carbon atoms and is intended to mean that each of these is described as an independent species. For example, the term C$_1$-C$_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "Alkyl" also encompasses cycloalkyl or carbocyclic groups. For example, when a term is used that includes "alk" then "cycloalkyl" or "carbocyclic" can be considered part of the definition, unless unambiguously excluded by the context. For example and without limitation, the terms alkyl, alkoxy, haloalkyl, etc. can all be considered to include the cyclic forms of alkyl, unless unambiguously excluded by context.

"Halo" or "halogen" means —Cl, —Br, —I or —F (and typically F). In certain embodiments, "halo" or "halogen" may refers independently to —Cl or —F.

"Haloalkyl" is a branched or straight-chain alkyl groups substituted with 1 or more halo atoms (typically F), up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

The term "heteroaryl" denotes stable aromatic ring systems that contain one or more heteroatoms selected from O, N, and S, wherein the ring nitrogen and sulfur atom(s) are optionally oxidized, and nitrogen atom(s) are optionally quarternized. Examples include but are not limited to, unsaturated 5 to 6 membered heteromonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]. In one embodiment the "heteroaryl" group is a 8, 9, or 10 membered bicyclic ring system. Examples of 8, 9, or 10 membered bicyclic heteroaryl groups include benzofurazanyl, benzothiophenyl, benzothiazolyl, benzoxazolyl, quinazolinyl, quinoxalinyl, naphthyridinyl, quinolinyl, isoquinolinyl, benzofuranyl, indolyl, indazolyl, and benzotriazolyl.

"Arylalkyl" is an aryl group as defined herein attached through an alkyl group. Non-limiting examples of arylalkyl groups include:

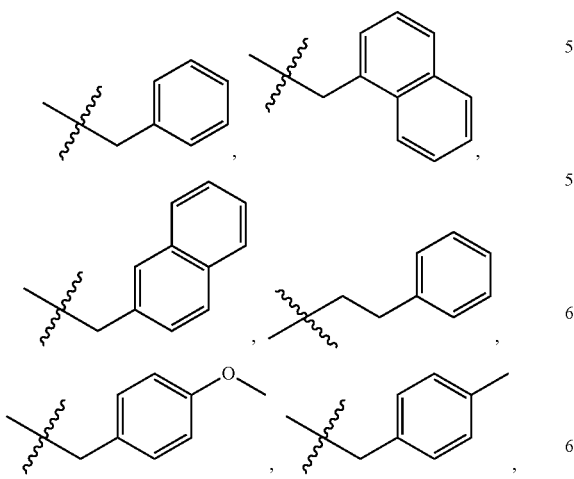

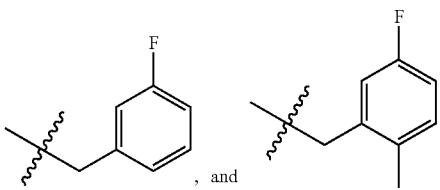

, and

"Heteroarylalkyl" is a heteroaryl group as defined herein attached through an alkyl group. Non-limiting examples of heteroarylalkyl groups include:

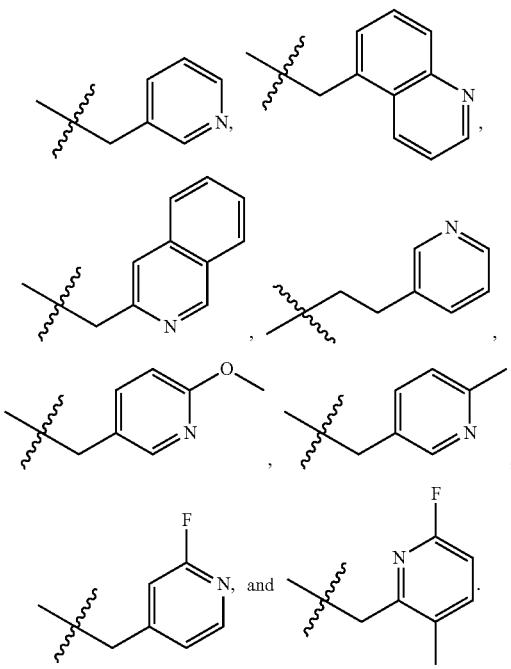

"Aryloxy" is an aryl group as defined herein attached through a —O— linker. Non-limiting examples of aryloxy groups include:

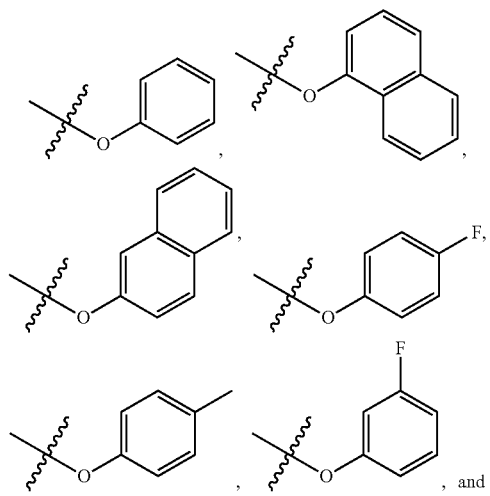

, and

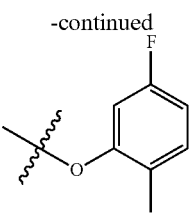

The term "heterocycle", "heterocyclyl", or "heterocyclo" includes saturated, and partially saturated heteroatom-containing ring radicals, where the heteroatoms may be selected from nitrogen, sulfur and oxygen (and typically nitrogen). It does not include rings containing —O—O—, —O—S— or —S—S— portions. In one embodiment the "heterocycle" group is optionally substituted with 1 to 3 substituents that include but are not limited to, hydroxyl, Boc, halo, haloalkyl, cyano, alkyl, arylalkyl, heteroarylalkyl, oxo, alkoxy, and amino. Examples of heterocycle groups include 3- to 6-membered heteromonocyclic groups containing 1 to 4 nitrogen atoms (e.g. pyrrolidinyl, imidazolidinyl, piperidinyl, pyrrolinyl, piperazinyl); saturated 3 to 6-membered heteromonocyclic group containing 1 to 2 oxygen atoms and 1 to 3 nitrogen atoms (e.g. morpholinyl); saturated 3 to 6-membered heteromonocyclic group containing 1 to 2 sulfur atoms and 1 to 3 nitrogen atoms (e.g., thiazolidinyl). Examples of partially saturated heterocycle radicals include but are not limited to, dihydrothienyl, dihydropyranyl, dihydrofuryl, and dihydrothiazolyl. Examples of partially saturated and saturated heterocycle groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydroquinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl. The terms "heterocycle", "heterocyclyl", and "heterocyclo" are used interchangeably herein. The term "heterocycle" except where excluded by context, includes bicyclic and tricyclic heterocycles. For example 2-azabicyclo[2.1.1]hexane would be considered a 6-membered heterocycle, and 3-azabicyclo[3.2.0]heptane would be considered a 7-membered heterocycle.

As used herein the term "bicyclic heterocycle" refers to a heterocycle as defined herein with additional fused rings. Non-limiting examples of bicyclic heterocycles include:

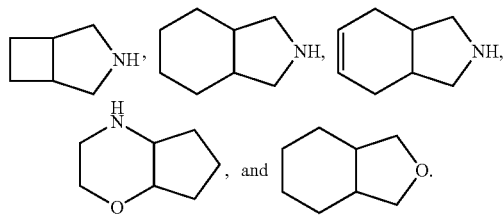

Unless otherwise drawn or clear from the context, the term "bicyclic heterocycle" includes cis and trans diastereomers. Non-limiting examples of chiral bicyclic heterocycles include:

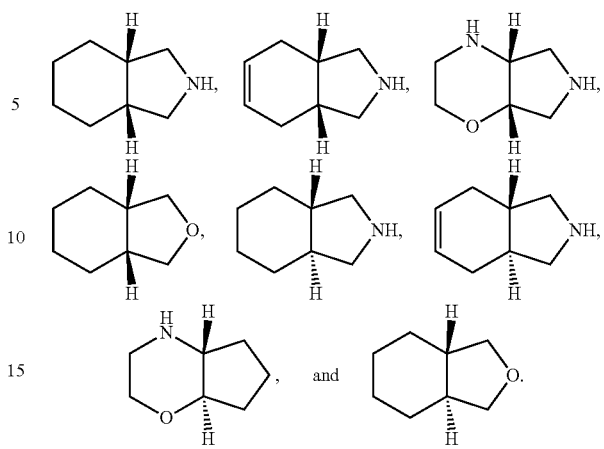

As used herein the term "bridged heterocycle" refers to a heterocycle as defined herein with at least one bridging carbon atom. Non-limiting examples of bridged heterocycles include:

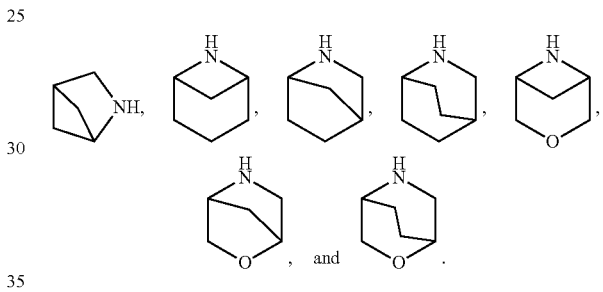

Heterocycle groups also include radicals where heterocyclic radicals are fused/condensed with aryl radicals: such as unsaturated condensed heterocyclic group containing 1 to 5 nitrogen atoms, for example, indoline, isoindoline, unsaturated condensed heterocyclic group containing 1 to 2 oxygen atoms and 1 to 3 nitrogen atoms, unsaturated condensed heterocyclic group containing 1 to 2 sulfur atoms and 1 to 3 nitrogen atoms, and saturated, partially unsaturated and unsaturated condensed heterocyclic group containing 1 to 2 oxygen or sulfur atoms.

"Pharmaceutically acceptable salt" refers to both acid and base addition salts.

"Treating" or "treatment" refer to the treatment of a disease or disorder described herein, in a subject, preferably a human, and includes:

i. inhibiting a disease or disorder, i.e., arresting its development;

ii. relieving a disease or disorder, i.e., causing regression of the disorder;

iii. slowing progression of the disorder; and/or iv. inhibiting, relieving, or slowing progression of one or more symptoms of the disease or disorder "Host" refers to a warm-blooded animal such as a mammal, typically a human, which is afflicted with one or more diseases and disorders described herein.

A "prodrug" as used herein, means a compound which when administered to a host in vivo is converted into a parent drug. As used herein, the term "parent drug" means any of the presently described chemical compounds described herein. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

The present invention includes compounds of Formula I, II, III, and IV with at least one desired isotopic substitution of an atom, at an amount above the natural abundance of the isotope, i.e., enriched. Isotopes are atoms having the same atomic number but different mass numbers, i.e., the same number of protons but a different number of neutrons.

The present invention also includes combination treatment and pharmaceutical compositions including compounds of Formula V with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, fluorine and chlorine such as $^2$H, $^3$H, $^{11}$C, $^{13}$C, $^{14}$C, $^{15}$N, $^{17}$O, $^{18}$O, $^{18}$F, $^{35}$S, $^{36}$Cl, and respectively. In one non-limiting embodiment, isotopically labelled compounds can be used in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2$H) and tritium ($^3$H) may be used anywhere in described structures that achieves the desired result. Alternatively, or in addition, isotopes of carbon, e.g., $^{13}$C and $^{14}$C, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in a compound of Formula I, II, III, IV, V. In one non-limiting embodiment, the substitution of a hydrogen atom for a deuterium atom occurs within a group selected from any of X, Y, A, Z, $R^1$, $R^2$, $R^3$, $R^4$, $R^5$, $R^{11}$, $R^{12}$, $R^{13}$, $R^{14}$, $R^{15}$, and $R^x$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

RAD1901 is a compound of structure

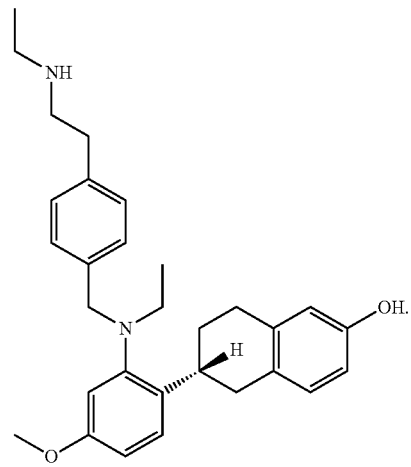

AZD9496 is a compound of structure

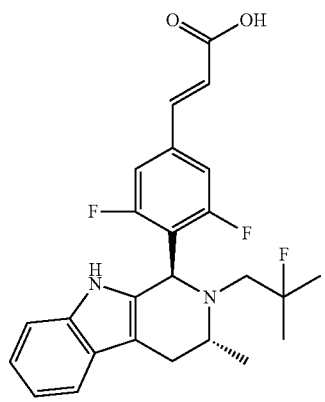

Compounds

Benzothiophene based estrogen receptor ligands of the invention includes compounds of Formula I, II, III, or IV, or a pharmaceutically acceptable salt thereof:

In one embodiment, a compound of Formula I is provided:

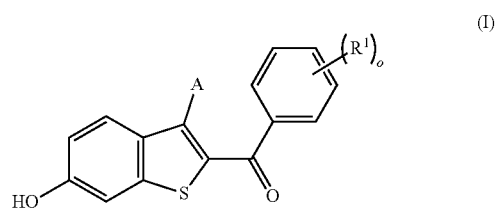

or a pharmaceutically acceptable salt, N-oxide, isotopic derivative, or prodrug, optionally in a pharmaceutically acceptable carrier to form a pharmaceutically acceptable composition thereof;

wherein A is:

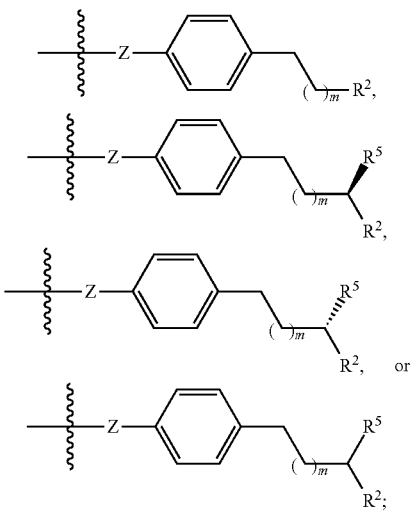

m is 0, 1, or 2;
o is 0, 1, 2, 3, 4, or 5 (and typically 1, 2 or 3);
Z is selected from —O—, —C($R^3$)$_2$—, —CHR$^3$—, —CH$_2$—, —CHF—, —CF$_2$—, and —S—;
each $R^1$ is independently selected from $C_1$-$C_3$alkyl, halogen, and $C_1$-$C_3$haloalkyl;
$R^2$ is selected from 4-6 membered heterocycle optionally substituted with one, two, or three groups (and typically one group) independently selected from $R^4$; or
$R^2$ is selected from —NH$_2$, —NH($C_1$-$C_3$alkyl or $C_2$-$C_3$haloalkyl), and —N((independently)$C_1$-$C_3$alkyl or $C_2$-$C_3$haloalkyl)$_2$;
$R^3$ is independently selected from —F, —Cl, —Br, —CH$_3$, —CH$_2$F, —CHF$_2$, and —CF$_3$; and
$R^4$ and $R^5$ are independently selected from hydrogen, halogen, $C_1$-$C_3$alkyl, and $C_1$-$C_3$haloalkyl.

In an alternative embodiment of Formula I, $R^2$ is selected from monocyclic 7-8 membered heterocycle optionally substituted with one, two, or three groups (and typically one group) independently selected from $R^4$.

In another alternative embodiment of Formula I, $R^2$ is selected from 6-12 membered bicyclic or bridged heterocycle optionally substituted with one, two, or three groups (and typically one group) independently selected from $R^4$.

In another alternative embodiment of Formula I, $R^2$ is —NH—(CH$_2$)$_{n1}$—NH$_2$, —NH—(CH$_2$)$_{n1}$—NH($C_1$-$C_{12}$alkyl or $C_2$-$C_{12}$haloalkyl), —NH—(CH$_2$)$_{n1}$—N((independently)$C_1$-$C_{12}$alkyl or $C_2$-$C_{12}$haloalkyl)$_2$, —NHC$_4$-$C_{12}$alkyl, or N($C_1$-$C_{12}$alkyl)$_2$, wherein n1 is 2, 3, 4, 5, or 6.

In one embodiment, a compound of Formula II is provided:

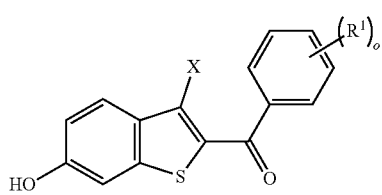

(II)

or a pharmaceutically acceptable salt, N-oxide, isotopic derivative, or prodrug, optionally in a pharmaceutically acceptable carrier to form a pharmaceutically acceptable composition thereof;
wherein
X is

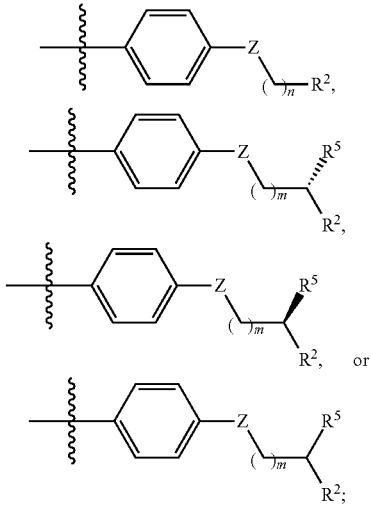

m is 0, 1, or 2;
n is 1, 2, or 3;
o is 0, 1, 2, 3, 4, or 5 (and typically 1, 2 or 3);
Z is selected from —O—, —C($R^3$)$_2$—, —CHR$^3$—, —CH$_2$—, —CHF—, —CF$_2$—, and —S—;
each $R^1$ is independently selected from $C_1$-$C_3$alkyl (for example methyl), halogen (for example F), and $C_1$-$C_3$haloalkyl (typically F substituted alkyl);
$R^2$ is selected from 4-6 membered heterocycle optionally substituted with one, two, or three groups (and typically one group) independently selected from $R^4$; or
$R^2$ is selected from —NH$_2$, —NH($C_1$-$C_3$alkyl or $C_2$-$C_3$haloalkyl), and —N((independently)$C_1$-$C_3$alkyl or $C_2$-$C_3$haloalkyl)$_2$;
$R^3$ is independently selected from —F, —Cl, —Br, —CH$_3$, —CH$_2$F, —CHF$_2$, and —CF$_3$; and
$R^4$ and $R^5$ are independently selected from hydrogen, halogen (for example F), $C_1$-$C_3$alkyl, and $C_1$-$C_3$haloalkyl.

In an alternative embodiment of Formula II, $R^2$ is selected from monocyclic 7-8 membered heterocycle optionally substituted with one, two, or three groups (and typically one group) independently selected from $R^4$.

In another alternative embodiment of Formula II, $R^2$ is selected from 6-12 membered bicyclic or bridged heterocycle optionally substituted with one, two, or three groups (and typically one group) independently selected from $R^4$.

In another alternative embodiment of Formula II, $R^2$ is —NH—(CH$_2$)$_{n1}$—NH$_2$, —NH—(CH$_2$)$_{n1}$—NH($C_1$-$C_{12}$alkyl or $C_2$-$C_{12}$haloalkyl), —NH—(CH$_2$)$_{n1}$—N((independently)$C_1$-$C_{12}$alkyl or $C_2$-$C_{12}$haloalkyl)$_2$, —NHC$_4$-$C_{12}$alkyl, or —N($C_1$-$C_{12}$alkyl)$_2$, wherein n1 is 2, 3, 4, 5, or 6.

In one embodiment, a compound of Formula III is provided:

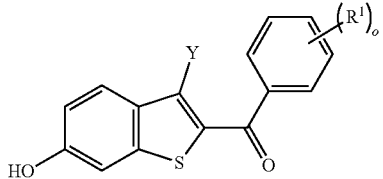

(III)

or a pharmaceutically acceptable salt, N-oxide, isotopic derivative, or prodrug, optionally in a pharmaceutically acceptable carrier to form a pharmaceutically acceptable composition thereof;
wherein:
m is 0, 1, or 2;
n is 1, 2, or 3;
o is 0, 1, 2, 3, 4, or 5;
Y is

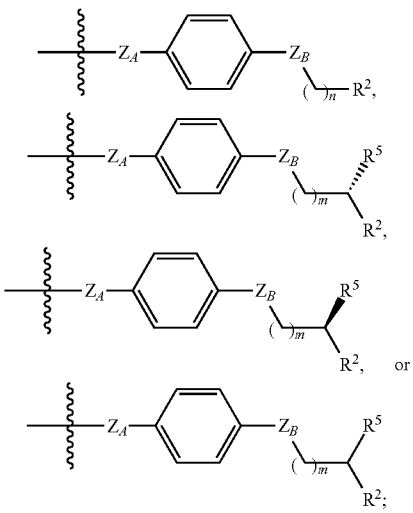

$Z_A$ and $Z_B$ are independently selected from —O—, —C(R$^3$)$_2$—, —CHR$^3$—, —CH$_2$—, —CHF—, —CF$_2$—, and —S—;

each $R^1$ is independently selected from $C_1$-$C_3$alkyl, halogen (for example F), and $C_1$-$C_3$haloalkyl (for example F substituted substituted);

$R^2$ is selected from 4-6 membered heterocycle optionally substituted with one, two, or three groups (and typically one group) independently selected from $R^4$; or
$R^2$ is selected from —NH$_2$, —NH($C_1$-$C_3$alkyl or $C_2$-$C_3$haloalkyl), and —N((independently)$C_1$-$C_3$alkyl or $C_2$-$C_3$haloalkyl)$_2$;

$R^3$ is independently selected from —F, —Cl, —Br, —CH$_3$, —CH$_2$F, —CHF$_2$, and —CF$_3$; and $R^4$ and $R^5$ are independently selected from hydrogen, halogen (for example F), $C_1$-$C_3$alkyl, and $C_1$-$C_3$haloalkyl.

In an alternative embodiment of Formula III, $R^2$ is selected from monocyclic 7-8 membered heterocycle optionally substituted with one, two, or three groups (and typically one group) independently selected from $R^4$.

In another alternative embodiment of Formula III, $R^2$ is selected from 6-12 membered bicyclic or bridged heterocycle optionally substituted with one, two, or three groups (and typically one group) independently selected from $R^4$.

In another alternative embodiment of Formula III, $R^2$ is —NH—(CH$_2$)$_{n1}$—NH$_2$, —NH—(CH$_2$)$_{n1}$—NH($C_1$-$C_{12}$alkyl or $C_2$-$C_{12}$haloalkyl), —NH—(CH$_2$)$_{n1}$—N((independently)$C_1$-$C_{12}$alkyl or $C_2$-$C_{12}$haloalkyl)$_2$, —NHC$_4$-$C_{12}$alkyl, or —N($C_1$-$C_{12}$alkyl)$_2$, wherein n1 is 2, 3, 4, 5, or 6.

In one embodiment the compound of Formula I is of Formula I-A:

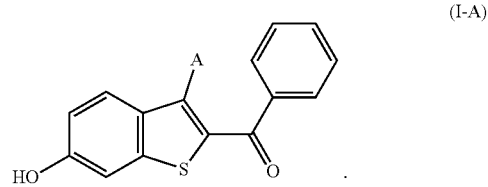

(I-A)

In one embodiment the compound of Formula I is of Formula I-B:

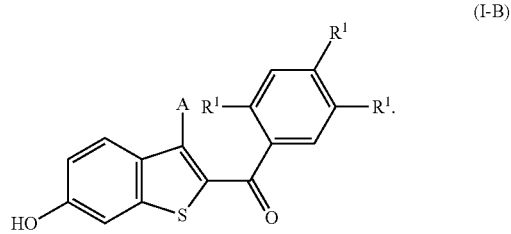

(I-B)

In one embodiment the compound of Formula I is of Formula I-C:

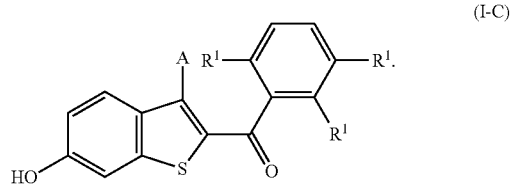

(I-C)

In one embodiment the compound of Formula I is of Formula I-D:

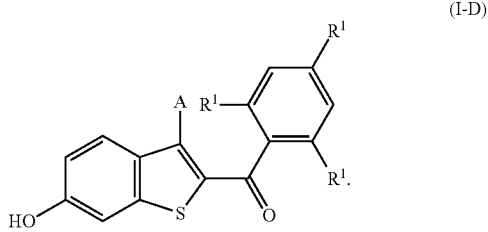

(I-D)

In one embodiment the compound of Formula I is of Formula I-E:

(I-E)

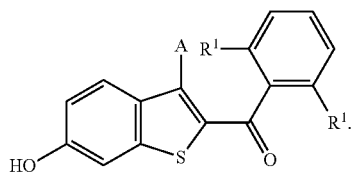

In one embodiment the compound of Formula I is of Formula I-F:

(I-F)

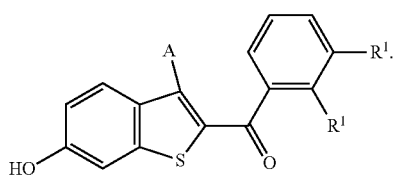

In one embodiment the compound of Formula I is of Formula I-G:

(I-G)

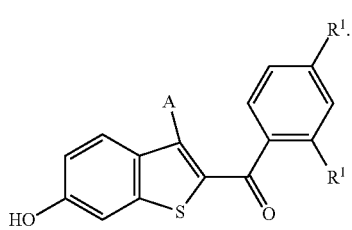

In one embodiment the compound of Formula I is of Formula I-H:

(I-H)

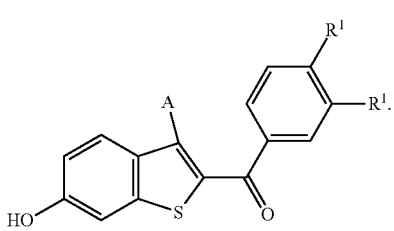

In one embodiment the compound of Formula I is of Formula I-J:

(I-J)

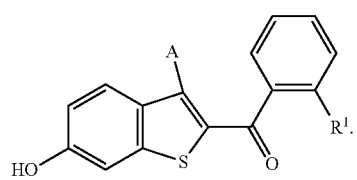

In one embodiment the compound of Formula I is of Formula I-K:

(I-K)

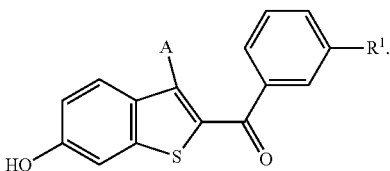

In one embodiment the compound of Formula I is of Formula I-L:

(I-L)

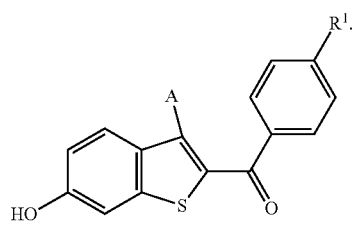

In one embodiment the compound of Formula II is of Formula II-A:

(II-A)

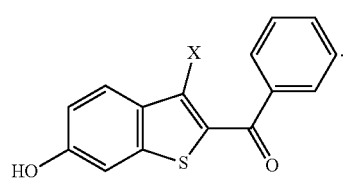

In one embodiment the compound of Formula II is of Formula II-B:

(II-B)

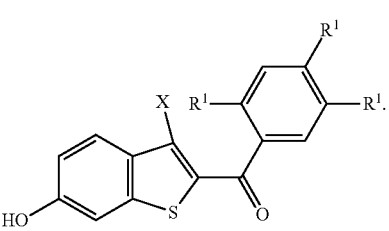

In one embodiment the compound of Formula II is of Formula II-C:

(II-C)

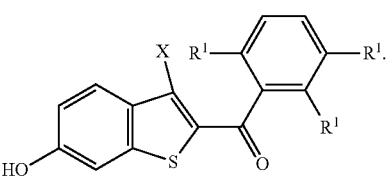

In one embodiment the compound of Formula II is of Formula II-D:

In one embodiment the compound of Formula II is of Formula II-E:

(II-D)

In one embodiment the compound of Formula II is of Formula II-F:

(II-E)

In one embodiment the compound of Formula II is of Formula II-G:

(II-F)

In one embodiment the compound of Formula II is of Formula II-H:

(II-G)

In one embodiment the compound of Formula II is of Formula II-J:

(II-H)

In one embodiment the compound of Formula II is of Formula II-K:

(II-J)

In one embodiment the compound of Formula II is of Formula II-L:

(II-K)

In one embodiment the compound of Formula III is of Formula III-A:

(II-L)

In one embodiment the compound of Formula III is of Formula III-B:

(III-A)

In one embodiment the compound of Formula III is of Formula III-C:

(III-B)

(III-C)

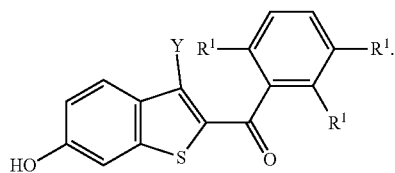

In one embodiment the compound of Formula III is of Formula III-D:

(III-D)

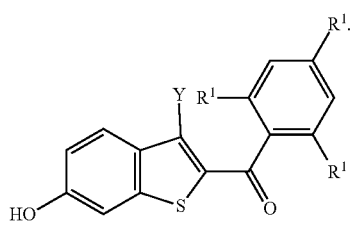

In one embodiment the compound of Formula III is of Formula III-E:

(III-E)

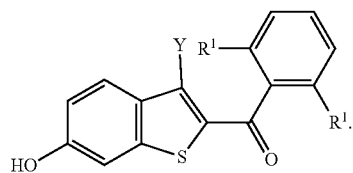

In one embodiment the compound of Formula III is of Formula III-F:

(III-F)

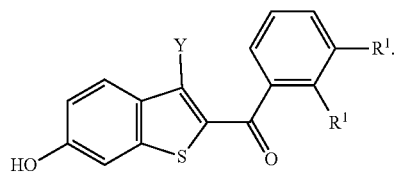

In one embodiment the compound of Formula III is of Formula III-G:

(III-G)

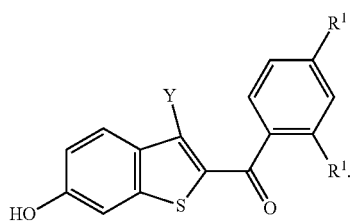

In one embodiment the compound of Formula III is of Formula III-H:

(III-H)

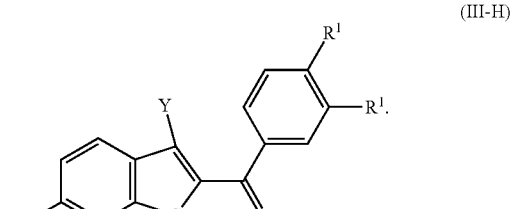

In one embodiment the compound of Formula III is of Formula III-J:

(III-J)

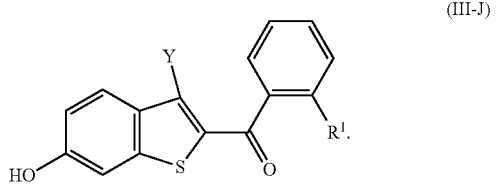

In one embodiment the compound of Formula III is of Formula III-K:

(III-K)

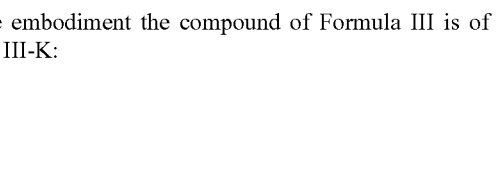

In one embodiment the compound of Formula III is of Formula III-L:

(III-L)

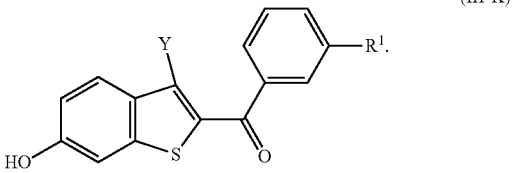

In one embodiment the compound of Formula I is:
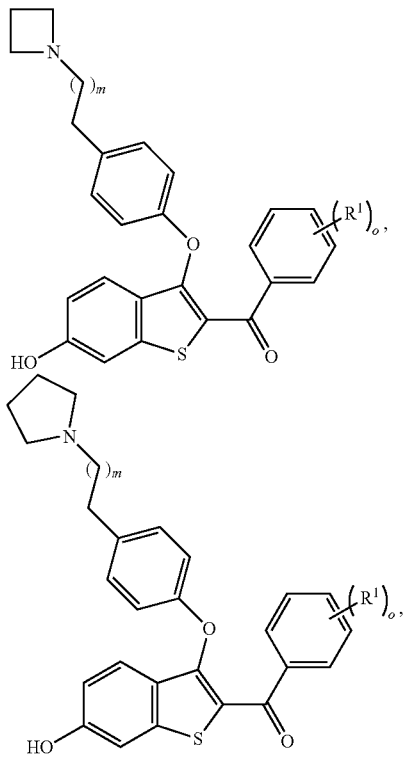
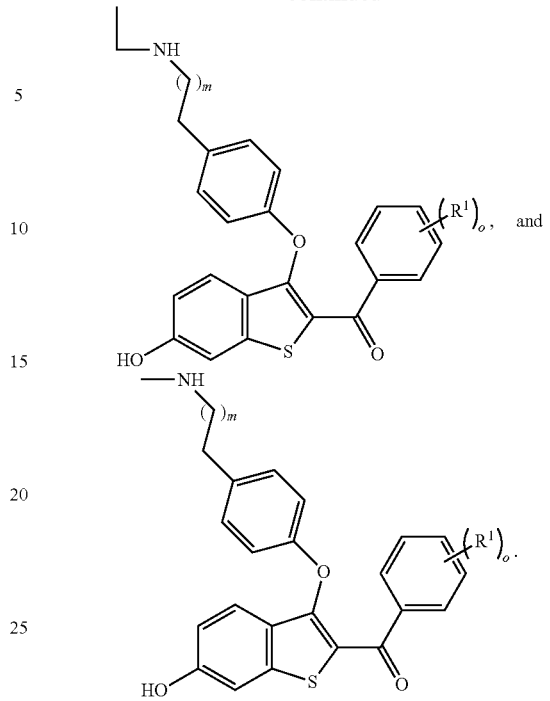
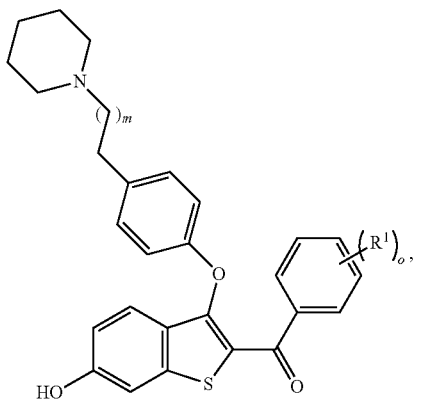
In one embodiment the compound of Formula II is:
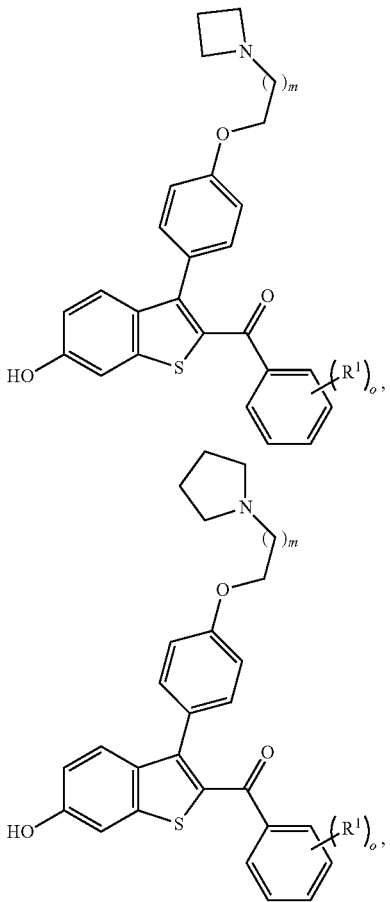

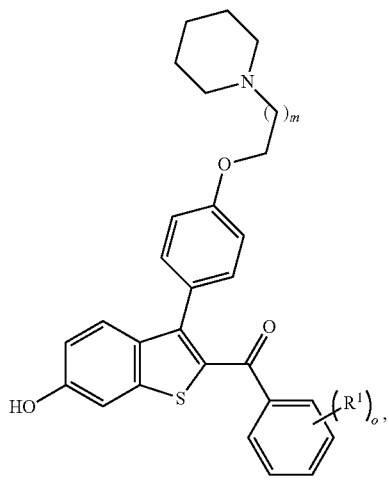
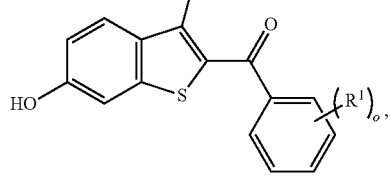
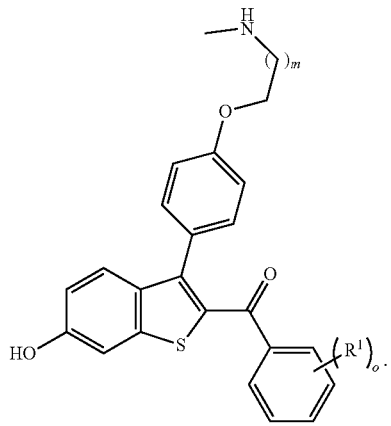
In one embodiment the compound of Formula V is:
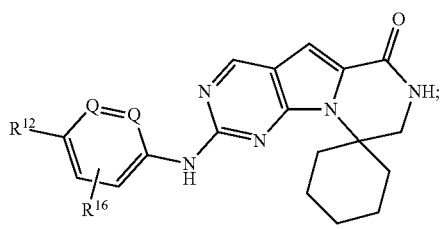
or a pharmaceutically acceptable salt thereof.
In one embodiment the compound of Formula V is:
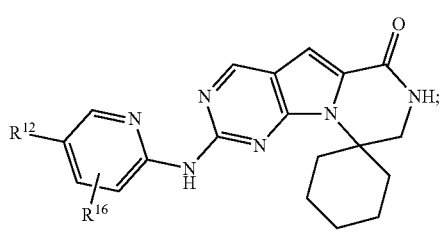
or a pharmaceutically acceptable salt thereof.
In one embodiment the compound of Formula V is:
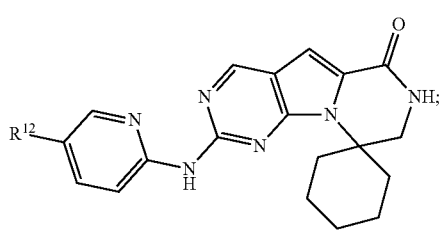
or a pharmaceutically acceptable salt thereof.

In one embodiment the compound of Formula V is:

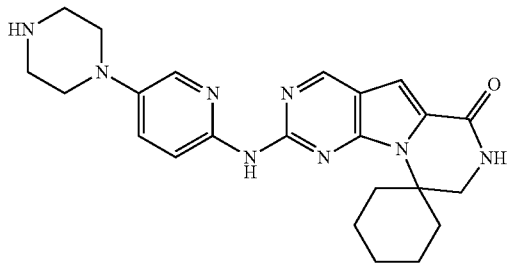 [SMILES: O=C1NCC2(CCCCC2)n2c1cc1cnc(Nc3ccc(N4CCNCC4)cn3)nc12]

or a pharmaceutically acceptable salt thereof.

In one embodiment the compound of Formula V is:

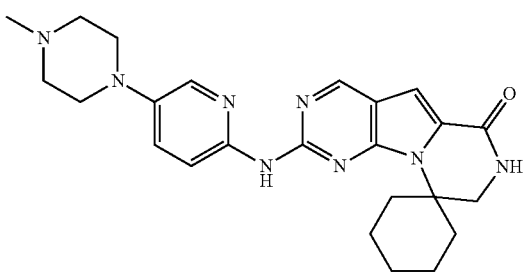 [SMILES: CN1CCN(c2ccc(Nc3ncc4cc5n(c4n3)C3(CCCCC3)CNC5=O)nc2)CC1]

or a pharmaceutically acceptable salt thereof.

In one embodiment the compound of Formula V is:

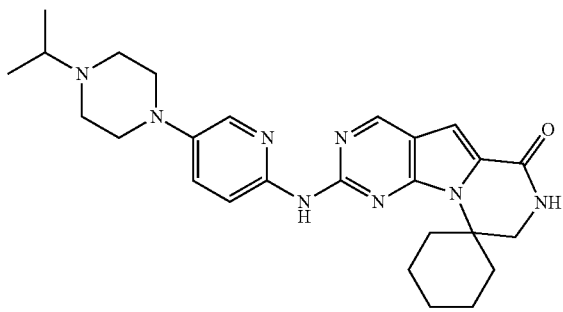 [SMILES: CC(C)N1CCN(c2ccc(Nc3ncc4cc5n(c4n3)C3(CCCCC3)CNC5=O)nc2)CC1]

or a pharmaceutically acceptable salt thereof.

In one embodiment the compound of Formula V is:

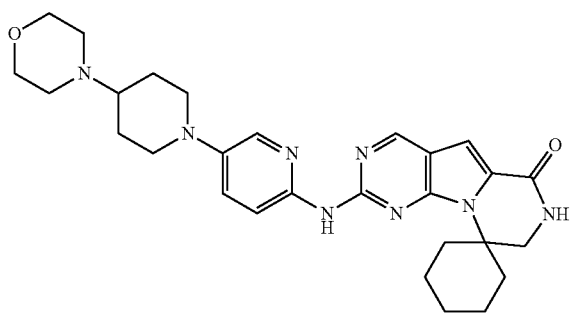 [SMILES: O=C1NCC2(CCCCC2)n2c1cc1cnc(Nc3ccc(N4CCC(N5CCOCC5)CC4)cn3)nc12]

or a pharmaceutically acceptable salt thereof.

Embodiments of $R^1$

In one embodiment $R^1$ is fluoro.
In one embodiment $R^1$ is chloro.
In one embodiment $R^1$ is bromo.
In one embodiment $R^1$ is trifluoromethane.
In one embodiment $R^1$ is difluoromethane.
In one embodiment $R^1$ is monofluoromethane.
In one embodiment $R^1$ is methyl.
In one embodiment $R^1$ is ethyl.
In one embodiment $R^1$ is propyl.
In one embodiment $R^1$ is cyclopropyl.
In various independent embodiments there are 2, 3, 4, or 5, $R^1$s and at least one $R^1$ is fluoro.
In various independent embodiments there are 2, 3, 4, or 5, $R^1$s and at least one $R^1$ is chloro.
In various independent embodiments there are 2, 3, 4, or 5, $R^1$s and at least one $R^1$ is bromo.
In various independent embodiments there are 2, 3, 4, or 5, $R^1$s and at least one $R^1$ is trifluoromethane.
In various independent embodiments there are 2, 3, 4, or 5, $R^1$s and at least one $R^1$ is methyl.
In various independent embodiments there are 2, 3, 4, or 5, $R^1$s and at least one $R^1$ is ethyl.
In various independent embodiments there are 2, 3, 4, or 5, $R^1$s and at least one $R^1$ is propyl.
In various independent embodiments there are 2, 3, 4, or 5, $R^1$s and at least one $R^1$ is cyclopropyl.
In various independent embodiments there are 2, 3, 4, or 5, $R^1$s and at least one $R^1$ is difluoromethane.
In various independent embodiments there are 2, 3, 4, or 5, $R^1$s and at least one $R^1$ is monofluoromethane.

Embodiments of "Alkyl"

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_8$alkyl, $C_1$-$C_4$alkyl, $C_1$-$C_3$alkyl, or $C_1$-$C_2$alkyl.
In one embodiment "alkyl" has one carbon.
In one embodiment "alkyl" has two carbons.
In one embodiment "alkyl" has three carbons.
In one embodiment "alkyl" has four carbons.
In one embodiment "alkyl" has five carbons.
In one embodiment "alkyl" has six carbons.
Non-limiting examples of "alkyl" include: methyl, ethyl, propyl, butyl, pentyl, and hexyl.
Additional non-limiting examples of "alkyl" include: isopropyl, isobutyl, isopentyl, and isohexyl.
Additional non-limiting examples of "alkyl" include: sec-butyl, sec-pentyl, and sec-hexyl.
Additional non-limiting examples of "alkyl" include: tert-butyl, tert-pentyl, and tert-hexyl.
Additional non-limiting examples of "alkyl" include: neopentyl, 3-pentyl, and active pentyl.

Embodiments of "Haloalkyl"

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_8$haloalkyl, $C_1$-$C_4$haloalkyl, $C_1$-$C_3$haloalkyl, and $C_1$-$C_2$haloalkyl.
In one embodiment "haloalkyl" has one carbon.
In one embodiment "haloalkyl" has one carbon and one halogen.
In one embodiment "haloalkyl" has one carbon and two halogens.
In one embodiment "haloalkyl" has one carbon and three halogens.
In one embodiment "haloalkyl" has two carbons.
In one embodiment "haloalkyl" has three carbons.
In one embodiment "haloalkyl" has four carbons.

In one embodiment "haloalkyl" has five carbons.
In one embodiment "haloalkyl" has six carbons.
Non-limiting examples of "haloalkyl" include:

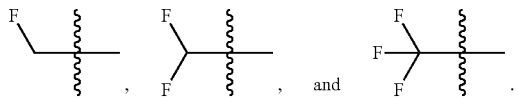

Additional non-limiting examples of "haloalkyl" include:

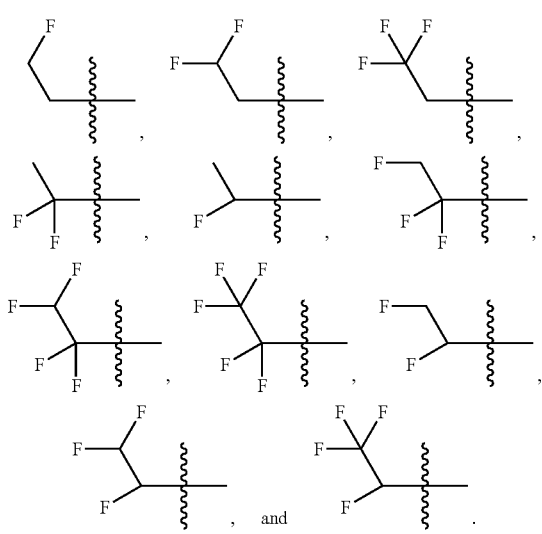

Additional non-limiting examples of "haloalkyl" include:

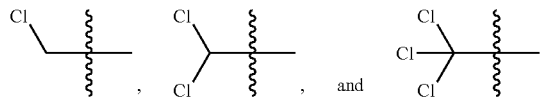

Additional non-limiting examples of "haloalkyl" include:

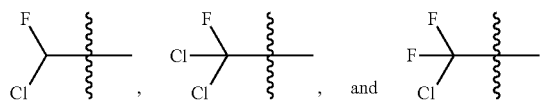

Embodiments of "Aryl"

In one embodiment "aryl" is a 6 carbon aromatic group (phenyl)

In one embodiment "aryl" is a 10 carbon aromatic group (napthyl)

In one embodiment "aryl" is a 6 carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example,

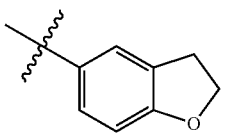 [SMILES: *c1ccc2c(c1)CCO2]

is an "aryl" group.
However,

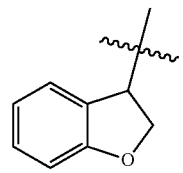 [SMILES: *C1COc2ccccc21]

is a "heterocycle" group.

In one embodiment "aryl" is a 6 carbon aromatic group fused to a cycloalkyl wherein the point of attachment is the aryl ring. Non-limiting examples of "aryl" include dihydroindene and tetrahydronaphthalene wherein the point of attachment for each group is on the aromatic ring.

For example,

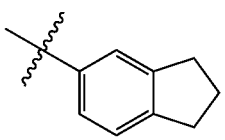 [SMILES: *c1ccc2c(c1)CCC2]

is an "aryl" group.
However,

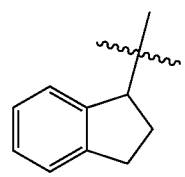 [SMILES: *C1CCc2ccccc21]

is a "cycloalkyl" group.

Embodiments of "Heteroaryl"

In one embodiment "heteroaryl" is a 5 membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

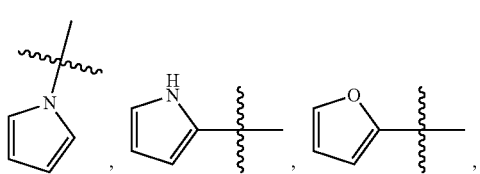

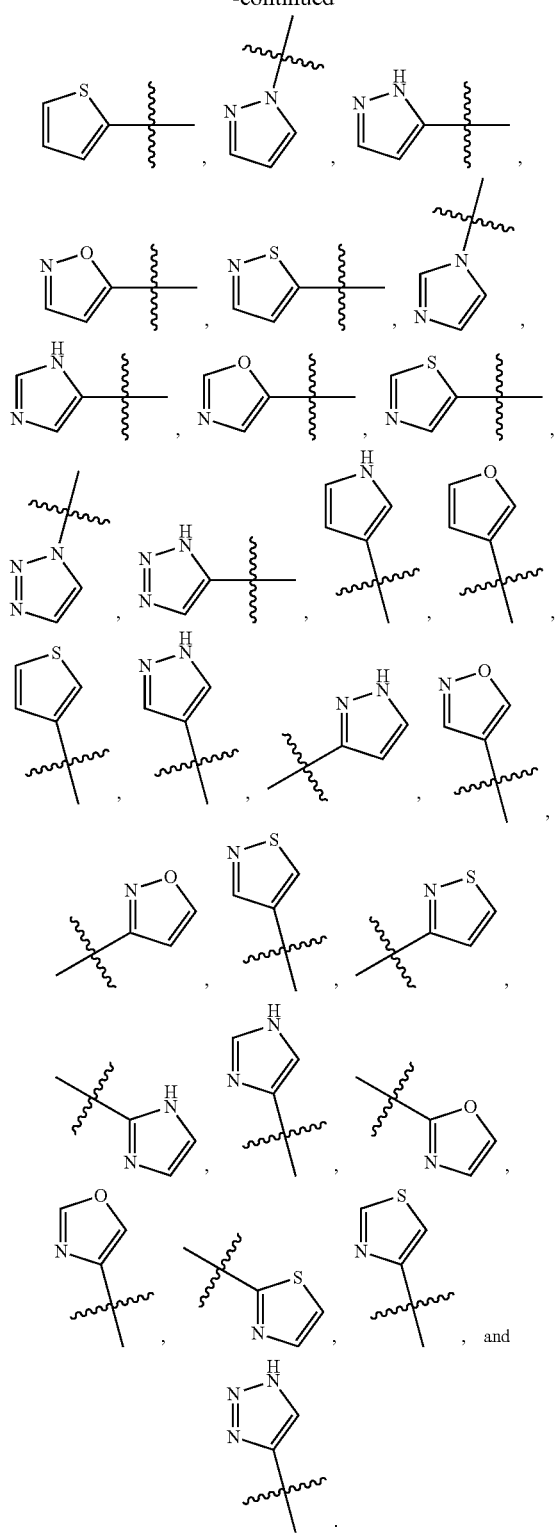

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

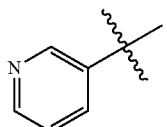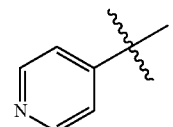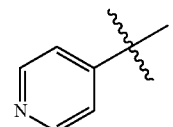

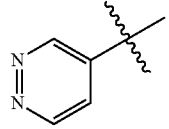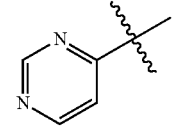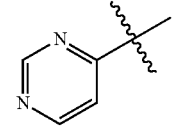

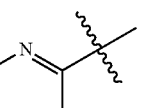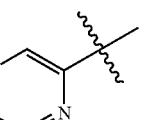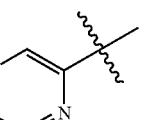, and

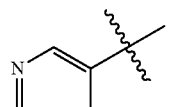.

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

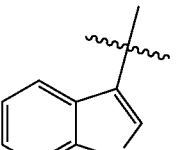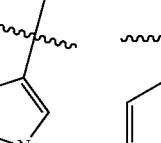

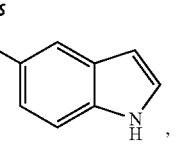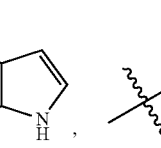

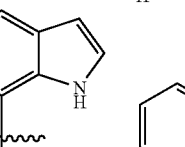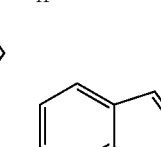, and

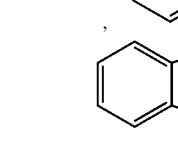

Additional non-limiting examples of "heteroaryl" groups that are bicyclic include:

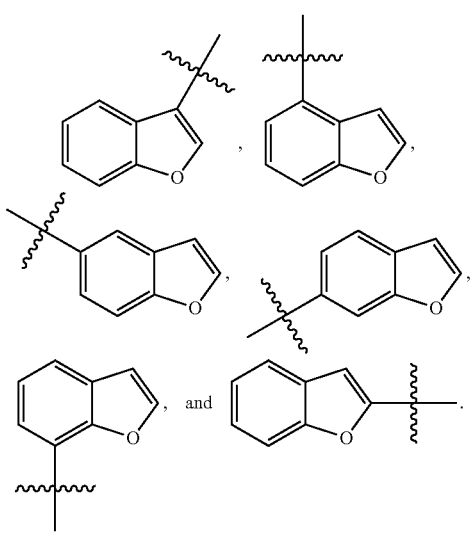

Additional non-limiting examples of "heteroaryl" groups that are bicyclic include:

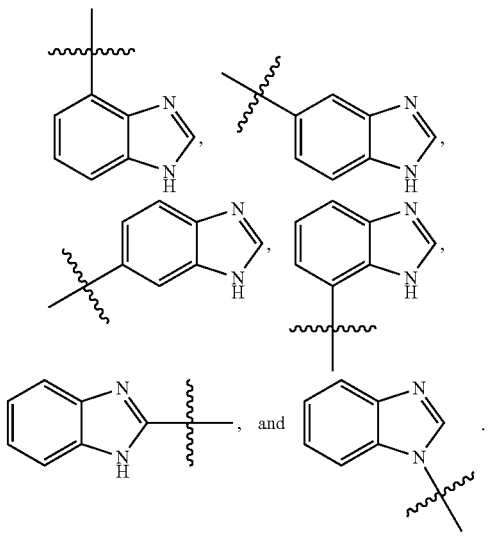

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

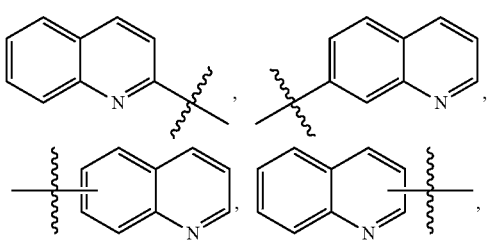

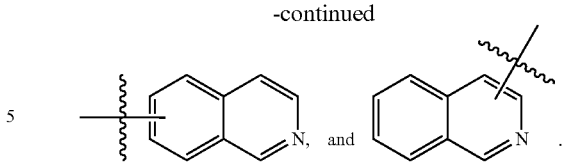

Embodiments of "Cycloalkyl"

In one embodiment "cycloalkyl" is a $C_3$-$C_8$cycloalkyl, $C_3$-$C_7$cycloalkyl, $C_3$-$C_6$cycloalkyl, $C_3$-$C_8$cycloalkyl, $C_3$-$C_4$cycloalkyl, $C_4$-$C_8$cycloalkyl, $C_5$-$C_8$cycloalkyl, or $C_6$-$C_8$cycloalkyl.

In one embodiment "cycloalkyl" has three carbons.
In one embodiment "cycloalkyl" has four carbons.
In one embodiment "cycloalkyl" has five carbons.
In one embodiment "cycloalkyl" has six carbons.
In one embodiment "cycloalkyl" has seven carbons.
In one embodiment "cycloalkyl" has eight carbons.
In one embodiment "cycloalkyl" has nine carbons.
In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

Additional non-limiting examples of "cycloalkyl" include dihydro-indene and tetrahydronaphthalene wherein the point of attachment for each group is on the cycloalkyl ring.

For example,

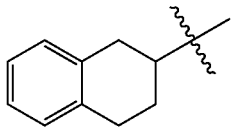 [SMILES: *C1CCc2ccccc2C1]

is an "cycloalkyl" group.

However,

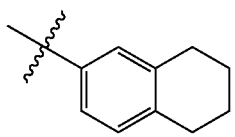 [SMILES: *c1ccc2c(c1)CCCC2]

is an "aryl" group.

Embodiments of "Heterocycle"

In one embodiment "heterocycle" refers to a cyclic ring with one nitrogen and 3, 4, 5, 6, 7, or 8 carbon atoms.

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocyclic ring.

For example,

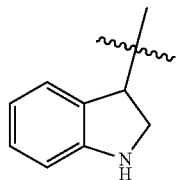 [SMILES: *C1CNc2ccccc21]

is a "heterocycle" group.

However,

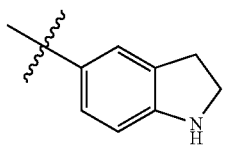 [SMILES: *c1ccc2c(c1)CCN2]

is an "aryl" group.

Embodiments of "Arylalkyl"

In one embodiment the "arylalkyl" refers to a 1 carbon alkyl group substituted with an aryl group.

Non-limiting examples of "arylalkyl" include:

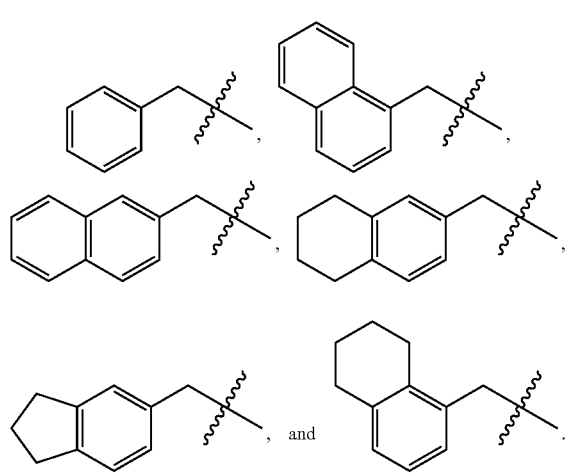

In one embodiment "arylalkyl" is

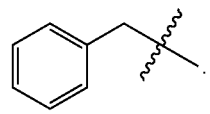 [SMILES: *Cc1ccccc1]

In one embodiment the "arylalkyl" refers to a 2 carbon alkyl group substituted with an aryl group.

Non-limiting examples of "arylalkyl" include:

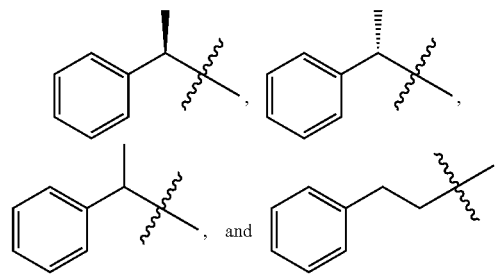

In one embodiment the "arylalkyl" refers to a 3 carbon alkyl group substituted with an aryl group.

Embodiments of $R^2$

In one embodiment $R^2$ is 4-6 membered heterocycle optionally substituted with one, two, or three groups selected from $R^4$.

In one embodiment $R^2$ is —$NH_2$.
In one embodiment $R^2$ is —NHalkyl.
In one embodiment $R^2$ is —$NHCH_3$.
In one embodiment $R^2$ is —$NHCH_2CH_3$.
In one embodiment $R^2$ is —N(alkyl)$_2$.
In one embodiment $R^2$ is —$N(CH_3)_2$.
In one embodiment $R^2$ is —$N(CH_2CH_3)_2$.
In one embodiment, $R^2$ is —OH.
In one embodiment $R^2$ is

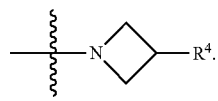

In one embodiment $R^2$ is

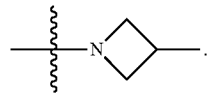 [SMILES: *N1CC(C)C1]

In one embodiment $R^2$ is

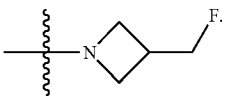 [SMILES: *N1CC(CF)C1]

In one embodiment R² is F

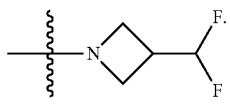 [SMILES: *N1CC(C(F)F)C1]

In one embodiment R² is

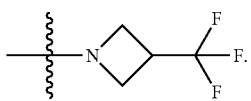

In one embodiment R² is

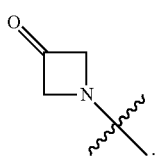

In one embodiment R² is

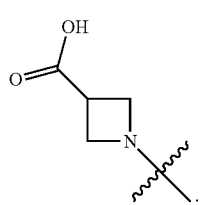 [SMILES: *N1CC(C(=O)O)C1]

In various independent embodiments R² is

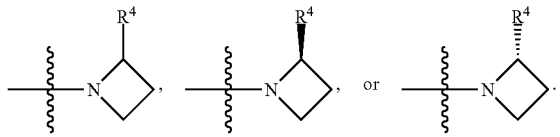

In various independent embodiments R² is

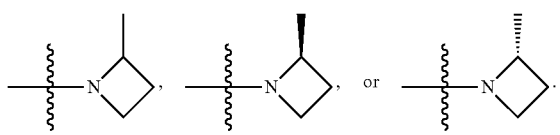

In various independent embodiments R² is

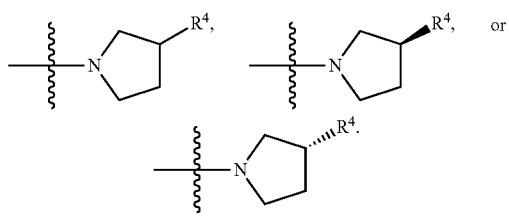

In various independent embodiments R² is

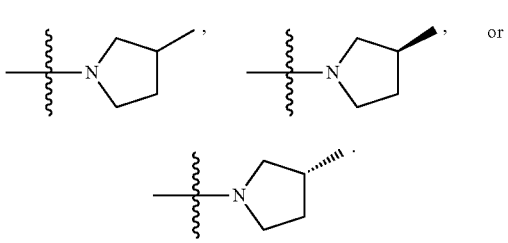

In various independent embodiments R² is

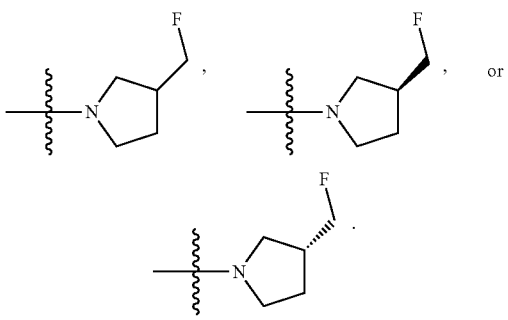

In various independent embodiments R² is

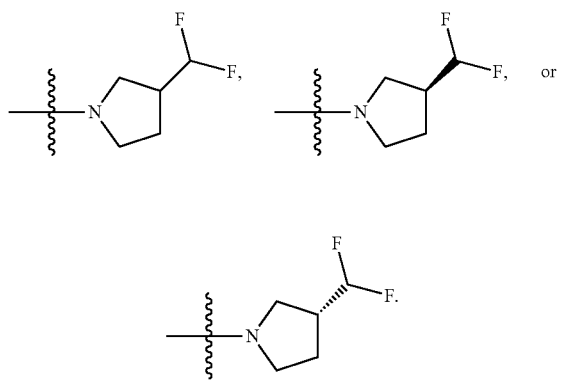

In various independent embodiments R² is

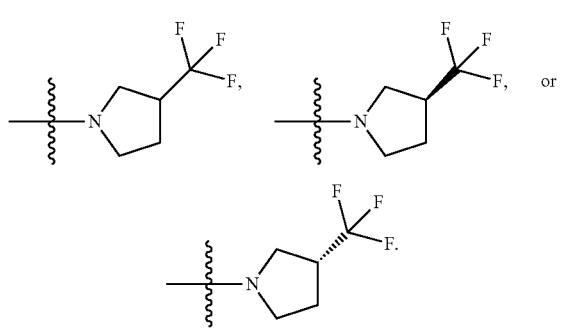

In various independent embodiments R² is

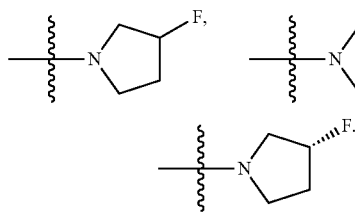

In various independent embodiments R² is

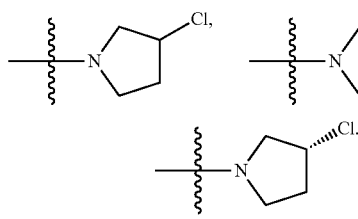

In various independent embodiments R² is

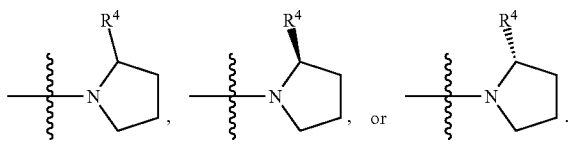

In various independent embodiments R² is

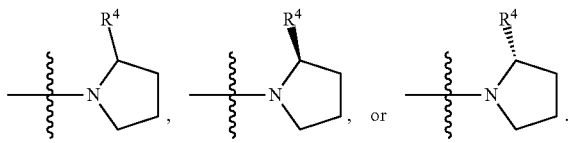

In various independent embodiments R² is

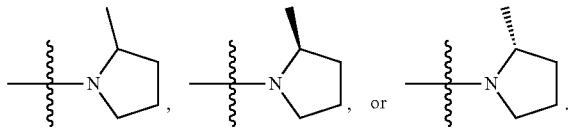

In various independent embodiments R² is

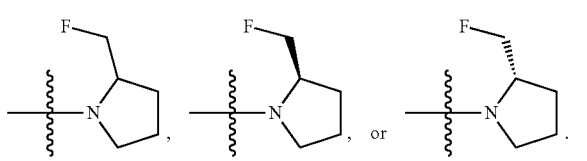 [SMILES: *N1CCCC1CF ; *N1CCC[C@@H]1CF ; *N1CCC[C@H]1CF]

In various independent embodiments R² is

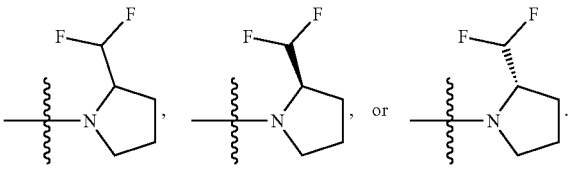 [SMILES: *N1CCCC1C(F)F ; *N1CCC[C@@H]1C(F)F ; *N1CCC[C@H]1C(F)F]

In various independent embodiments R² is

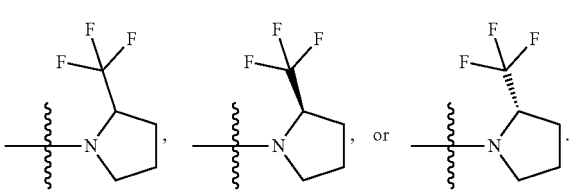 [SMILES: *N1CCCC1C(F)(F)F ; *N1CCC[C@@H]1C(F)(F)F ; *N1CCC[C@H]1C(F)(F)F]

In various independent embodiments R² is

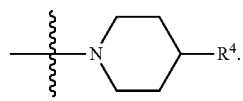

In various independent embodiments R² is

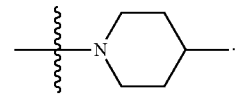

In various independent embodiments R² is

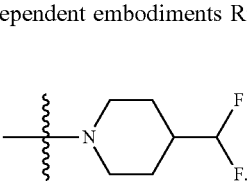

In various independent embodiments R² is F

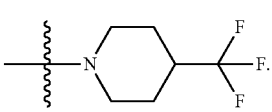

In various independent embodiments R² is

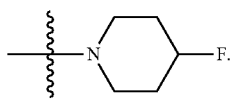

In various independent embodiments R² is

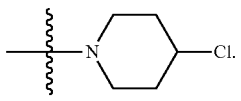

In various independent embodiments R² is

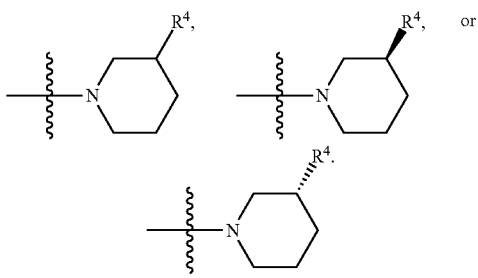

In various independent embodiments R²

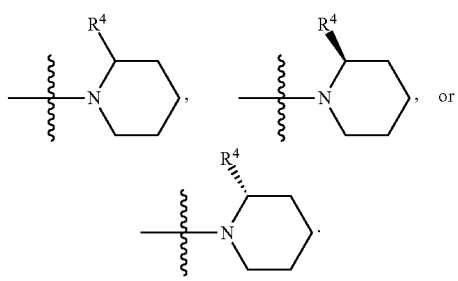

In various independent embodiments R² is

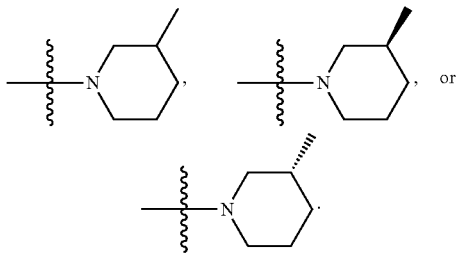

In various independent embodiments R² is

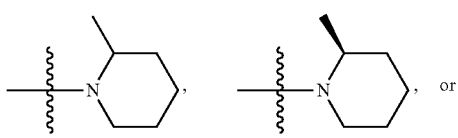

-continued

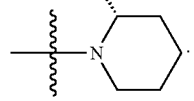

In various independent embodiments R² is

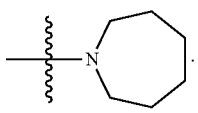

In various independent embodiments R² is

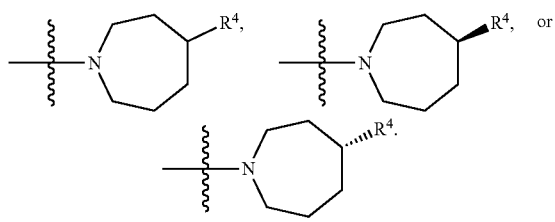

In various independent embodiments R² is

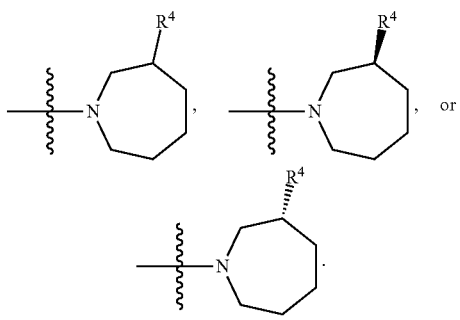

In various independent embodiments R² is

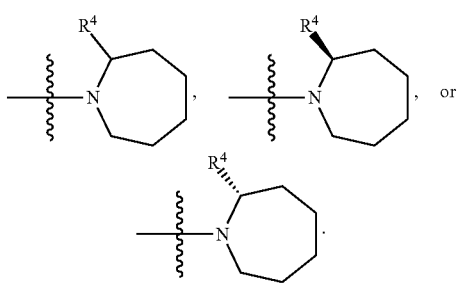

In various independent embodiments R² is

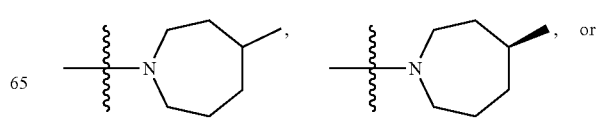

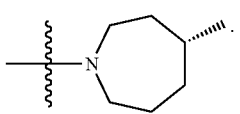
In various independent embodiments R² is
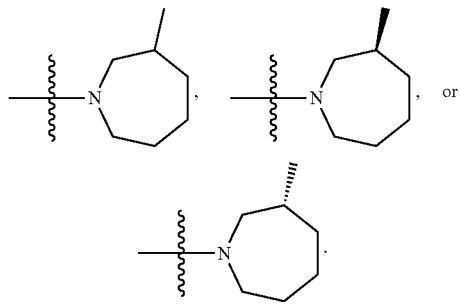
In various independent embodiments R² is
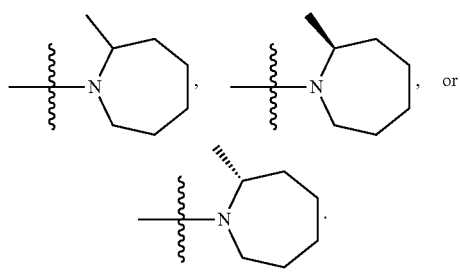
In various independent embodiments R² is
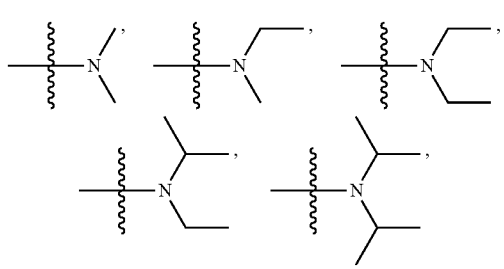
In various independent embodiments R² is
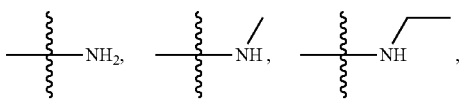
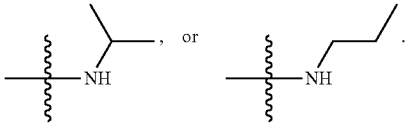
In various independent embodiments R² is
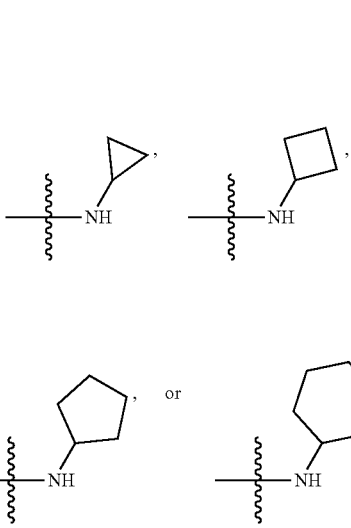
In various independent embodiments R² is
In various independent embodiments R² is Embodiments of A
In one embodiment, A is selected from:
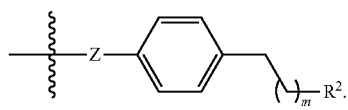
In another embodiment, A is selected from:
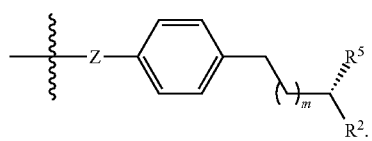
In another embodiment, A is selected from:
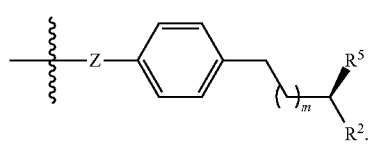
In various independent embodiments, A is selected from:
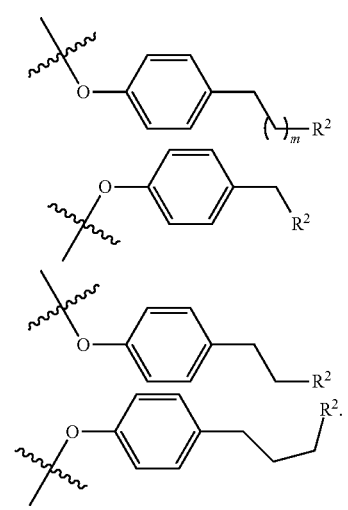
In various independent embodiments, A is selected from:
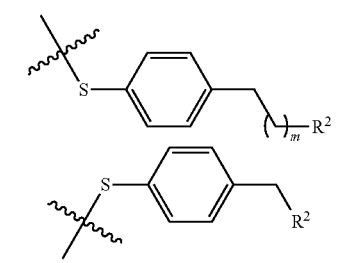
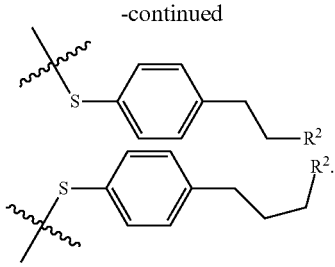
In various independent embodiments, A is selected from:
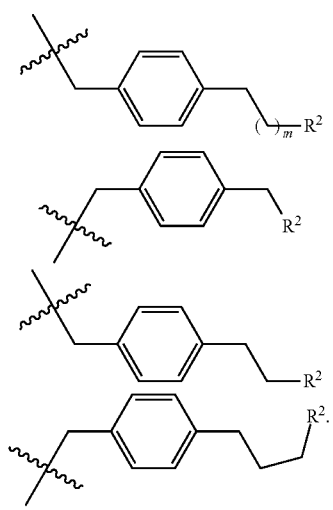
In various independent embodiments, A is selected from:
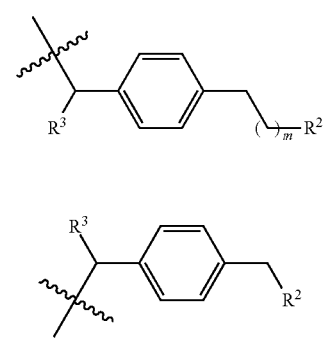
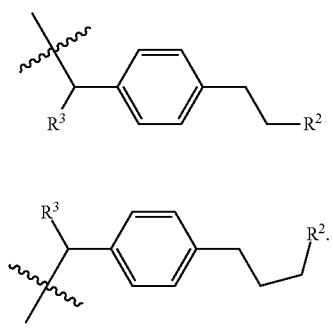

In various independent embodiments, A is selected from:
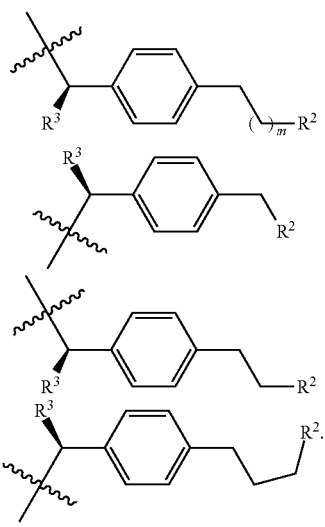
In various independent embodiments, A is selected from:
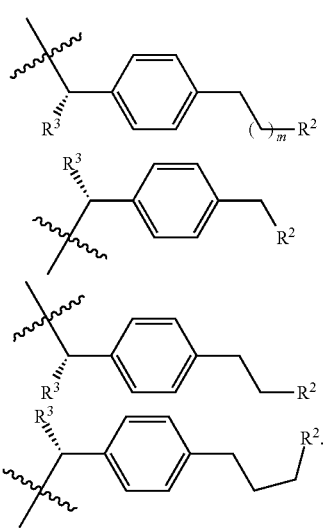
In various independent embodiments, A is selected from:
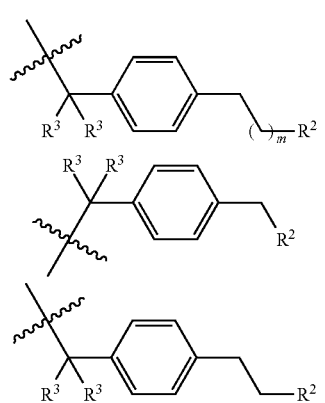
-continued
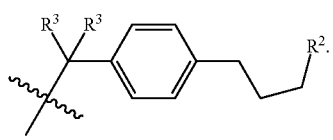
In various independent embodiments, A is selected from:
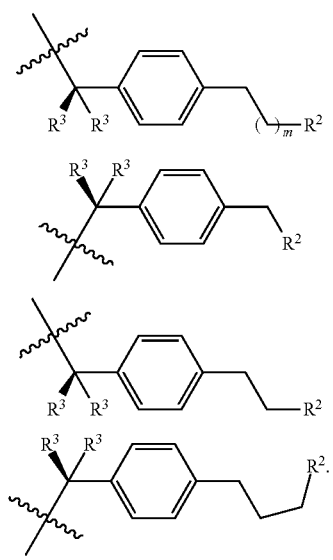
In various independent embodiments, A is selected from:
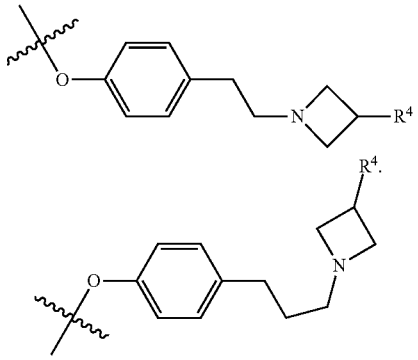

61
In various independent embodiments, A is selected from:
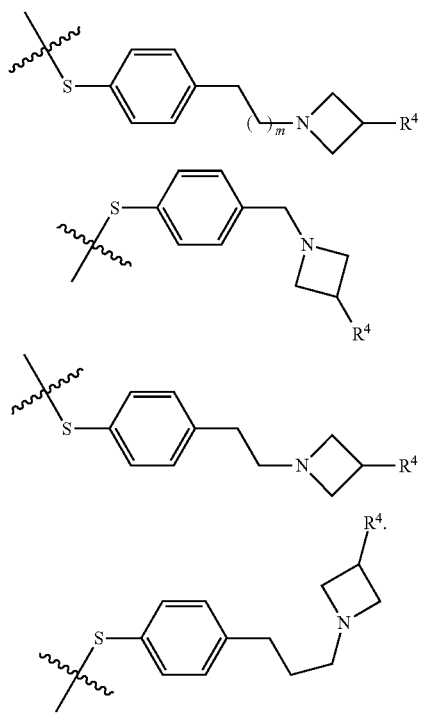
In various independent embodiments, A is selected from:
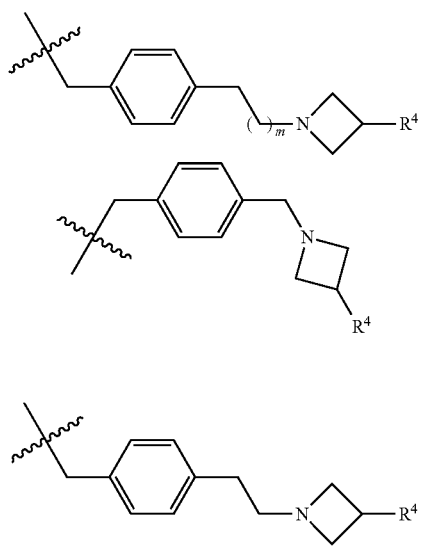
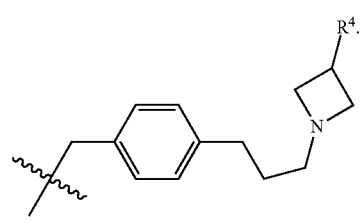
62
In various independent embodiments, A is selected from:
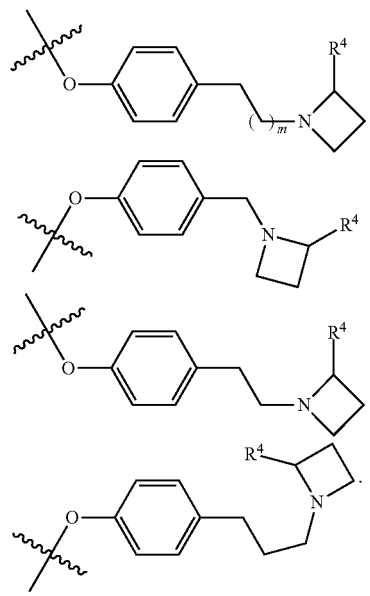
In various independent embodiments, A is selected from:
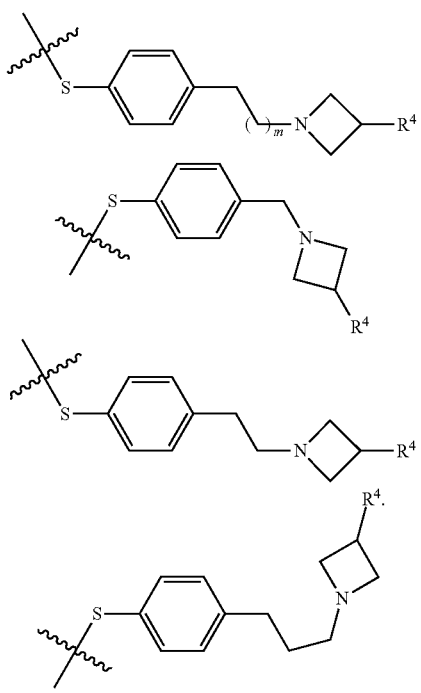
In various independent embodiments, A is selected from:
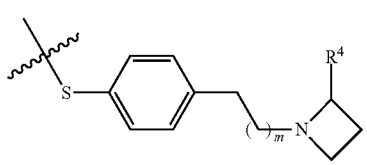

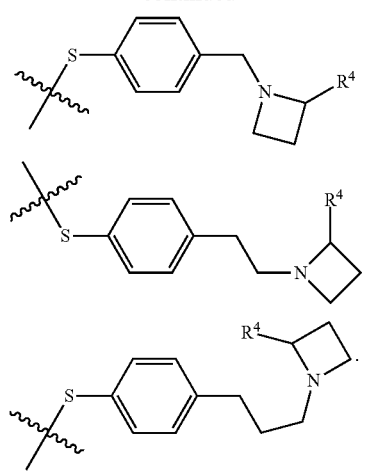
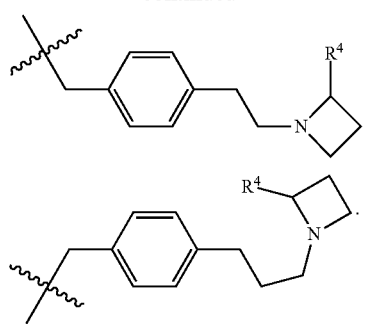
In various independent embodiments, A is selected from:
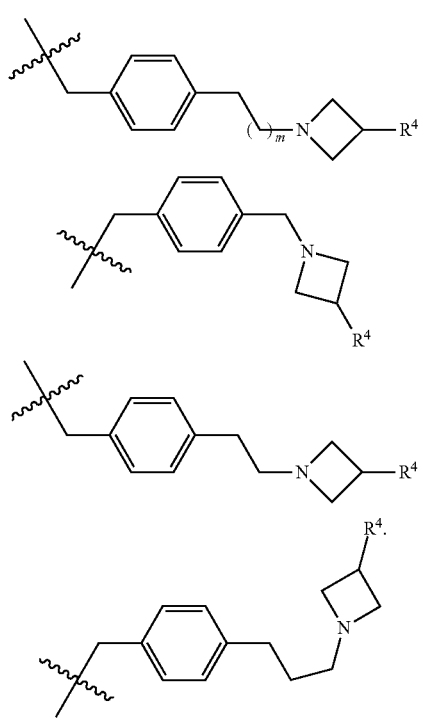
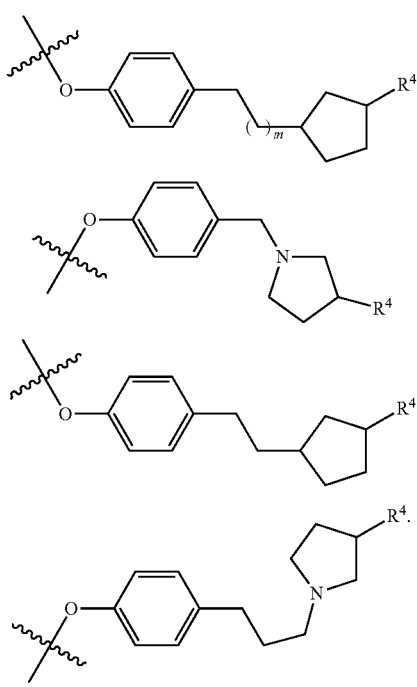
In various independent embodiments, A is selected from:
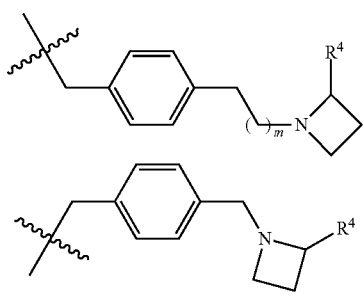
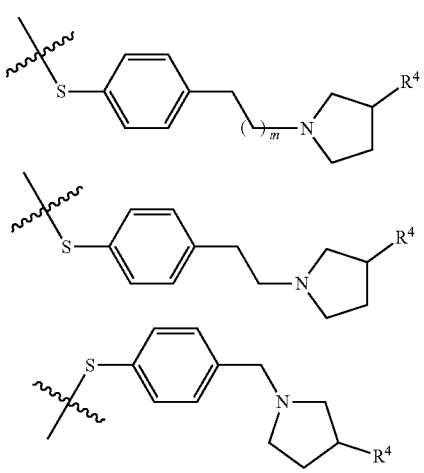

-continued
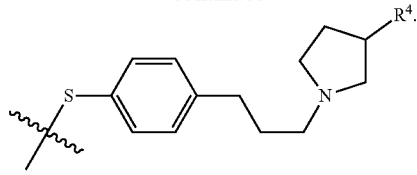
In various independent embodiments, A is selected from:
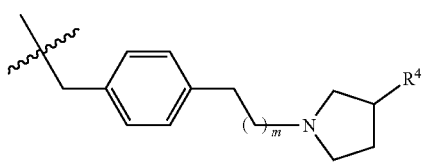
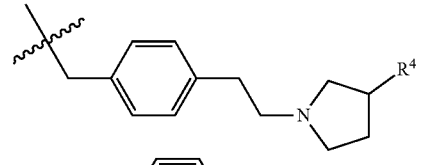
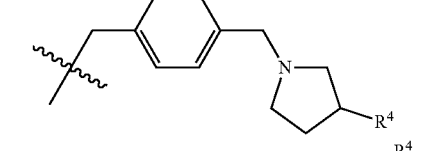
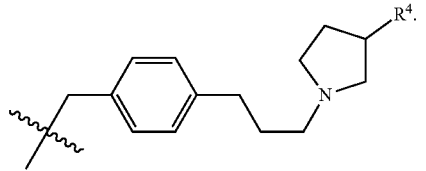
In various independent embodiments, A is selected from:
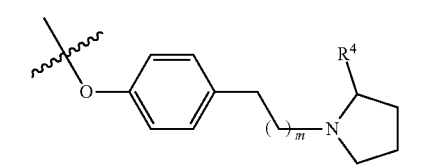
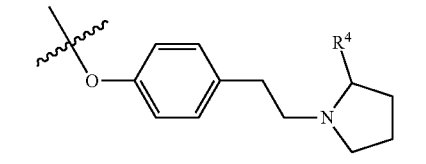
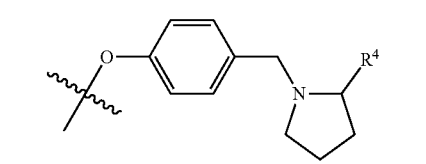
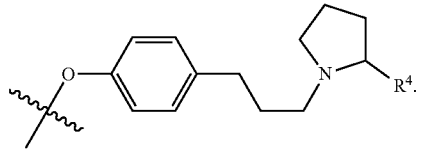
In various independent embodiments, A is selected from:
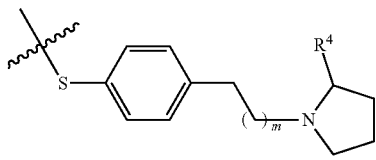
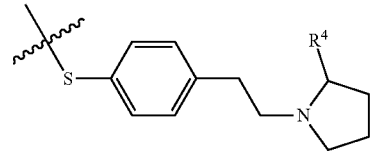
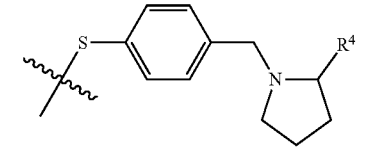
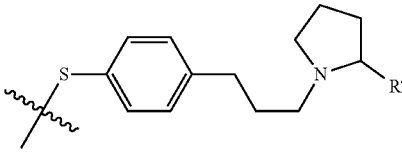
In various independent embodiments, A is selected from:
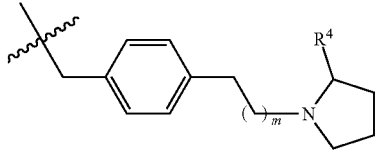
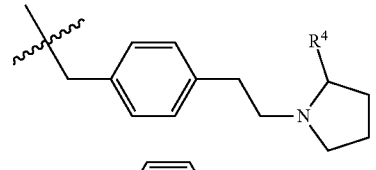
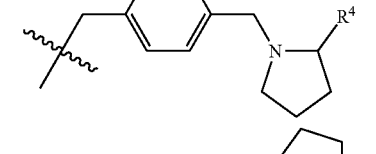
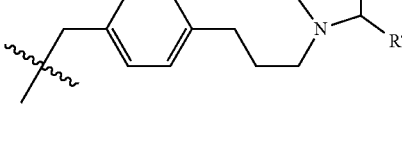
In various independent embodiments, A is selected from:
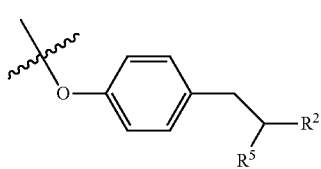

-continued
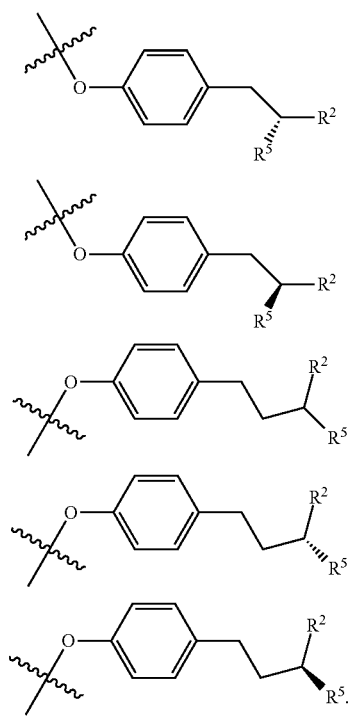
In various independent embodiments, A is selected from:
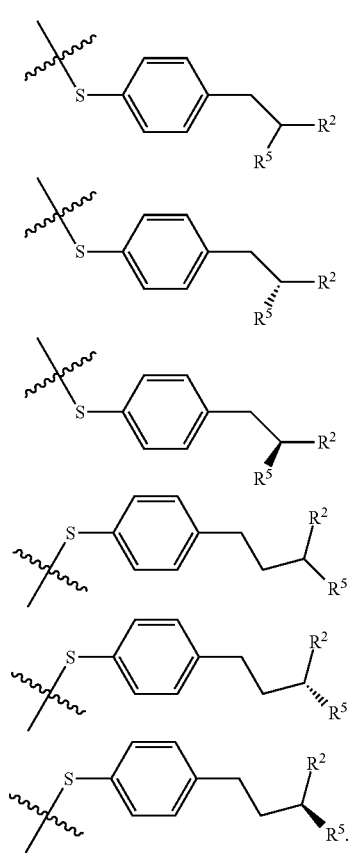
In various independent embodiment, A is selected from:
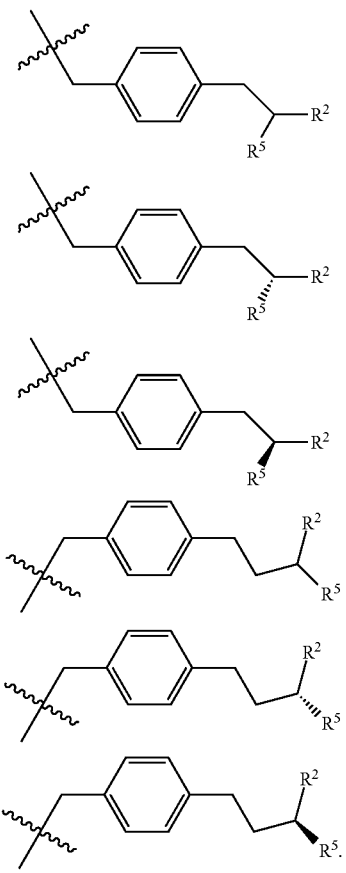
In an alternative embodiment, A is selected from:
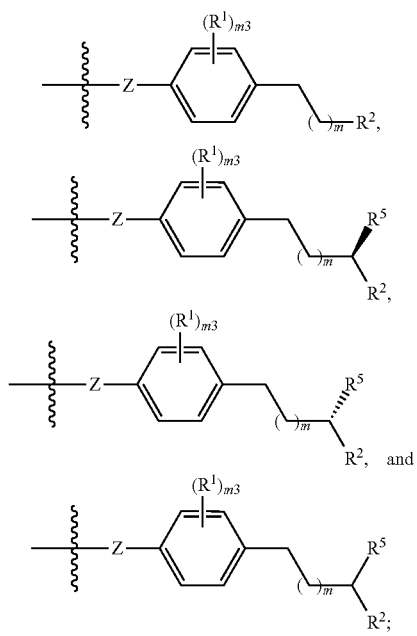
wherein m3 is 1, 2, 3, or 4.

Embodiments of X

In one embodiment, X is selected from:

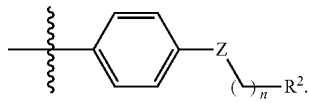

In another embodiment, X is selected from:

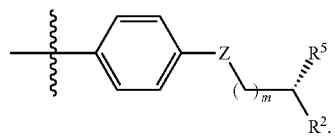

In another embodiment, X is selected from:

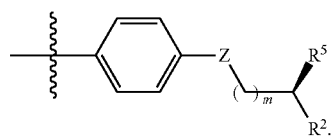

In various independent embodiments, X is selected from:

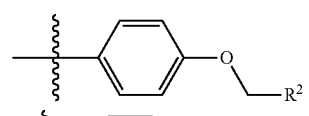

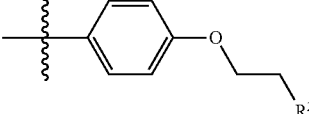

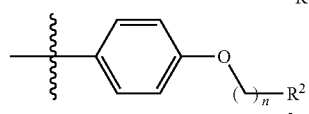

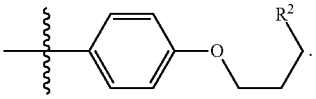

In various independent embodiments, X is selected from:

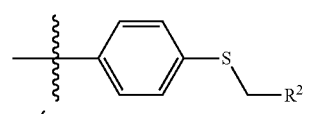

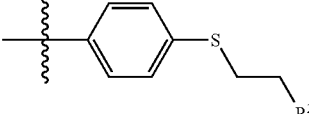

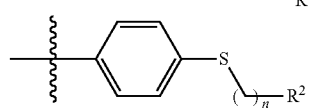

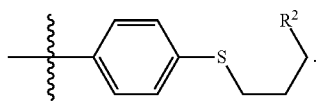

In various independent embodiments, X is selected from:

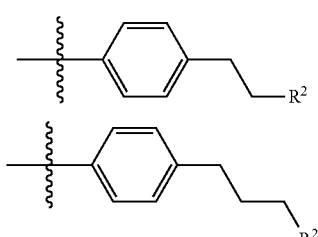

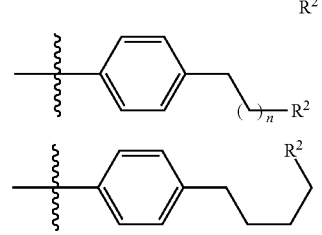

In various independent embodiments, X is selected from:

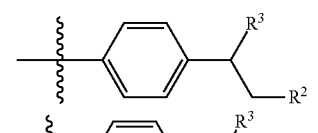

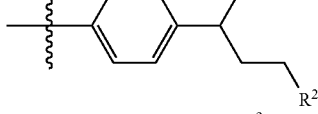

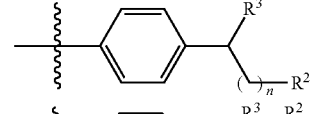

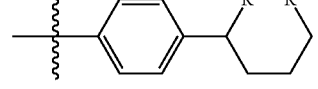

In various independent embodiments, X is selected from:

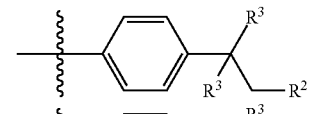

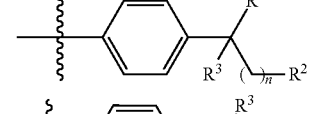

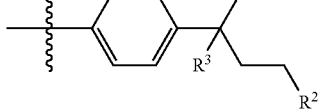

-continued
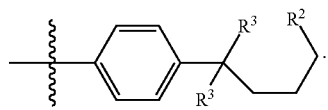
In various independent embodiments, X is selected from:
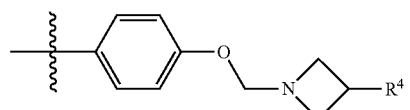
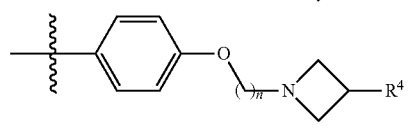
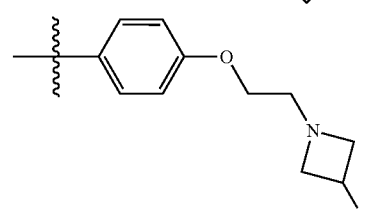
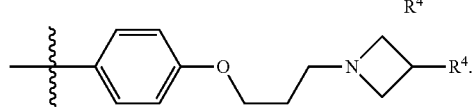
In various independent embodiments, X is selected from:
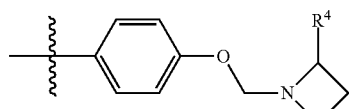
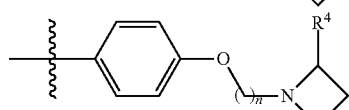
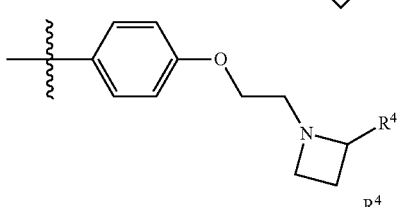
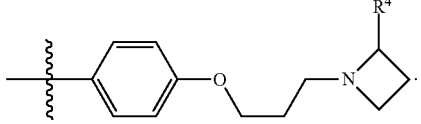
In various independent embodiments, X is selected from:
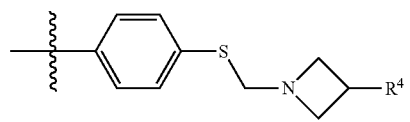
-continued
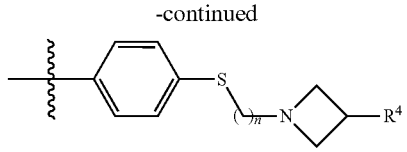
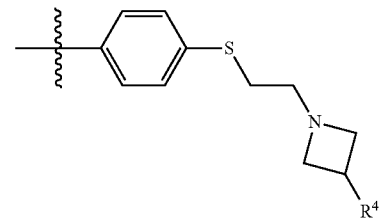
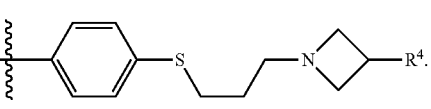
In various independent embodiments, X is selected from:
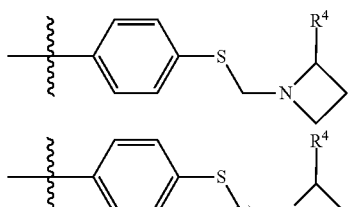
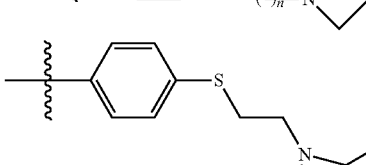
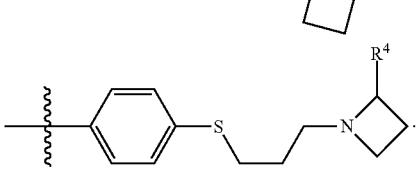
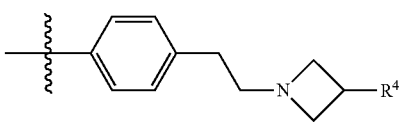
In various independent embodiments, X is selected from:
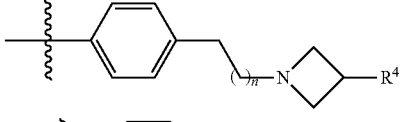
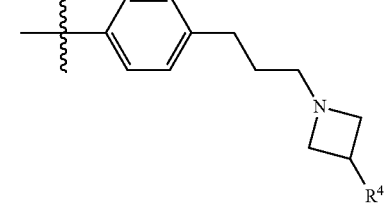

-continued
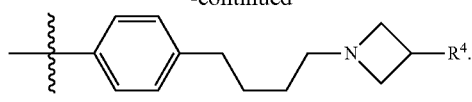
In various independent embodiments, X is selected from:
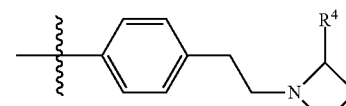
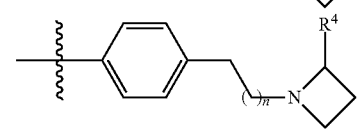
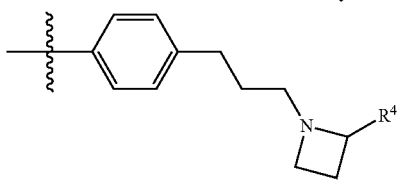
In various independent embodiments, X is selected from:
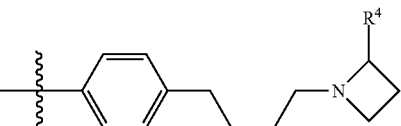
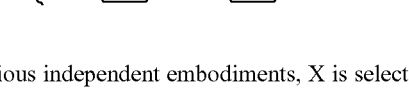
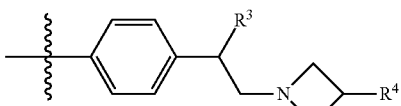
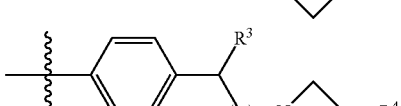
In various independent embodiments, X is selected from:
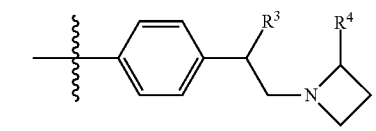
-continued
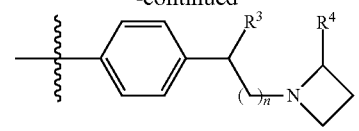
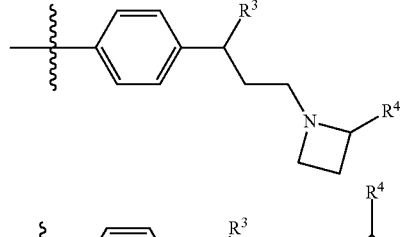
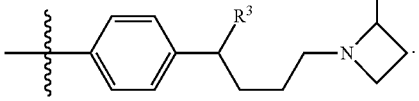
In various independent embodiments, X is selected from:
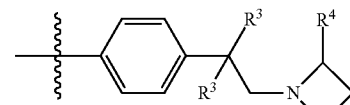
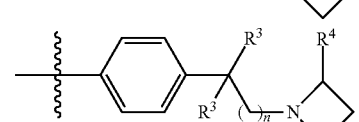
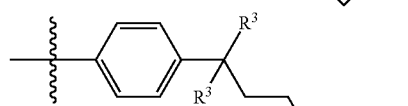
In various independent embodiments, X is selected from:
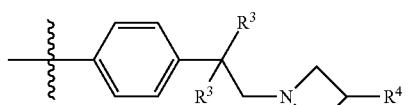
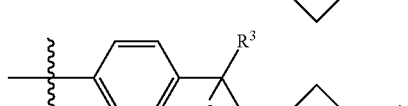
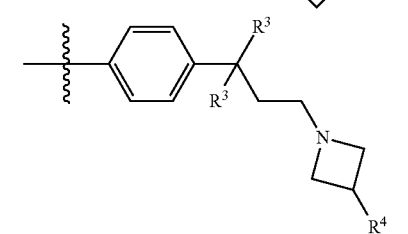

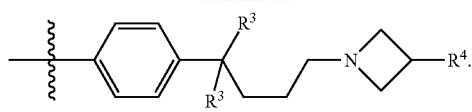
In various independent embodiments, X is selected from:
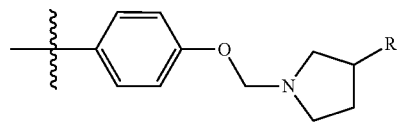
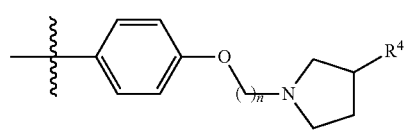
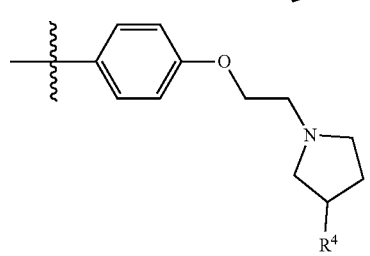
In an alternative embodiment, X is selected from:
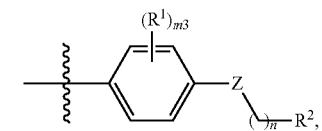
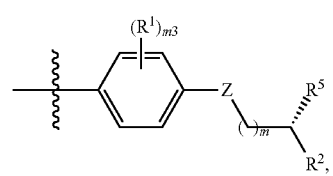
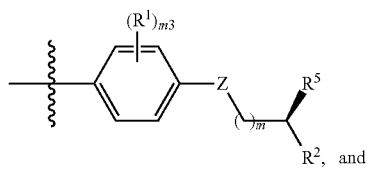
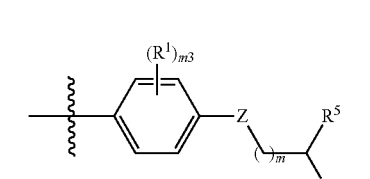
wherein m3 is 1, 2, 3, or 4.
In an alternative embodiment, Y is selected from:
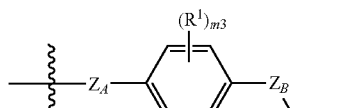
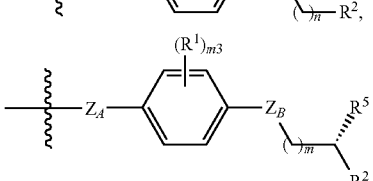
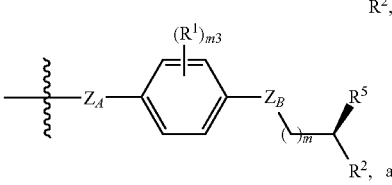
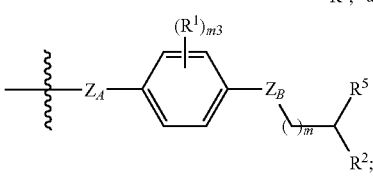
wherein m3 is 1, 2, 3, or 4.
Embodiments of $R^{12}$
In one embodiment $R^{12}$ is selected from:
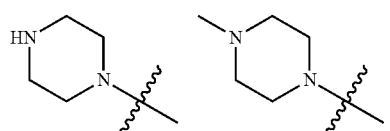
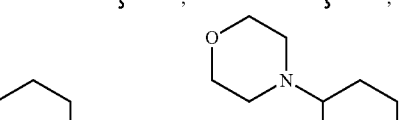
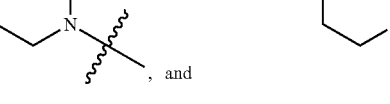
In one embodiment $R^{12}$ is
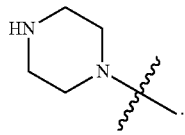 [SMILES: *N1CCNCC1]
In one embodiment $R^{12}$ is
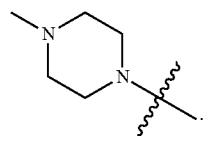 [SMILES: *N1CCN(C)CC1]

In one embodiment $R^{12}$ is
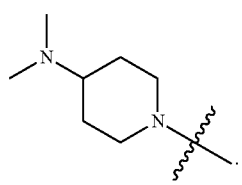 [SMILES: *N1CCC(N(C)C)CC1]
In one embodiment $R^{12}$ is
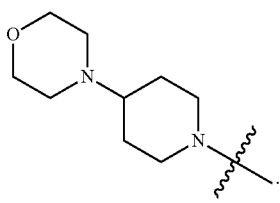 [SMILES: *N1CCC(N2CCOCC2)CC1]
Non-limiting examples of compounds of Formula I include:
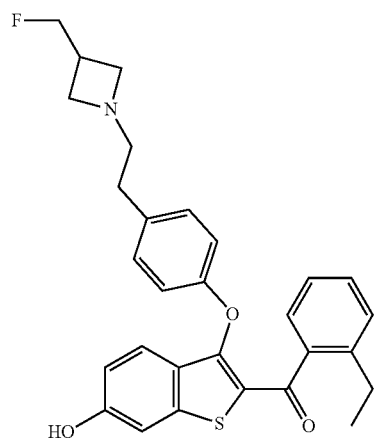
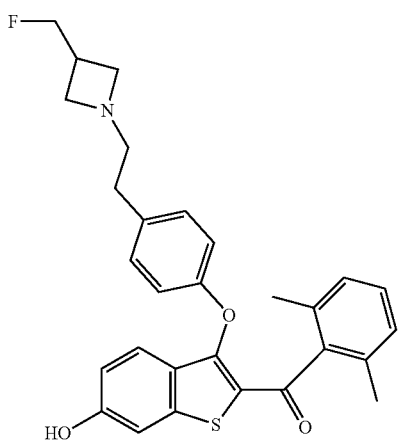
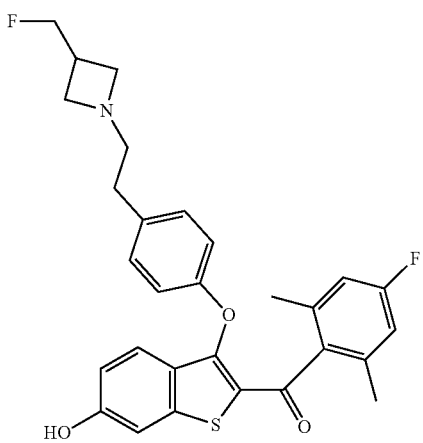
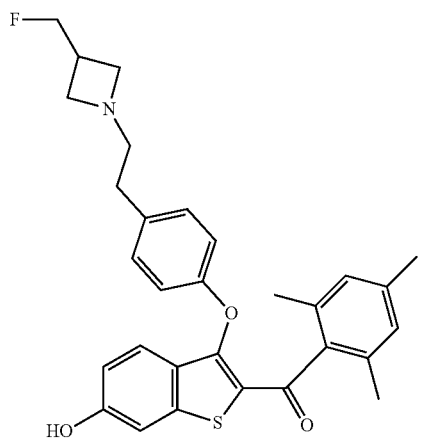
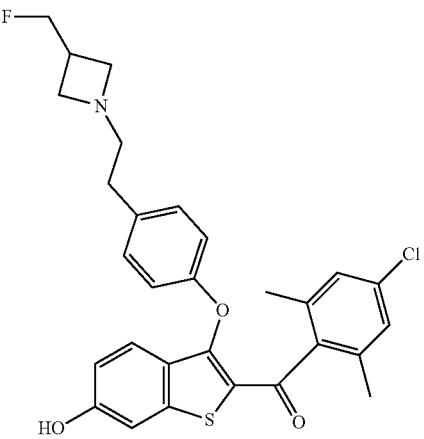

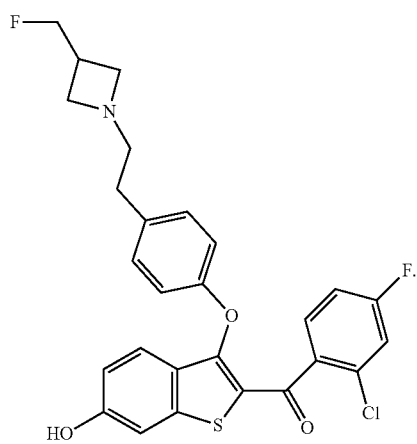
Non-limiting examples of compounds of Formula I include:
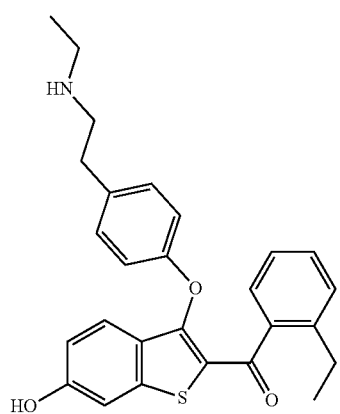
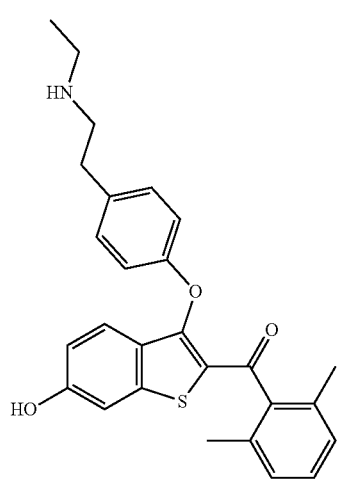
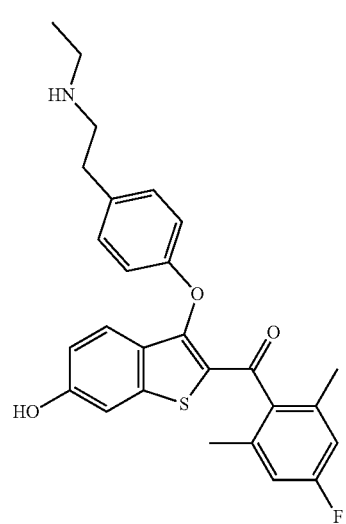
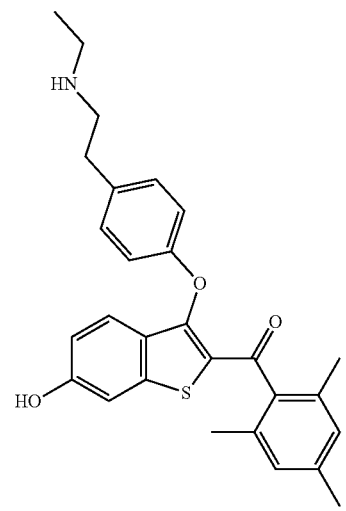
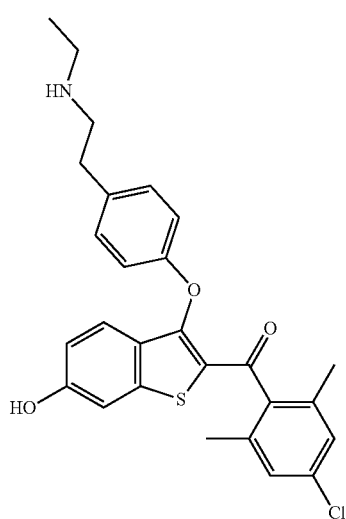

81
-continued
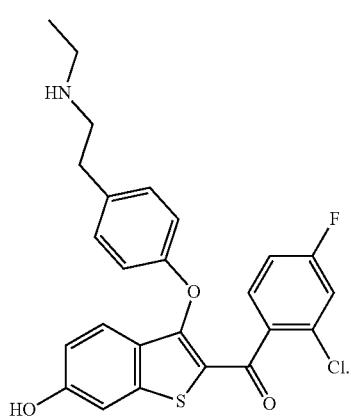
Non-limiting examples of compounds of Formula I include:
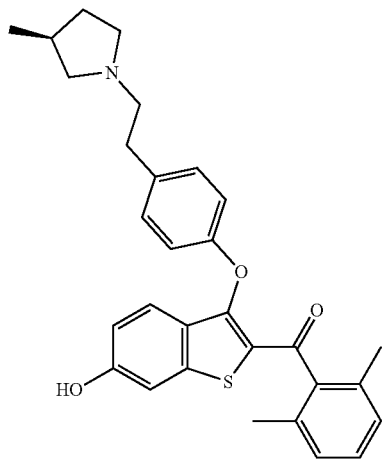
82
-continued
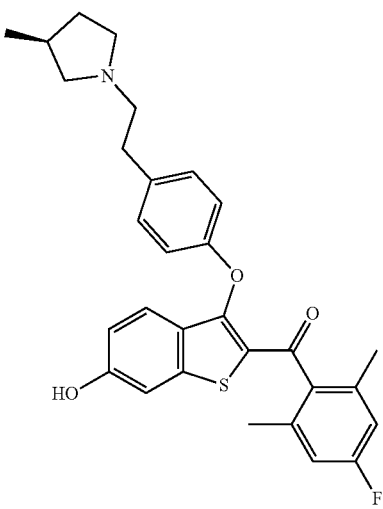
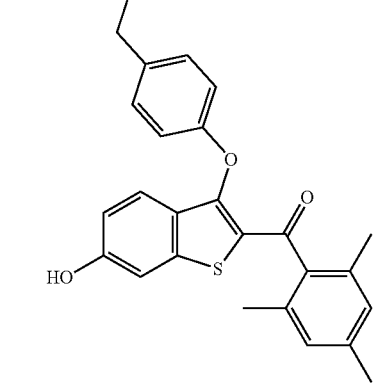
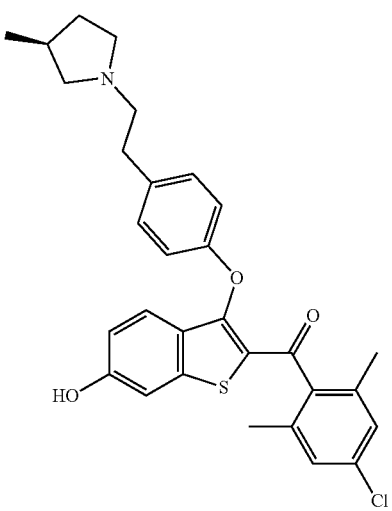

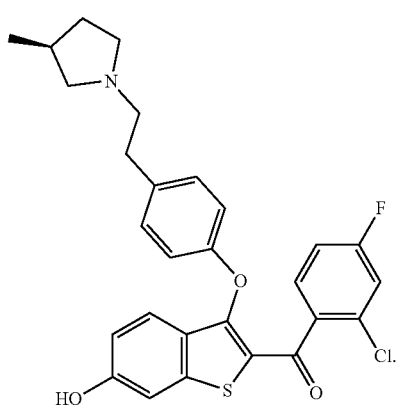
Non-limiting examples of compounds of Formula I include:
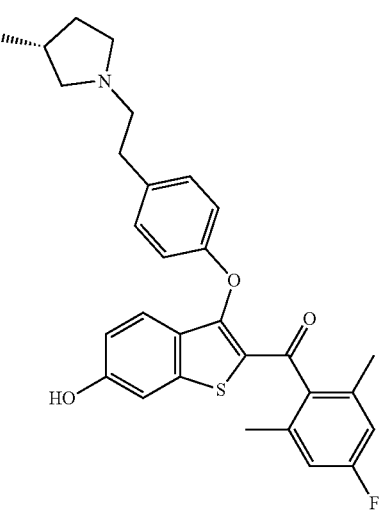
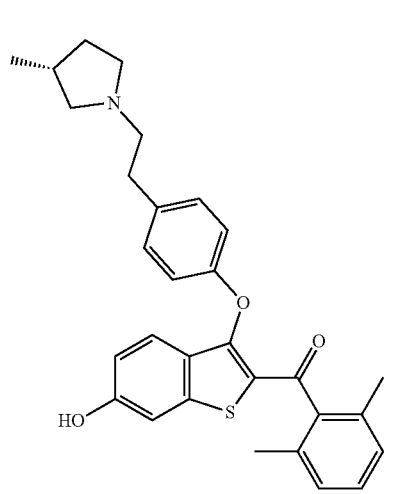
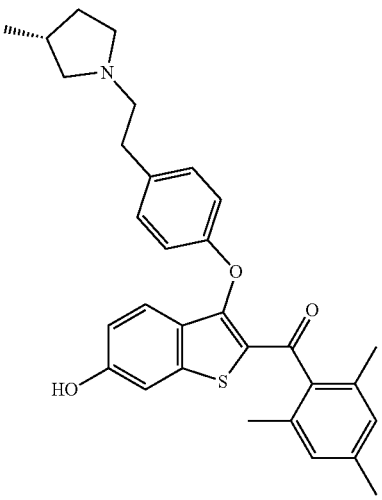

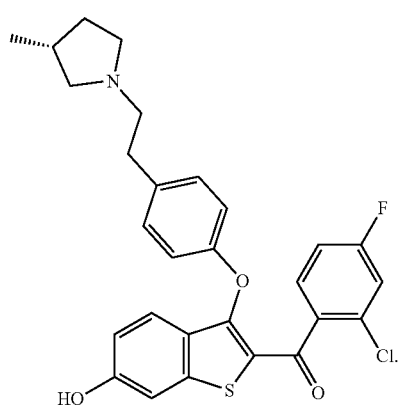
Non-limiting examples of compounds of Formula I include:
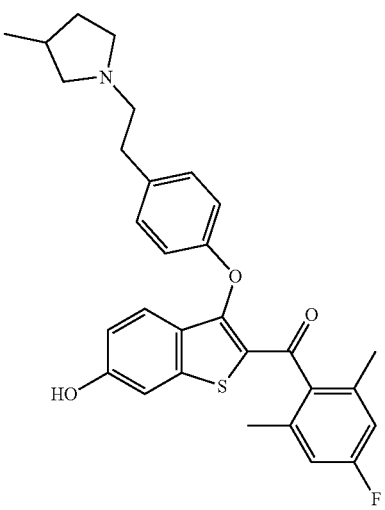
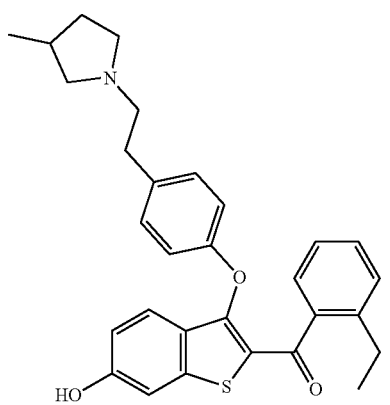
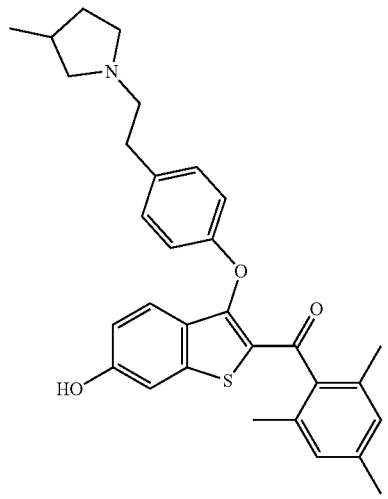
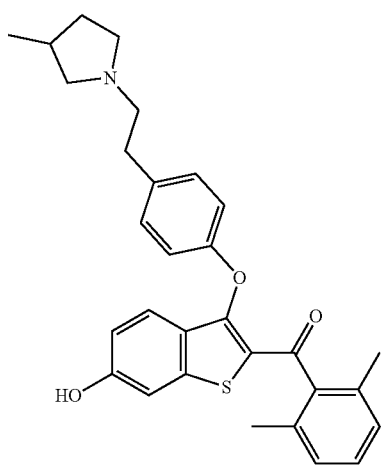
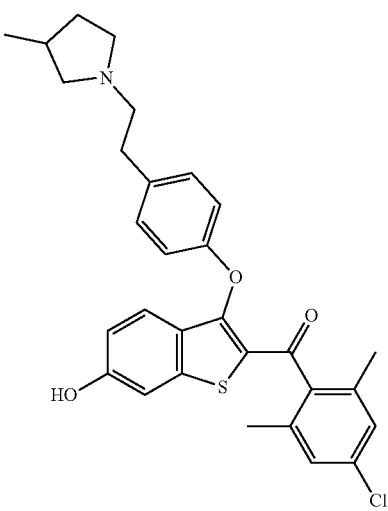

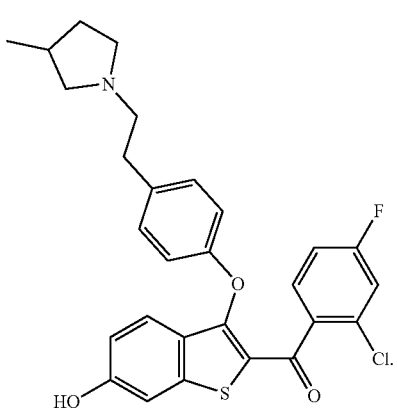
Non-limiting examples of compounds of Formula I include:
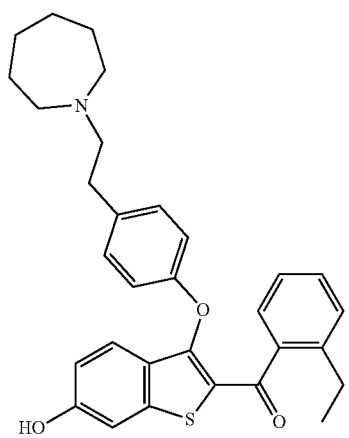
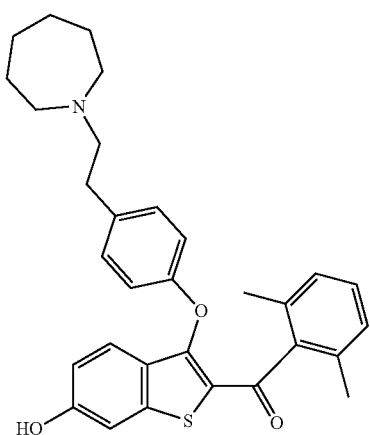
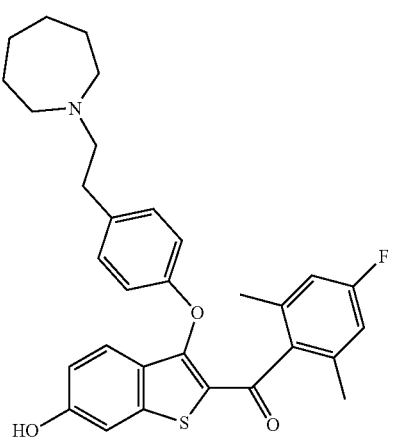
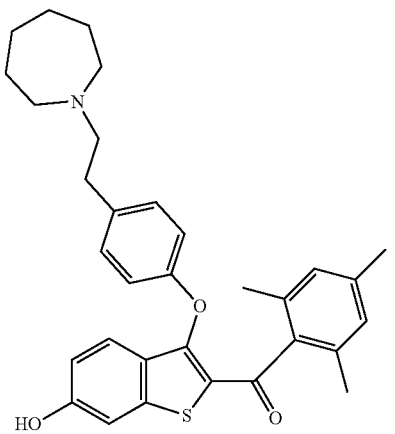
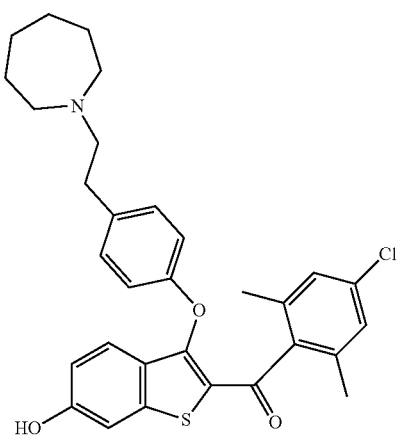

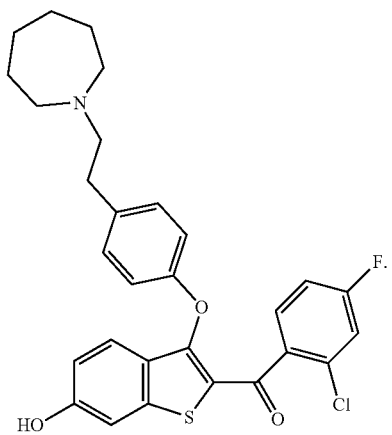
Non-limiting examples of compounds of Formula I include:
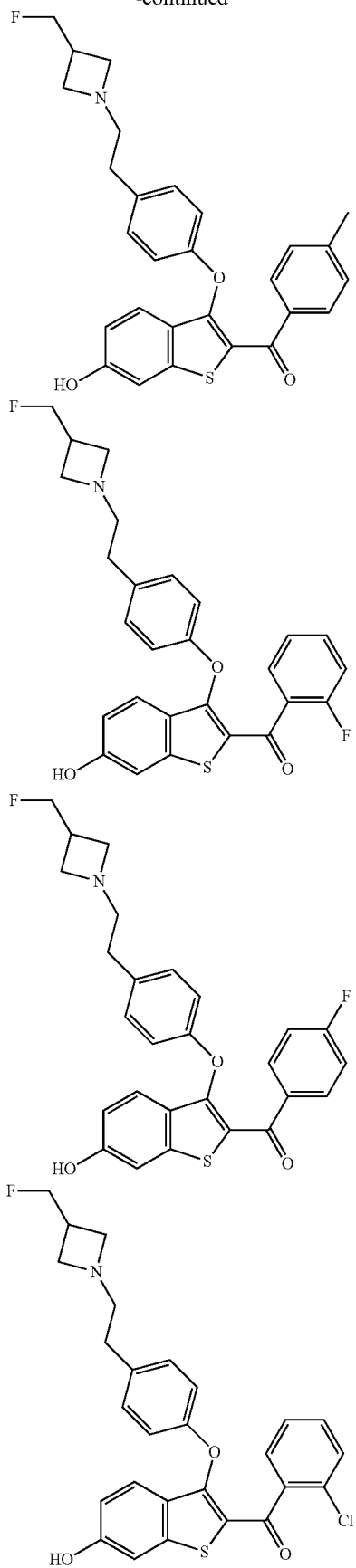

91
-continued
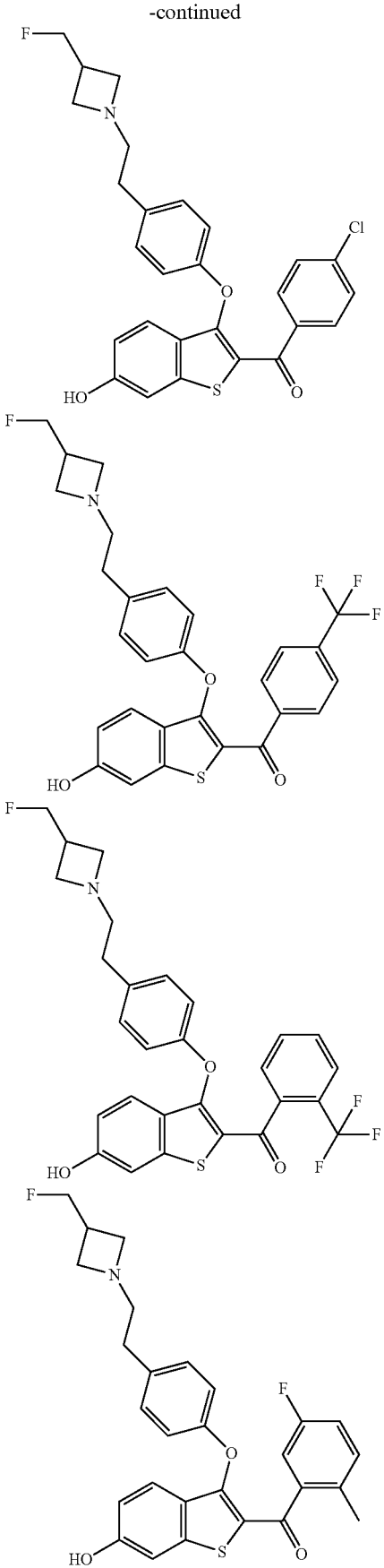
92
-continued
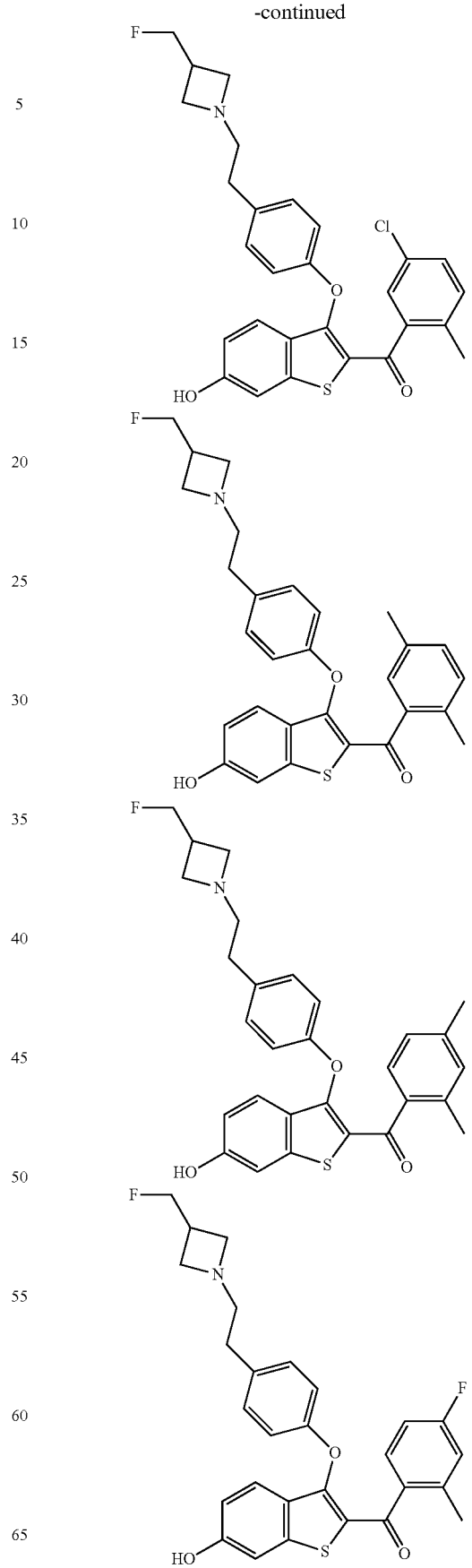

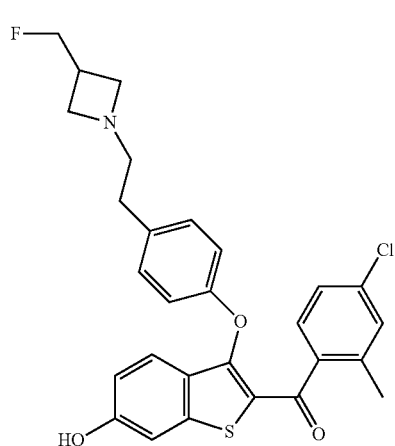
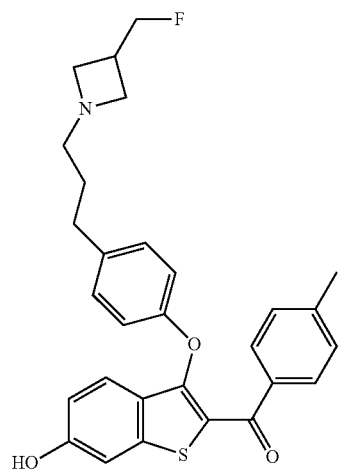
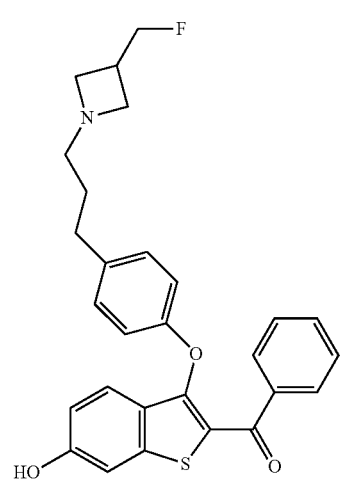
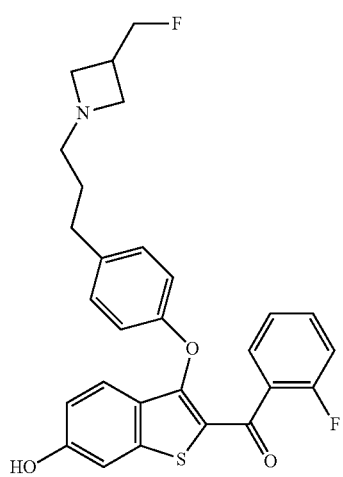
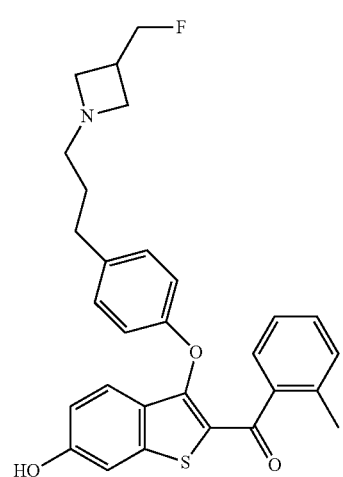
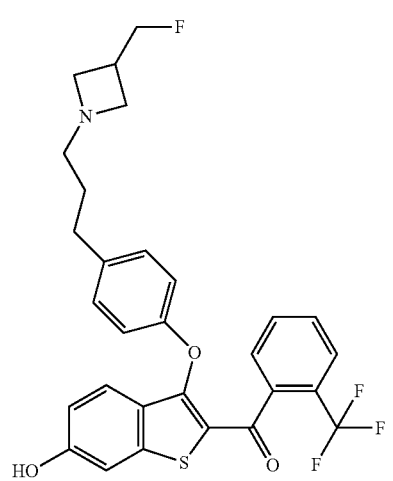

95
-continued
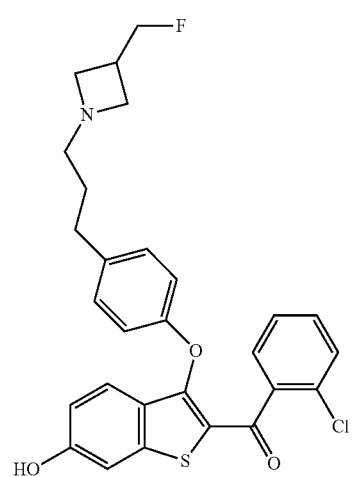
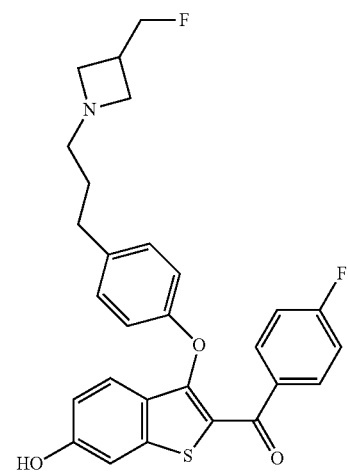
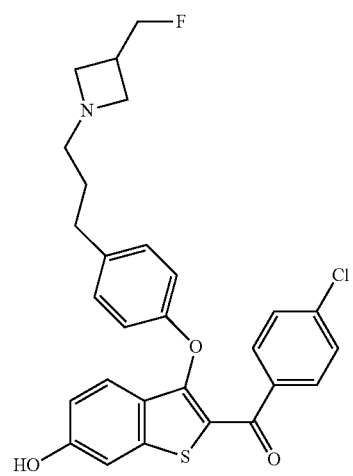
96
-continued
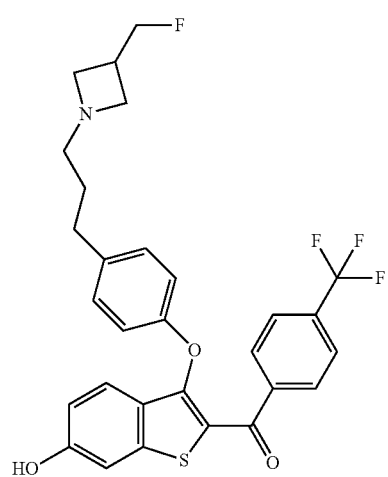
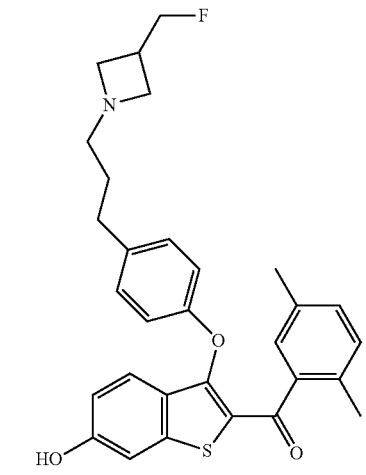
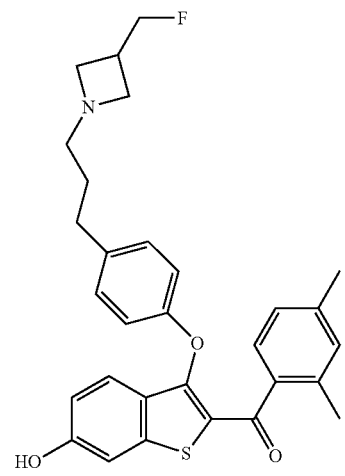

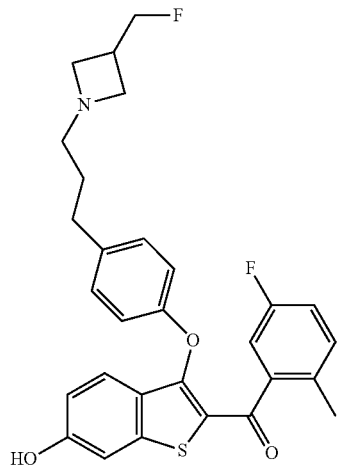
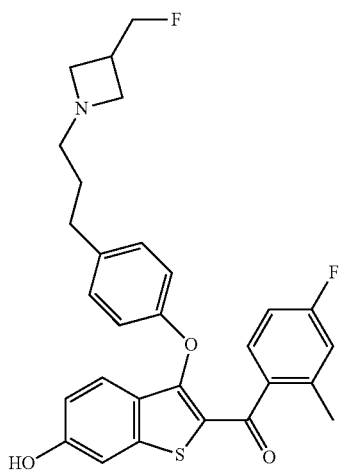
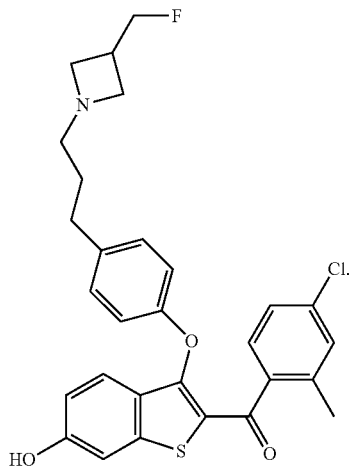
Additional non-limiting examples of compounds of Formula I include:
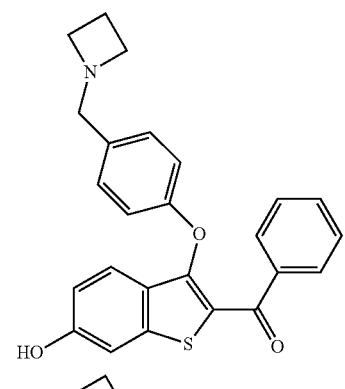
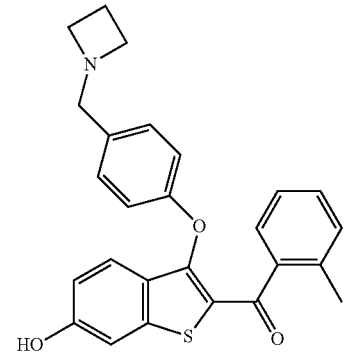
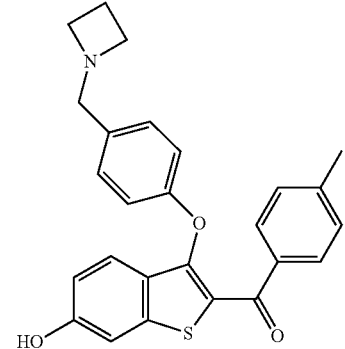

99
-continued
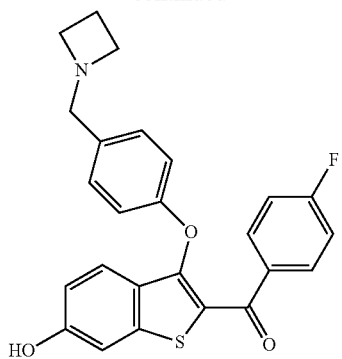
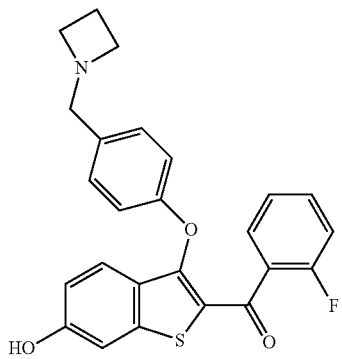
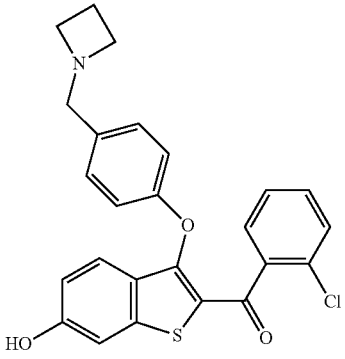
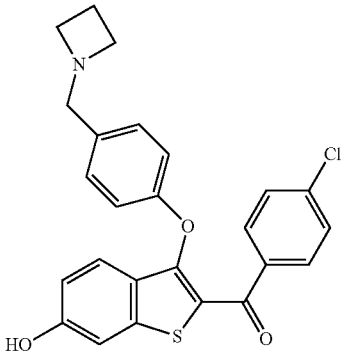
100
-continued
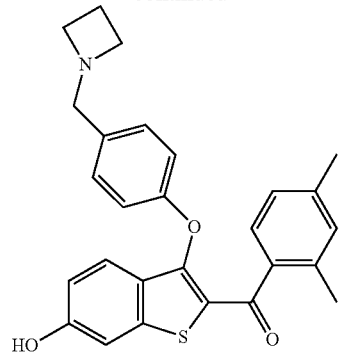
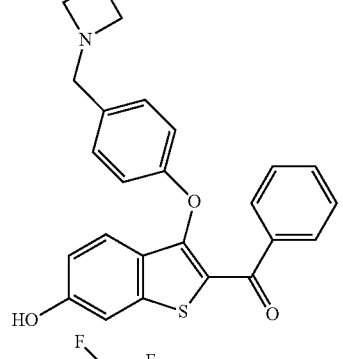
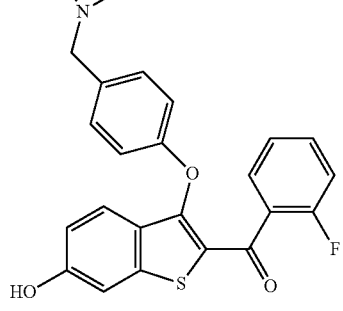
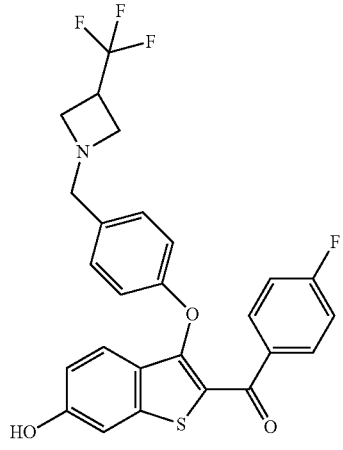

101
-continued
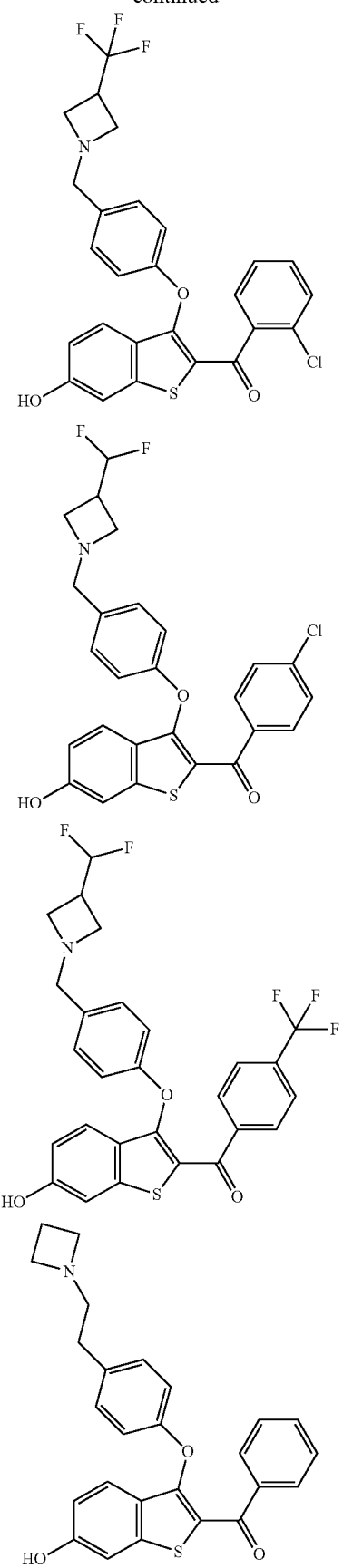
102
-continued
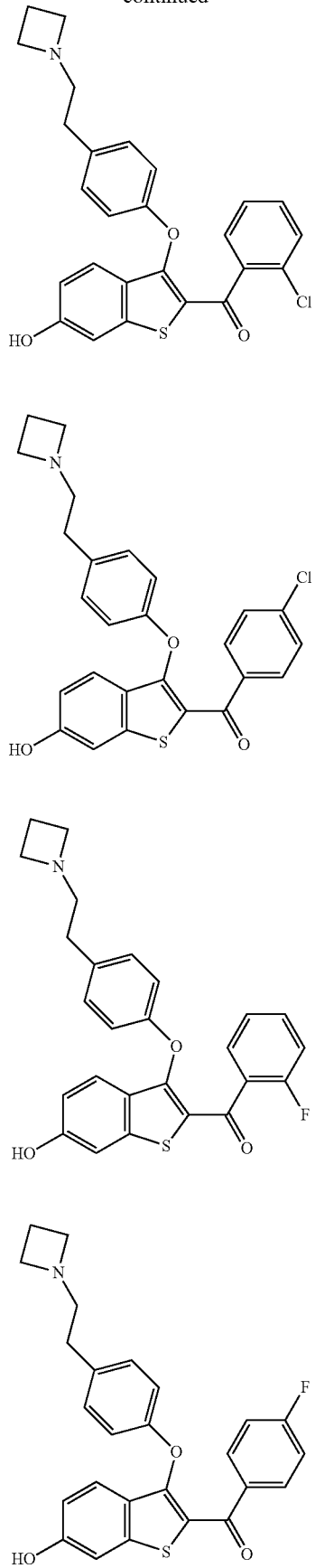

103
-continued
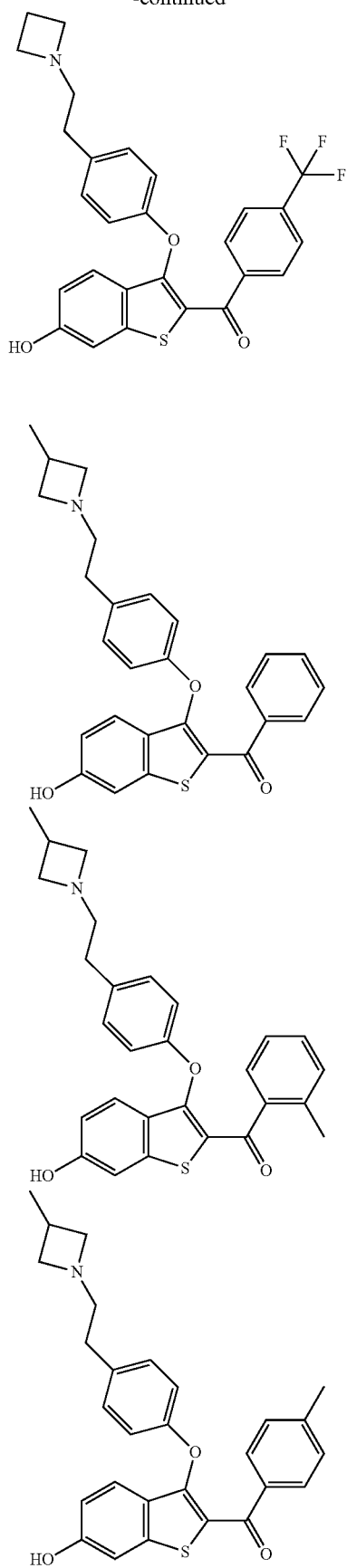
104
-continued
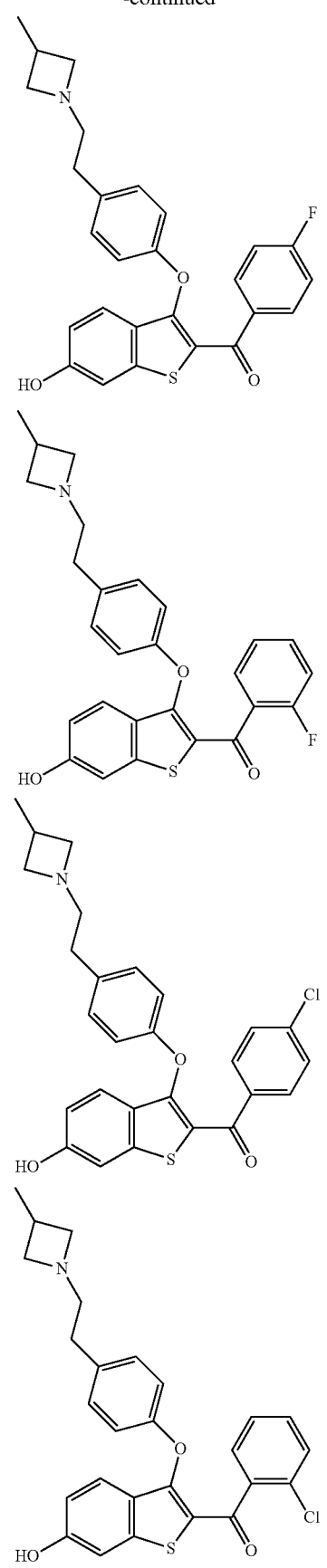

105
-continued
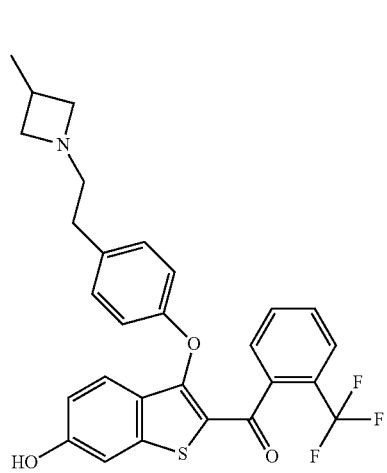
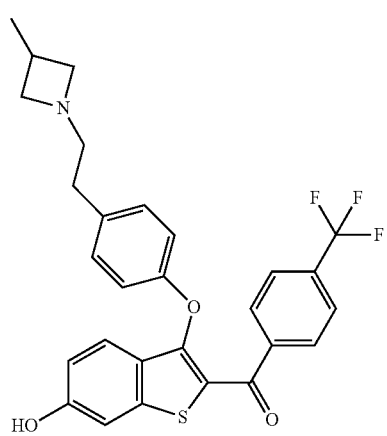
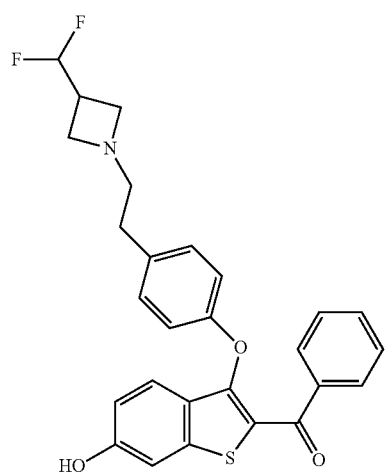
106
-continued
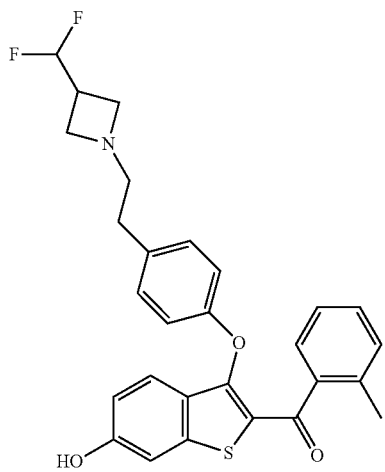
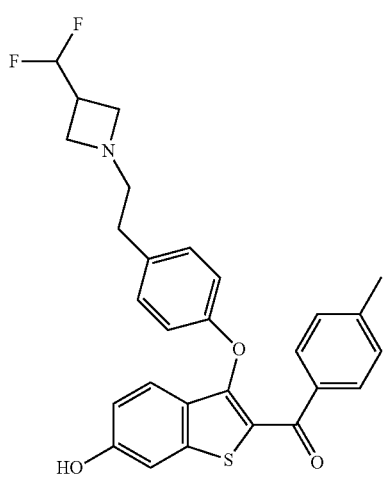
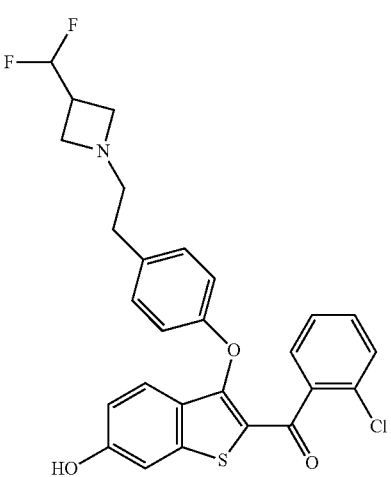

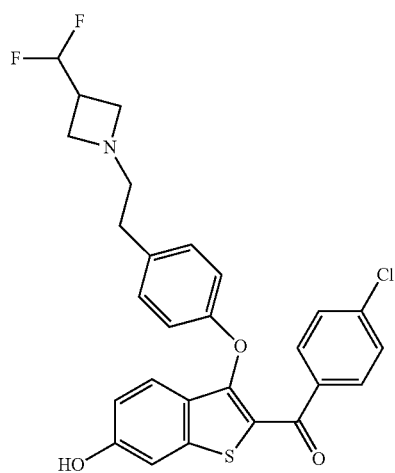
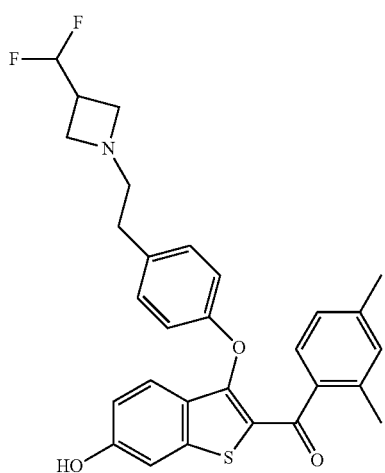
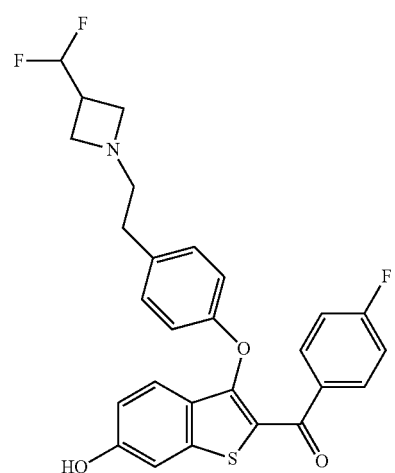
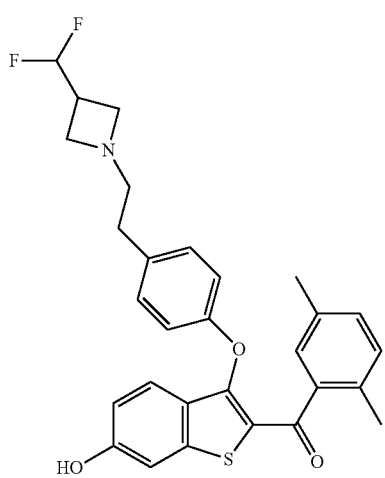
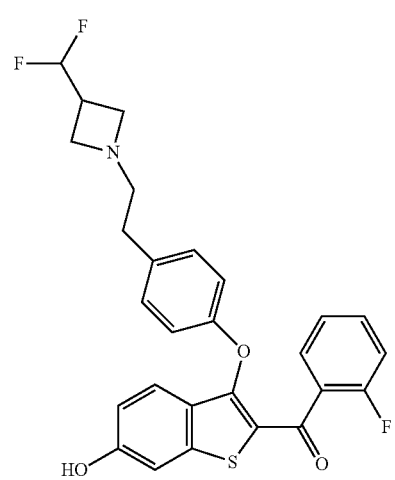
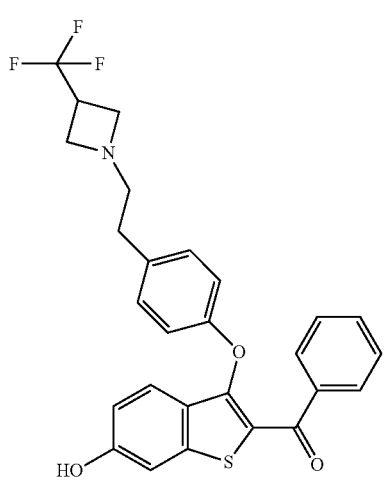

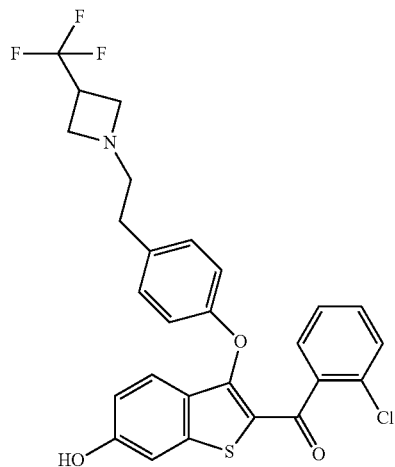
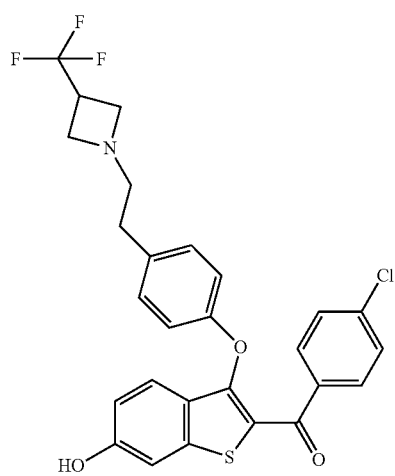
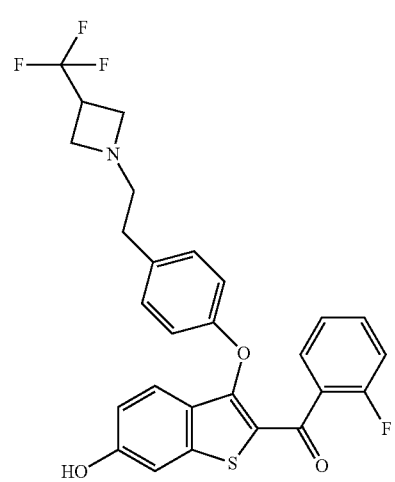
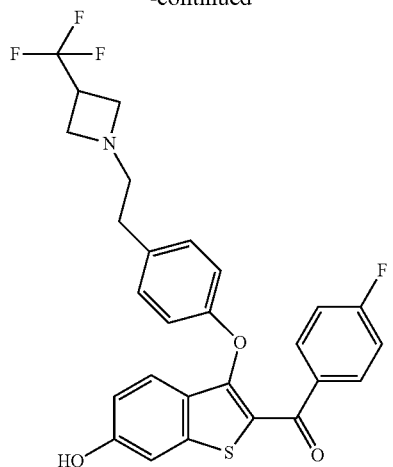
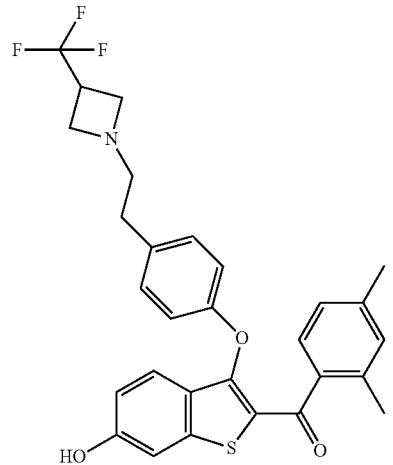
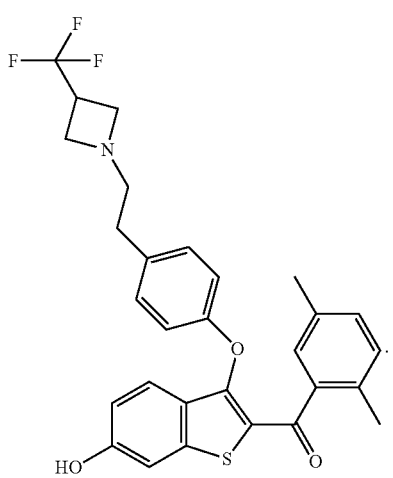
Non-limiting examples of compounds of Formula I include:

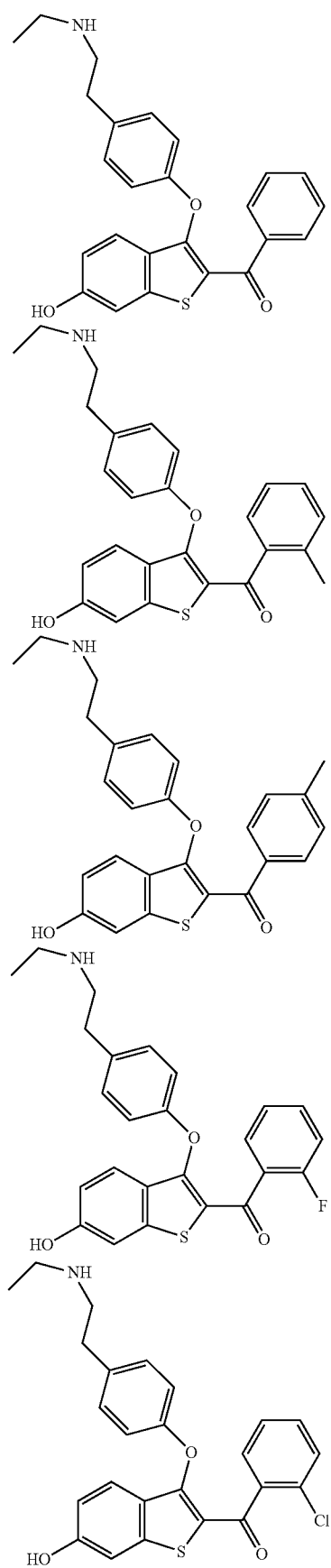
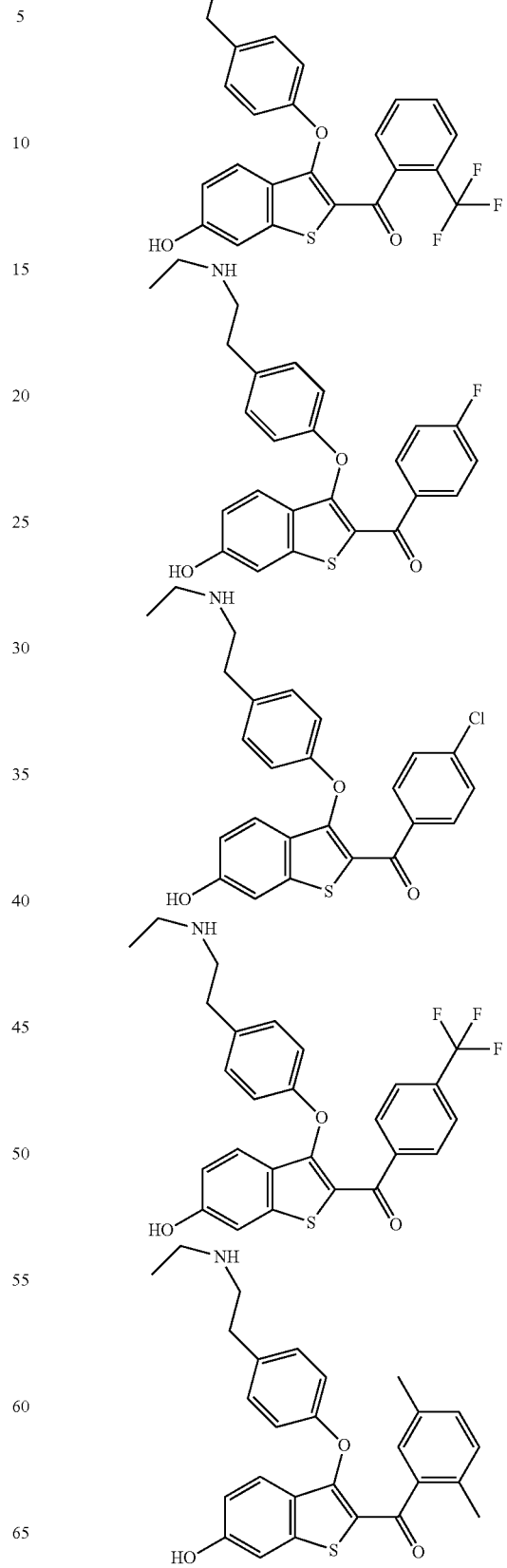
-continued

-continued
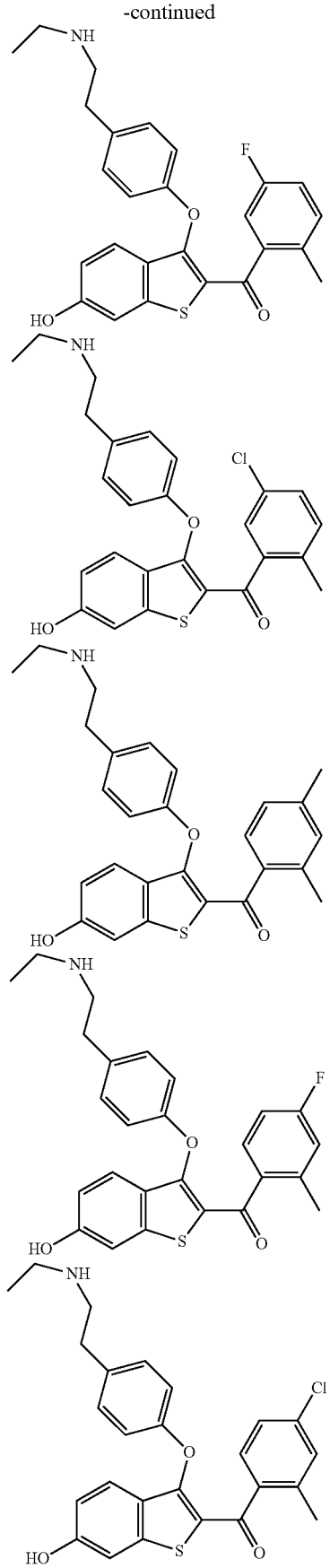
-continued
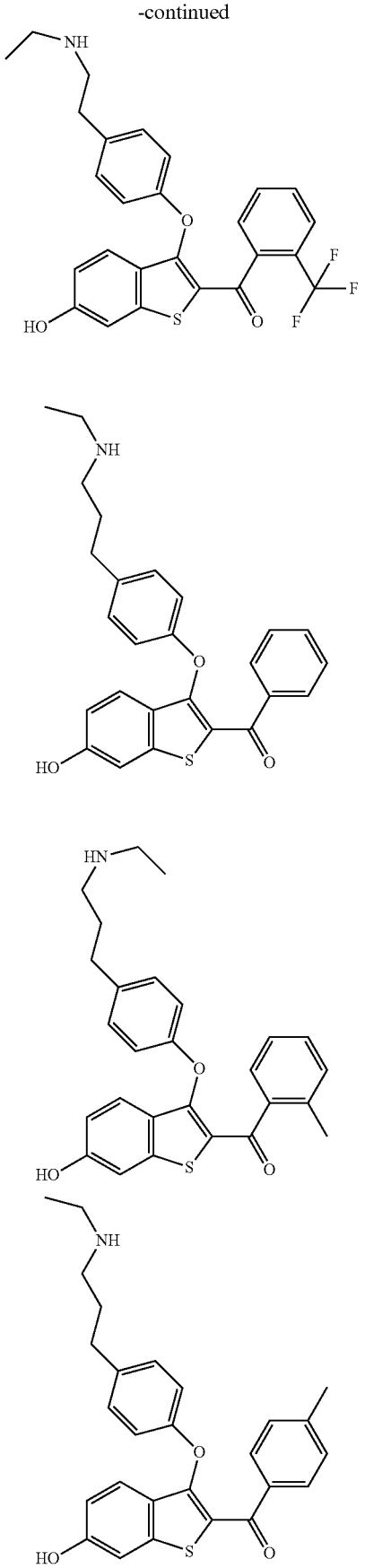

115
116
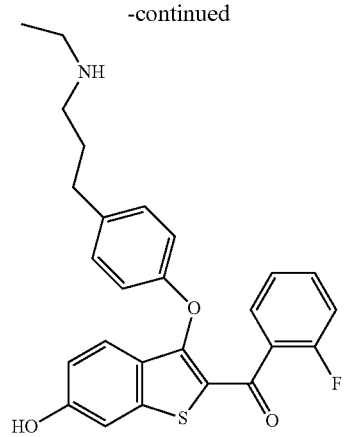
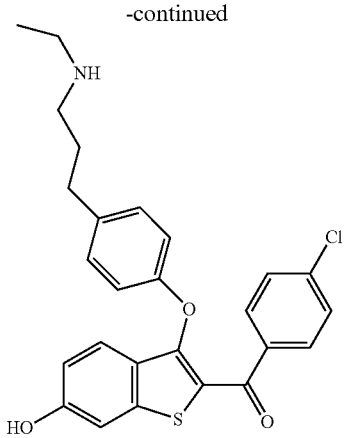

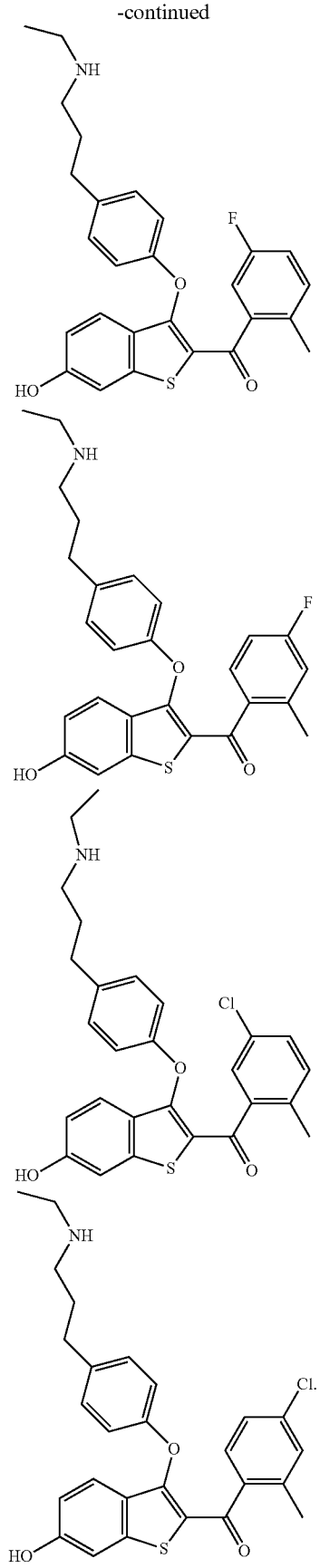
Non-limiting examples of compounds of Formula I include:
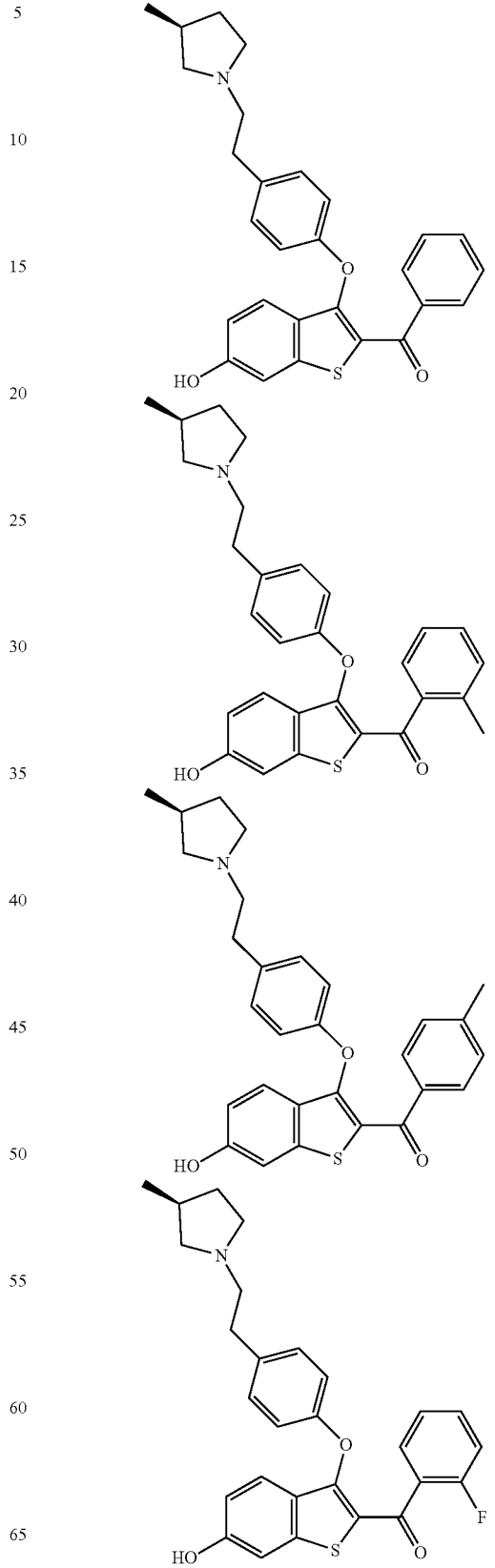

119
-continued
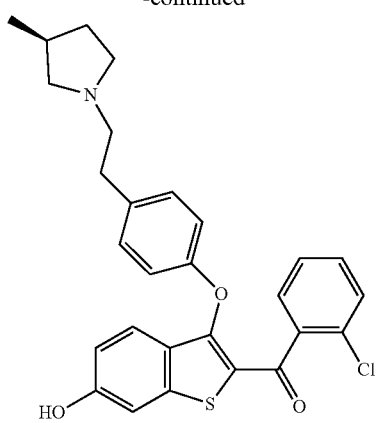
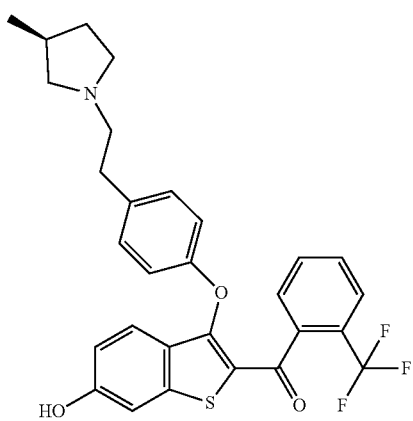
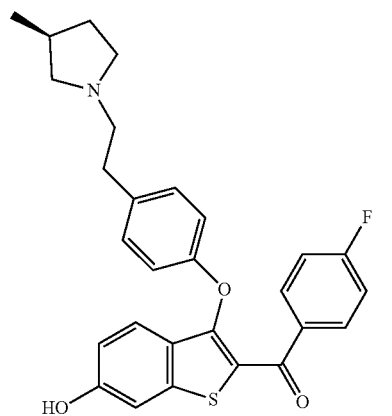
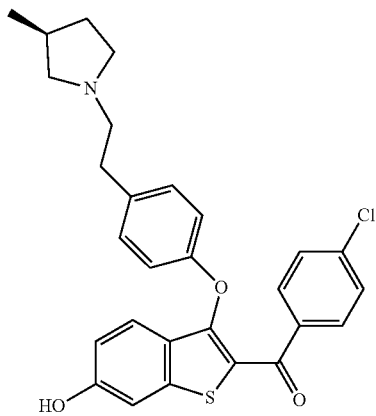
120
-continued
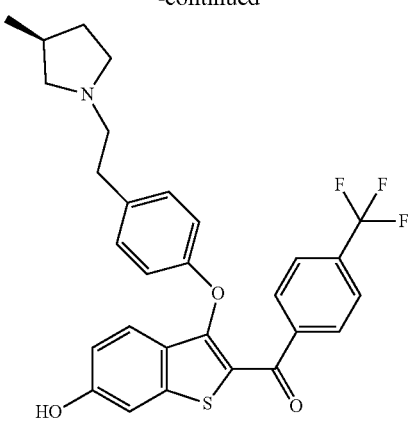
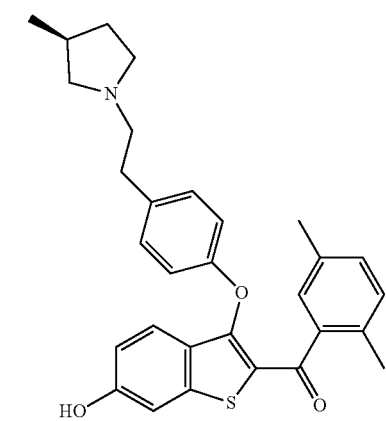
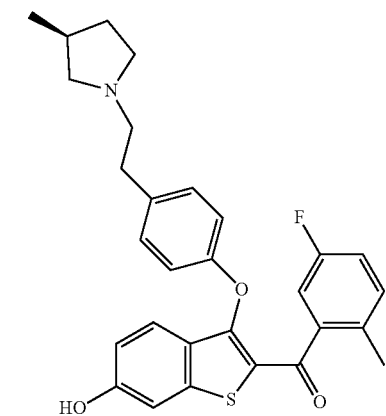
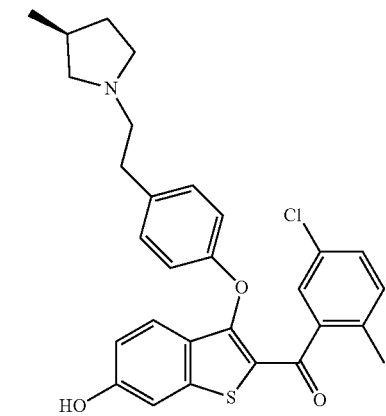

121
-continued
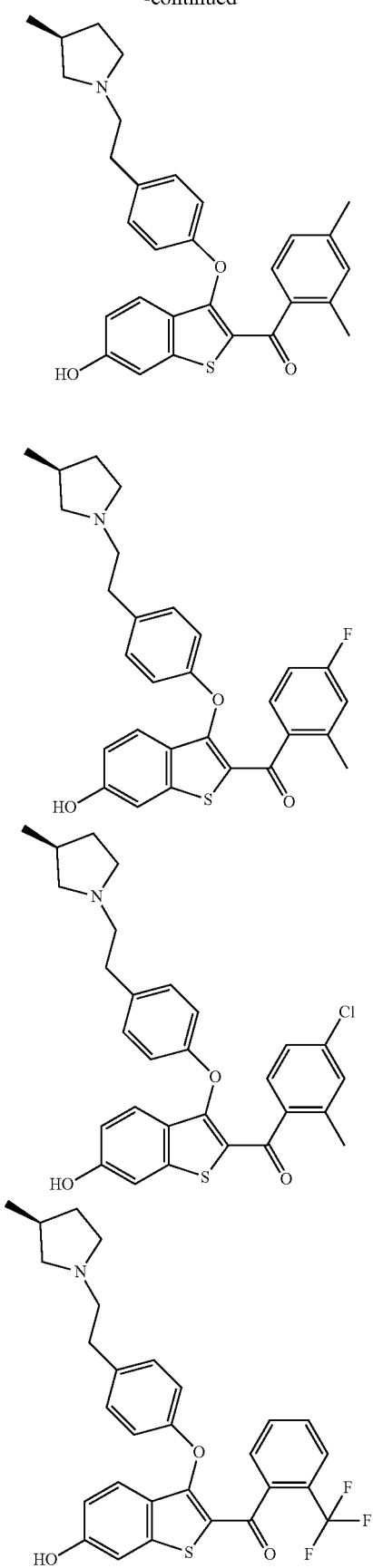
122
-continued
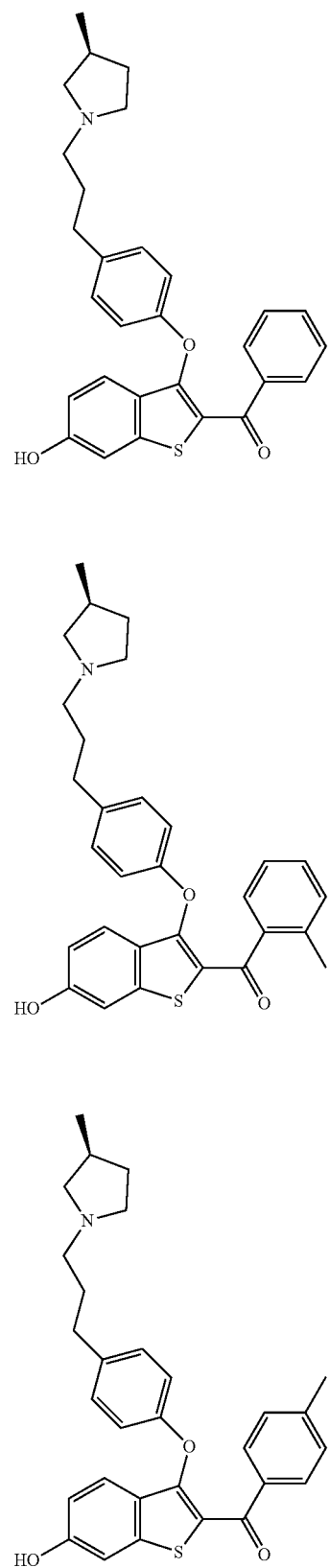

123
-continued
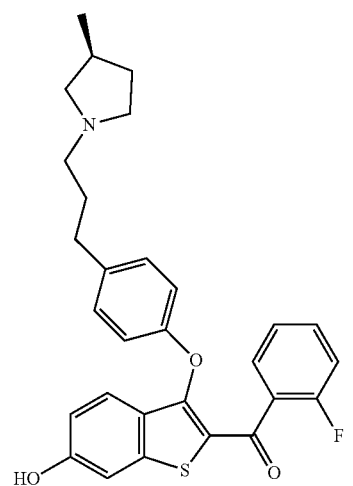
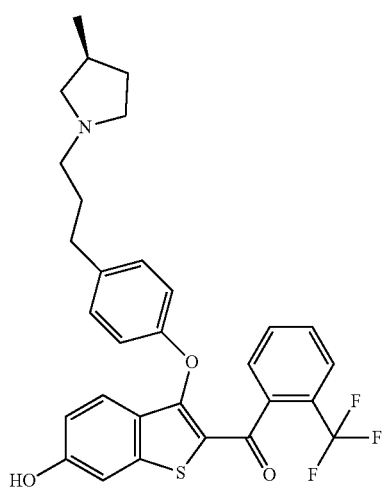
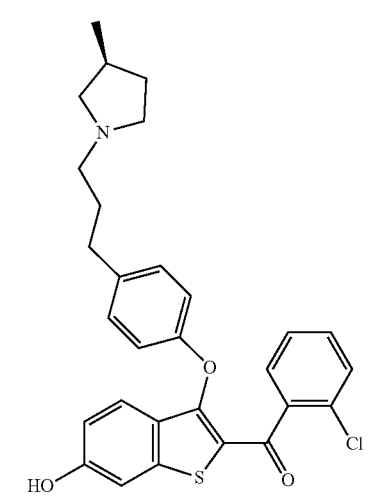
124
-continued
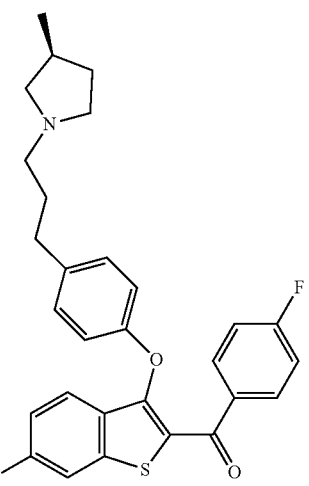
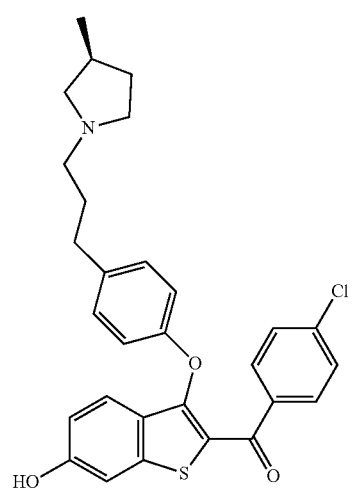
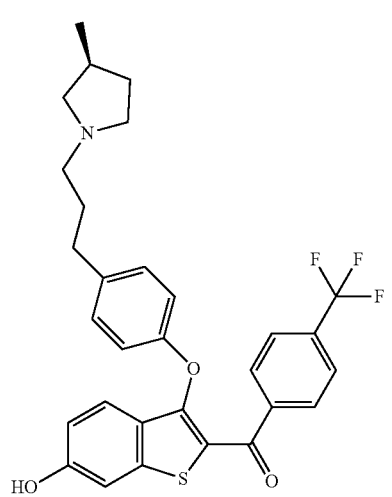

125
-continued
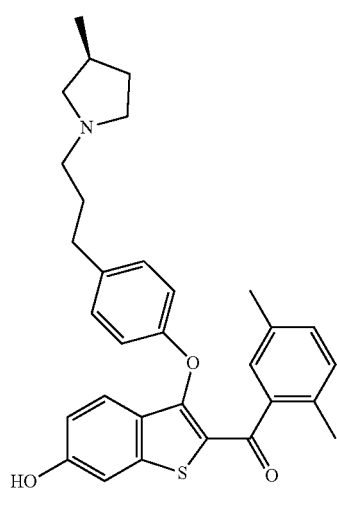
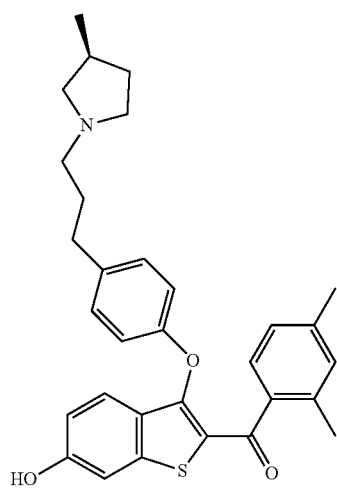
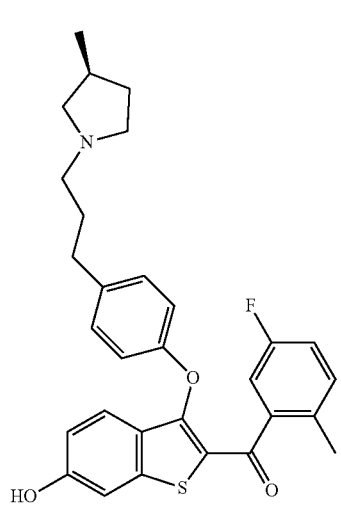
126
-continued
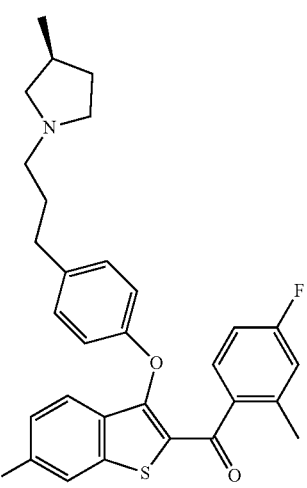
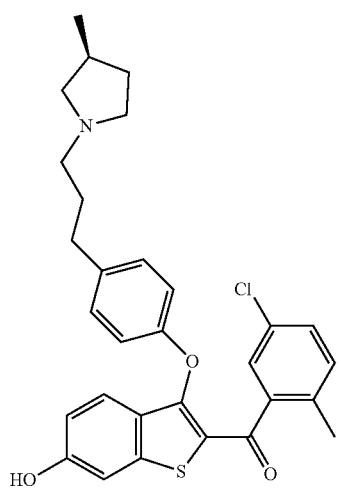
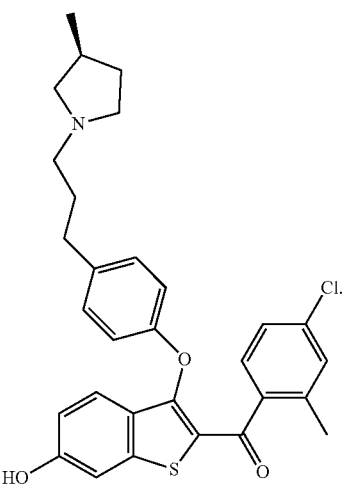
Non-limiting examples of compounds of Formula II include:

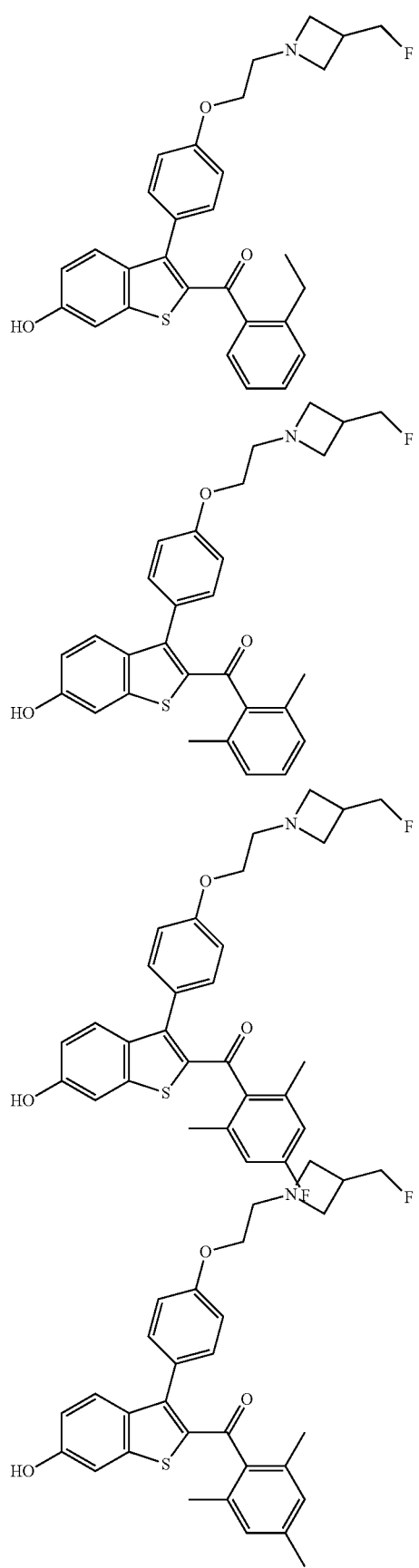
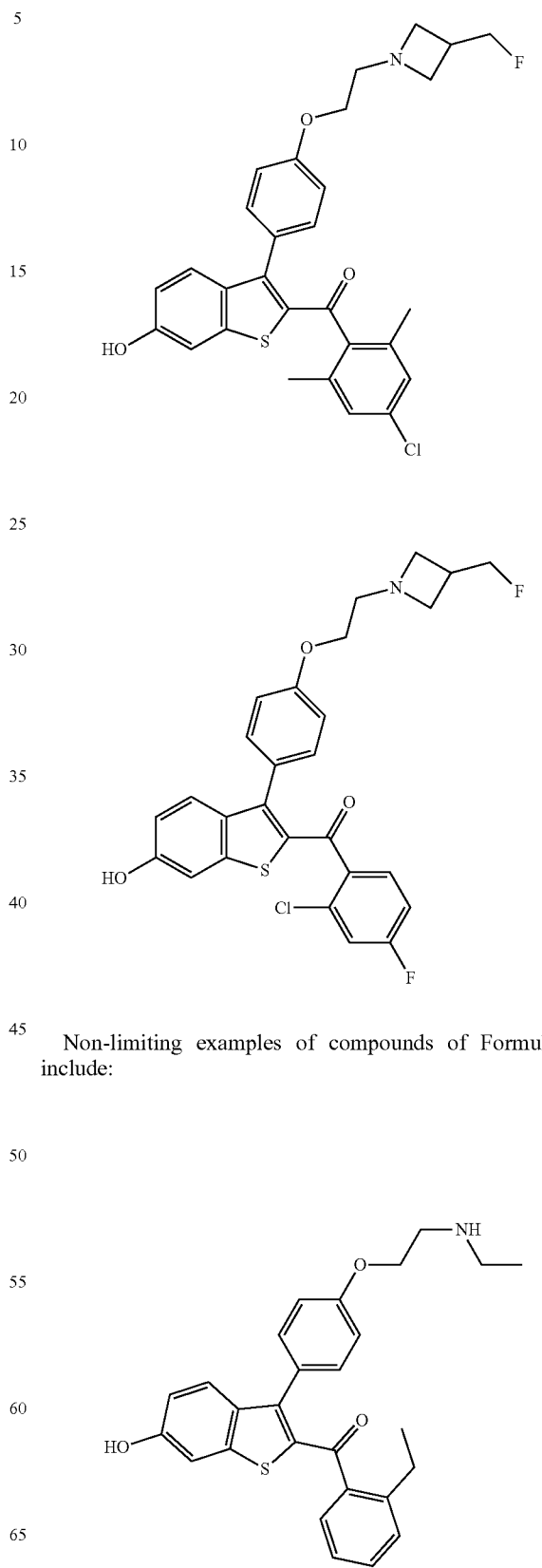
Non-limiting examples of compounds of Formula II include:

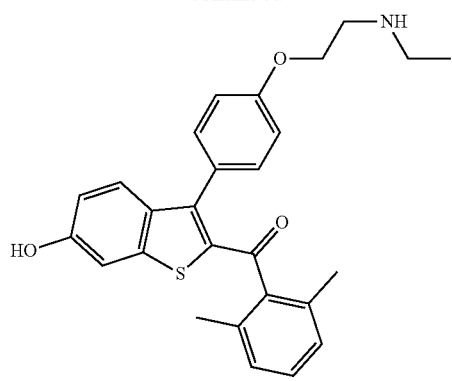
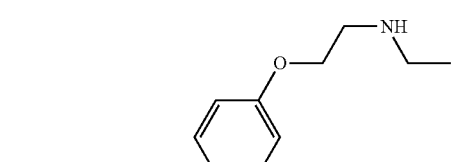
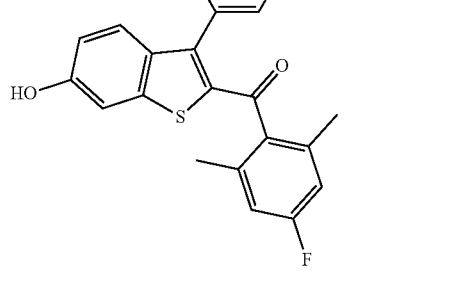
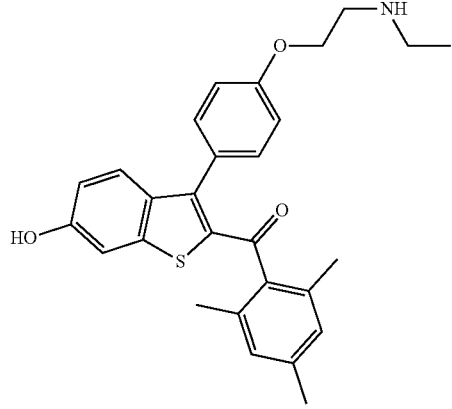
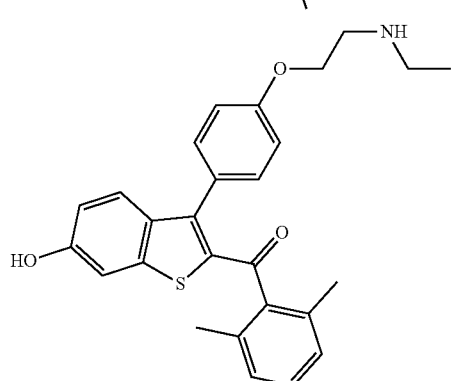
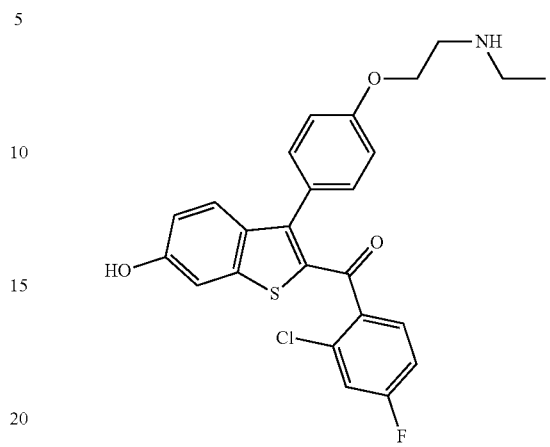
Non-limiting examples of compounds of Formula II include:
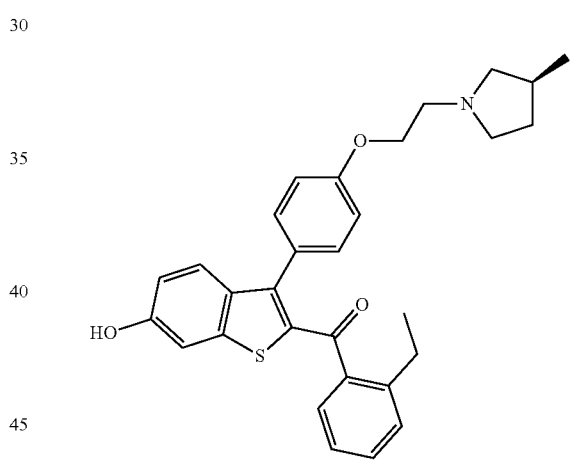
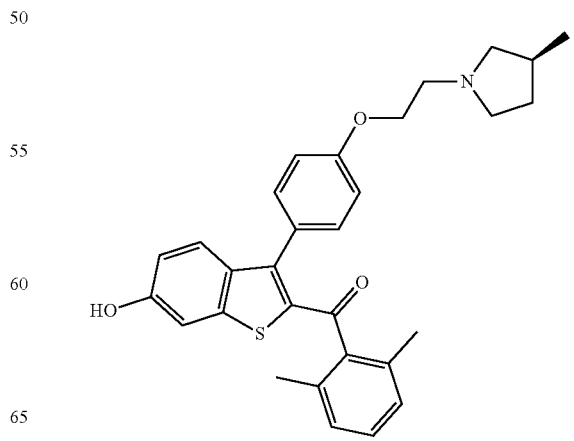

131
-continued
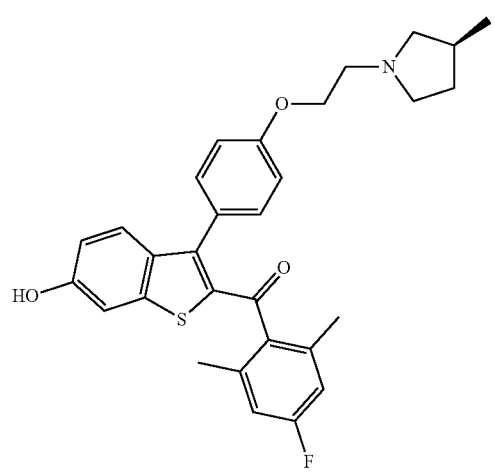
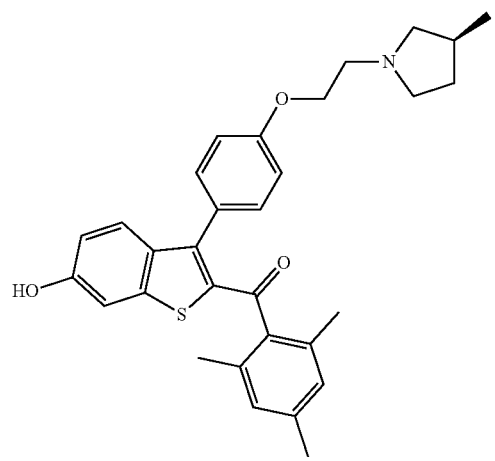
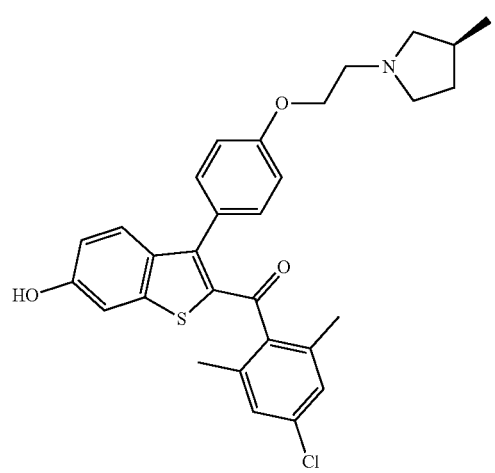
132
-continued
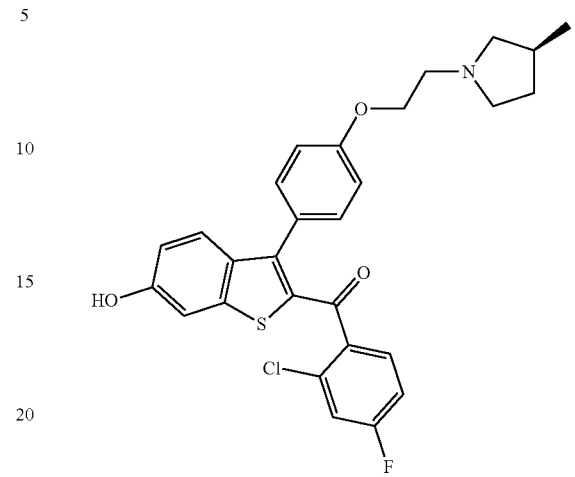
Non-limiting examples of compounds of Formula II include:
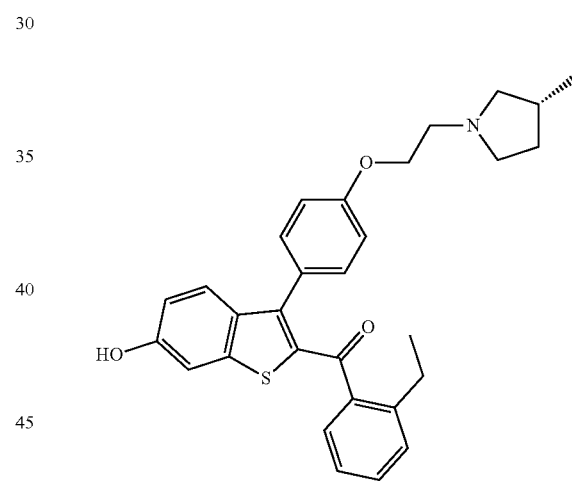
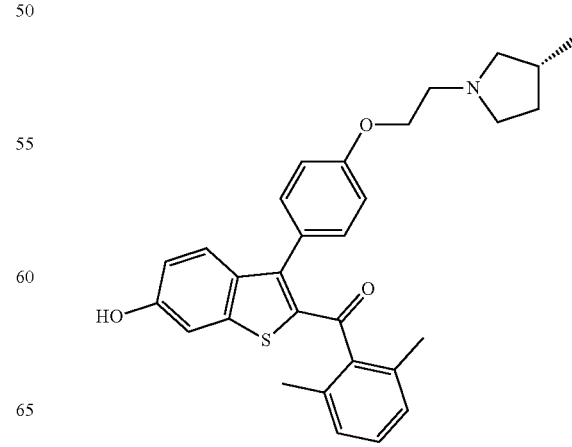

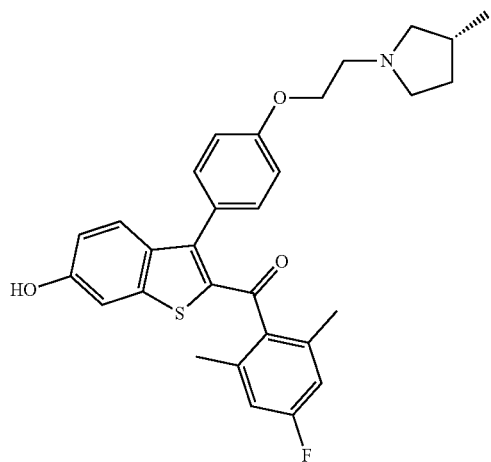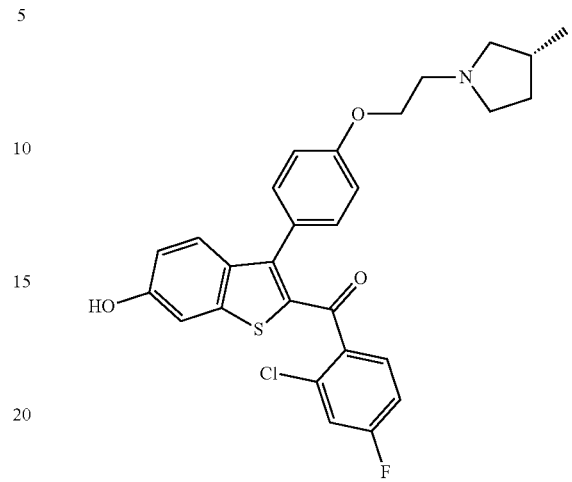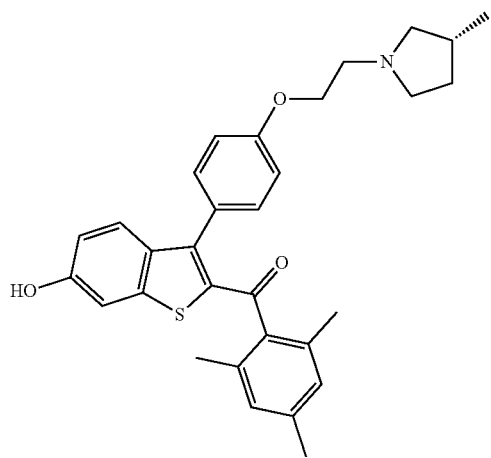
Non-limiting examples of compounds of Formula II include:
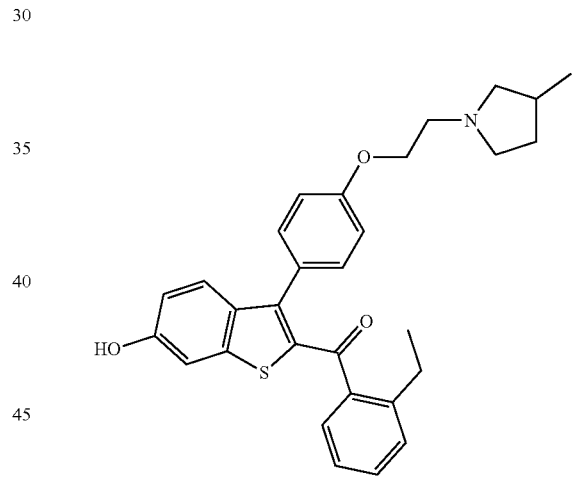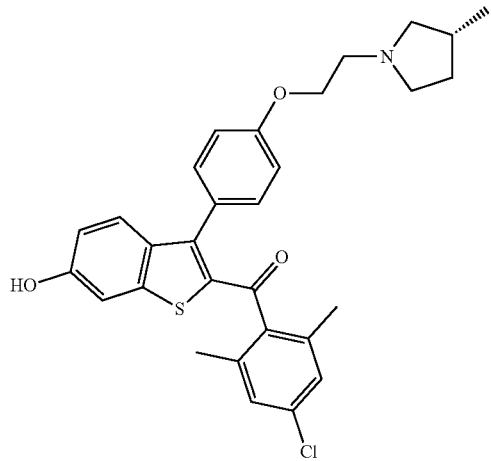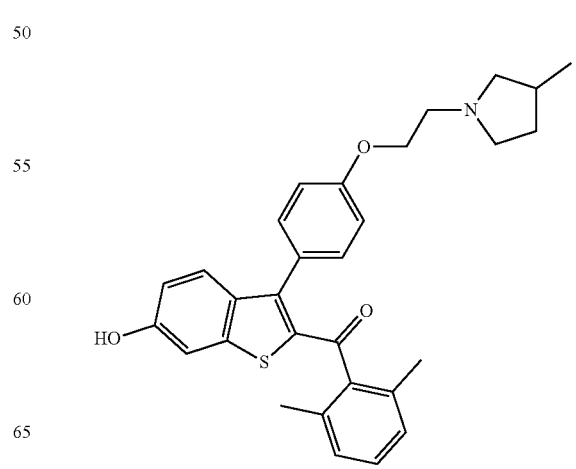

135
-continued
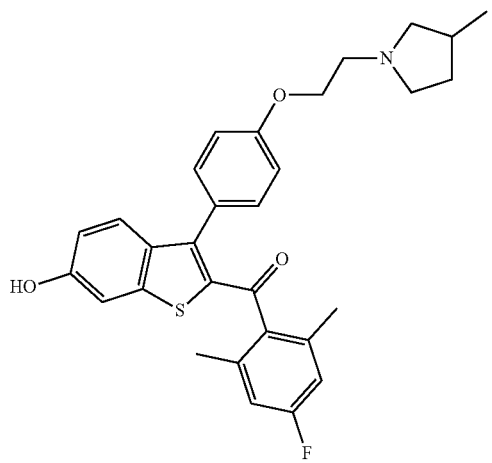
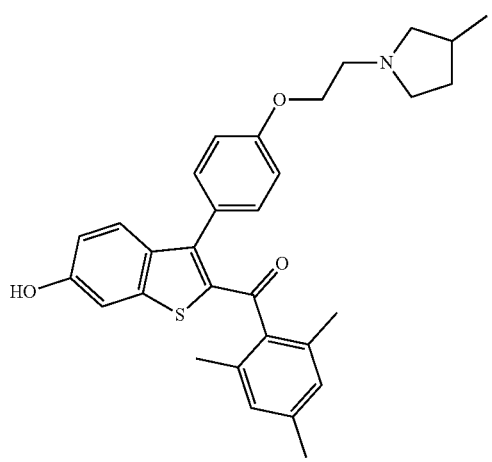
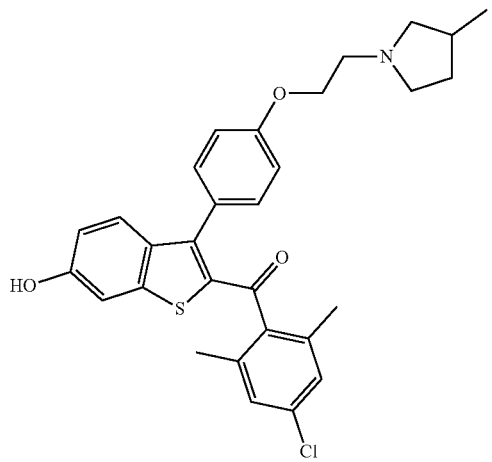
136
-continued
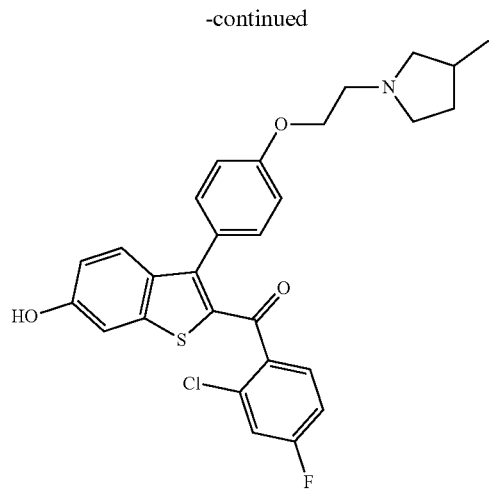
Non-limiting examples of compounds of Formula II include:
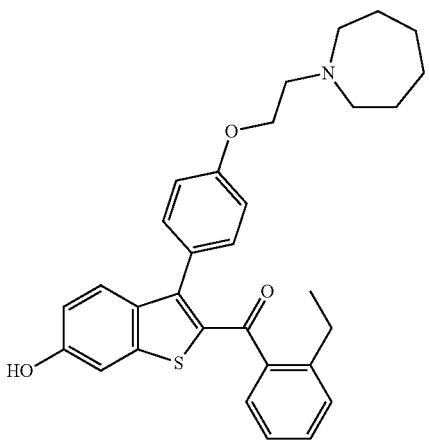
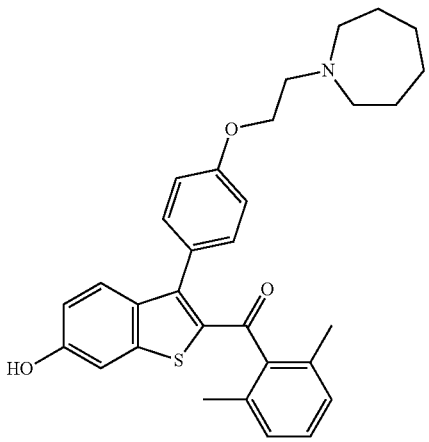

137
-continued
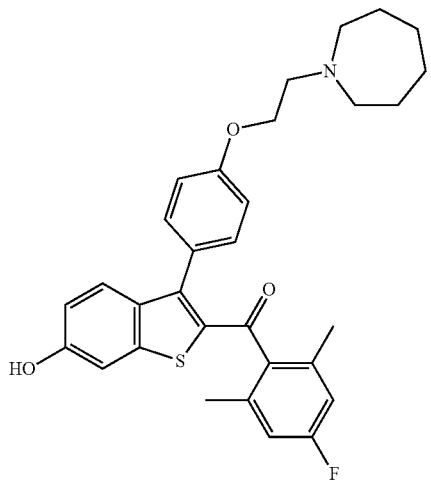
138
-continued
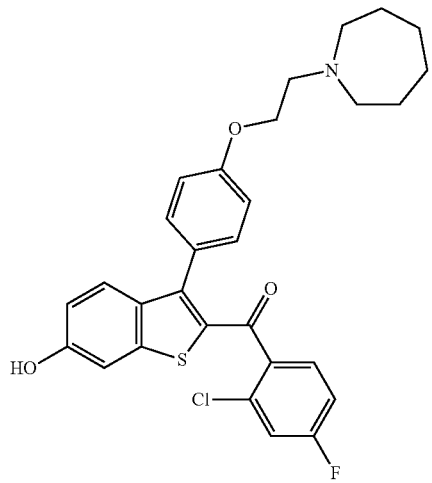
Non-limiting examples of compounds of Formula II include:
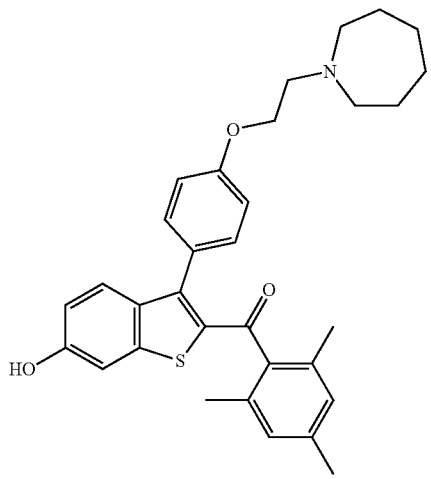
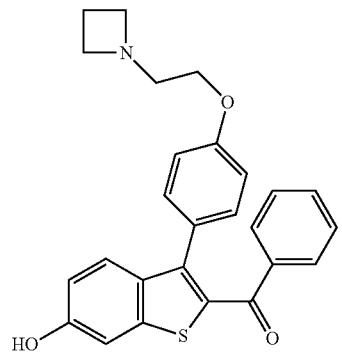
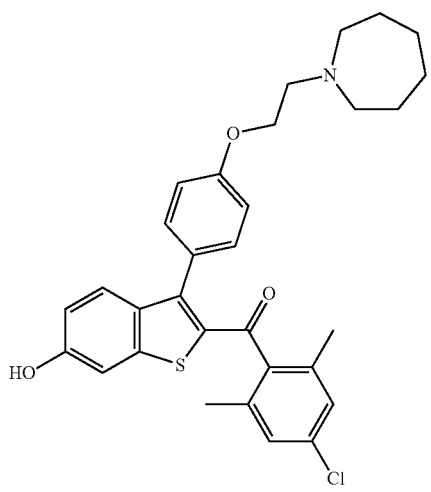
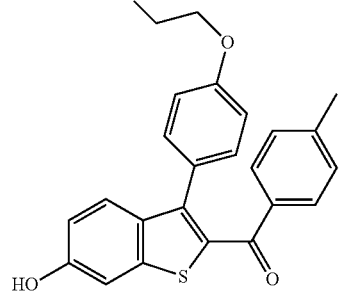

139
-continued
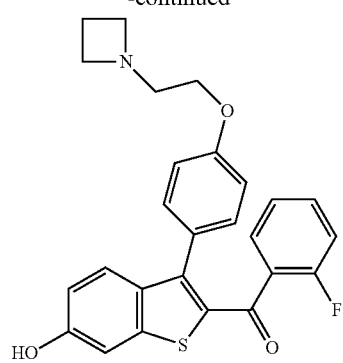
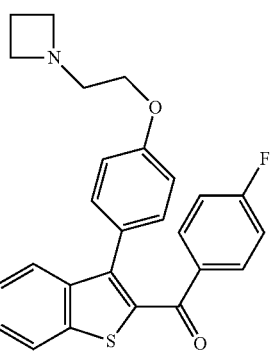
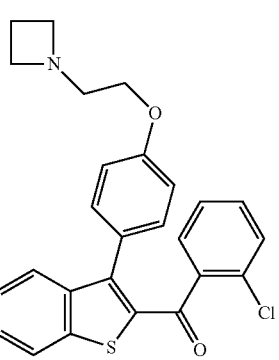
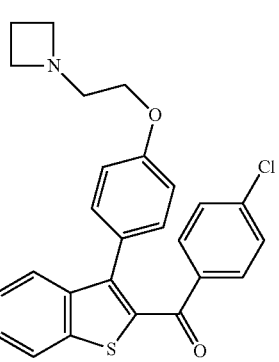
140
-continued
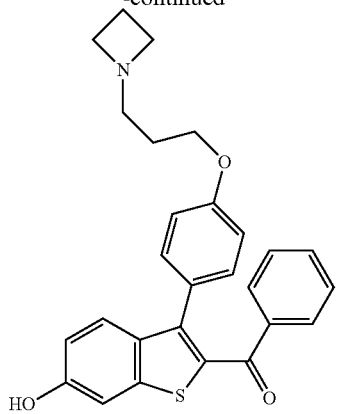
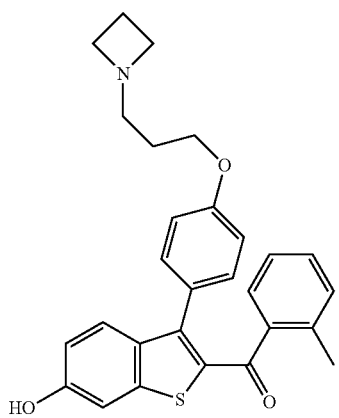
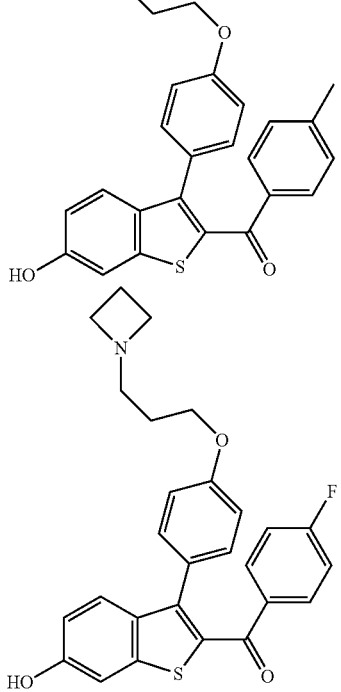
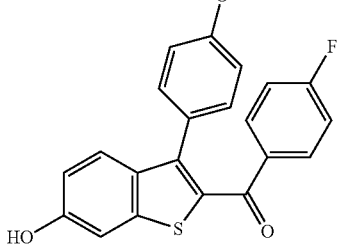

141
-continued
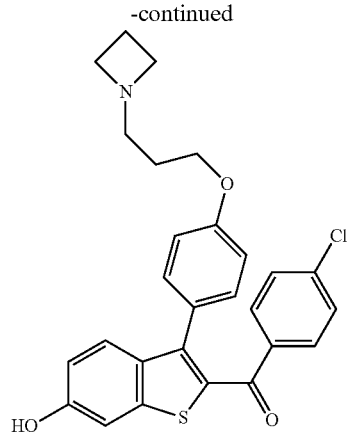
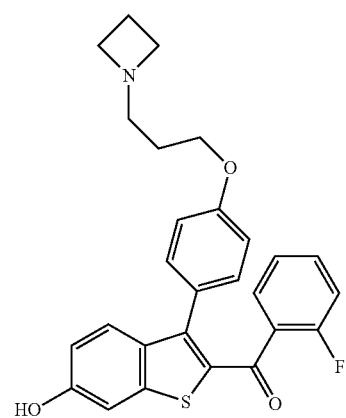
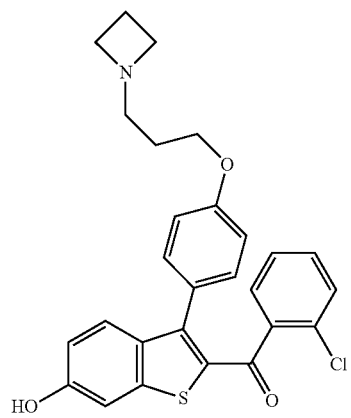
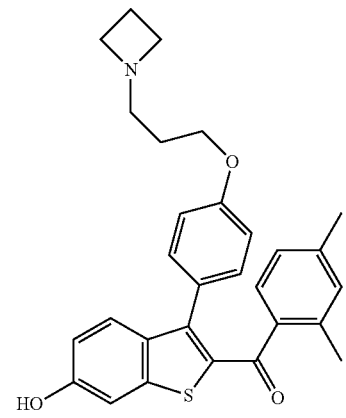
142
-continued
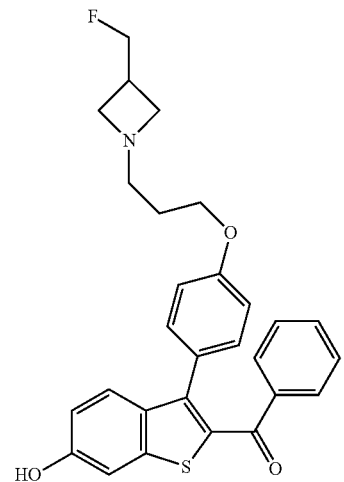
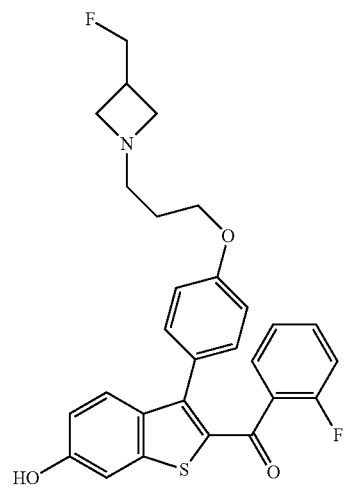
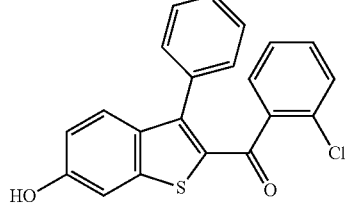

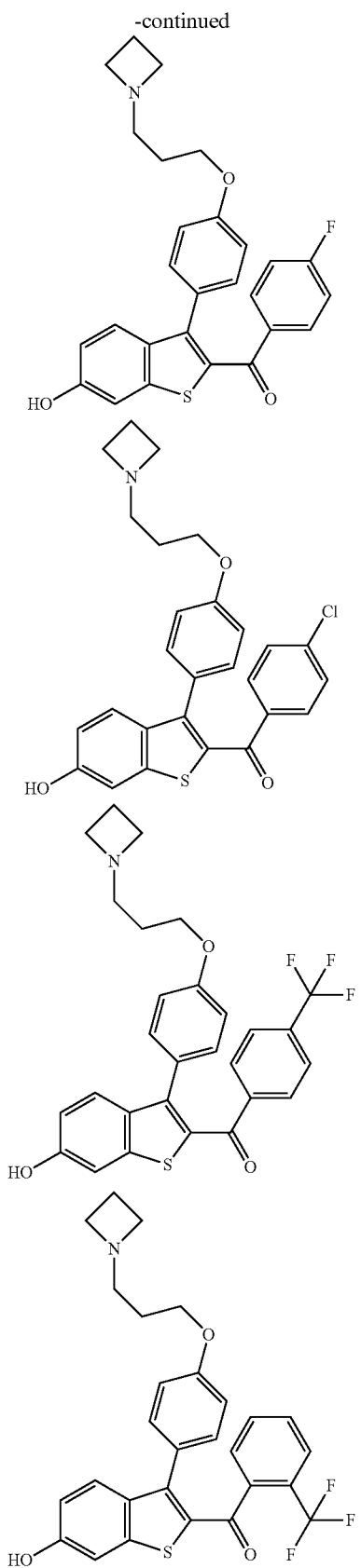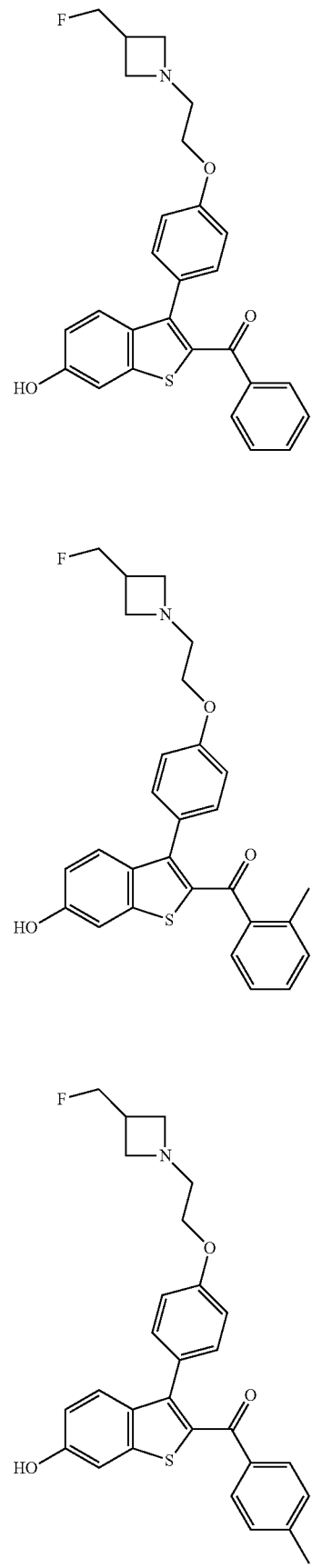
Non-limiting examples of compounds of Formula II include:

145
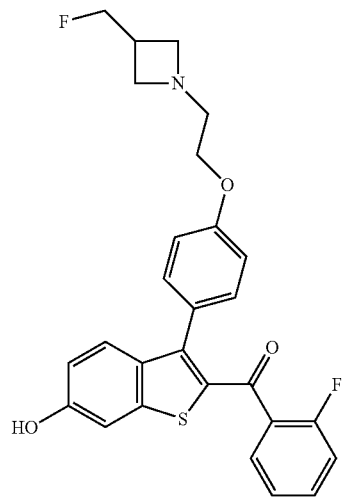
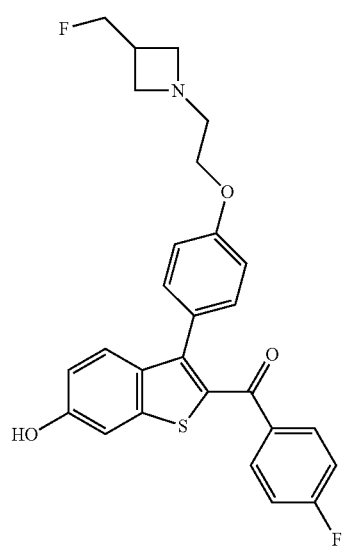
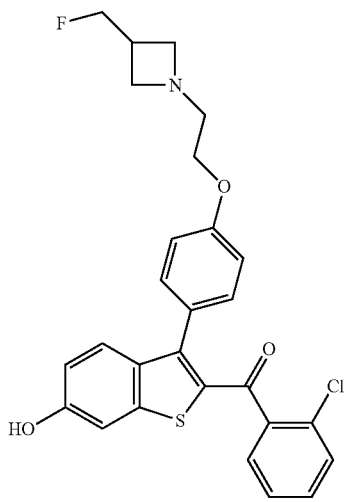
146
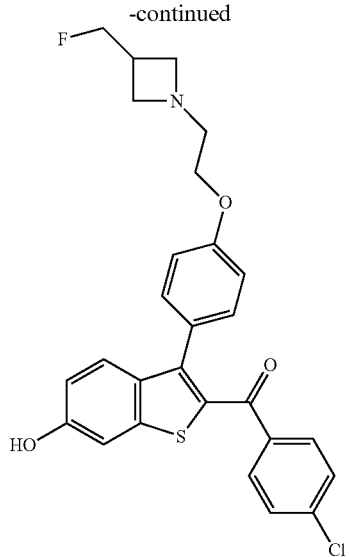
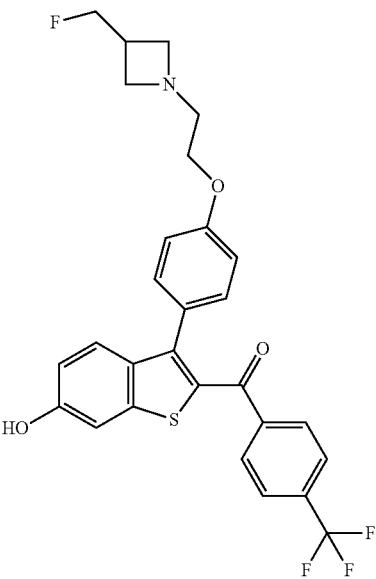
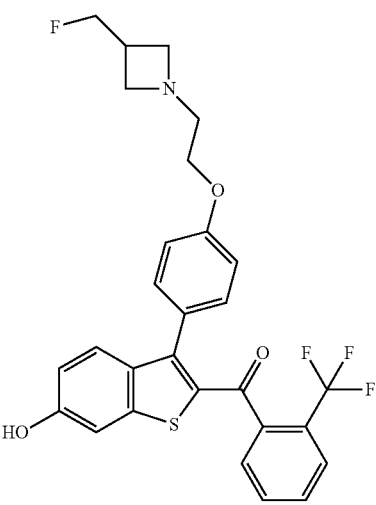

147
-continued
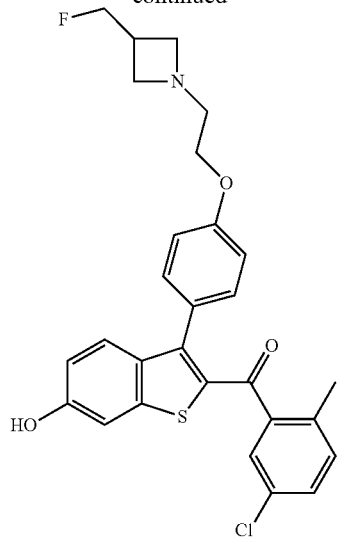
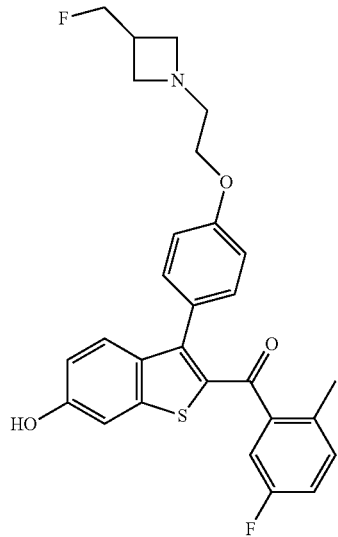
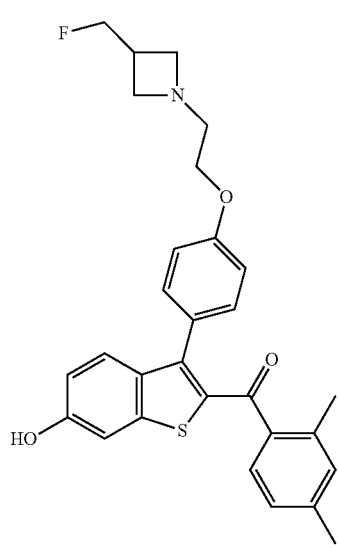
148
-continued
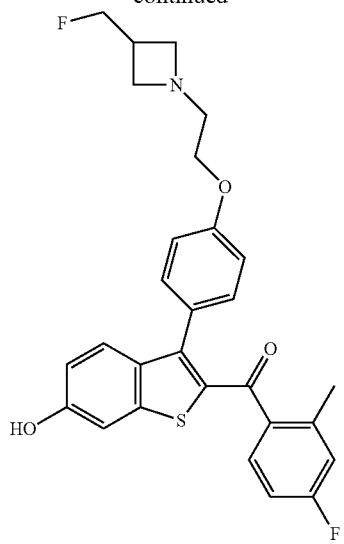
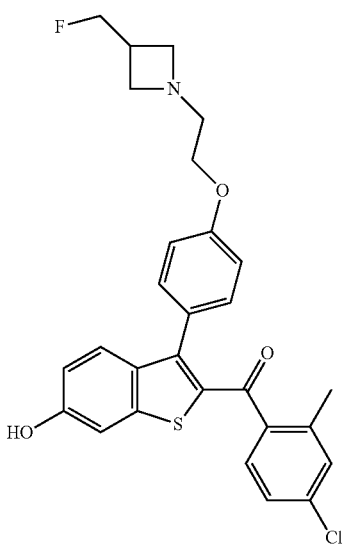
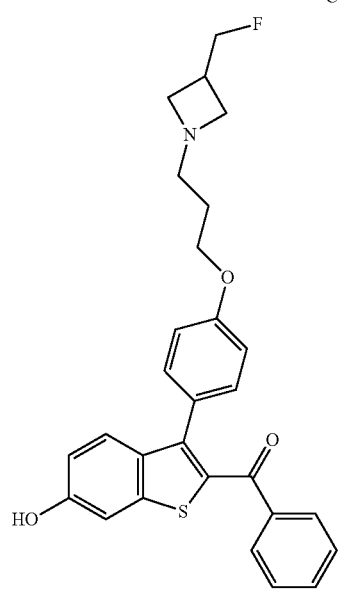

149
-continued
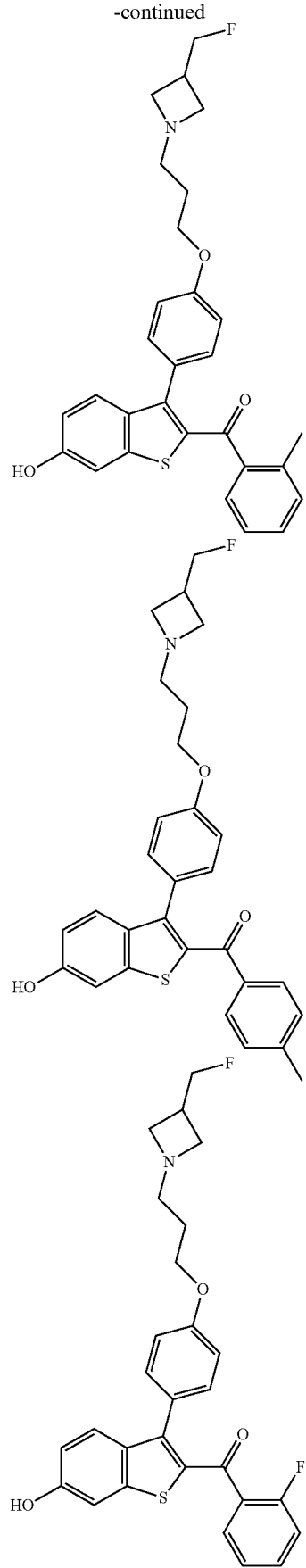
150
-continued
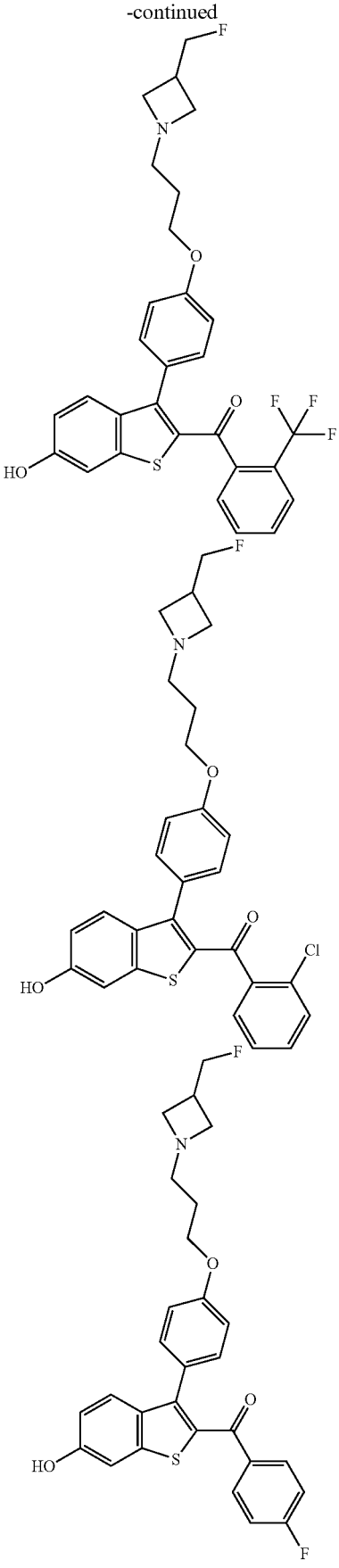

151
-continued
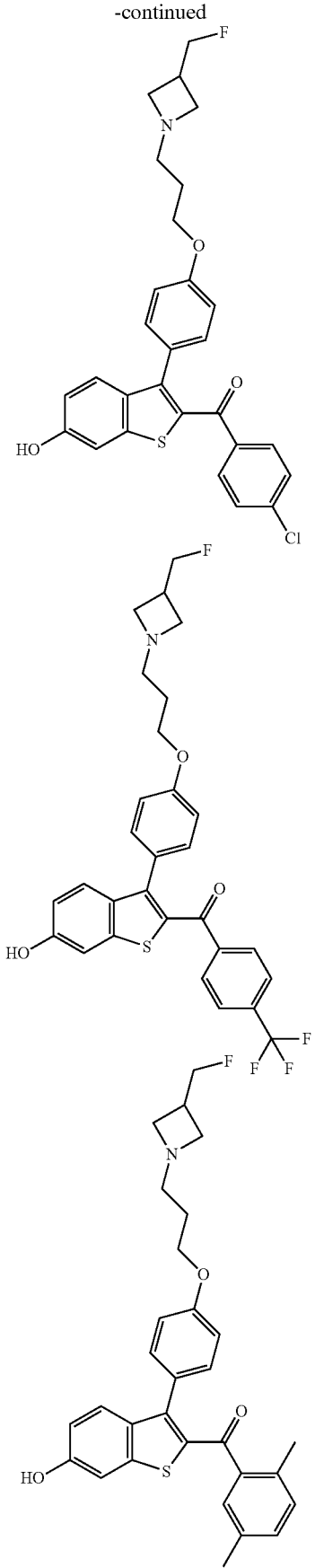
152
-continued
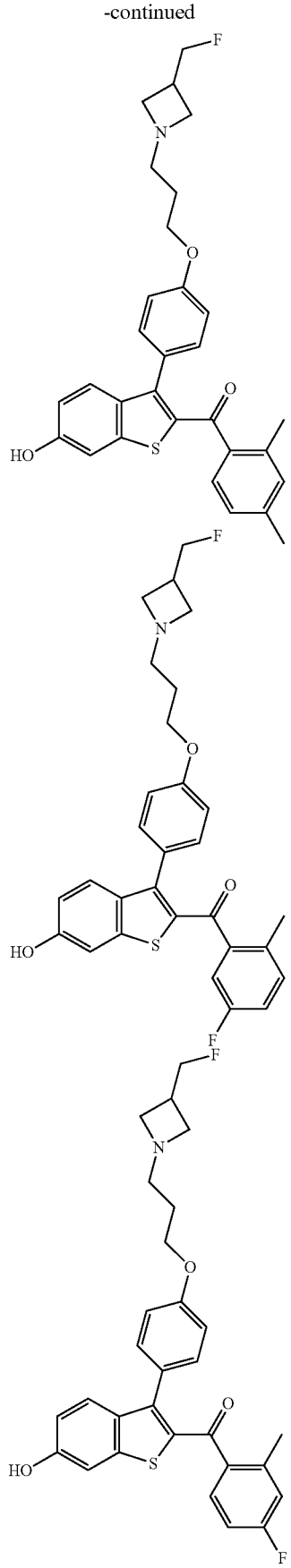

153
-continued
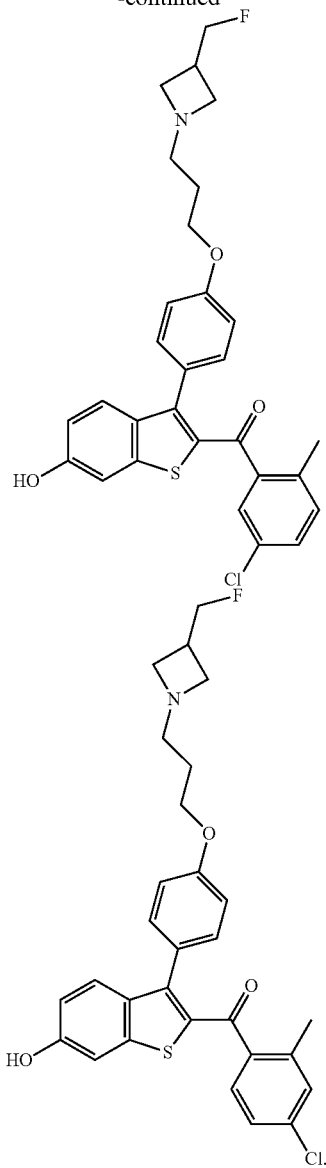
Non-limiting examples of compounds of Formula II include:
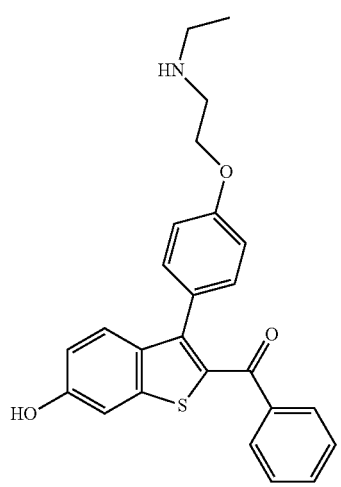
154
-continued
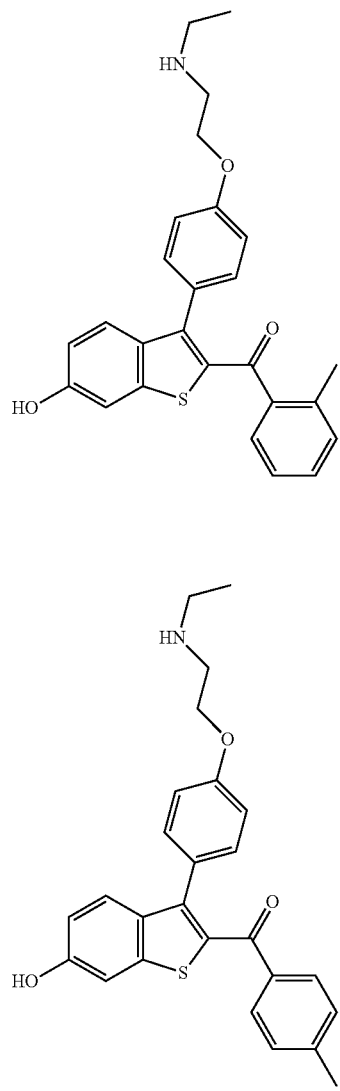
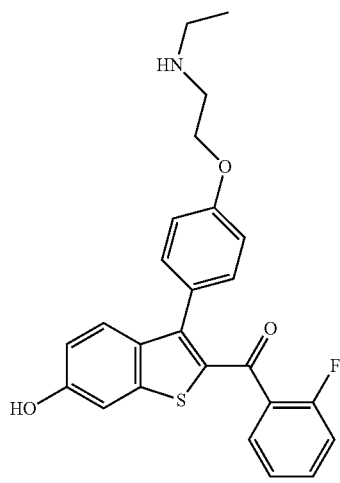

155
-continued
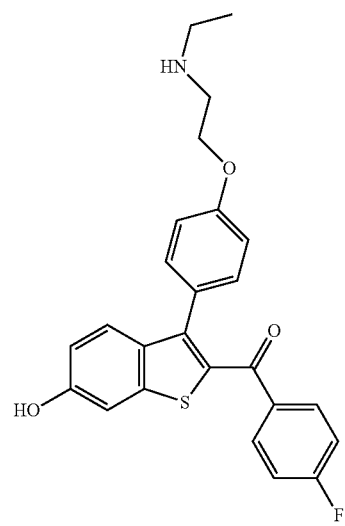
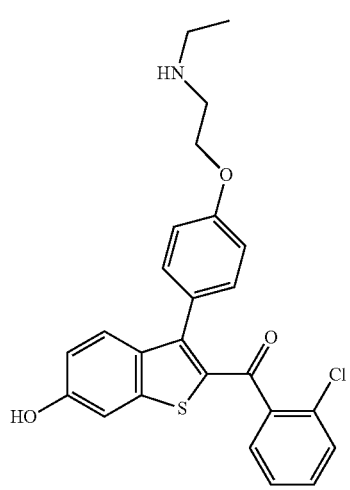
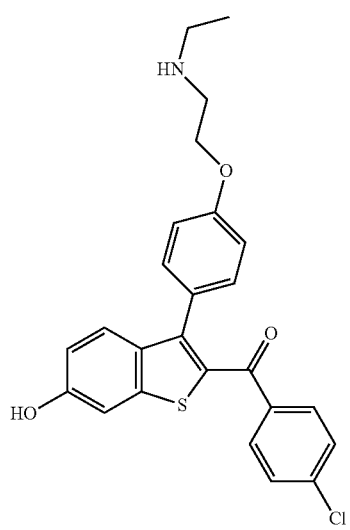
156
-continued
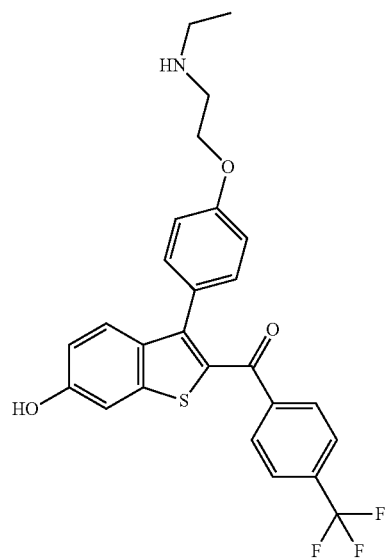
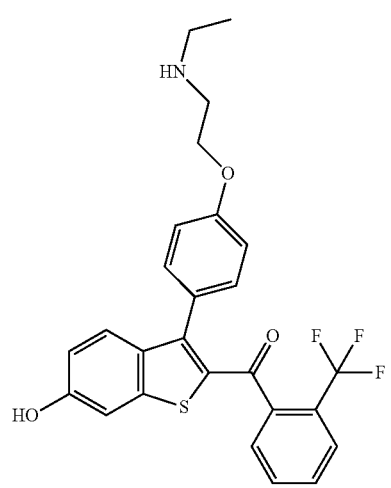
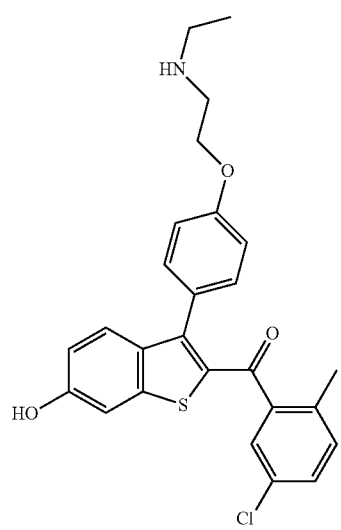

157
-continued
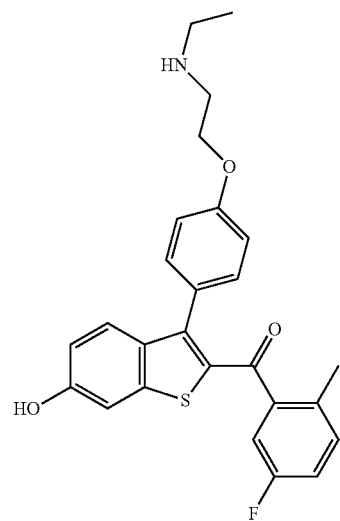
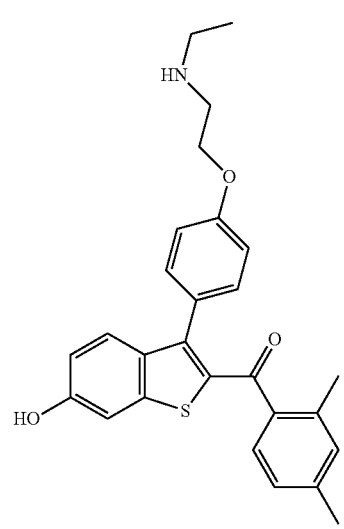
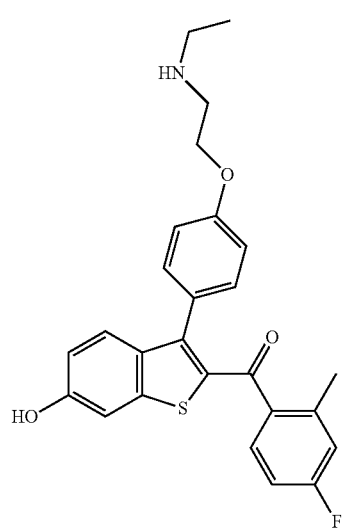
158
-continued
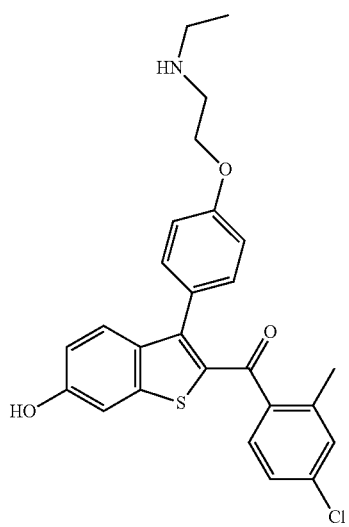
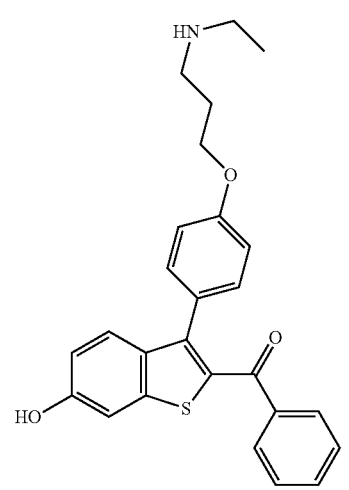
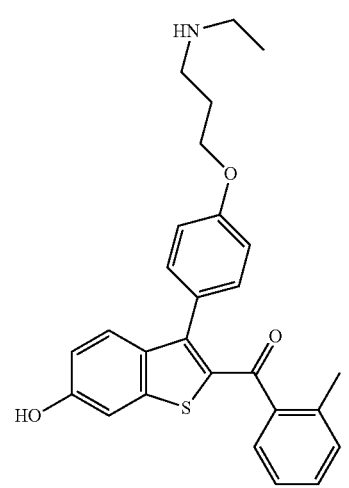

159
-continued
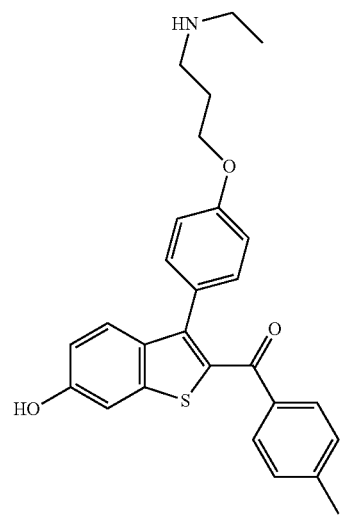
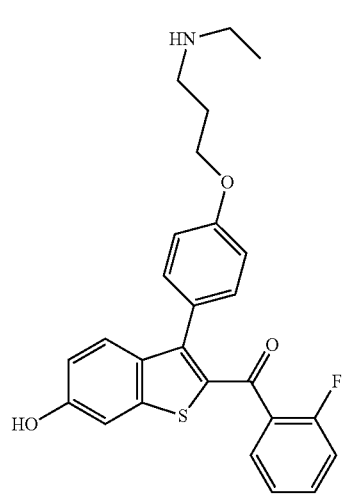
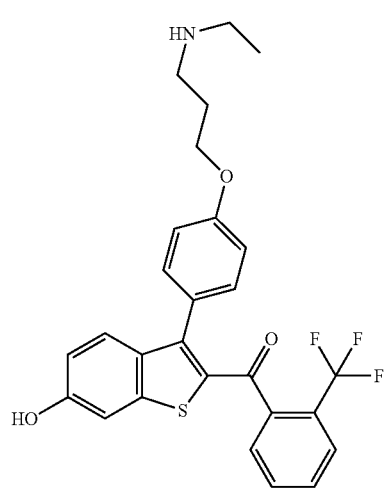
160
-continued
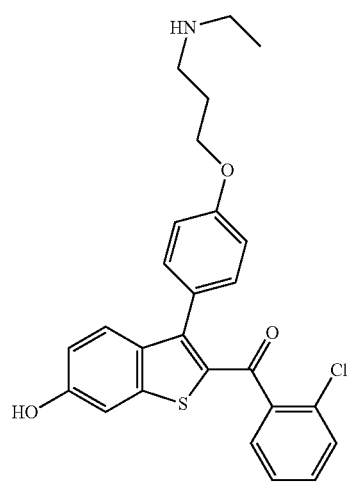
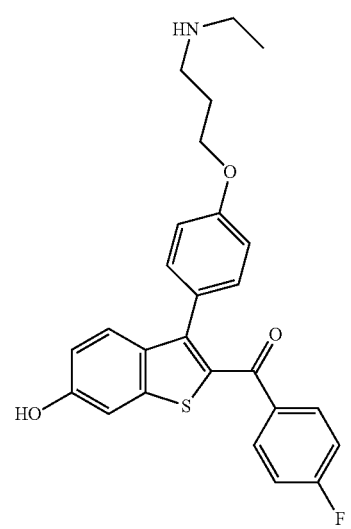
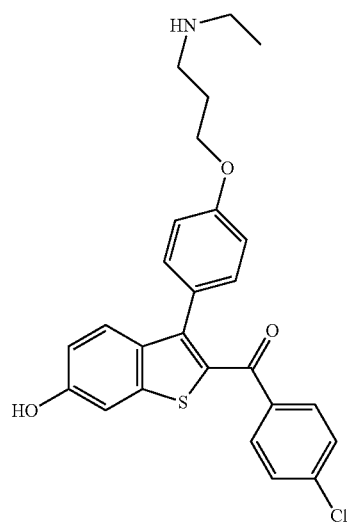

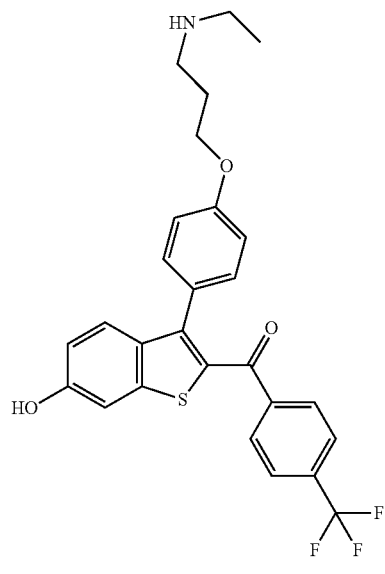
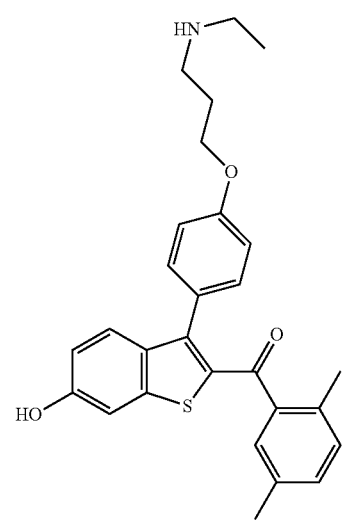
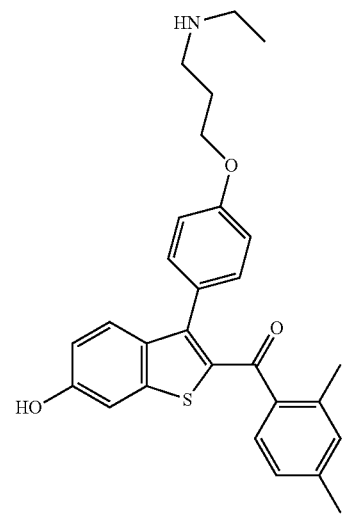
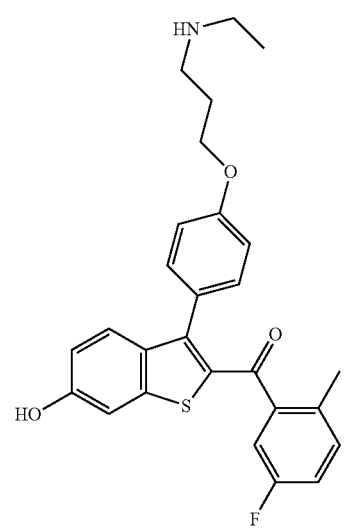
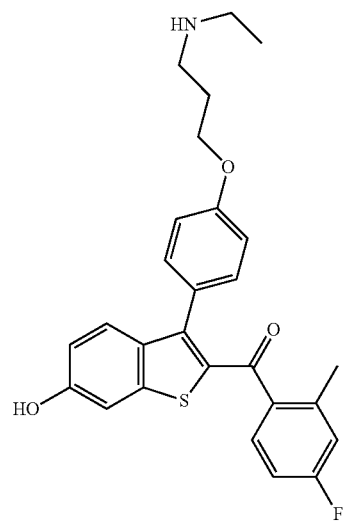
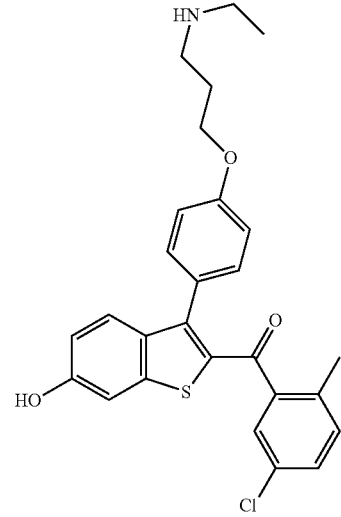

163
-continued
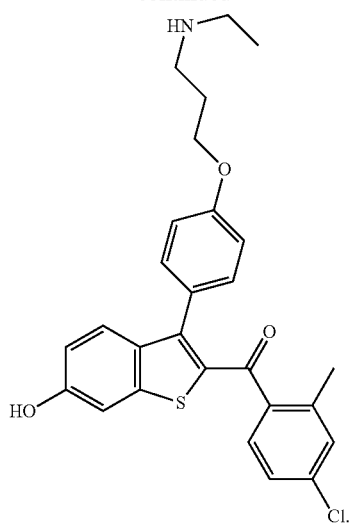
Non-limiting examples of compounds of Formula II include:
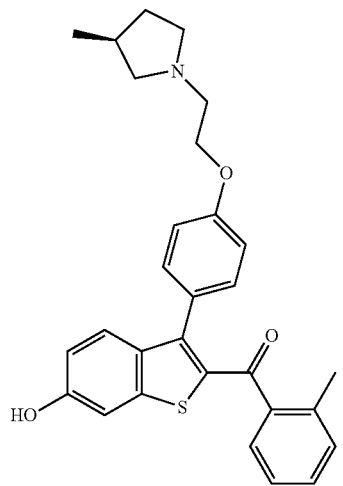
164
-continued
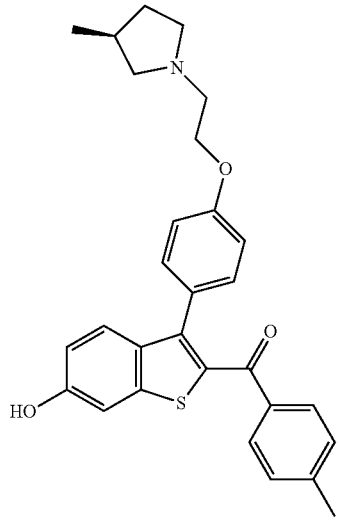
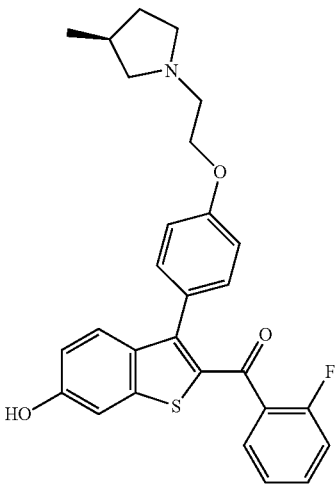
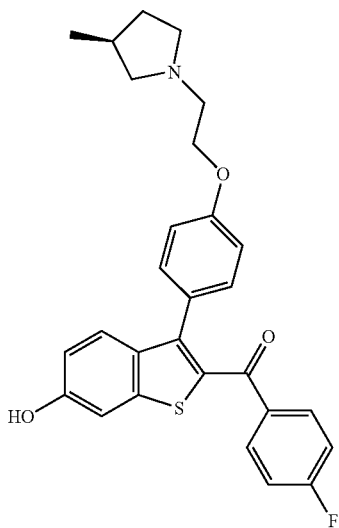

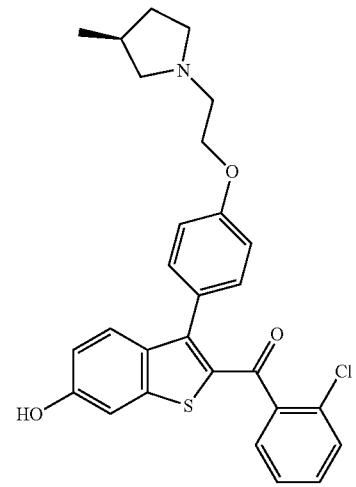
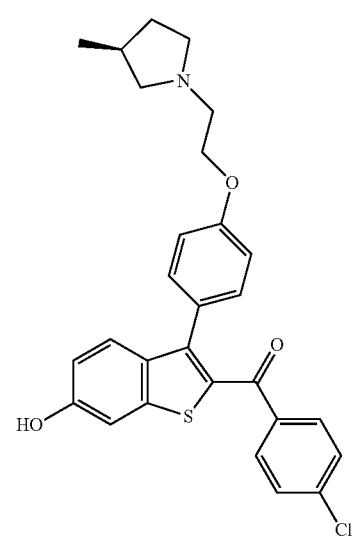
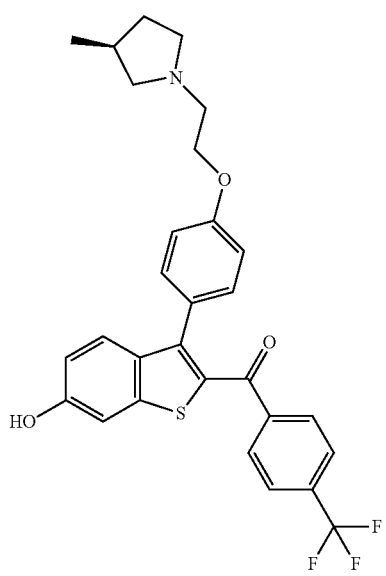
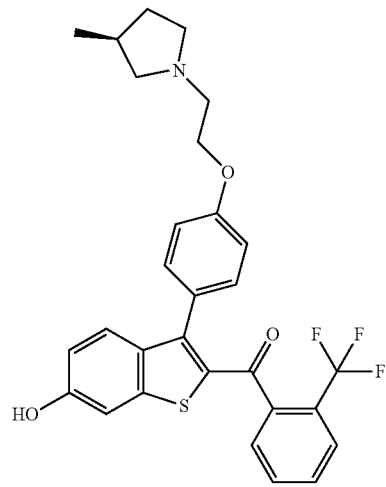
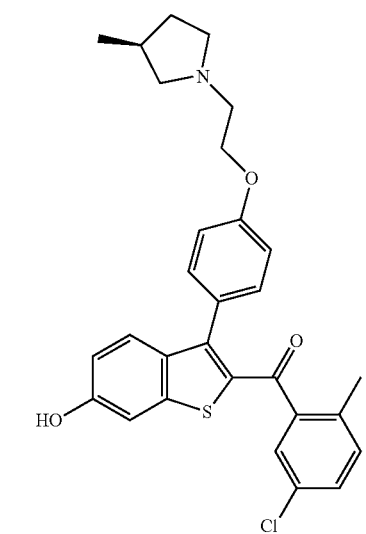
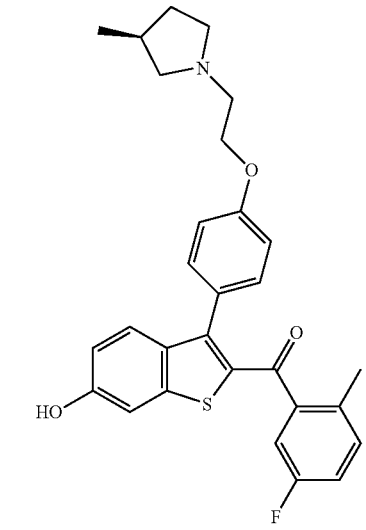

167
-continued
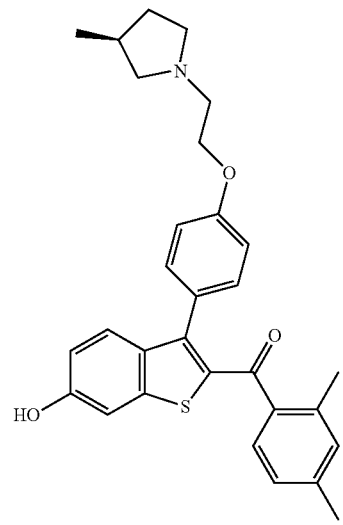
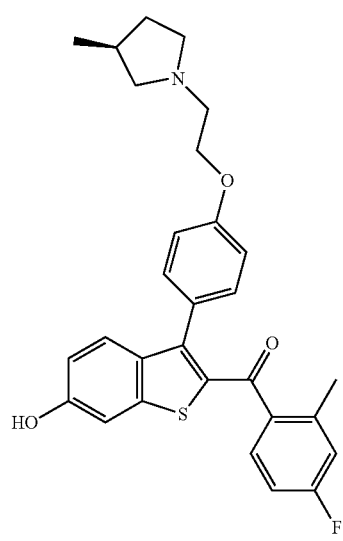
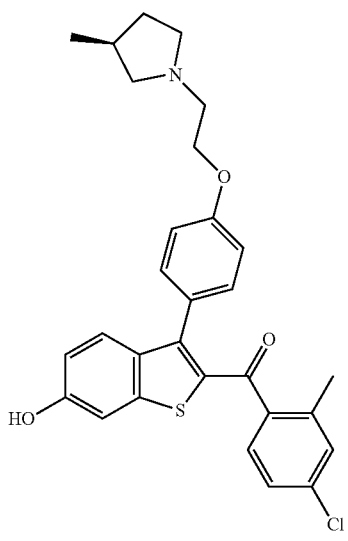
168
-continued
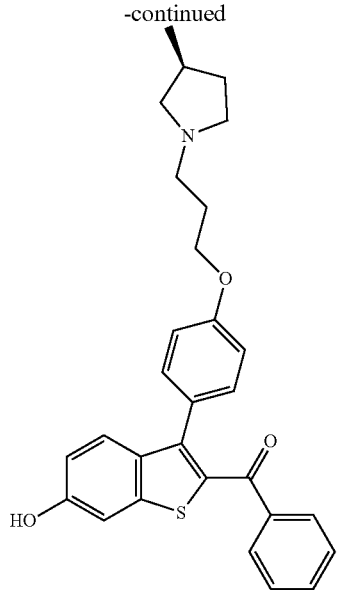
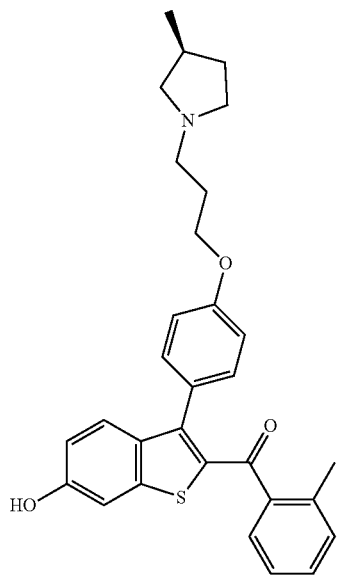
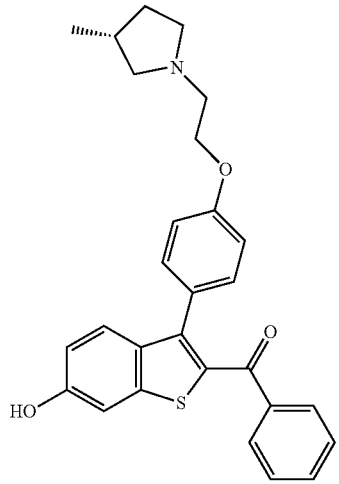

169
-continued
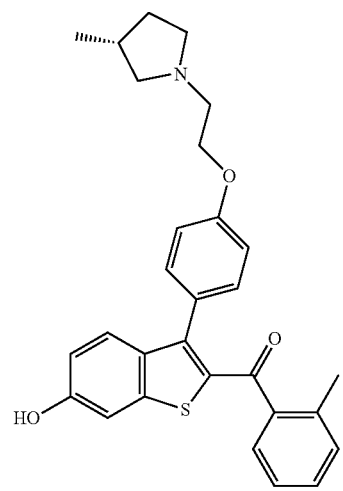
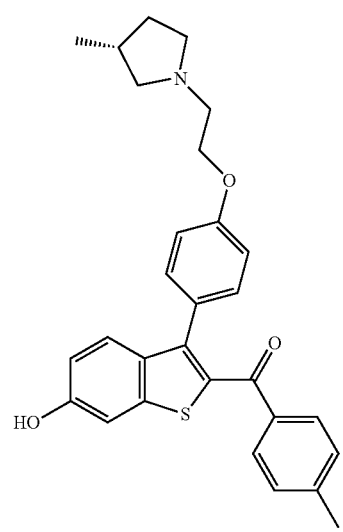
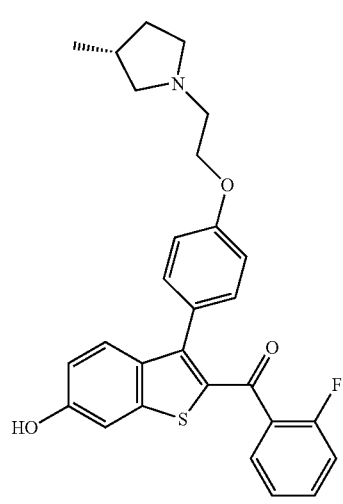
170
-continued
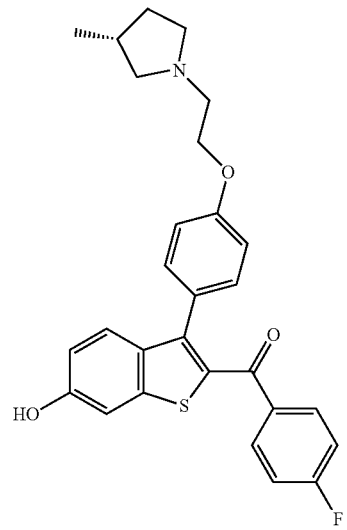
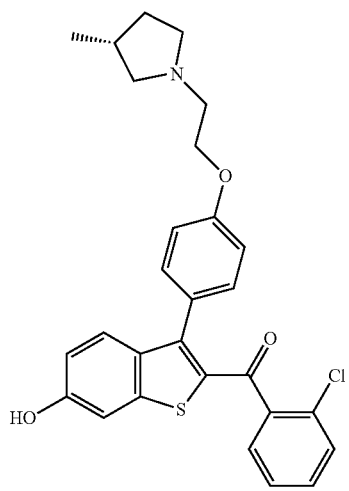
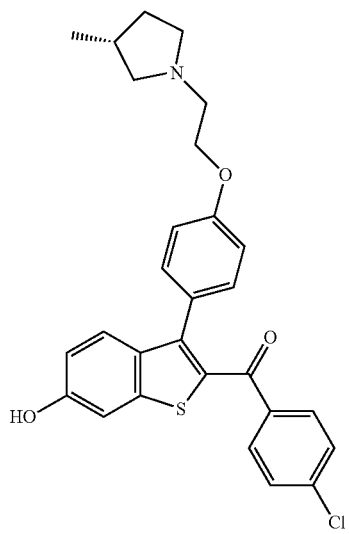

171
-continued
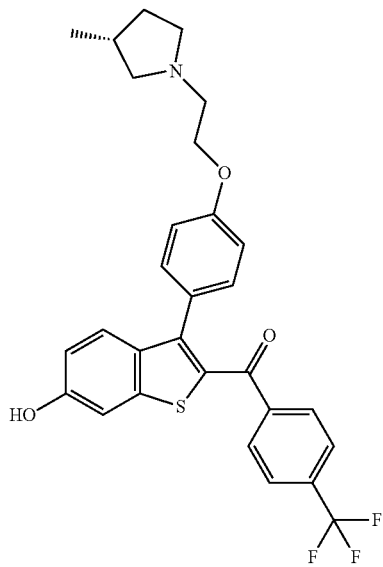
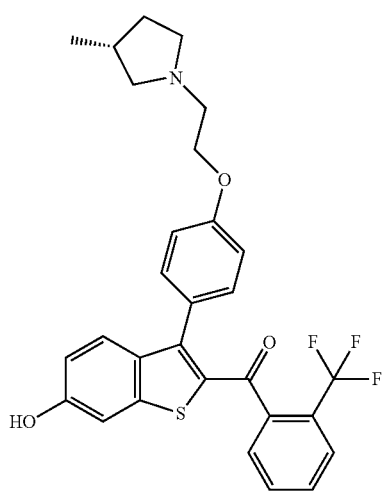
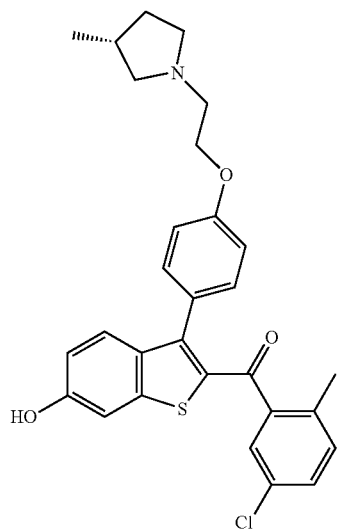
172
-continued
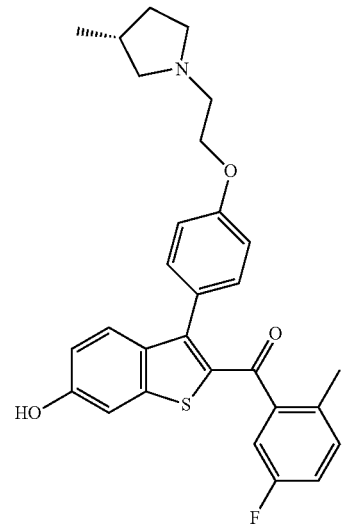
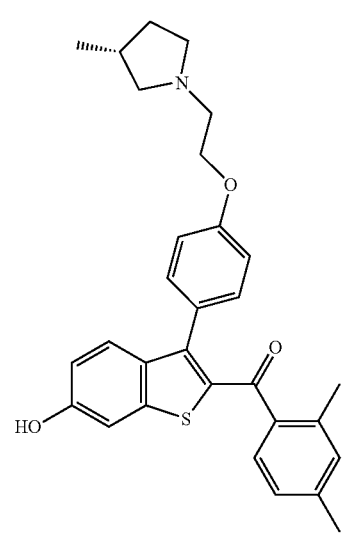
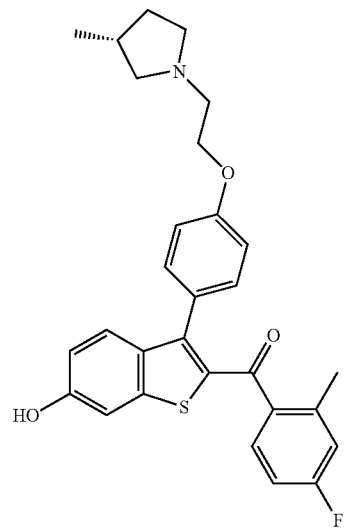

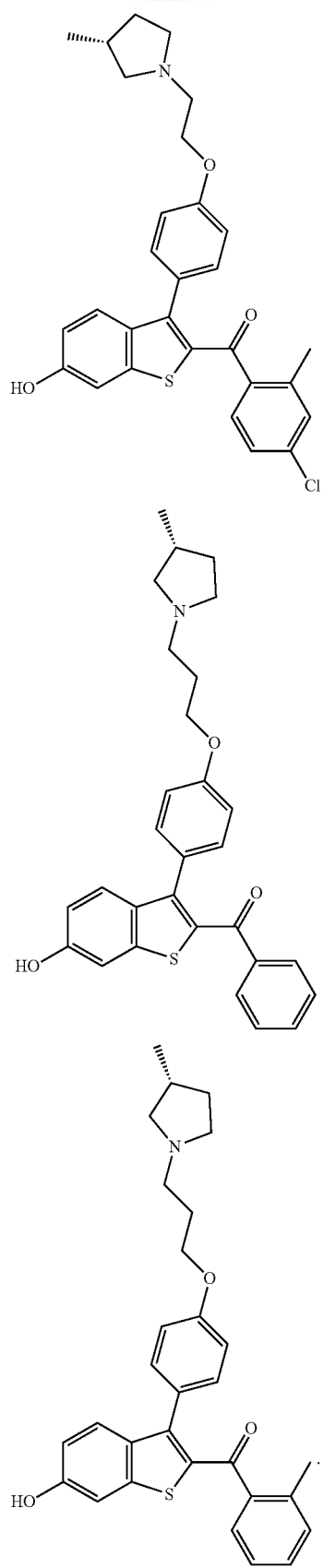
Non-limiting examples of compounds of Formula III include:
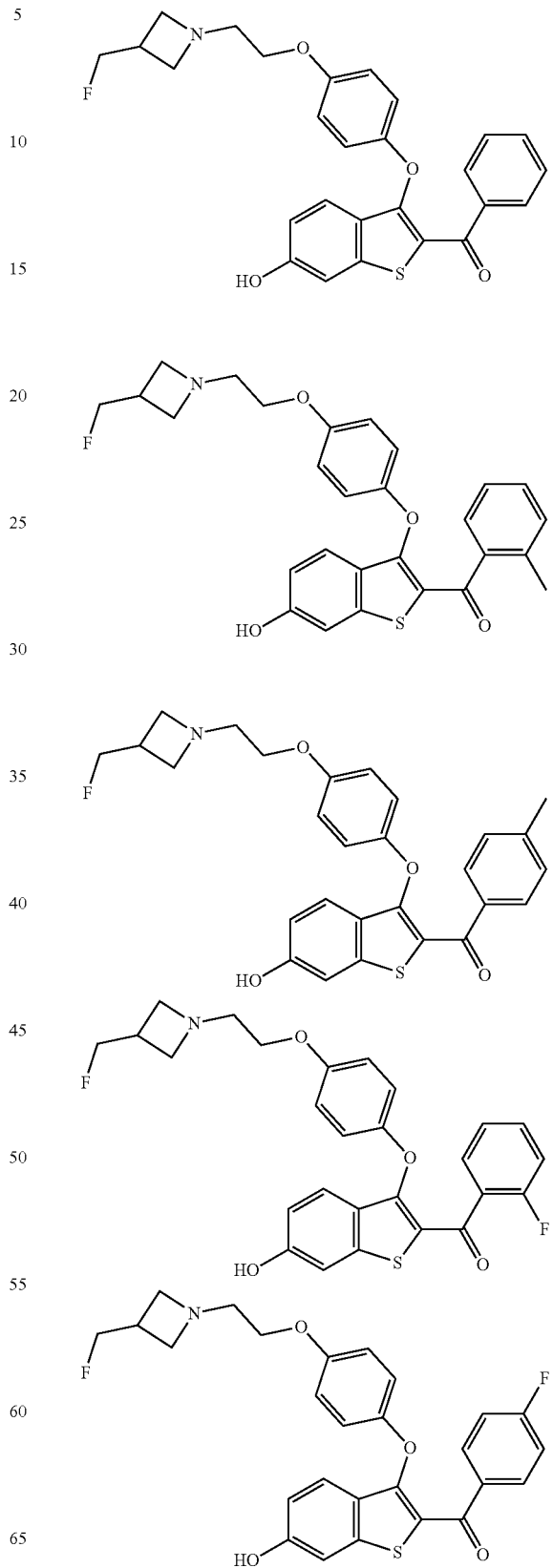

175
-continued
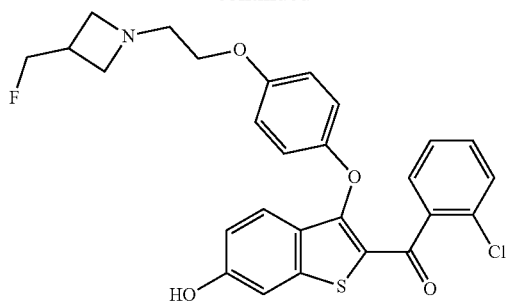
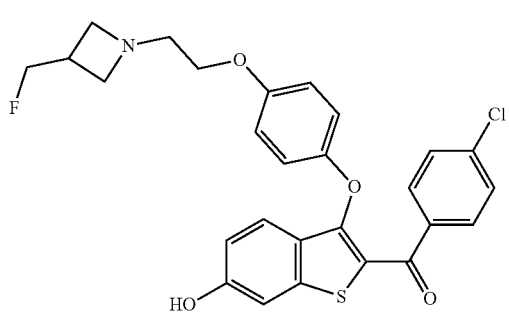
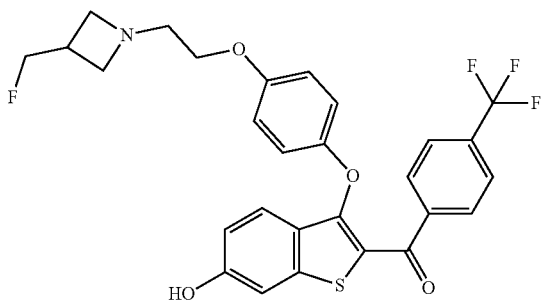
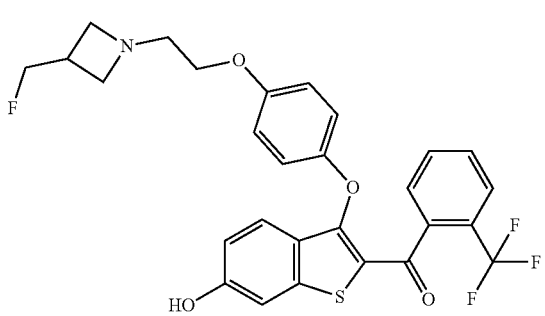
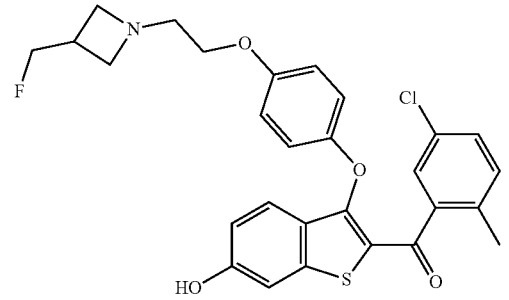
176
-continued
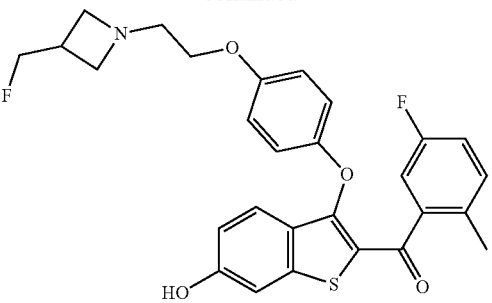
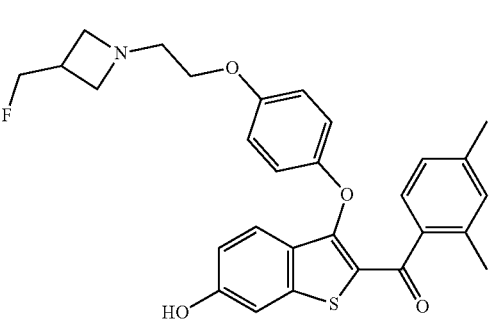
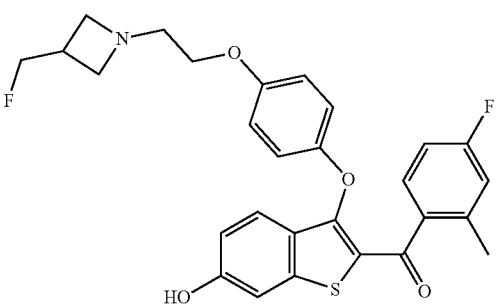
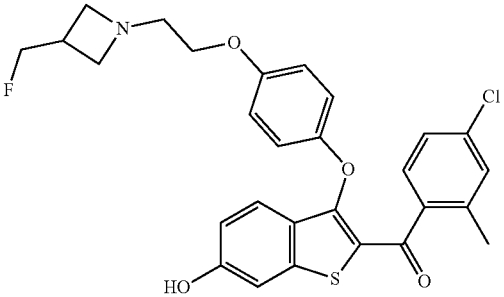
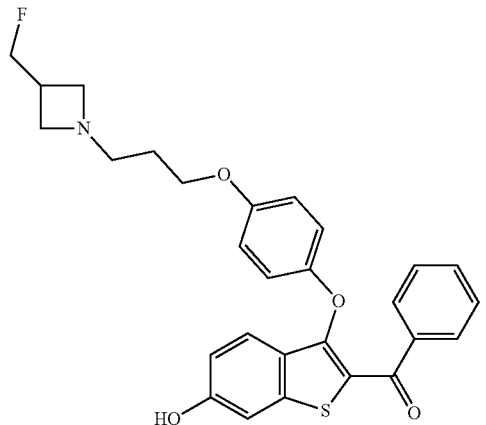

177
-continued
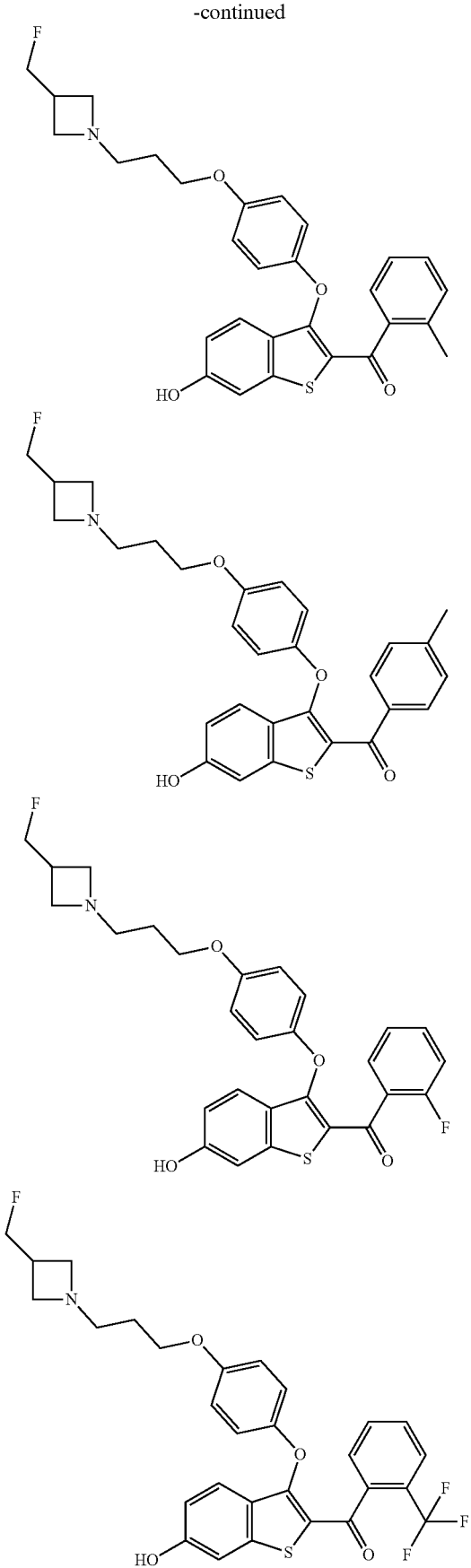
178
-continued
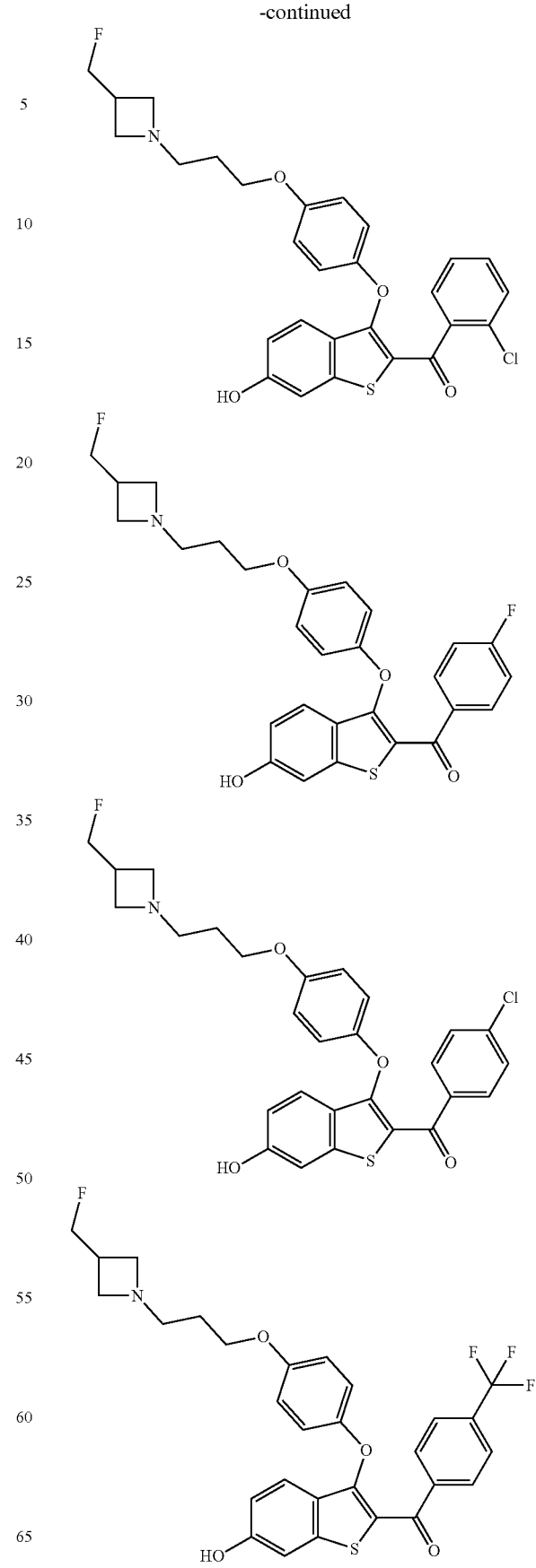

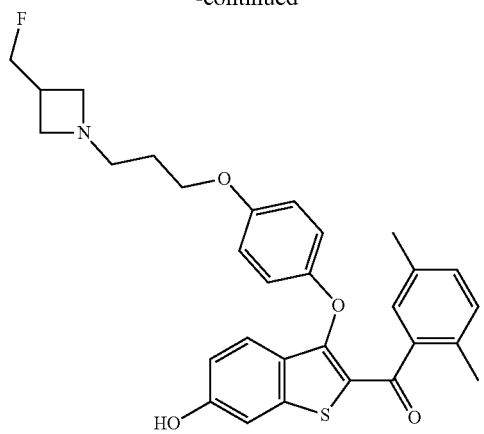
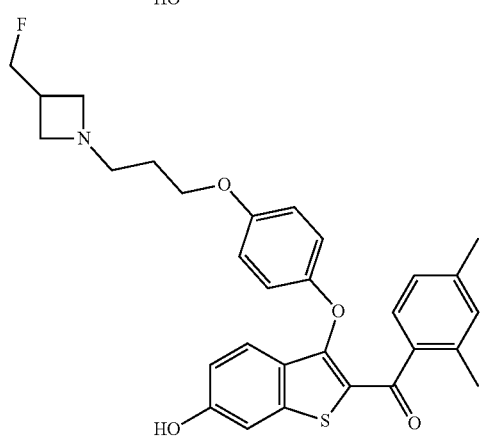
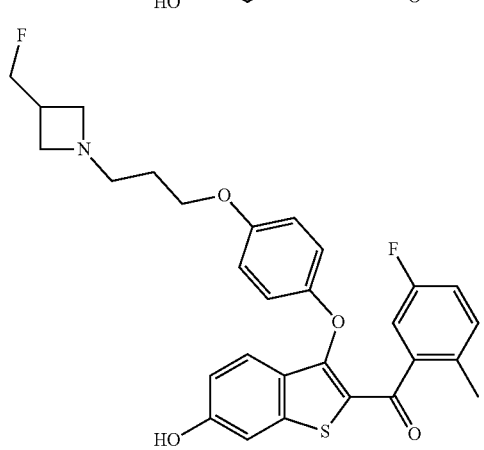
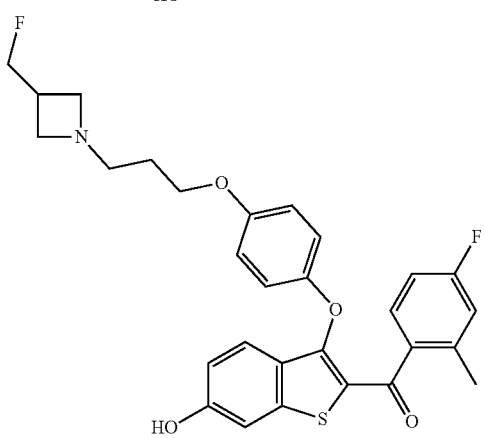
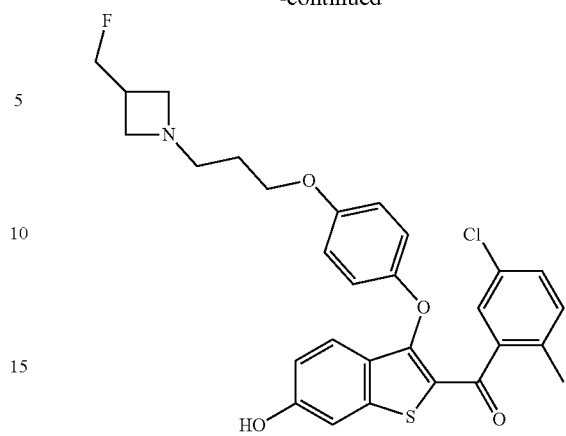
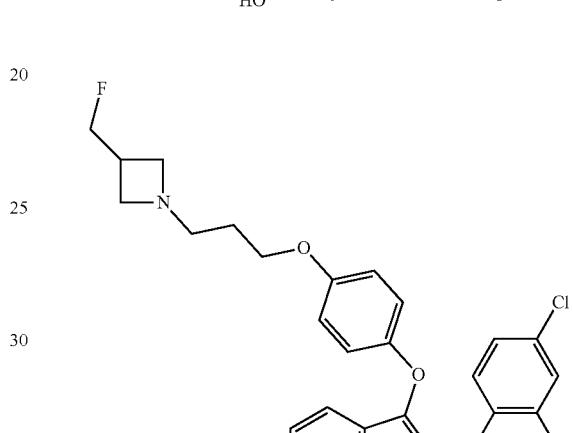
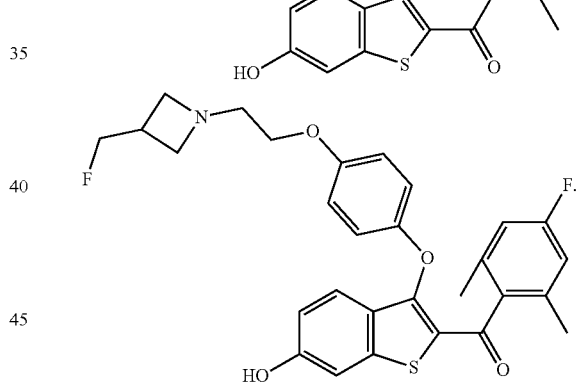
Non-limiting examples of compounds of Formula III include:
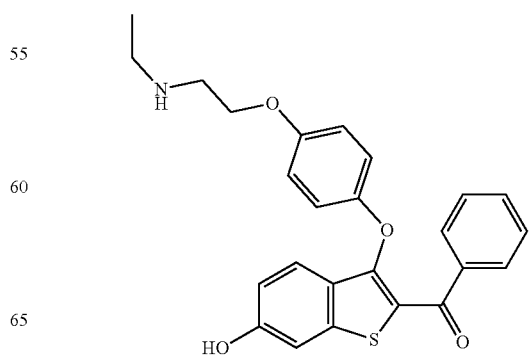

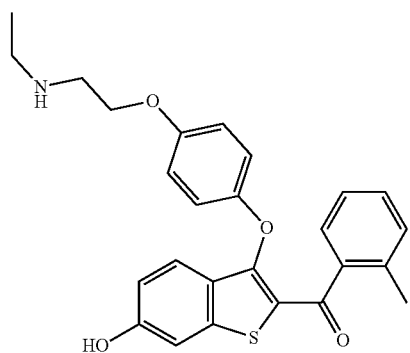
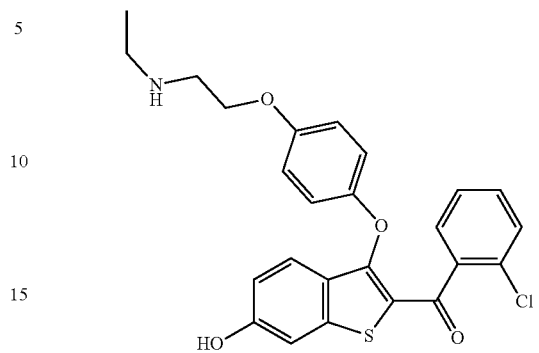
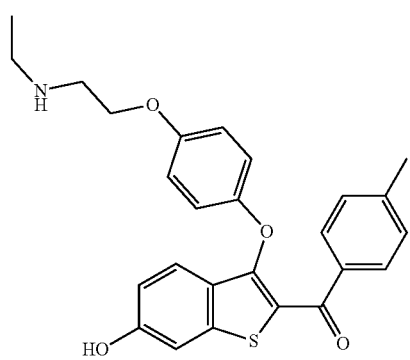
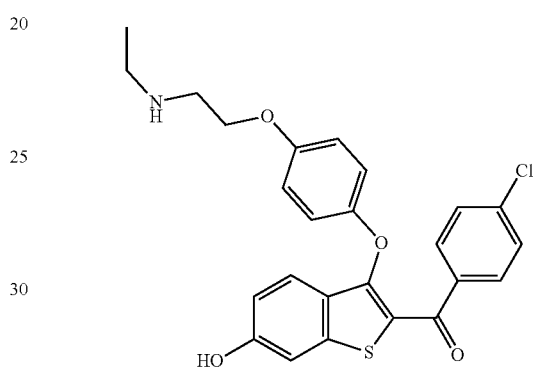
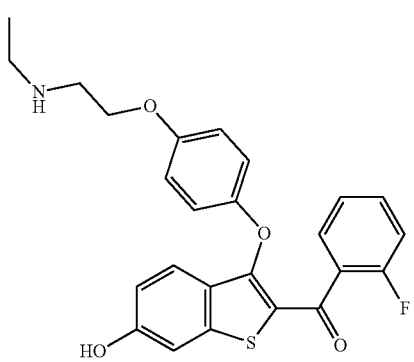
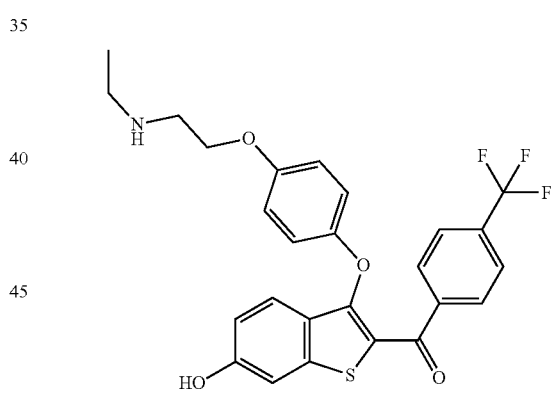
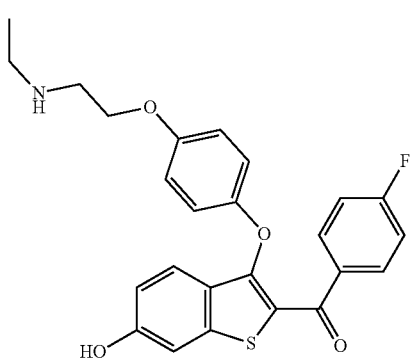
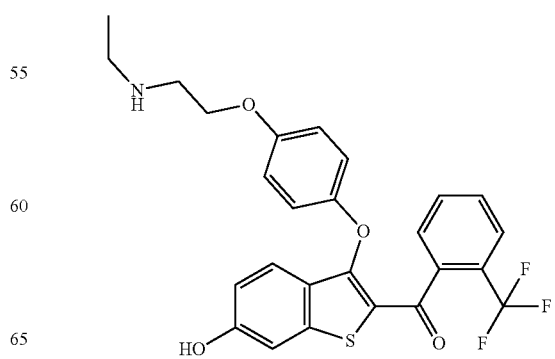

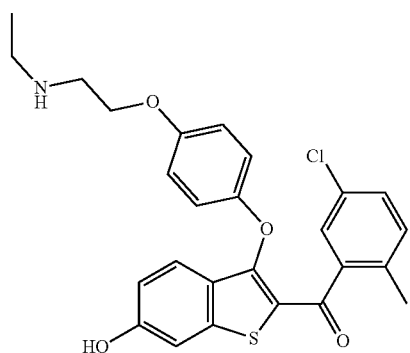
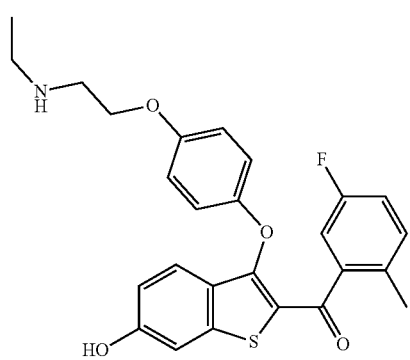
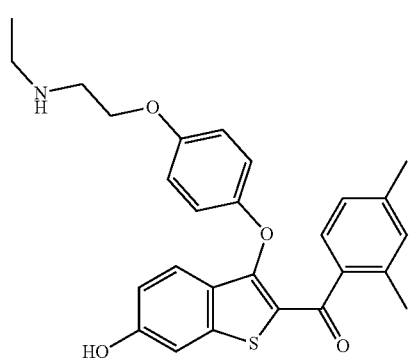
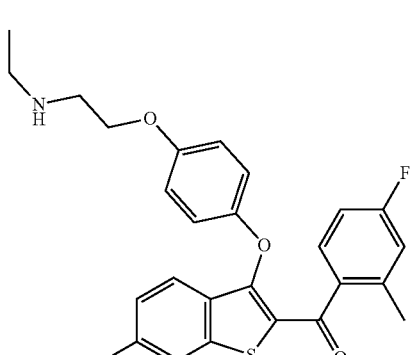
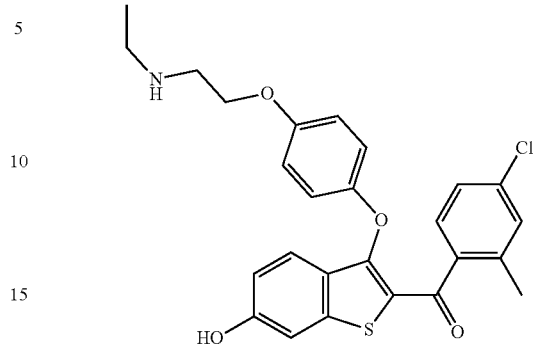
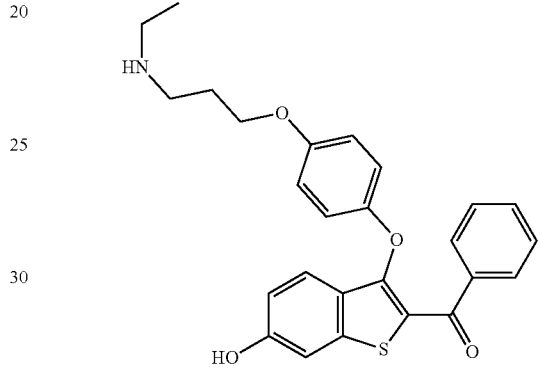
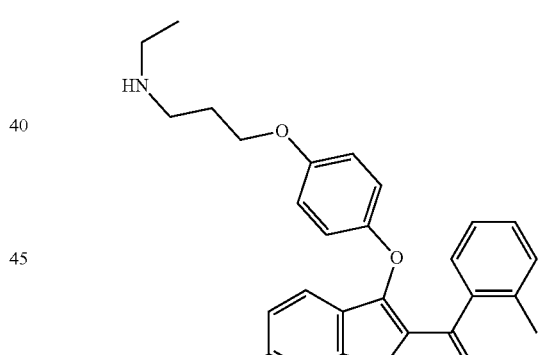
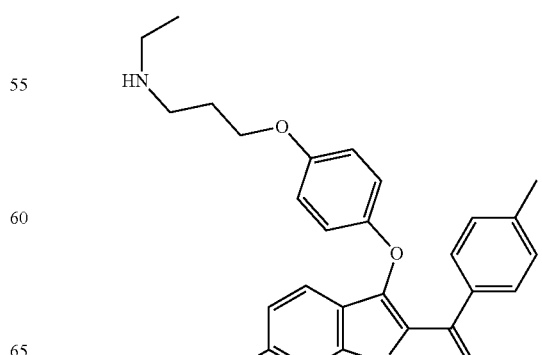

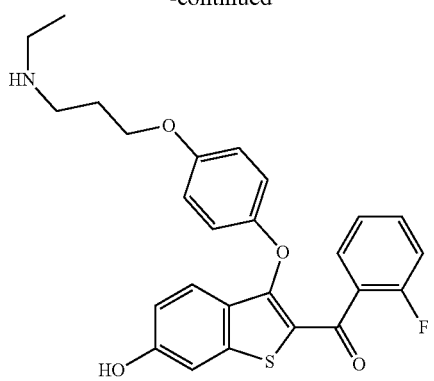
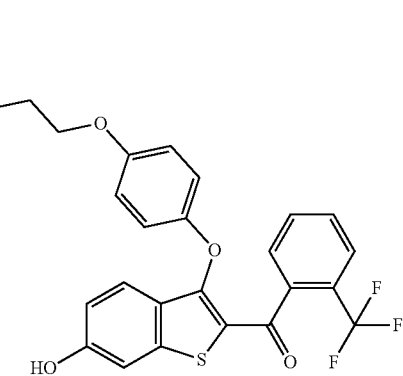
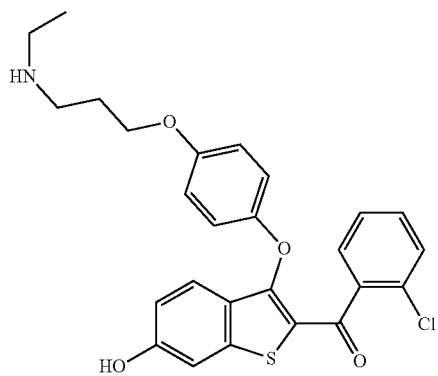
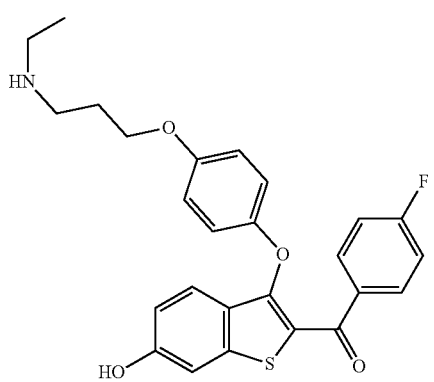
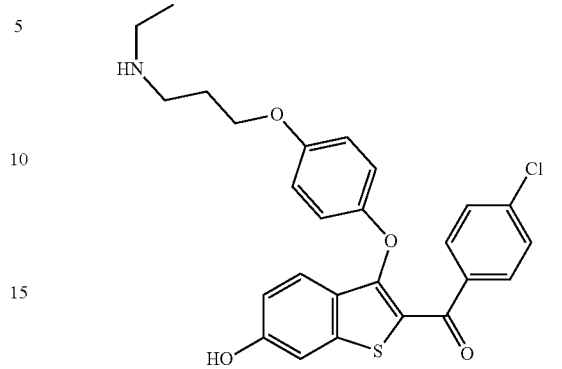
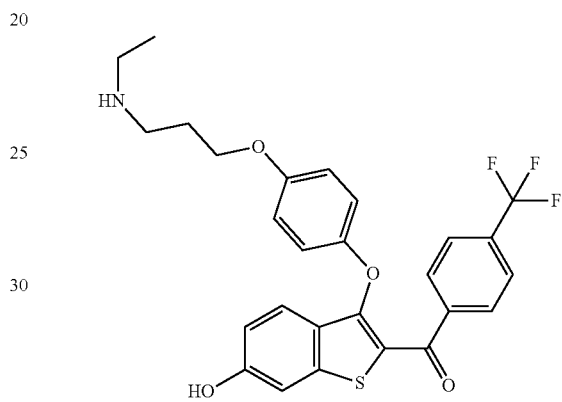
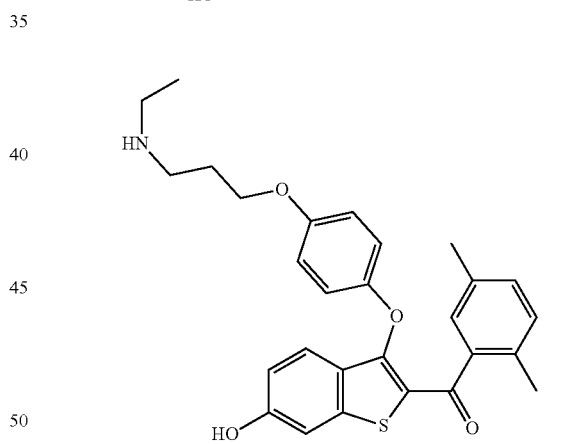
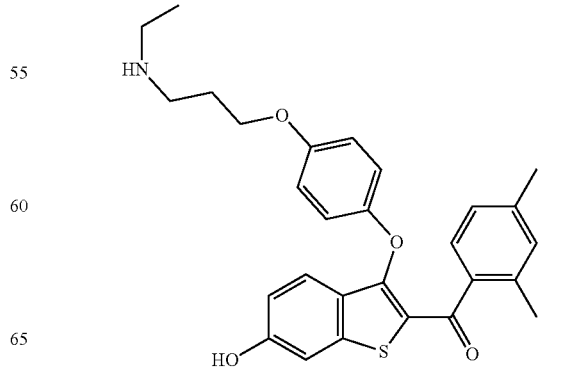

187
-continued
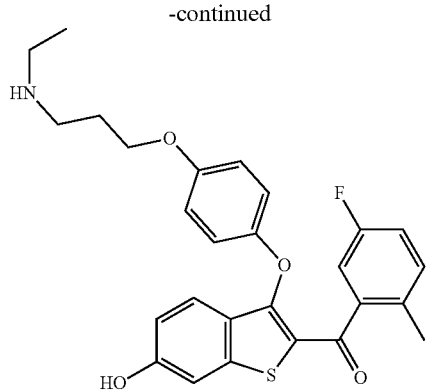
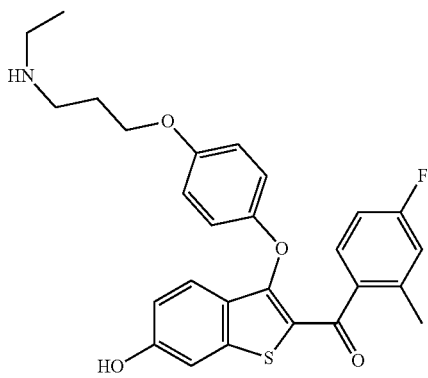
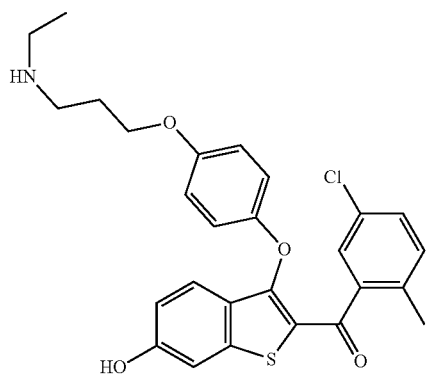
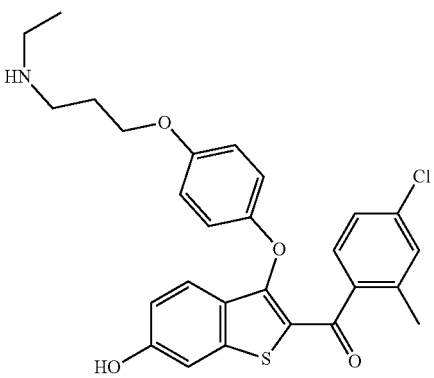
188
-continued
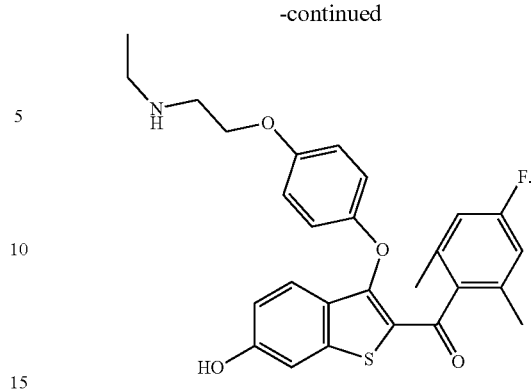
Non-limiting examples of compounds of Formula III include:
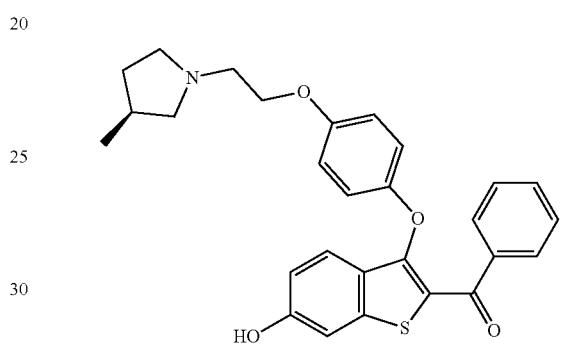
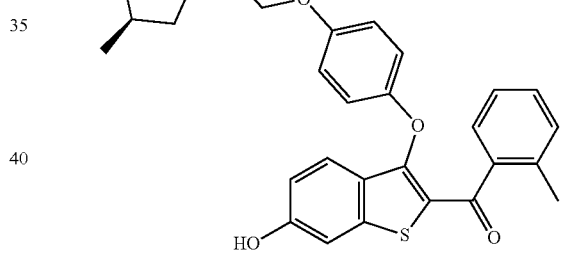
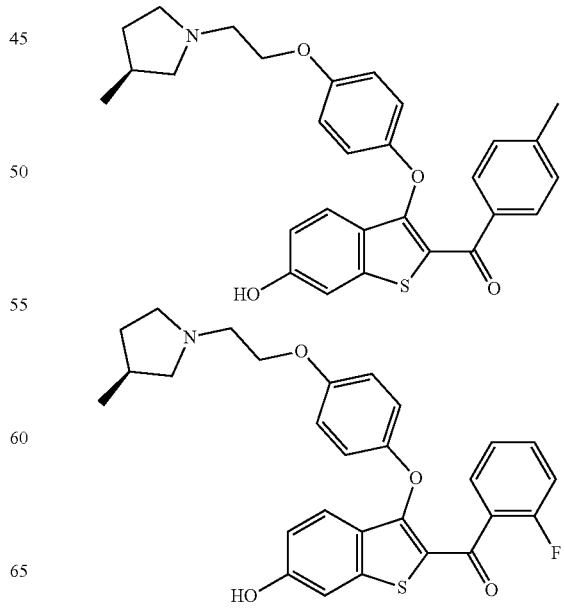

189
-continued
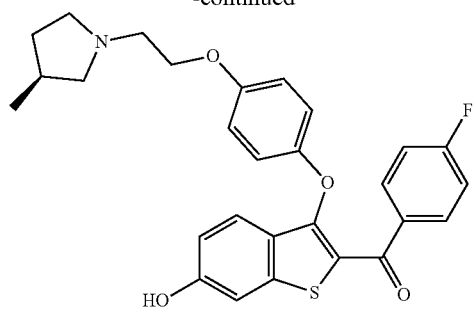
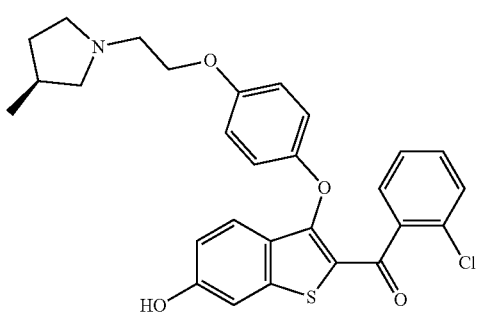
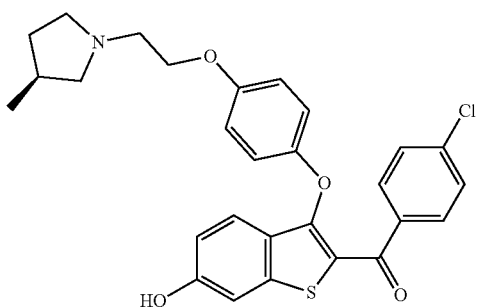
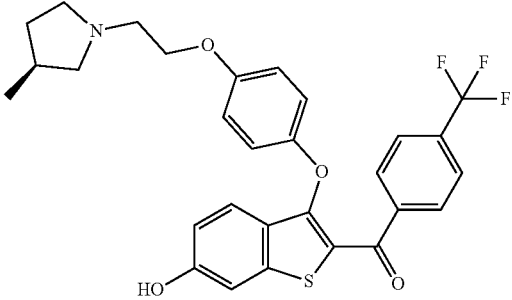
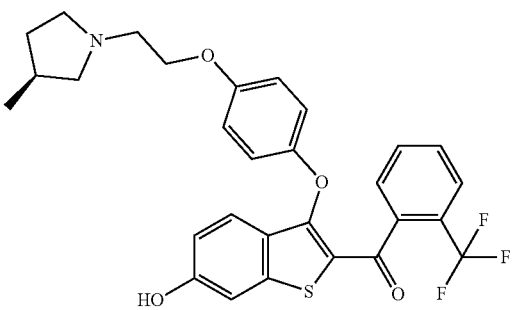
190
-continued
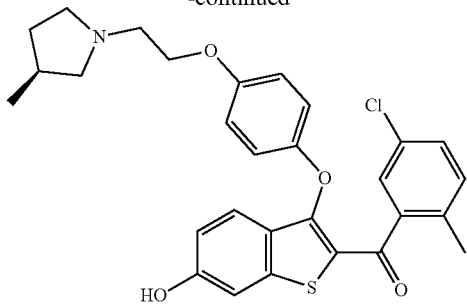
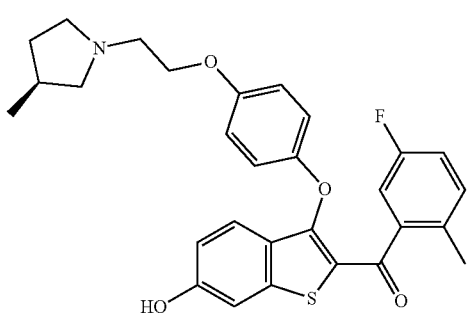
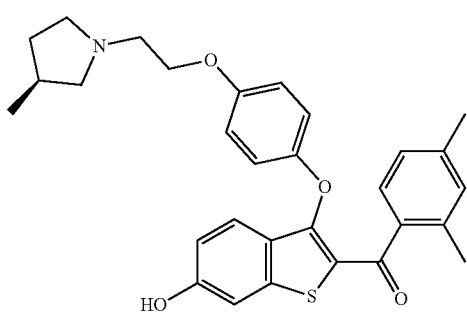
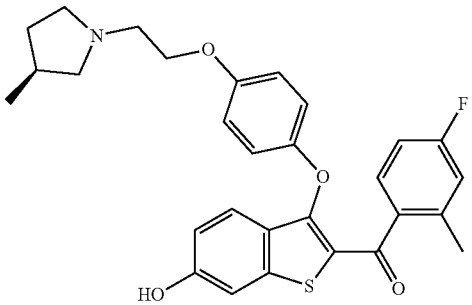
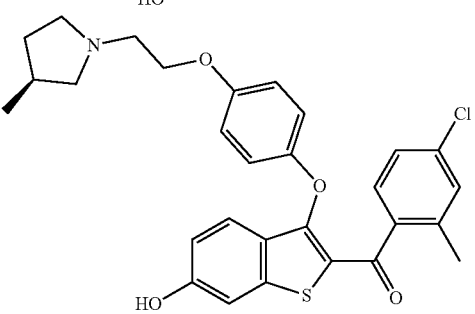

191
-continued
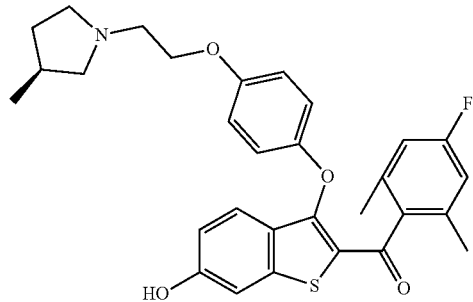
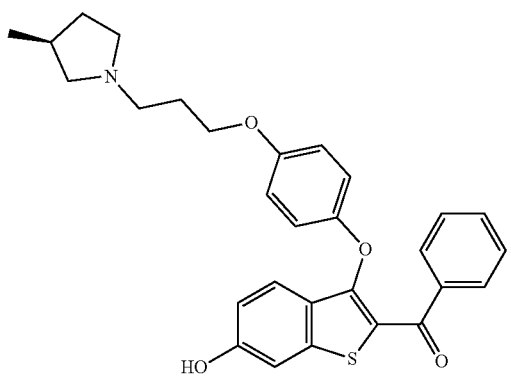
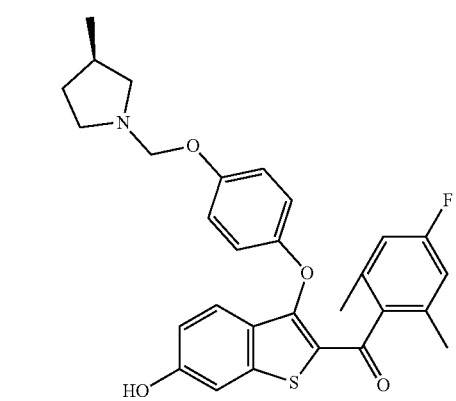
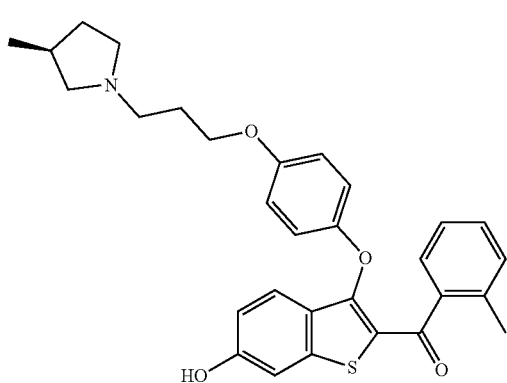
192
-continued
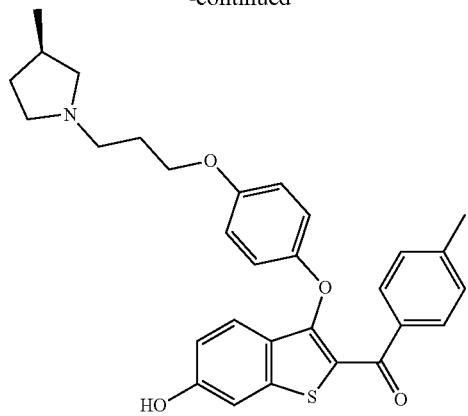
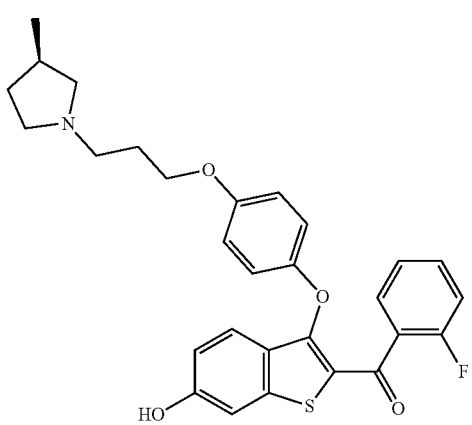
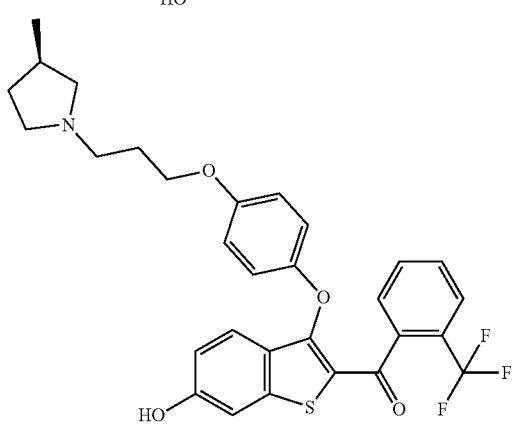
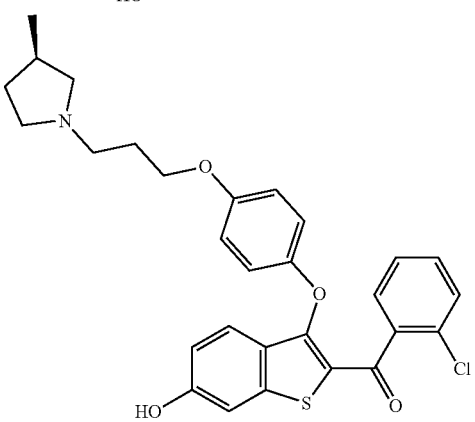

193
-continued
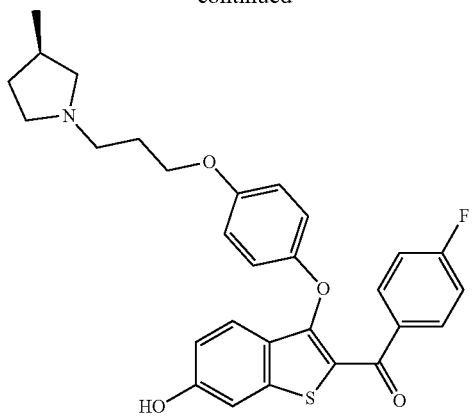
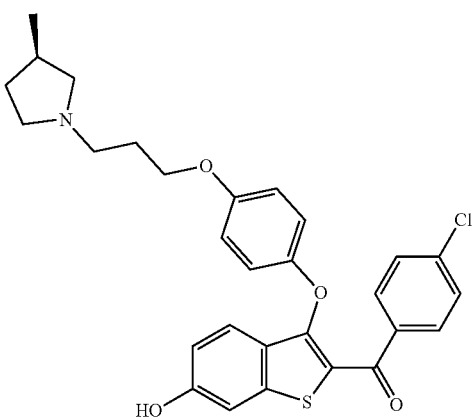
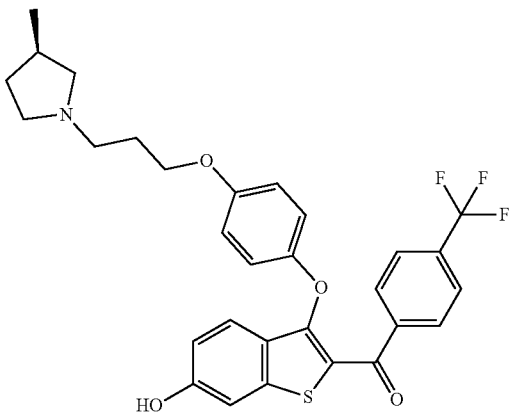
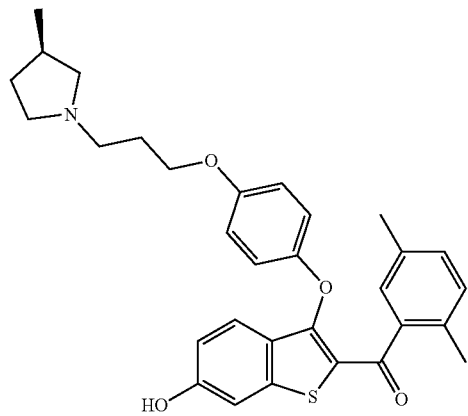
194
-continued
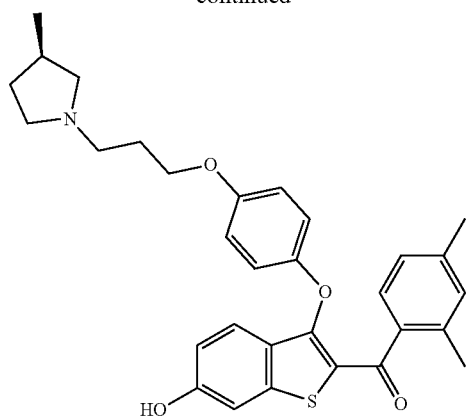
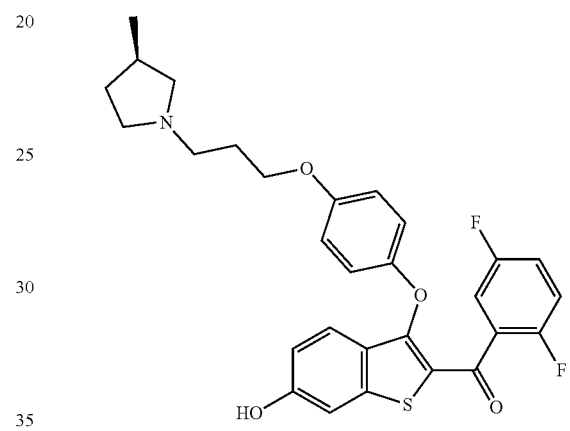
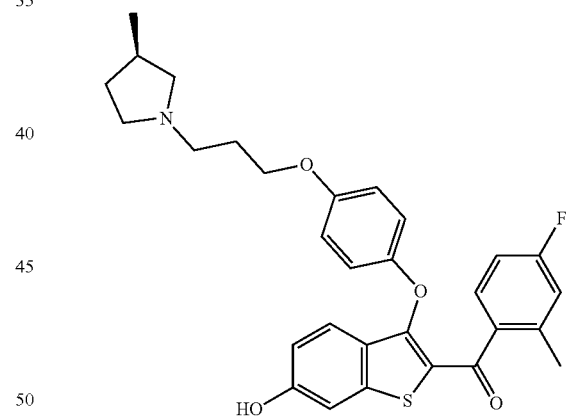
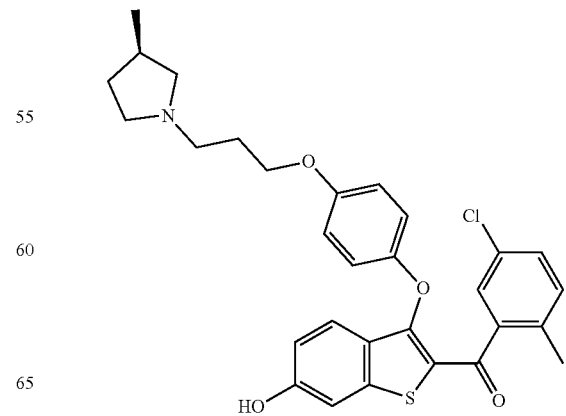

-continued

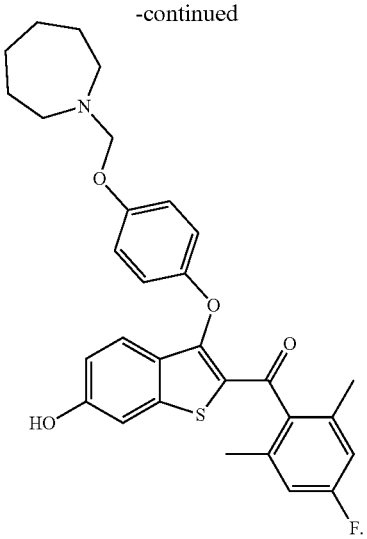

Pharmaceutical Compositions and Dosage Forms

In some aspects, this invention is a pharmaceutical composition comprising a therapeutically effective amount of a compound of Formula I, II, III, or IV as described herein, and one or more pharmaceutically acceptable diluents, preservatives, solubilizers, emulsifiers, adjuvants, excipients, or carriers. Such excipients include liquids such as water, saline, glycerol, polyethylene glycol, hyaluronic acid, ethanol, and the like.

The term "pharmaceutically acceptable carrier" refers to a diluent, adjuvant, excipient or carrier with which a compound of the disclosure is administered. The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. An appropriate "effective" amount in any individual case can be determined by one of ordinary skill in the art using routine experimentation. "Pharmaceutically acceptable carriers" for therapeutic use are well known in the pharmaceutical art, and are described, for example, in Remington's Pharmaceutical Sciences, 18th Edition (Easton, Pa.: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. Id. at 1449. In addition, antioxidants and suspending agents can be used. Id.

Suitable excipients for non-liquid formulations are also known to those of skill in the art. A thorough discussion of pharmaceutically acceptable excipients and salts is available in Remington's Pharmaceutical Sciences, 18th Edition (Easton, Pa.: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

In general, the compositions of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

Thus, the compositions of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a acceptably nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as an continuous infusion system. A formulation provided by the disclosure can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art. The compounds of the disclosure can also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compositions of the disclosure can be formulated for aerosol administration, particularly to the respiratory tract and including intranasal administration. The compound may, for example generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve. Alternatively the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. the effective amount for a given situation can be determined by routine experimentation. For purposes of the disclosure, a therapeutic amount may for example be in the range of about 0.01 mg/kg to about 250 mg/kg body weight, more preferably about 0.1 mg/kg to about 10 mg/kg, in at least one dose. In larger mammals the indicated daily dosage can be from about 1 mg to 300 mg, one or more times per day, more preferably in the range of about 10 mg to 200 mg. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

The therapeutically effective dosage of any active compound described herein will be determined by the health care practitioner depending on the condition, size and age of the patient as well as the route of delivery. In one non-limited embodiment, a dosage from about 0.1 to about 200 mg/kg has therapeutic efficacy, with all weights being calculated based upon the weight of the active compound, including the cases where a salt is employed. In some embodiments, the dosage may be the amount of compound needed to provide a serum concentration of the active compound of up to about 10 nM, 50 nM, 100 nM, 200 nM, 300 nM, 400 nM, 500 nM, 600 nM, 700 nM, 800 nM, 900 nM, 1 µM, 5 µM, 10 µM, 20 µM, 30 µM, or 40 µM.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples of dosage forms with at least 5, 10, 15, 20, 25, 50, 100, 200, 250, 300, 400, 500, 600, 700, 750, 800, 850, 900, 950 or 1000 mg of active compound, or its salt. The pharmaceutical composition may also include a molar ratio of the active compound and an additional active agent, in a ratio that achieves the desired results.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Methods of Treatment

The compounds and compositions of the invention may be used in methods for treatment or prevention of estrogen-related medical disorders, for example, cancer. The cancer may be a breast cancer, a uterine cancer, an ovarian cancer, a prostate cancer, and a lung cancer. Particularly, the breast cancer may be a tamoxifen resistant breast cancer or a triple negative breast cancer.

In one embodiment "cancer" refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

In one embodiment, the cancer or tumor is estrogen-mediated. In an alternative embodiment, the cancer or tumor is not estrogen-mediated. In variable embodiments, the cancer or tumor is not hormone-mediated. Non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, Wilms tumor.

The method of treatment may prevent or reduce the risk of cancer. The method of treatment may cause partial or complete regression of cancer in a subject.

The method of treatment may cause partial or complete regression of a tamoxifen resistant cancer or tumor. The method of treatment may cause partial or complete regression of a triple negative breast cancer.

In some embodiments, compounds disclosed herein are used to treat or prevent cancer or a tumor in a mammal, such as a human. In some embodiments, the cancer is breast cancer, ovarian cancer, endometrial cancer, prostate cancer, or uterine cancer. In some embodiments, the cancer is breast cancer, lung cancer, ovarian cancer, endometrial cancer, prostate cancer, or uterine cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, the cancer is a hormone-sensitive cancer or a hormone receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors.

In some embodiments, compounds disclosed herein are used to treat hormone receptor positive metastatic breast cancer in a postmenopausal woman with disease progression following anti-estrogen therapy.

In some embodiments, compounds disclosed herein are used to treat a hormonal dependent benign or malignant disease of the breast or reproductive tract in a mammal. In some embodiments, the benign or malignant disease is breast cancer.

In one embodiment a compound of the present invention is used for hormone therapy.

The foregoing may be better understood by reference to the following Examples, which are presented for purposes of illustration and are not intended to limit the scope of the invention.

In one aspect, a compound of the present invention or its pharmaceutically acceptable salt or prodrug, can be used to treat a hormone-related cancer or tumor that has metastasized to the brain, bone or other organ. In one embodiment of this aspect, the hormone-related cancer is estrogen mediated. In another embodiment, the estrogen mediated cancer is selected from breast, uterine, ovarian and endometrial. In other embodiments, a compound of the present invention or its pharmaceutically acceptable salt or prodrug, can be used to prevent a hormone-related cancer or tumor from metastasizing to the brain, bone or other organ, including a hormone-related cancer that is estrogen mediated, for example, breast, uterine, ovarian or endometrial.

Combination Therapy

In one aspect, a compound of Formula I, Formula II, Formula III, or Formula IV of the present invention is administered in combination with a compound of Formula V in a single fixed dosage form once, twice, or three times a day, which may have the benefit of treatment compliance. In another embodiment, the drugs are formulated together into two or more fixed dosage forms, which are taken simultaneously or over the course of the day, for example once, twice, or three times a day, as prescribed by a healthcare provider. In yet another embodiment, the drugs are provided in separate pills and are administered approximately simultaneously or at varying times throughout the day. When the drugs are provided in separate dosage forms, in one embodiment they are administered in a manner that an effective amount of both of the drugs ($C_{trough}$) is present simultaneously in the body.

In one aspect, a method for the treatment of a disorder of abnormal cellular proliferation in a host such as a human is provided that includes administering an effective amount of a combination of one or more of the active compounds described herein in combination or alternation with another active compound.

In one aspect of this embodiment, the additional active compound is an immune modulator, including but not limited to a checkpoint inhibitor. A checkpoint inhibitor for use in the methods described herein include, but are not limited to a PD-1 inhibitor, PD-L1 inhibitor, PD-L2 inhibitor, CTLA-4 inhibitor, LAG-3 inhibitor, TIM-3 inhibitor, and V-domain Ig suppressor of T-cell activation (VISTA) inhibitor, or combination thereof.

In one embodiment, the checkpoint inhibitor is a PD-1 inhibitor that blocks the interaction of PD-1 and PD-L1 by binding to the PD-1 receptor, and in turn inhibits immune suppression. In one embodiment, the checkpoint inhibitor is a PD-1 checkpoint inhibitor selected from nivolumab, pembrolizumab, pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.).

In one embodiment, the checkpoint inhibitor is a PD-L1 inhibitor that blocks the interaction of PD-1 and PD-L1 by binding to the PD-L1 receptor, and in turn inhibits immune suppression. PD-L1 inhibitors include, but are not limited to, avelumab, atezolizumab, durvalumab, KN035, and BMS-936559 (Bristol-Myers Squibb).

In one aspect of this embodiment, the checkpoint inhibitor is a CTLA-4 checkpoint inhibitor that binds to CTLA-4 and inhibits immune suppression. CTLA-4 inhibitors include, but are not limited to, ipilimumab, tremelimumab (AstraZeneca and MedImmune), AGEN1884 and AGEN2041 (Agenus).

In another embodiment, the checkpoint inhibitor is a LAG-3 checkpoint inhibitor. Examples of LAG-3 checkpoint inhibitors include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). In yet another aspect of this embodiment, the checkpoint inhibitor is a TIM-3 checkpoint inhibitor. A specific TIM-3 inhibitor includes, but is not limited to, TSR-022 (Tesaro).

In yet another embodiment, one of the active compounds described herein is administered in an effective amount for the treatment of abnormal tissue of the female reproductive system such as breast, ovarian, kidney, endometrial, or uterine cancer, in combination or alternation with an effective amount of an estrogen inhibitor including but not limited to a SERM (selective estrogen receptor modulator), a SERD (selective estrogen receptor downregulator), a complete estrogen receptor downregulator, or another form of partial or complete estrogen antagonist. Partial anti-estrogens like raloxifene and tamoxifen retain some estrogen-like effects, including an estrogen-like stimulation of uterine growth, and also, in some cases, an estrogen-like action during breast cancer progression which stimulates tumor growth. In contrast, fulvestrant, a complete anti-estrogen, is free of estrogen-like action on the uterus and is effective in tamoxifen-resistant tumors. Non-limiting examples of anti-estrogen compounds are provided in WO 2014/19176 assigned to AstraZeneca. Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone.

In another embodiment, one of the active compounds described herein is administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor downregulator and/or degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one aspect, a treatment regimen is provided comprising the administration of a compound of the present invention in combination with at least one additional chemotherapeutic agent. The combinations disclosed herein can be administered for beneficial, additive, or synergistic effect in the treatment of abnormal cellular proliferative disorders.

In specific embodiments, the treatment regimen includes the administration of a compound of the present invention in combination with at least one kinase inhibitor. In one embodiment, the at least one kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

PI3k inhibitors that may be used in the present invention are well known. Examples of PI3 kinase inhibitors include but are not limited to Wortmannin, demethoxyviridin, perifosine, idelalisib, pictilisib, Palomid 529, ZSTK474, PWT33597, CUDC-907, and AEZS-136, duvelisib, GS-9820, GDC-0032 (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)- furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl) thieno[3,2-d]pyrimidine), GDC-0980 ((S)-1-(4-((2-(2-aminopyrimidin-5-yl)-7-methyl-4-morpholinothieno[3,2-d] pyrimidin-6 yl)methyl)piperazin-1-yl)-2-hydroxypropan-1-one (also known as RG7422)), SF 1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10, 13,16-tetraazaoctadecan-18-oate), PF-05212384 (N-[4-[[4-(Dimethylamino)-1-piperidinyl]carbonyl]phenyl]-N-[4-(4, 6-di-4-morpholinyl-1,3,5-triazin-2-yl)phenyl]urea), LY3023414, BEZ23 5 (2-Methyl-2-{4-[3-methyl-2-oxo-8-(quinolin-3-yl)-2,3-dihydro-1H-imidazo[4,5-c]quinolin-1-yl]phenyl}propanenitrile), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl) amino]methylidene]-5-hydroxy-9-(methoxymethyl)-9a, 11a-dimethyl-1,4,7-trioxo-2,3,3a,9,10,11-hexahydroindeno [4,5h]isochromen-10-yl] acetate (also known as sonolisib)).

In one embodiment, the compound of the present invention is combined in a single dosage form with the PIk3 inhibitor.

BTK inhibitors for use in the present invention are well known. Examples of BTK inhibitors include ibrutinib (also known as PCI-32765)(Imbmvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl) phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo [h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, *Journal of Hematology & Oncology*, 2013, 6:59, the entirety of which is incorporated herein by reference. In one embodiment, the compound of the present invention is combined in a single dosage form with the BTK inhibitor.

Syk inhibitors for use in the present invention are well known, and include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a] pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl) amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), R09021 (6-[(1R, 2S)-2-Amino-cyclohexylamino]-4-(5,6-dimethyl-pyridin-2-ylamino)-pyridazine-3-carboxylic acid amide), imatinib (Gleevec; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R, 2S)-2-aminocyclohexyl)amino)-4-(m-tolylamino) pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl) bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4] oxazin-3(4H)-one), YM 193306 (see Singh et al. Discovery and Development of Spleen Tyrosine Kinase (SYK) Inhibitors, *J. Med. Chem.* 2012, 55, 3614-3643), 7-azaindole, piceatannol, ER-27319 (see Singh et al. Discovery and Development of Spleen Tyrosine Kinase (SYK) Inhibitors, *J. Med. Chem.* 2012, 55, 3614-3643 incorporated in its entirety herein), Compound D (see Singh et al. Discovery and Development of Spleen Tyrosine Kinase (SYK) Inhibitors, *J. Med. Chem.* 2012, 55, 3614-3643 incorporated in its entirety herein), PRT060318 (see Singh et al. Discovery and Development of Spleen Tyrosine Kinase (SYK) Inhibitors, *J. Med. Chem.* 2012, 55, 3614-3643 incorporated in its entirety herein), luteolin (see Singh et al. Discovery and Development of Spleen Tyrosine Kinase (SYK) Inhibitors, *J. Med. Chem.* 2012, 55, 3614-3643 incorporated in its entirety herein), apigenin (see Singh et al. Discovery and Development of Spleen Tyrosine Kinase (SYK) Inhibitors, *J. Med. Chem.* 2012, 55, 3614-3643 incorporated in its entirety herein), quercetin (see Singh et al. Discovery and Development of Spleen Tyrosine Kinase (SYK) Inhibitors, *J. Med. Chem.* 2012, 55, 3614-3643 incorporated in its entirety herein), fisetin (see Singh et al. Discovery and Development of Spleen Tyrosine Kinase (SYK) Inhibitors, *J. Med. Chem.* 2012, 55, 3614-3643 incorporated in its entirety herein), myricetin (see Singh et al. Discovery and Development of Spleen Tyrosine Kinase (SYK) Inhibitors, *J. Med. Chem.* 2012, 55, 3614-3643 incorporated in its entirety herein), morin (see Singh et al. Discovery and Development of Spleen Tyrosine Kinase (SYK) Inhibitors, *J. Med. Chem.* 2012, 55, 3614-3643 incorporated in its entirety herein). In one embodiment, the compound of the present invention is combined in a single dosage form with the Syk inhibitor.

In one embodiment, the at least one additional chemotherapeutic agent is a B-cell lymphoma 2 (Bcl-2) protein inhibitor. BCL-2 inhibitors are known in the art, and include, for example, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenyl sulfanylbutan-2-yl]amino]-3-nitrophenyl] sulfonylbenzamide), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), or G3139 (Oblimersen). In one embodiment, the compound of the present invention is combined in a single dosage form with the at least one BCL-2 inhibitor.

The compound of the present invention or its pharmaceutically active salt can be combined with an immunotherapy. As discussed in more detail below, the compound of the present invention can be conjugated to an antibody, radioactive agent, or other targeting agent that directs the compound to the diseased or abnormally proliferating cell.

In one embodiment, the additional therapy is a monoclonal antibody (MAb). Some MAbs stimulate an immune response that destroys cancer cells. Similar to the antibodies produced naturally by B cells, these MAbs "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs, which bind to cell surface growth factor receptors, prevent the targeted receptors from sending their normal growth-promoting signals. They may also trigger apoptosis and activate the immune system to destroy tumor cells.

In some embodiments, the combination can be administered to the subject in further combination with other chemotherapeutic agents. If convenient, the combination described herein can be administered at the same time as another chemotherapeutic agent in order to simplify the treatment regimen. In some embodiments, the combination and the other chemotherapeutic can be provided in a single formulation. In one embodiment, the use of the compounds described herein is combined in a therapeutic regime with other agents. Such agents may include, but are not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof), BCL-2 inhibitors, apoptotic compounds, AKT inhibitors, including but not limited to, MK-2206, GSK690693, Perifosine, (KRX-0401), GDC-0068, Triciribine, AZD5363, Honokiol, PF-04691502, and Miltefosine, PD-1 inhibitors including but not limited to, Nivolumab, CT-011, MK-3475, BMS936558, and AMP-514 or FLT-3 inhibitors, including but not limited to, P406, Dovitinib, Quizartinib (AC220), Amuvatinib (MP-470), Tandutinib (MLN518), ENMD-2076, and KW-2449, or combinations thereof. Examples of mTOR inhibitors include but are not limited to rapamycin and its analogs, everolimus (Afinitor), temsirolimus, ridaforolimus (Deforolimus), and sirolimus. Examples of MEK inhibitors include but are not limited to trametinib/GSK1120212 (N-(3-{3-cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-dihydroxypropoxy]-3,4-difluoro-2-[(2-fluoro-4-iodophenyl)amino]-benzamide), TAK733 ((R)-3-(2,3-dihydroxypropyl)-6-fluoro-5-(2-fluoro-4-iodophenylamino)-8-methylpyrido[2,3d]pyrimidine-4,7 (3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide). Examples of RAS inhibitors include but are not limited to Reolysin and siGl2D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol. In a particular embodiment, a compound described herein is administered in combination with letrozole and/or tamoxifen. Other chemotherapeutic agents that can be used in combination with the compounds described herein include, but are not limited to, chemotherapeutic agents that do not require cell cycle activity for their anti-neoplastic effect.

In one embodiment, a compound of the present invention described herein can be combined with a chemotherapeutic selected from, but are not limited to, Imatinib mesylate (Gleevec®), Dasatinib (Sprycel®), Nilotinib (Tasigna®), Bosutinib (Bosulif®), Trastuzumab (Herceptin®), Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Targretin®), Alitretinoin (Panretin®), Tretinoin (Vesanoid®), Carfilzomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the additional therapeutic agent is an anti-inflammatory agent, a chemotherapeutic agent, a radiotherapeutic, additional therapeutic agents, or immunosuppressive agents.

Suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil, dacarbazine, 6-mercaptopurine, 6-thioguanine, actinomycin D, adriamycin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucovorin, calicheamicin, capecitabine, carboplatin, lomustine (CCNU), carmustine (BSNU), Chlorambucil, Cisplatin, Cladribine, Colchicine, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunorubicin HCl, daunorubicin citrate, denileukin diftitox, Dexrazoxane, Dibromomannitol, dihydroxy anthracin dione, Docetaxel, dolasetron mesylate, doxorubicin HCl, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrovorum factor, etoposide phosphate, filgrastim, floxuridine, fluconazole, fludarabine phosphate, fluorouracil, flutamide, folinic acid, gemcitabine HCl, glucocorticoids, goserelin acetate, gramicidin D, granisetron HCl, hydroxyurea, idarubicin HCl, ifosfamide, interferon α-2b, irinotecan HCl, letrozole, leucovorin calcium, leuprolide acetate, levamisole HCl, lidocaine, lomustine, maytansinoid, mechlorethamine HCl, medroxyprogesterone acetate, megestrol acetate, melphalan HCl, mercaptopurine, Mesna, methotrexate, methyltestosterone, mithramycin, mitomycin C, mitotane, mitoxantrone, nilutamide, octreotide acetate, ondansetron HCl, paclitaxel, pamidronate disodium, pentostatin, pilocarpine HCl, plicamycin, polifeprosan 20 with carmustine implant, porfimer sodium, procaine, procarbazine HCl, propranolol, sargramostim, streptozotocin, tamoxifen, taxol, teniposide, teniposide, testolactone, tetracaine, thioepa chlorambucil, thioguanine, thiotepa, topotecan HCl, toremifene citrate, trastuzumab, tretinoin, valrubicin, vinblastine sulfate, vincristine sulfate, and vinorelbine tartrate.

Additional therapeutic agents that can be administered in combination with a compound disclosed herein can include 2-methoxyestradiol or 2ME2, finasunate, vatalanib, volociximab, etaracizumab (MEDI-522), cilengitide, dovitinib, figitumumab, atacicept, rituximab, alemtuzumab, aldesleukin, atlizumab, tocilizumab, lucatumumab, dacetuzumab, HLL1, huN901-DM1, atiprimod, natalizumab, bortezomib, marizomib, tanespimycin, saquinavir mesylate, ritonavir, nelfinavir mesylate, indinavir sulfate, belinostat, panobinostat, mapatumumab, lexatumumab, dulanermin, plitidepsin, talmapimod, P276-00, enzastaurin, tipifarnib, lenalidomide, thalidomide, pomalidomide, simvastatin, and celecoxib.

In one aspect of the present invention, a compound described herein can be combined with at least one immunosuppressive agent. The immunosuppressive agent in one embodiment is selected from the group consisting of a calcineurin inhibitor, e.g. a cyclosporin or an ascomycin, e.g. Cyclosporin A (Neoral®), FK506 (tacrolimus), pimecrolimus, a mTOR inhibitor, e.g. rapamycin or a derivative thereof, e.g. Sirolimus (Rapamune®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CellCept®), OKT3 (Orthoclone OKT3®), Prednisone, ATGAM®, Thymoglobulin®, Brequinar Sodium, OKT4, T10B9.A-3A, 33B3.1, 15-deoxyspergualin, tresperimus, Leflunomide Arava®, anti-CD25, anti-IL2R, Basiliximab (Simulect®), Daclizumab (Zenapax®), mizoribine, methotrexate, dexamethasone, ISAtx-247, SDZ ASM 981 (pimecrolimus, Elidel®), CTLA41g, Abatacept, belatacept, LFA31g, etanercept (sold as Enbrel® by ImmuneXcite), adalimumab (Humira®), infliximab (Remicade®), an anti-LFA-1 antibody, natalizumab (Antegren®), Enlimomab, gavilimomab, Golimumab, antithymocyte immunoglobulin, siplizumab, Alefacept, efalizumab, Pentasa, mesalazine, asacol, codeine phosphate, benorylate, fenbufen, naprosyn, diclofenac, etodolac, indomethacin, aspirin, and ibuprofen.

In certain embodiments, a compound described herein is administered to the subject prior to treatment with another chemotherapeutic agent, during treatment with another chemotherapeutic agent, after administration of another chemotherapeutic agent, or a combination thereof.

Synthetic Methods

The compounds described herein can be prepared by methods known by those skilled in the art. In one non-limiting example the disclosed compounds can be prepared using the schemes.

Some of the compounds described herein can have a chiral center, and the compound can exist in isomeric or diastereomeric form. When multiple chiral variables are present on formulas of the present invention, the formula further encompasses every possible diastereomer unless indicated otherwise or clear from the text. For example (R,R), (S,R), (S,S), and (R,S) for a molecule with two chiral centers. One skilled in the art will recognize that pure enantiomers, diastereomers, and cis/trans isomers can be prepared by methods known in the art. Examples of methods to obtain optically active materials include at least the following:

i) Physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) Simultaneous crystallization—a technique whereby the individual enantiomers are separately crystallized from a solution of the racemate, possible only if the latter is a conglomerate in the solid state;

iii) Enzymatic resolutions—a technique whereby partial or complete separation of a racemate by virtue of differing rates of reaction for the enantiomers with an enzyme;

iv) Enzymatic asymmetric synthesis—a synthetic technique whereby at least one step of the synthesis uses an enzymatic reaction to obtain an enantiomerically pure or enriched synthetic precursor of the desired enantiomer;

v) Chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) Diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) First- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) Kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) Enantiospecific synthesis from non-racemic precursors—a synthetic technique whereby the desired enantiomer is obtained from non-chiral starting materials and where the stereochemical integrity is not or is only minimally compromised over the course of the synthesis;

x) Chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) Chiral gas chromatography—a technique whereby the racemate is volatilized and enantiomers are separated by virtue of their differing interactions in the gaseous mobile phase with a column containing a fixed non-racemic chiral adsorbent phase;

xii) Extraction with chiral solvents—a technique whereby the enantiomers are separated by virtue of preferential dissolution of one enantiomer into a particular chiral solvent;

xiii) Transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through;

xiv) Simulated moving bed chromatography, is used in one embodiment. A wide variety of chiral stationary phases are commercially available.

General Synthetic Route 1:

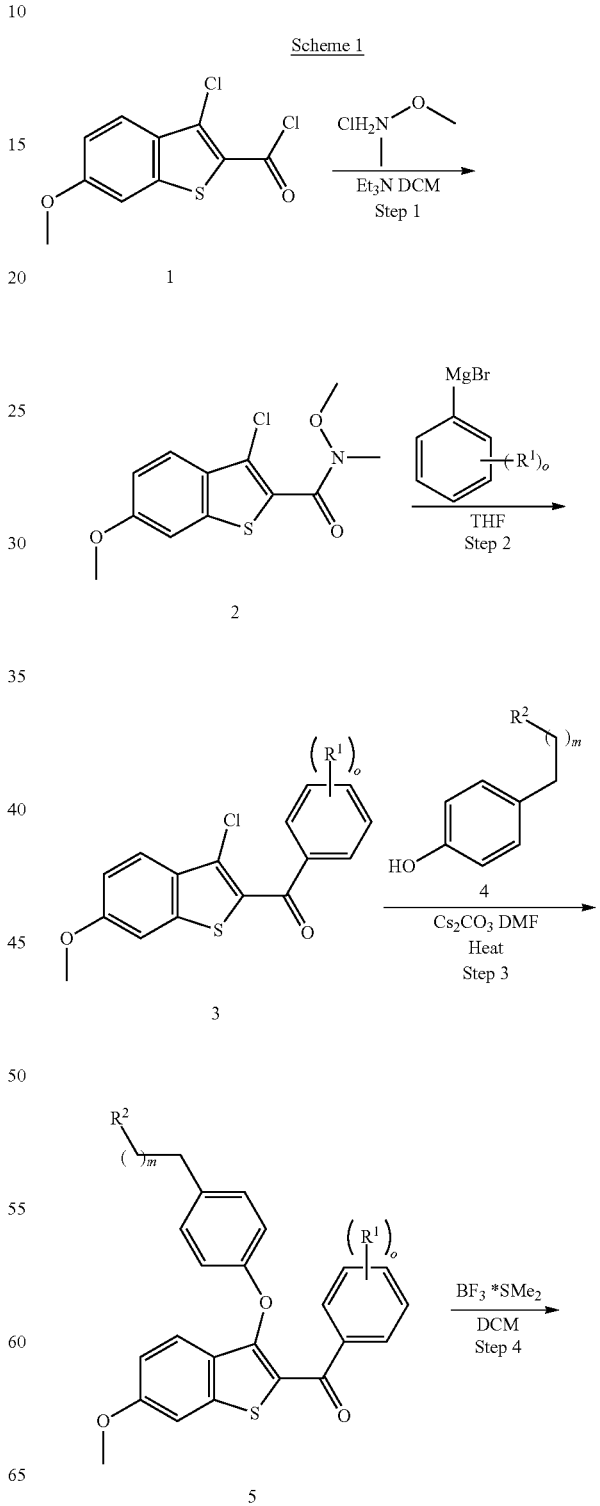

213

-continued

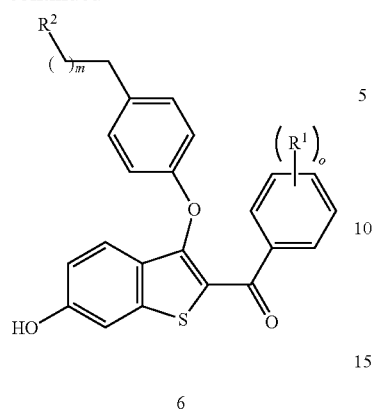

6

To a solution of commercially available 3-chloro-6-methoxybenzo[b]thiophene-2-carbonyl chloride (Compound 1) is added Weinreb's amine and base to afford Weinreb's amide 2. Weinreb's amide 2 is then subjected to the appropriate Grignard reagent to afford Compound 3. Compound 3 undergoes nucleophilic attack of intermediate 4 to afford Compound 5. Compound 5 is then demethylated to afford Compound 6.

Scheme 2

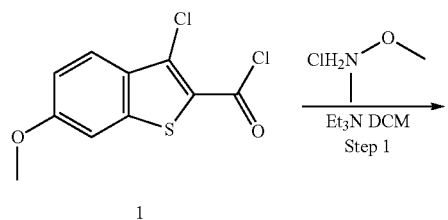

1

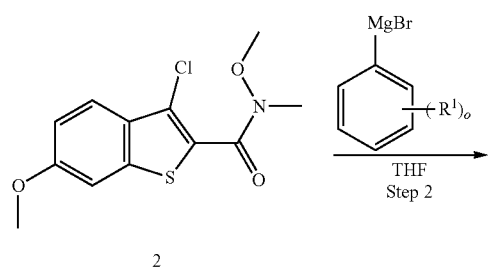

2

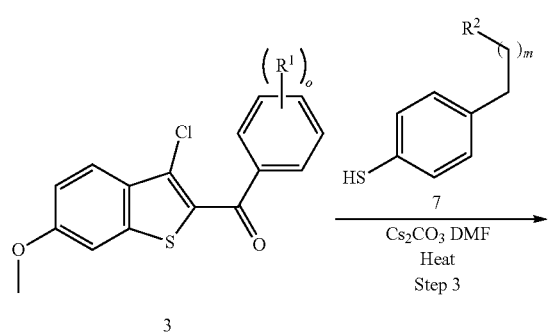

3

214

-continued

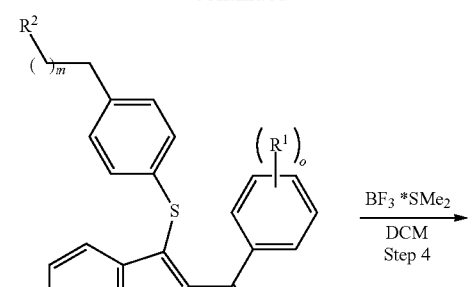

8

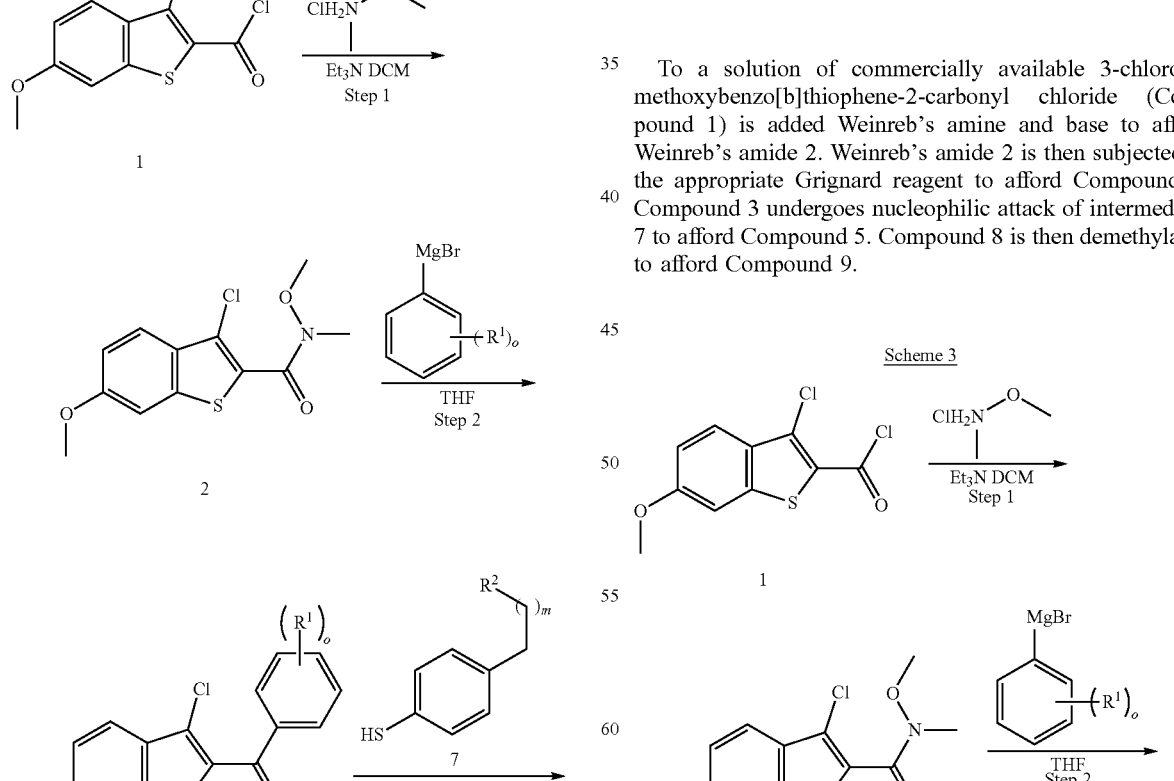

9

To a solution of commercially available 3-chloro-6-methoxybenzo[b]thiophene-2-carbonyl chloride (Compound 1) is added Weinreb's amine and base to afford Weinreb's amide 2. Weinreb's amide 2 is then subjected to the appropriate Grignard reagent to afford Compound 3. Compound 3 undergoes nucleophilic attack of intermediate 7 to afford Compound 5. Compound 8 is then demethylated to afford Compound 9.

Scheme 3

215
-continued

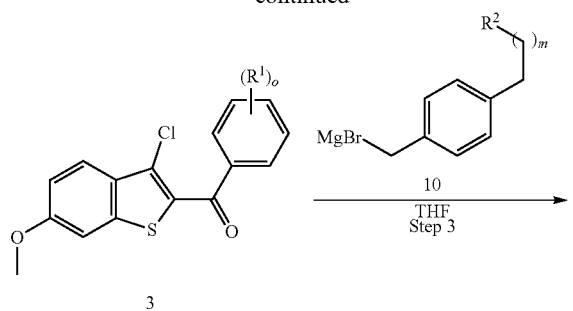

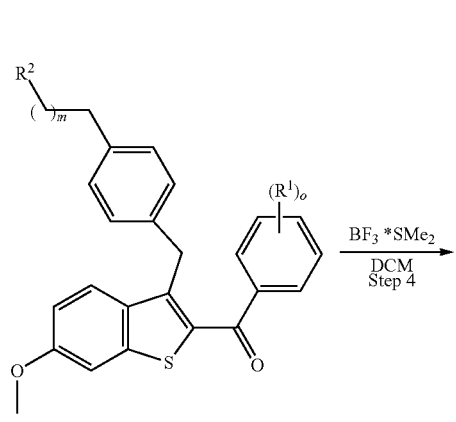

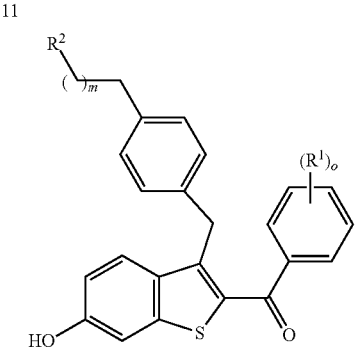

To a solution of commercially available 3-chloro-6-methoxybenzo[b]thiophene-2-carbonyl chloride (Compound 1) is added Weinreb's amine and base to afford Weinreb's amide 2. Weinreb's amide 2 is then subjected to the appropriate Grignard reagent to afford Compound 3. Compound 3 undergoes nucleophilic attack of intermediate 10 to afford Compound 11. Compound 11 is then demethylated to afford Compound 12.

Scheme 4

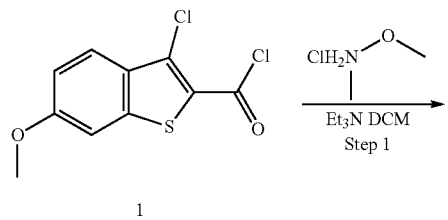

216
-continued

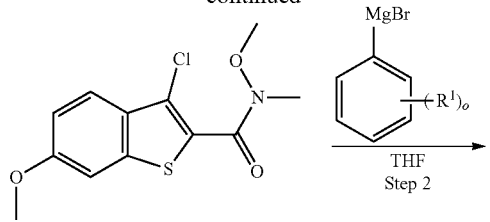

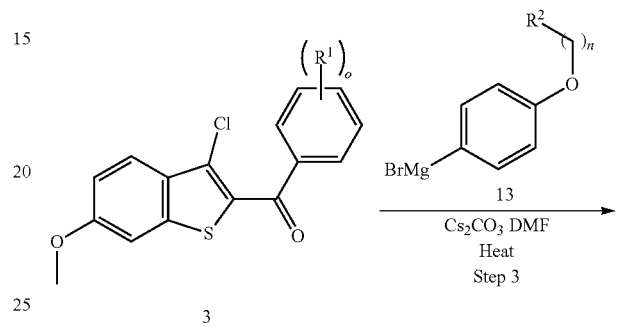

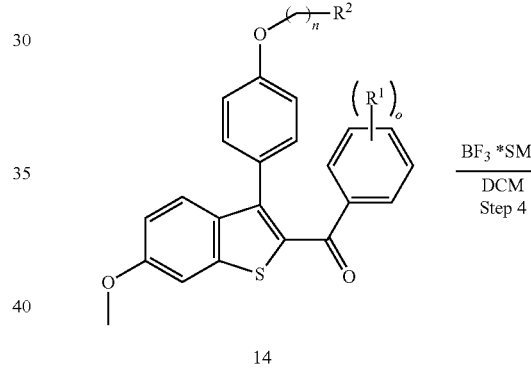

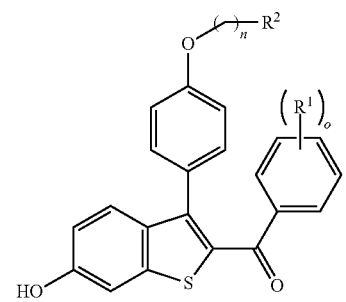

To a solution of commercially available 3-chloro-6-methoxybenzo[b]thiophene-2-carbonyl chloride (Compound 1) is added Weinreb's amine and base to afford Weinreb's amide 2. Weinreb's amide 2 is then subjected to the appropriate Grignard reagent to afford Compound 3. Compound 3 undergoes nucleophilic attack of intermediate 13 to afford Compound 14. Compound 14 is then demethylated to afford Compound 15.

Scheme 5

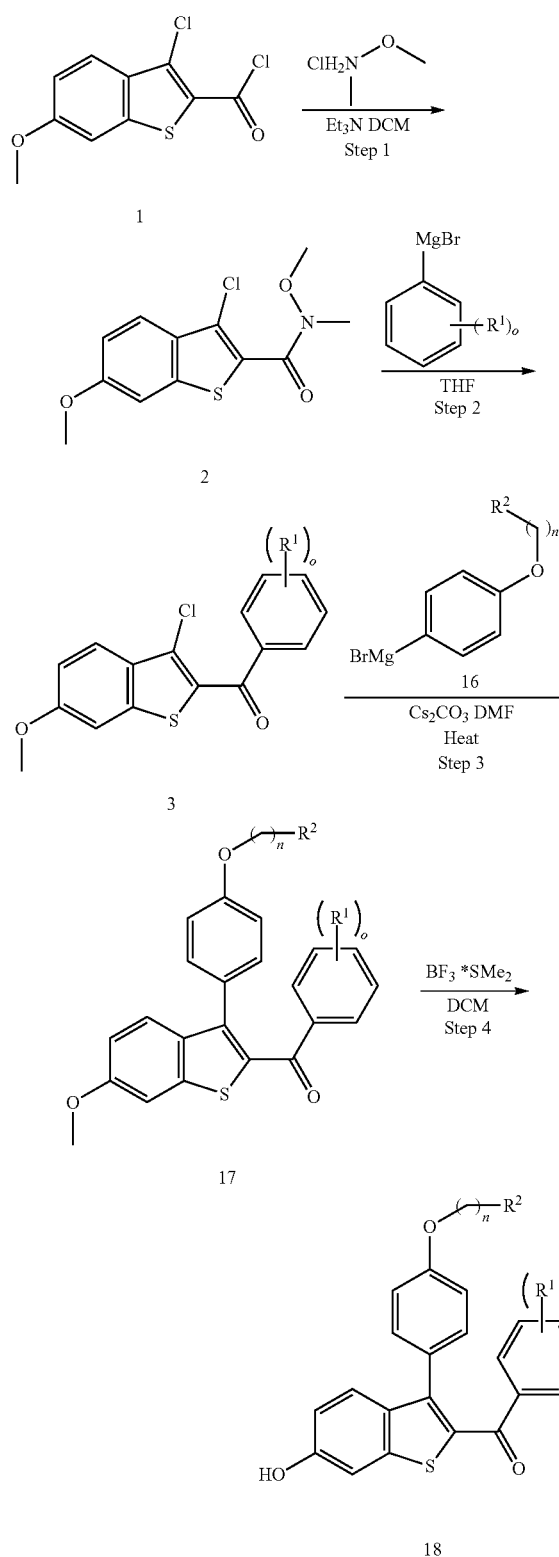

the appropriate Grignard reagent to afford Compound 3. Compound 3 undergoes nucleophilic attack of intermediate 16 to afford Compound 17. Compound 17 is then demethylated to afford Compound 18.

Scheme 6

To a solution of commercially available 3-chloro-6-methoxybenzo[b]thiophene-2-carbonyl chloride (Compound 1) is added Weinreb's amine and base to afford Weinreb's amide 2. Weinreb's amide 2 is then subjected to To a solution of commercially available 3-chloro-6-methoxybenzo[b]thiophene-2-carbonyl chloride (Compound 1) is added Weinreb's amine and base to afford Weinreb's amide 2. Weinreb's amide 2 is then subjected to the appropriate Grignard reagent to afford Compound 3. Compound 3 undergoes nucleophilic attack of intermediate 19 to afford Compound 20. Compound 20 is then demethylated to afford Compound 21

Scheme 7

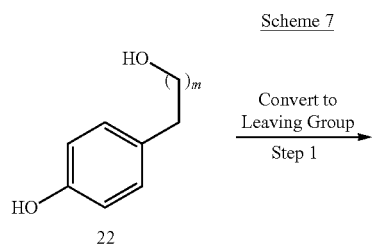

In Step 1 the primary alcohol of commercially available Compound 22 is converted to Compound 23 by methods known in the art. In Step 2 Compound 23 is subjected to nucleophilic attack by a $R^2$ group to afford Intermediate 4 which is used in Scheme 1.

Scheme 8

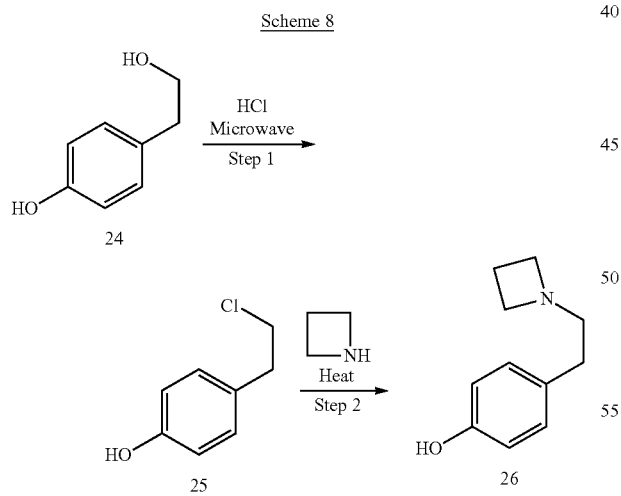

Scheme 8 is a non-limiting example of the method described in Scheme 7. In Step 1 the primary alcohol of commercially available 4-(2-Hydroxyethyl)phenol 24 is subjected to concentrated hydrochloric acid in a microwave to afford Compound 25. In Step 2 Compound 25 is mixed with azetidine in nucleophilic conditions to afford Compound 26 which can be used in Scheme 1.

Scheme 9

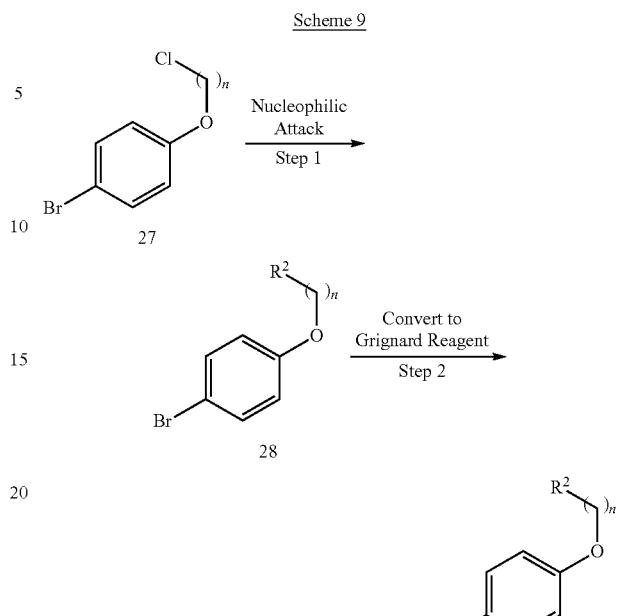

In Step 1 the chloro group of commercially available Compound 27 is subjected to nucleophilic attack by a $R^2$ group to afford Intermediate 28. In Step 2 Compound 28 is converted to a Grignard Reagent as known in the art to afford Intermediate 16 which is used in Scheme 4.

Scheme 10

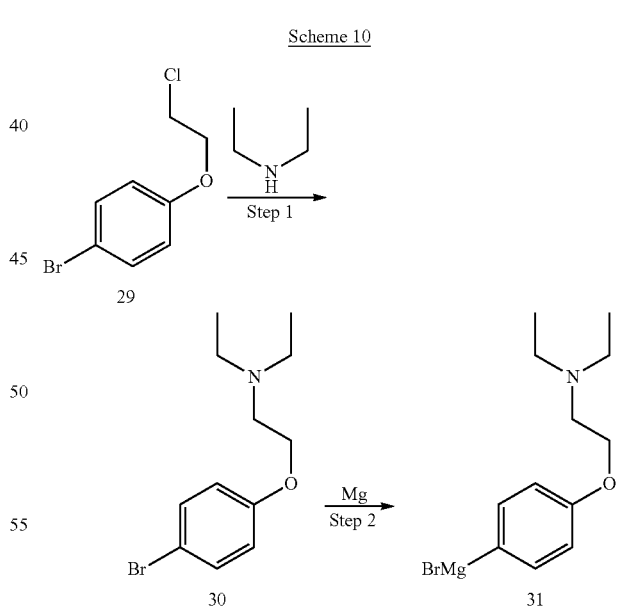

Scheme 10 is a non-limiting example of the method described in Scheme 8. In Step 1 the chloro group of commercially available 1-bromo-4-(2-chloroethoxy)benzene 29 is subjected to diethyl amine under nucleophilic conditions to afford Compound 30. In Step 2 Compound 30 is mixed with magnesium to afford Compound 31 which can be used in Scheme 4.

Example 1 Representative Compounds of the Present Invention

Table 1 and Table 2 provide non-limiting examples of compounds of the present invention which can be made according to the procedures above or in Example 2. Example 2 also provides detailed synthetic procedures for compounds 100-112 and compounds 120 and 121. One of ordinary skill in the art will be able to use these procedures or routine modifications thereof to prepare compounds described herein.

TABLE 1

| Compound # | Structure | Name |
|---|---|---|
| 100 | 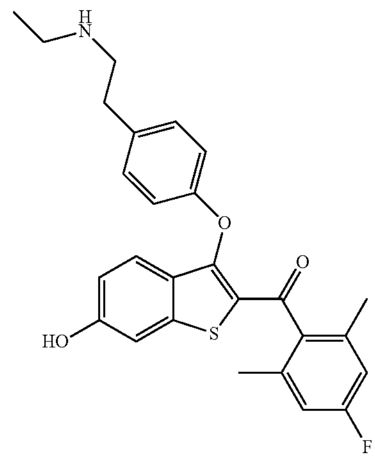 [SMILES: CCNCCc1ccc(Oc2c(C(=O)c3c(C)cc(F)cc3C)sc3cc(O)ccc23)cc1] | (3-(4-(2-(ethylamino)ethyl)phenoxy)-6-hydroxybenzo[b]thiophen-2-yl)(4-fluoro-2,6-dimethylphenyl)methanone |
| 101 | 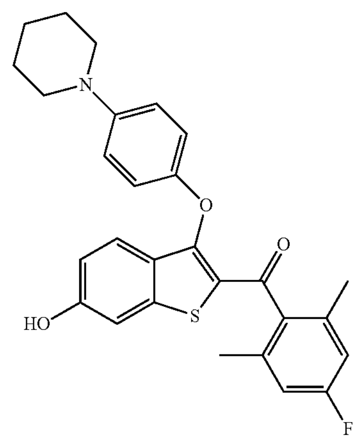 [SMILES: Cc1cc(F)cc(C)c1C(=O)c1sc2cc(O)ccc2c1Oc1ccc(N2CCCCC2)cc1] | (4-fluoro-2,6-dimethylphenyl)(6-hydroxy-3-(4-(piperidin-1-yl)phenoxy)benzo[b]thiophen-2-yl)methanone |
| 102 | 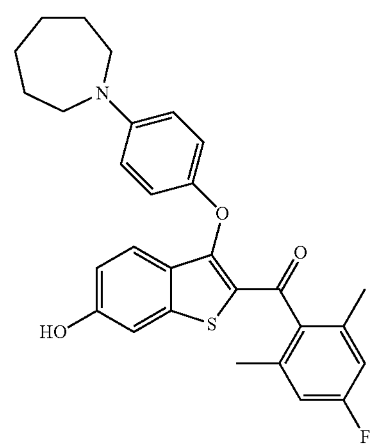 [SMILES: Cc1cc(F)cc(C)c1C(=O)c1sc2cc(O)ccc2c1Oc1ccc(N2CCCCCC2)cc1] | (3-(4-(azepan-1-yl)phenoxy)-6-hydroxybenzo[b]thiophen-2-yl)(4-fluoro-2,6-dimethylphenyl)methanone |

TABLE 1-continued

| Compound # | Structure | Name |
|---|---|---|
| 103 | 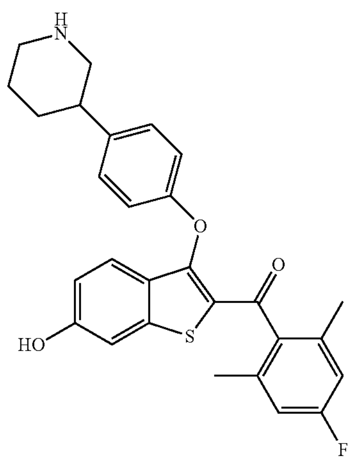 [SMILES: Cc1cc(F)cc(C)c1C(=O)c1sc2cc(O)ccc2c1Oc1ccc(C2CCCNC2)cc1] | (4-fluoro-2,6-dimethylphenyl)(6-hydroxy-3-(4-(piperidin-3-yl)phenoxy)benzo[b]thiophen-2-yl)methanone |
| 104 | 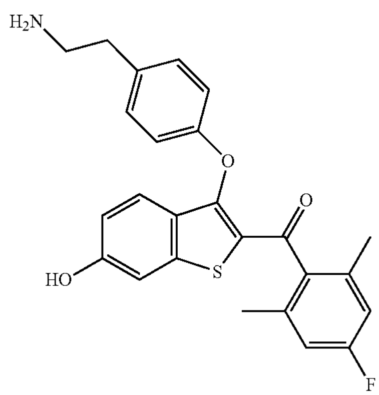 [SMILES: Cc1cc(F)cc(C)c1C(=O)c1sc2cc(O)ccc2c1Oc1ccc(CCN)cc1] | (3-(4-(2-aminoethyl)phenoxy)-6-hydroxybenzo[b]thiophen-2-yl)(4-fluoro-2,6-dimethylphenyl)methanone |
| 105 | 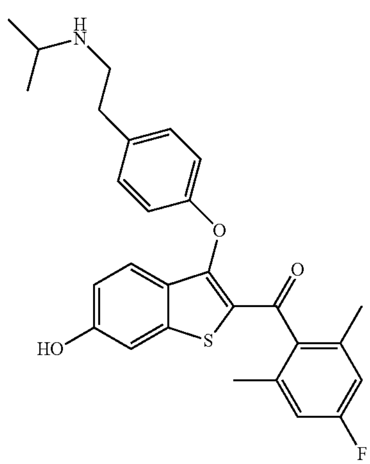 [SMILES: Cc1cc(F)cc(C)c1C(=O)c1sc2cc(O)ccc2c1Oc1ccc(CCNC(C)C)cc1] | (4-fluoro-2,6-dimethylphenyl)(6-hydroxy-3-(4-(2-(isopropylamino)ethyl)phenoxy)benzo[b]thiophen-2-yl)methanone |

TABLE 1-continued
| Compound # | Structure | Name |
|---|---|---|
| 106 | 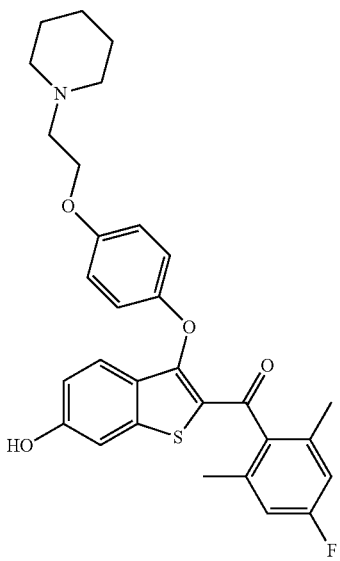 [SMILES: Cc1cc(F)cc(C)c1C(=O)c1sc2cc(O)ccc2c1Oc1ccc(OCCN2CCCCC2)cc1] | (4-fluoro-2,6-dimethylphenyl)(6-hydroxy-3-(4-(2-(piperidin-1-yl)ethoxy)phenoxy)benzo[b]thiophen-2-yl)methanone |
| 107 | 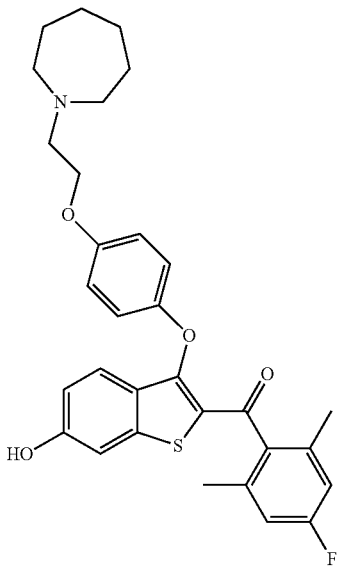 [SMILES: Cc1cc(F)cc(C)c1C(=O)c1sc2cc(O)ccc2c1Oc1ccc(OCCN2CCCCCC2)cc1] | (3-(4-(2-(azepan-1-yl)ethoxy)phenoxy)-6-hydroxybenzo[b]thiophen-2-yl)(4-fluoro-2,6-dimethylphenyl)methanone |

TABLE 1-continued
| Compound # | Structure | Name |
|---|---|---|
| 108 | 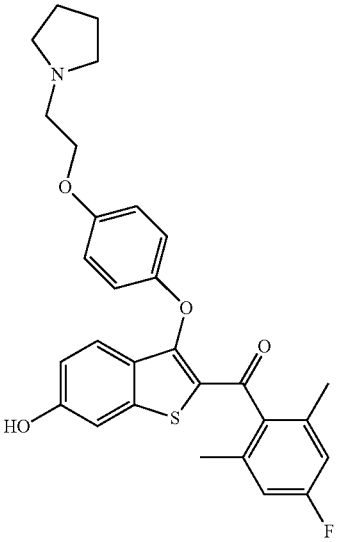 [SMILES: Cc1cc(F)cc(C)c1C(=O)c1sc2cc(O)ccc2c1Oc1ccc(OCCN2CCCC2)cc1] | (4-fluoro-2,6-dimethylphenyl)(6-hydroxy-3-(4-(2-(pyrrolidin-1-yl)ethoxy)phenoxy)benzo[b]thiophen-2-yl)methanone |
| 109 | 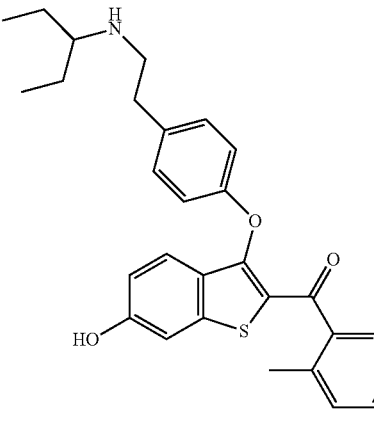 | (4-fluoro-2,6-dimethylphenyl)(6-hydroxy-3-(4-(2-(pentan-3-ylamino)ethyl)phenoxy)benzo[b]thiophen-2-yl)methanone |
| 110 | 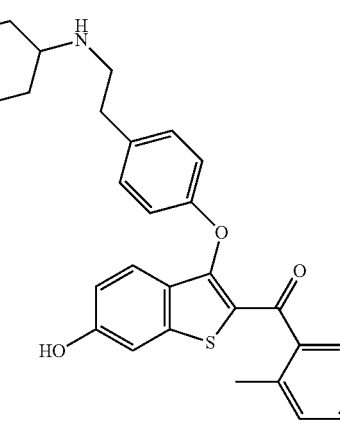 | (3-(4-(2-(cyclohexylamino)ethyl)phenoxy)-6-hydroxybenzo[b]thiophen-2-yl)(4-fluoro-2,6-dimethylphenyl)methanone |

TABLE 1-continued

| Compound # | Structure | Name |
|---|---|---|
| 111 | 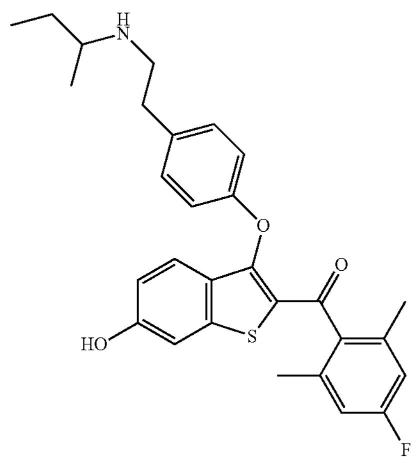 [SMILES: CCC(C)NCCc1ccc(Oc2c(C(=O)c3c(C)cc(F)cc3C)sc3cc(O)ccc23)cc1] | (3-(4-(2-(sec-butylamino)ethyl)phenoxy)-6-hydroxybenzo[b]thiophen-2-yl)(4-fluoro-2,6-dimethylphenyl)methanone |
| 112 | 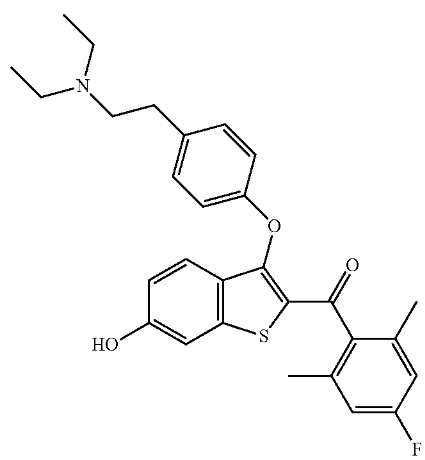 [SMILES: CCN(CC)CCc1ccc(Oc2c(C(=O)c3c(C)cc(F)cc3C)sc3cc(O)ccc23)cc1] | (3-(4-(2-(diethylamino)ethyl)phenoxy)-6-hydroxybenzo[b]thiophen-2-yl)(4-fluoro-2,6-dimethylphenyl)methanone |
| 113 | 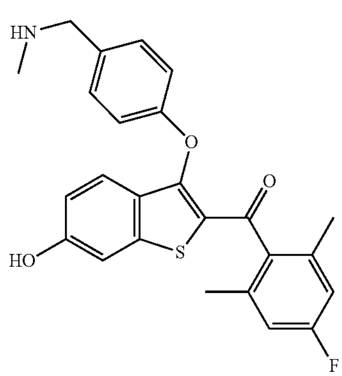 | (4-fluoro-2,6-dimethylphenyl)(6-hydroxy-3-(4-((methylamino)methyl)phenoxy)benzo[b]thiophen-2-yl)methanone |

TABLE 1-continued
| Compound # | Structure | Name |
|---|---|---|
| 114 | 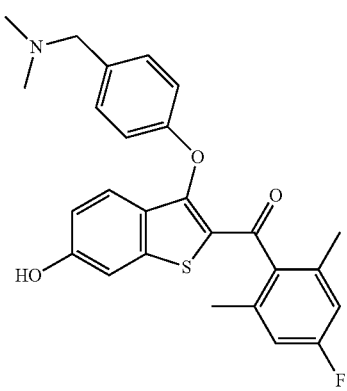 | (3-(4-((dimethylamino)methyl)phenoxy)-6-hydroxybenzo[b]thiophen-2-yl)(4-fluoro-2,6-dimethylphenyl)methanone |
| 115 | 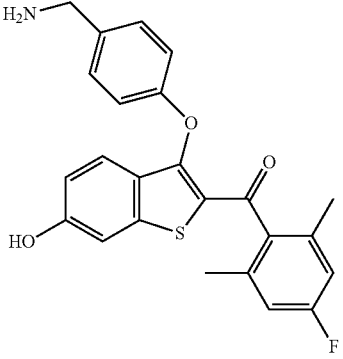 [SMILES: Cc1cc(F)cc(C)c1C(=O)c1sc2cc(O)ccc2c1Oc1ccc(CN)cc1] | (3-(4-(aminomethyl)phenoxy)-6-hydroxybenzo[b]thiophen-2-yl)(4-fluoro-2,6-dimethylphenyl)methanone |
| 116 | 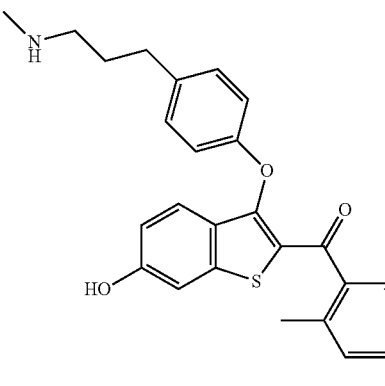 | (4-fluoro-2,6-dimethylphenyl)(6-hydroxy-3-(4-(3-(methylamino)propyl)phenoxy)benzo[b]thiophen-2-yl)methanone |

TABLE 1-continued

| Compound # | Structure | Name |
|---|---|---|
| 117 | 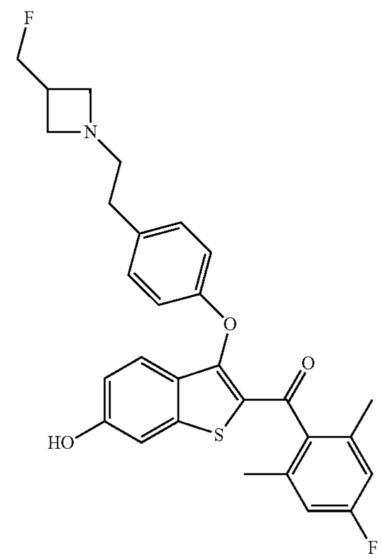 [SMILES: Cc1cc(F)cc(C)c1C(=O)c1sc2cc(O)ccc2c1Oc1ccc(CCN2CC(CF)C2)cc1] | (4-fluoro-2,6-dimethylphenyl)(3-(4-(2-(3-(fluoromethyl)azetidin-1-yl)ethyl)phenoxy)-6-hydroxybenzo[b]thiophen-2-yl)methanone |
| 118 | 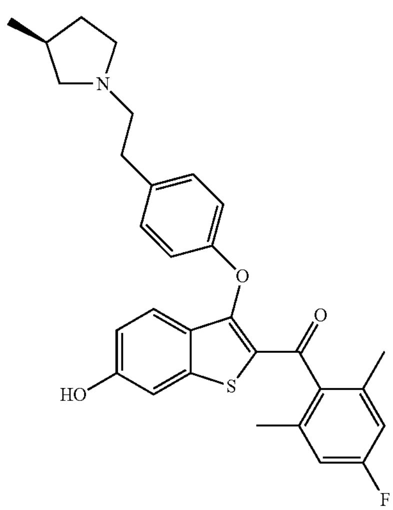 | (S)-(4-fluoro-2,6-dimethylphenyl)(6-hydroxy-3-(4-(2-(3-methylpyrrolidin-1-yl)ethyl)phenoxy)benzo[b]thiophen-2-yl)methanone |

TABLE 1-continued
| Compound # | Structure | Name |
|---|---|---|
| 119 | 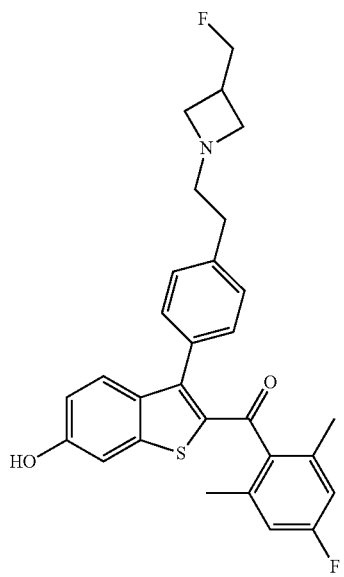 [SMILES: Cc1cc(F)cc(C)c1C(=O)c1sc2cc(O)ccc2c1-c1ccc(CCN2CC(CF)C2)cc1] | (4-fluoro-2,6-dimethylphenyl)(3-(4-(2-(3-(fluoromethyl)azetidin-1-yl)ethyl)phenyl)-6-hydroxybenzo[b]thiophen-2-yl)methanone |
| 120 | 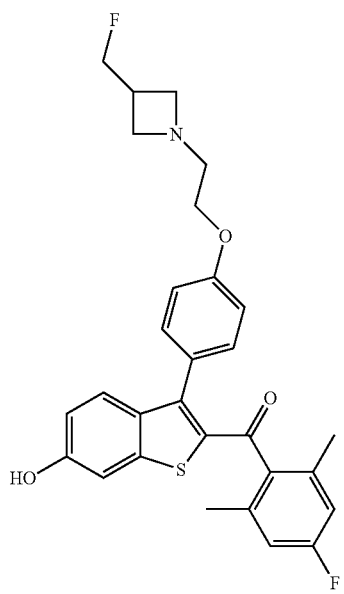 [SMILES: Cc1cc(F)cc(C)c1C(=O)c1sc2cc(O)ccc2c1-c1ccc(OCCN2CC(CF)C2)cc1] | (4-fluoro-2,6-dimethylphenyl)(3-(4-(2-(3-(fluoromethyl)azetidin-1-yl)ethoxy)phenyl)-6-hydroxybenzo[b]thiophen-2-yl)methanone |

TABLE 1-continued
| Compound # | Structure | Name |
|---|---|---|
| 121 | 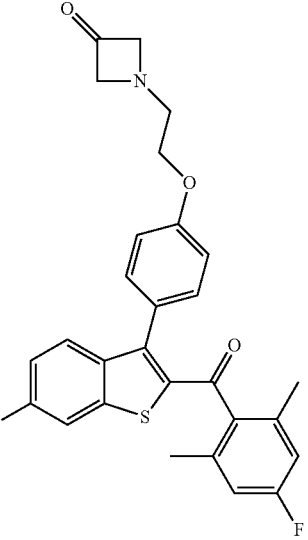 | 1-(2-(4-(2-(4-fluoro-2,6-dimethylbenzoyl)-6-hydroxybenzo[b]thiophen-3-yl)phenoxy)ethyl)azetidin-3-one |
| 122 | 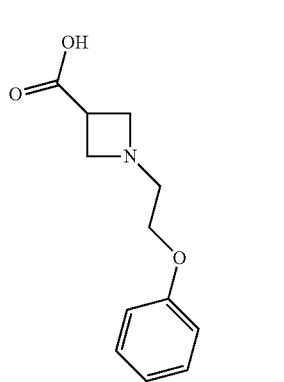 | 1-(2-(4-(2-(4-fluoro-2,6-dimethylbenzoyl)-6-hydroxybenzo[b]thiophen-3-yl)phenoxy)ethyl)azetidine-3-carboxylic acid |

TABLE 1-continued
| Compound # | Structure | Name |
|---|---|---|
| 123 | 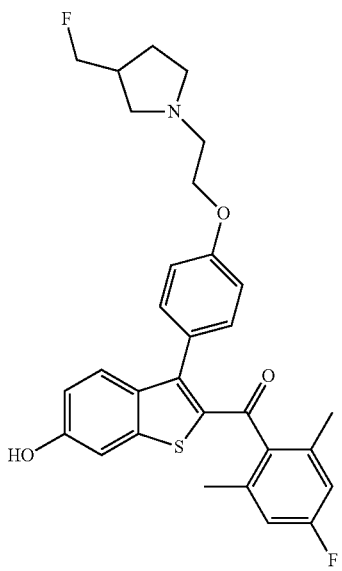 [SMILES: Cc1cc(F)cc(C)c1C(=O)c1sc2cc(O)ccc2c1-c1ccc(OCCN2CCC(CF)C2)cc1] | (4-fluoro-2,6-dimethylphenyl)(3-(4-(2-(3-(fluoromethyl)pyrrolidin-1-yl)ethoxy)phenyl)-6-hydroxybenzo[b]thiophen-2-yl)methanone |
| 124 | 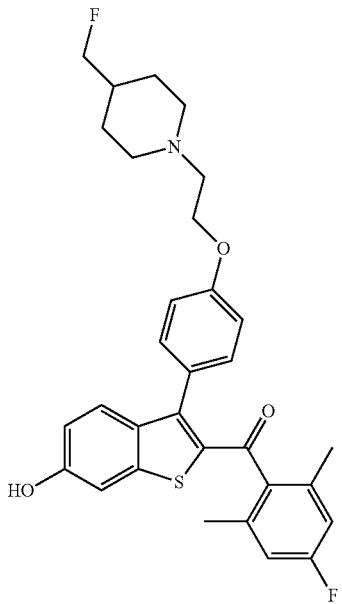 [SMILES: Cc1cc(F)cc(C)c1C(=O)c1sc2cc(O)ccc2c1-c1ccc(OCCN2CCC(CF)CC2)cc1] | (4-fluoro-2,6-dimethylphenyl)(3-(4-(2-(4-(fluoromethyl)piperidin-1-yl)ethoxy)phenyl)-6-hydroxybenzo[b]thiophen-2-yl)methanone |

TABLE 1-continued

| Compound # | Structure | Name |
|---|---|---|
| 125 | 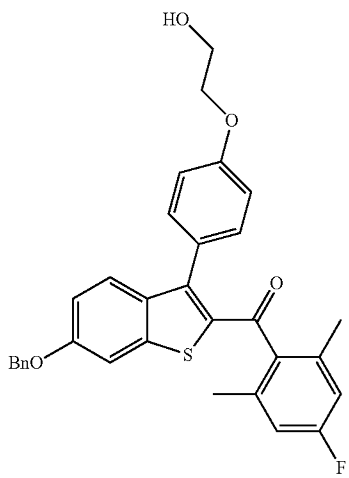 [SMILES: Cc1cc(F)cc(C)c1C(=O)c1sc2cc(OCc3ccccc3)ccc2c1-c1ccc(OCCO)cc1] | (6-(benzyloxy)-3-(4-(2-hydroxyethoxy)phenyl)benzo[b]thiophen-2-yl)(4-fluoro-2,6-dimethylphenyl)methanone |

TABLE 2

| Compound # | Structure | Name |
|---|---|---|
| 126 | 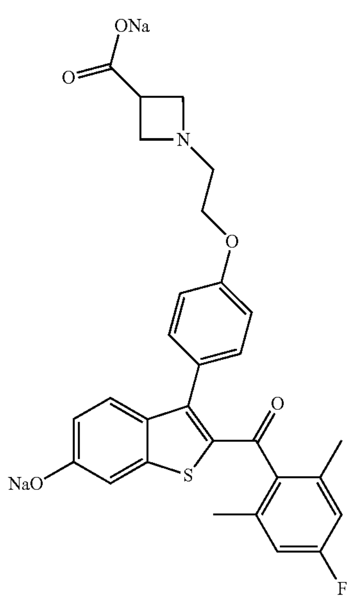 | sodium 1-(2-(4-(2-(4-fluoro-2,6-dimethylbenzoyl)-6-oxidobenzo[b]thiophen-3-yl)phenoxy)ethyl)azetidine-3-carboxylate |

TABLE 2-continued

| Compound # | Structure | Name |
|---|---|---|
| 127 | 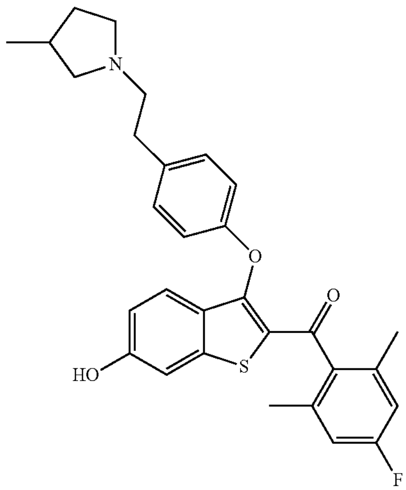 | (4-fluoro-2,6-dimethylphenyl)(6-hydroxy-3-(4-(2-(3-methylpyrrolidin-1-yl)ethyl)phenoxy)benzo[b]thiophen-2-yl)methanone |
| 128 | 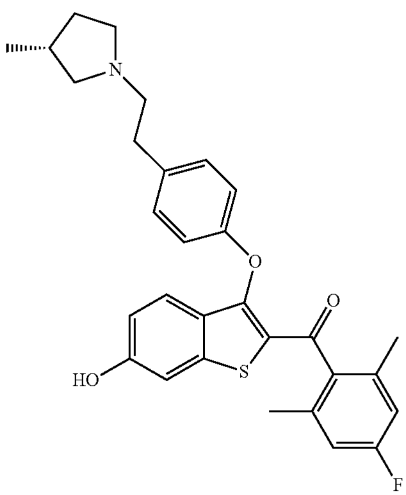 | (R)-(4-fluoro-2,6-dimethylphenyl)(6-hydroxy-3-(4-(2-(3-methylpyrrolidin-1-yl)ethyl)phenoxy)benzo[b]thiophen-2-yl)methanone |
| 129 | 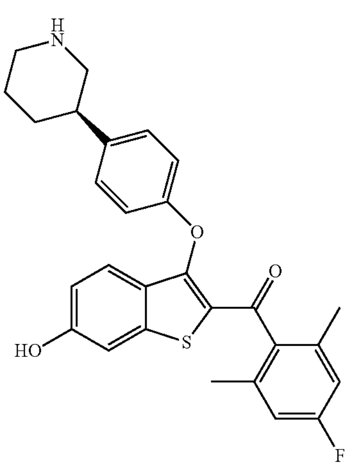 [SMILES: Cc1cc(F)cc(C)c1C(=O)c1sc2cc(O)ccc2c1Oc1ccc([C@H]2CCCNC2)cc1] | (R)-(4-fluoro-2,6-dimethylphenyl)(6-hydroxy-3-(4-(piperidin-3-yl)phenoxy)benzo[b]thiophen-2-yl)methanone |

TABLE 2-continued
| Compound # | Structure | Name |
|---|---|---|
| 130 | 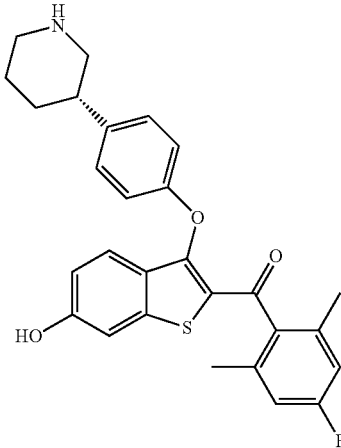 | (S)-(4-fluoro-2,6-dimethylphenyl)(6-hydroxy-3-(4-(piperidin-3-yl)phenoxy)benzo[b]thiophen-2-yl)methanone |
| 131 | 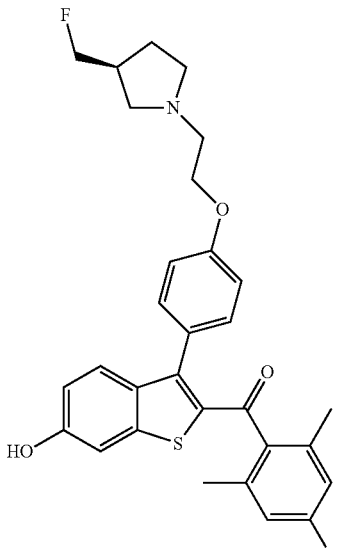 | (S)-(4-fluoro-2,6-dimethylphenyl)(3-(4-(2-(3-(fluoromethyl)pyrrolidin-1-yl)ethoxy)phenyl)-6-hydroxybenzo[b]thiophen-2-yl)methanone |
| 132 | 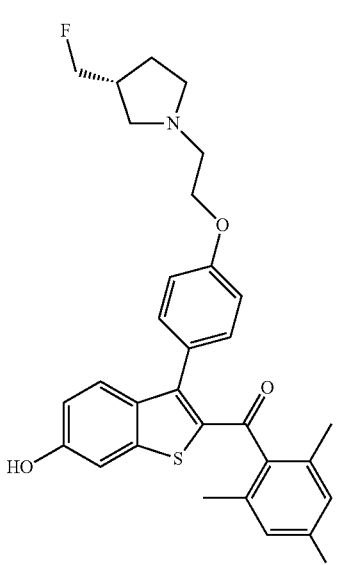 | (R)-(4-fluoro-2,6-dimethylphenyl)(3-(4-(2-(3-(fluoromethyl)pyrrolidin-1-yl)ethoxy)phenyl)-6-hydroxybenzo[b]thiophen-2-yl)methanone |

TABLE 2-continued
| Compound # | Structure | Name |
|---|---|---|
| 133 | 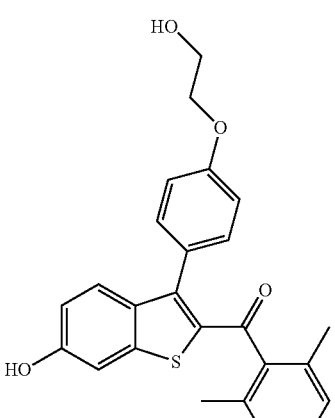 | (4-fluoro-2,6-dimethylphenyl)(6-hydroxy-3-(4-(2-hydroxyethoxy)phenyl)benzo[b]thiophen-2-yl)methanone |
Example 2. Representative Synthetic Procedures
Synthesis of Compound 100 ((3-(4-(2-(Ethylamino)ethyl)phenoxy)-6-hydroxybenzo[b]thiophen-2-yl)(4-fluoro-2,6-dimethylphenyl)methanone)
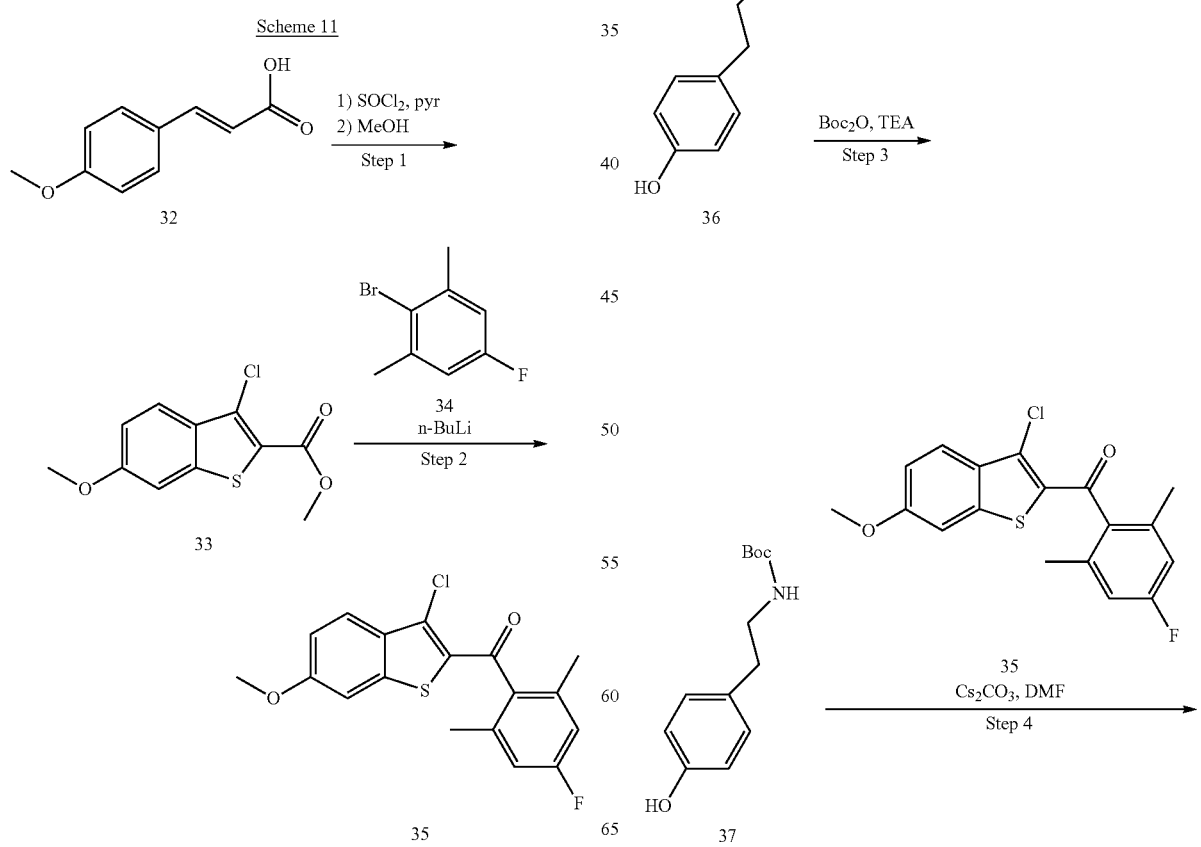

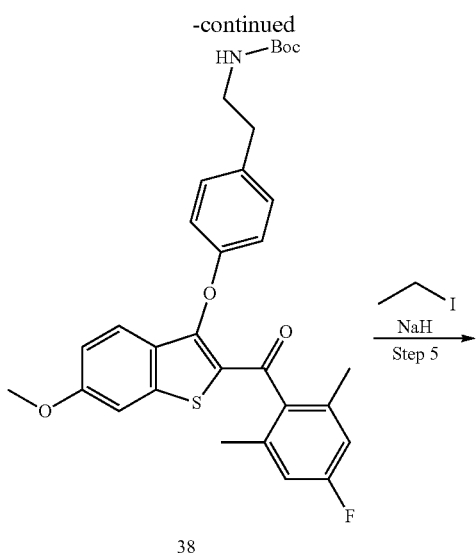

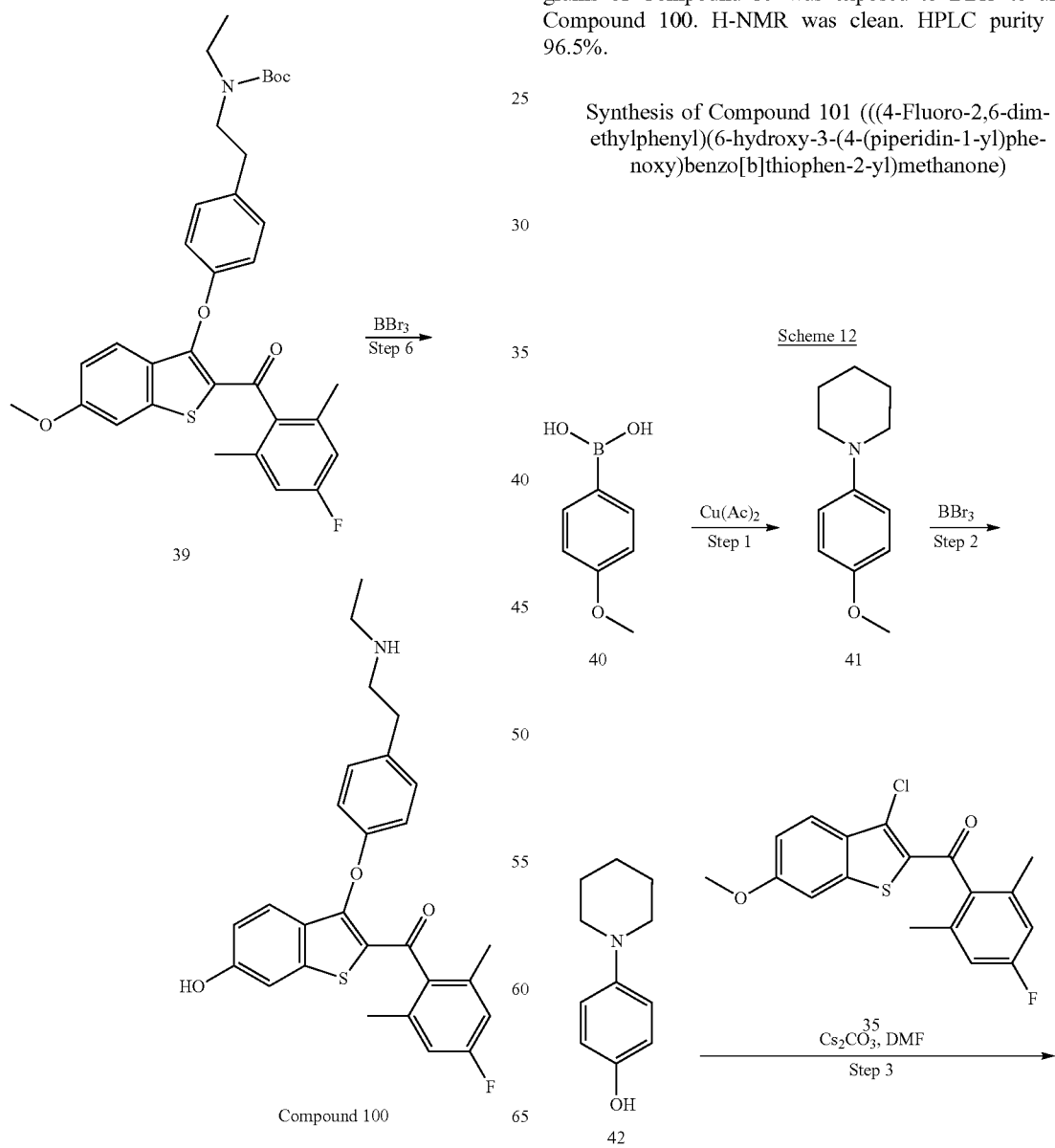

In Step 1, 100 grams of Compound 32 was dissolved thionyl chloride and pyridine. Methanol was added to the solution to afford Compound 33. Compound 33 was recrystallized to obtain 50 grams of pure product. The H-NMR was clean. In Step 2, 25 grams of Compound 32 was subjected to 1.3 eq of n-butyl lithium and Compound 34. After column purification 9.8 grams of pure Compound 35 was isolated. The H-NMR was clean. In Step 3, 3.5 grams of Compound 35 was reacted with Boc-anhydride in the presence of triethylamine to afford 5 grams of Compound 37 after work-up and purification. In Step 4, 4.5 grams of Compound 37 was dissolved in DMF and then Cesium Carbonate and Compound 35 were added to afford Compound 38. Compound 38 was purified by column chromatography to afford 6.8 grams of pure compound. H-NMR was clean and HPLC purity was 96%. In Step 5, to a solution of 6.2 grams of Compound 38 in DMF was added iodoethane and sodium hydride. After work-up and column purification 4.4 grams of Compound 39 was isolated. H-NMR was clean. In Step 6, 2 grams of Compound 39 was exposed to BBr3 to afford Compound 100. H-NMR was clean. HPLC purity was 96.5%.

Synthesis of Compound 101 (((4-Fluoro-2,6-dimethylphenyl)(6-hydroxy-3-(4-(piperidin-1-yl)phenoxy)benzo[b]thiophen-2-yl)methanone)

251
-continued

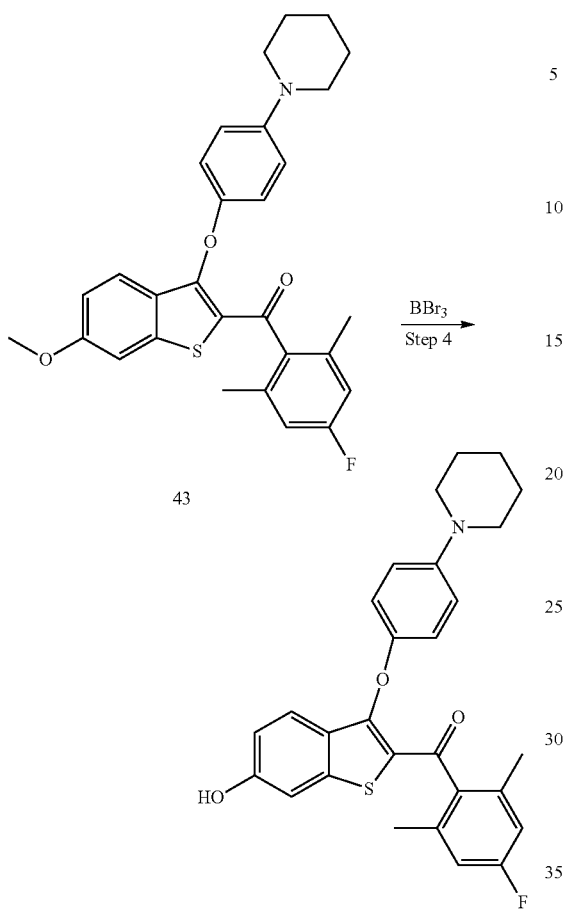

43

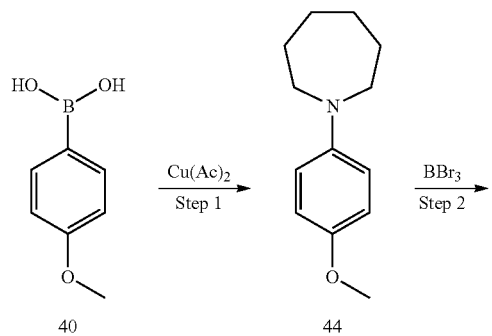

Compound 101

In Step 1, 1.67 grams of Compound 40 was converted to Compound 41 by the Cham lam coupling with copper acetate. The H-NMR was clean. In Step 2, 0.51 grams of Compound 41 was subjected to BBr$_3$ to afford 130 milligrams of Compound 42. The H-NMR was clean. In Step 3, 85 milligrams of Compound 42 was dissolved in DMF and then Cesium Carbonate and Compound 35 were added to afford 81 milligrams of Compound 43. H-NMR was clean. In Step 4, 50 milligrams of Compound 43 was exposed to BBr$_3$ to afford 10 milligrams of Compound 101 after purification. H-NMR was clean. HPLC purity was 95.3%.

Synthesis of Compound 102 ((3-(4-(Azepan-1-yl)phenoxy)-6-hydroxybenzo[b]thiophen-2-yl)(4-fluoro-2,6-dimethylphenyl)methanone)

Scheme 13

252
-continued

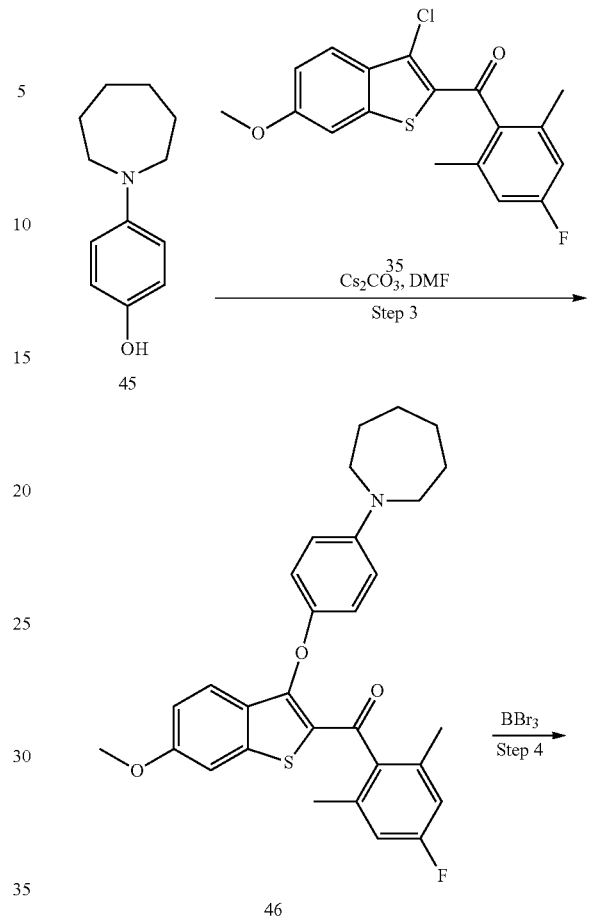

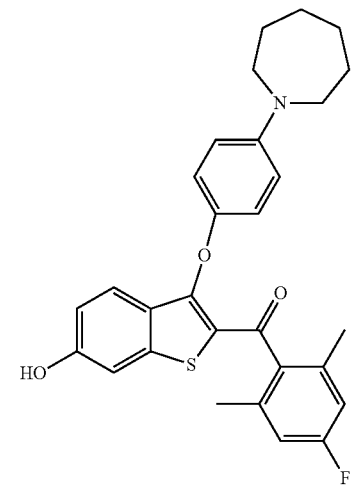

Compound 102

In Step 1, 1 gram of Compound 40 and 3 equivalents of azepane were converted to 353 milligrams of Compound 44 by the Cham lam coupling with copper acetate. In Step 2, 353 milligrams of Compound 44 was subjected to BBr$_3$ to afford 235 milligrams of Compound 45 after column chromatography. In Step 4, 210 milligrams of Compound 46 was exposed to BBr$_3$ in DCM to afford 30 milligrams of Compound 102 after work-up and column chromatography. H-NMR was clean. HPLC purity was 98.8%.

253

Synthesis of Compound 103 ((4-fluoro-2,6-dimethylphenyl)(6-hydroxy-3-(4-(piperidin-3-yl)phenoxy)benzo[b]thiophen-2-yl)methanone)

Scheme 14

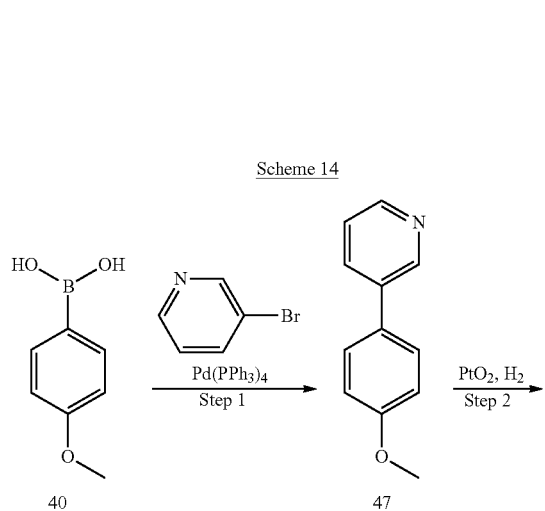

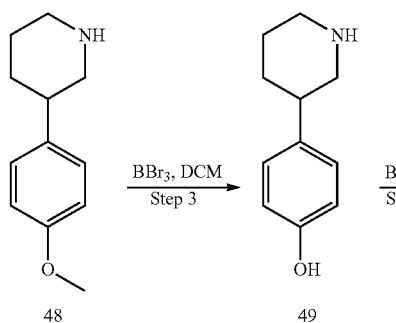

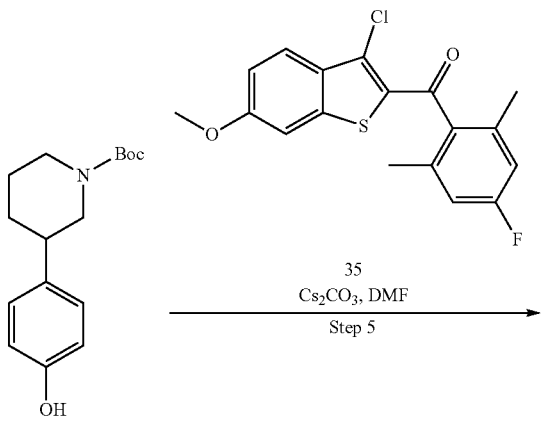

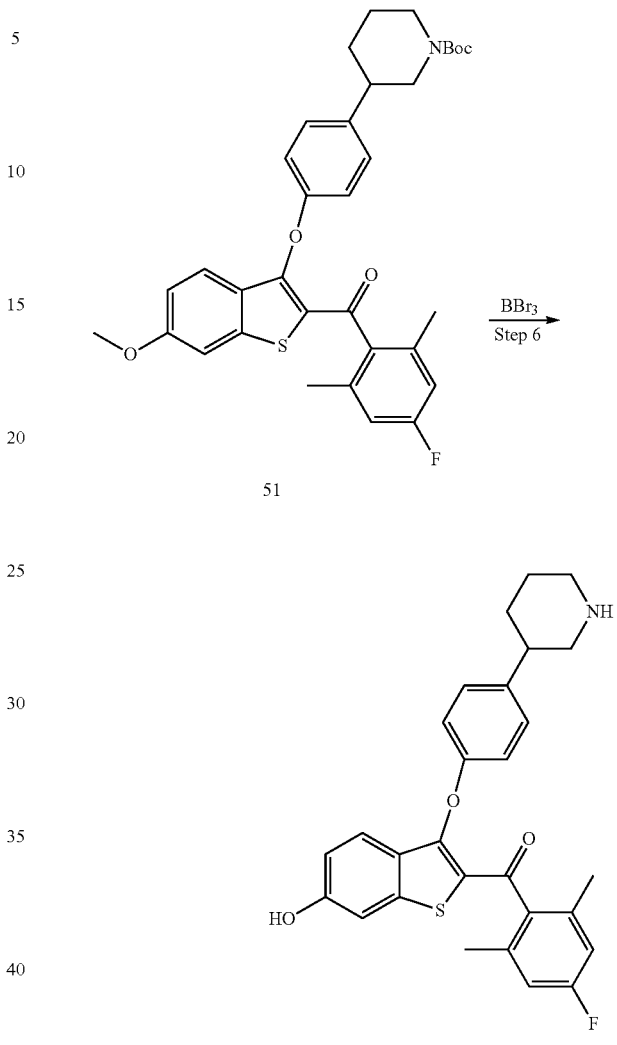

Compound 103

In Step 1, 1.6 grams of Compound 40 was converted to 1.6 grams of Compound 47 by the Suzuki coupling. The H-NMR was clean. In Step 2, 800 milligrams of Compound 47 was reduced by Platinum Oxide in the presence of hydrogen gas, isopropyl amine, and 6N HCl to afford 600 milligrams of Compound 48. The H-NMR was clean. In Step 3, 186 milligrams of Compound 48 was dissolved in DCM and then subjected to BBr$_3$ to afford Compound 49. The crude mixture of Compound 49 was then quenched with water and adjusted to pH 9 with potassium carbonate. The resulting mixture was exposed in Step 4 to Boc-anhydride to afford 100 milligrams of Compound 50 after work-up and purification. The H-NMR was clean. In Step 5, 100 milligrams of Compound 50 was dissolved in DMF and then Cesium Carbonate and Compound 35 were added to at 70° C. to afford 169 milligrams of Compound 51 after work-up and purification. In Step 6, 40 milligrams of Compound 51 was exposed to BBr$_3$ to afford 20 milligrams of Compound 103 after purification. H-NMR was clean. HPLC purity was 97%.

255

Synthesis of Compound 104 (((3-(4-(2-Aminoethyl)phenoxy)-6-hydroxybenzo[b]thiophen-2-yl)(4-fluoro-2,6-dimethylphenyl)methanone) and Compound 105 ((4-Fluoro-2,6-dimethylphenyl)(6-hydroxy-3-(4-(2-(isopropylamino)ethyl)phenoxy)benzo[b]thiophen-2-yl)methanone)

Scheme 15

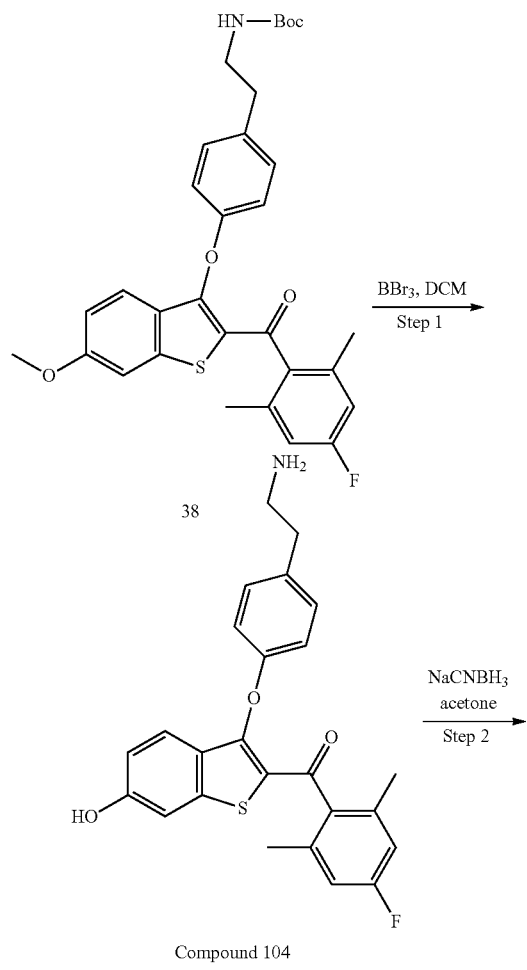

256

-continued

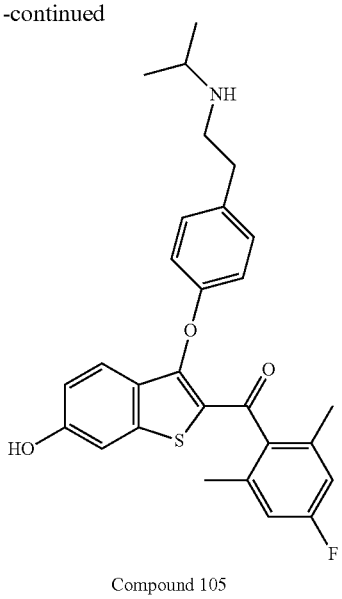

Compound 105

In Step 1, 100 milligrams of Compound 38 was dissolved in DCM and then subjected to BBr₃ to afford 86 milligrams of Compound 104. HPLC purity was 96.5%. The H-NMR was clean. In Step 2, 86 milligrams of Compound 104 was subjected to reductive amination conductions with sodium cyanoborohydride, acetone, and acetic acid to afford crude Compound 105. The crude mixture was worked-up and purified by column chromatography and then concentrated under high vacuum for 24 hours and then dissolved in methanol and concentrated to dryness to afford 15 milligrams of Compound 105. The H-NMR was clean. HPLC purity was >99%.

Synthesis of Compound 106 (((3-(4-(2-Aminoethyl)phenoxy)-6-hydroxybenzo[b]thiophen-2-yl)(4-fluoro-2,6-dimethylphenyl)methanone)

Scheme 16

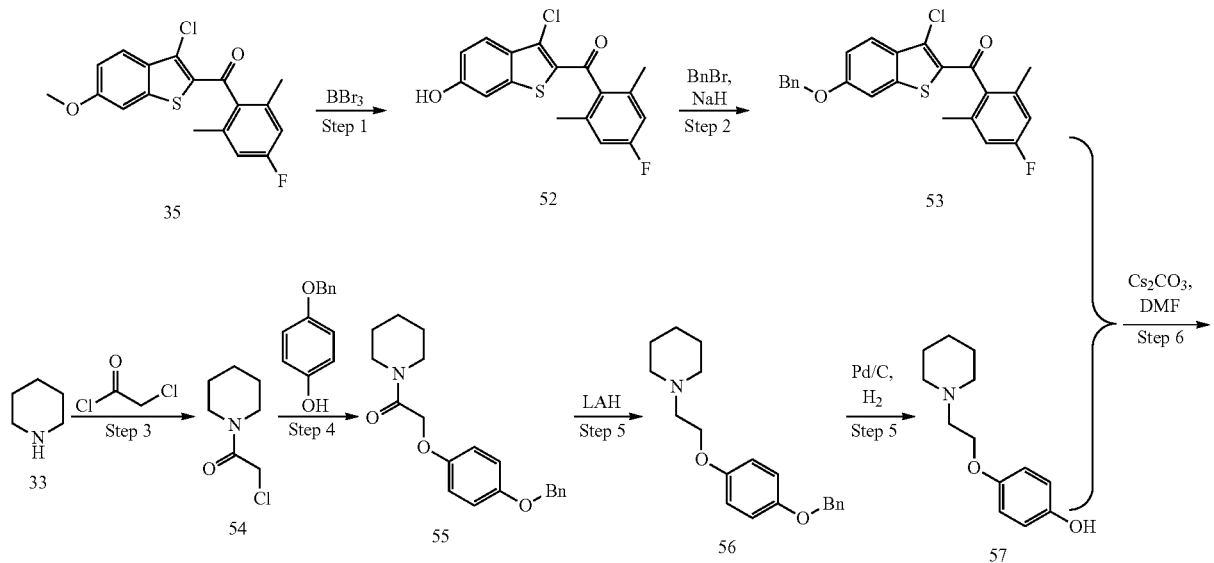

-continued

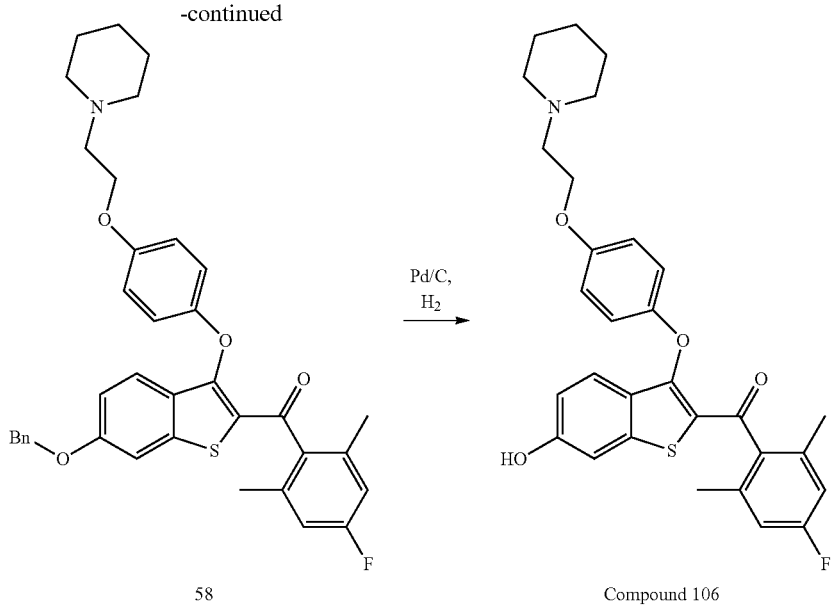

In Step 1, 1 gram of Compound 35 was dissolved in DCM and then subjected to BBr₃ to afford 930 milligrams of Compound 52. The H-NMR was clean. In Step 2, Compound 52 was reacted with sodium hydride and benzyl bromide to afford Compound 53. In Step 3, 200 milligrams of Compound 33 was dissolved in DCM and triethylamine and reacted with 2-chloroacetyl chloride to afford 240 milligrams of Compound 54 after work-up and purification. In Step 4 Compound 54 was then dissolved in DMF and reacted with sodium hydride and 4-(benzyloxy)phenol to afford 300 milligrams of Compound 55 after work-up and purification. In Step 5, 300 milligrams of Compound 55 was reduced by lithium aluminum hydride to afford 260 milligrams of Compound 56 as an oil after work-up and purification. The H-NMR was clean. In Step 6, 260 milligrams of Compound 56 was hydrogenated to afford 200 milligrams of Compound 57. The H-NMR was clean. In Step 8, 100 milligrams of Compound 57 was mixed with Compound 53 in DMF in the presence of cesium carbonate to afford 160 milligrams of Compound 58. In Step 10, 30 milligrams of Compound 58 was hydrogenated with palladium on carbon in the presence of hydrogen gas to afford 20 milligrams of Compound 106 after work-up and purification.

Synthesis of Compound 107 ((3-(4-(2-(Azepan-1-yl)ethoxy)phenoxy)-6-hydroxybenzo[b]thiophen-2-yl)(4-fluoro-2,6-dimethylphenyl)methanone)

Scheme 17

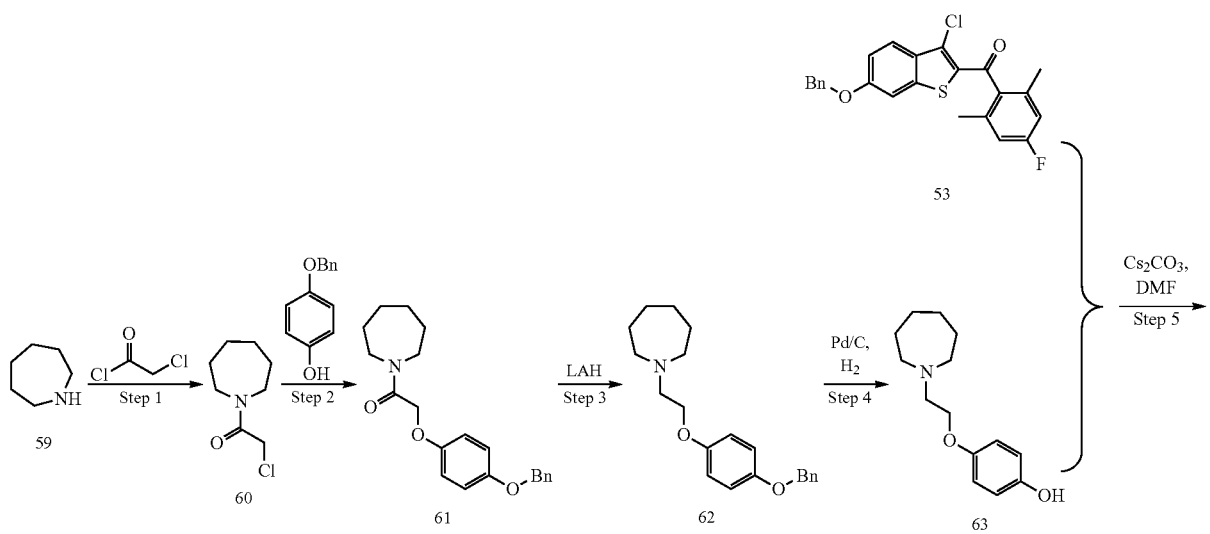

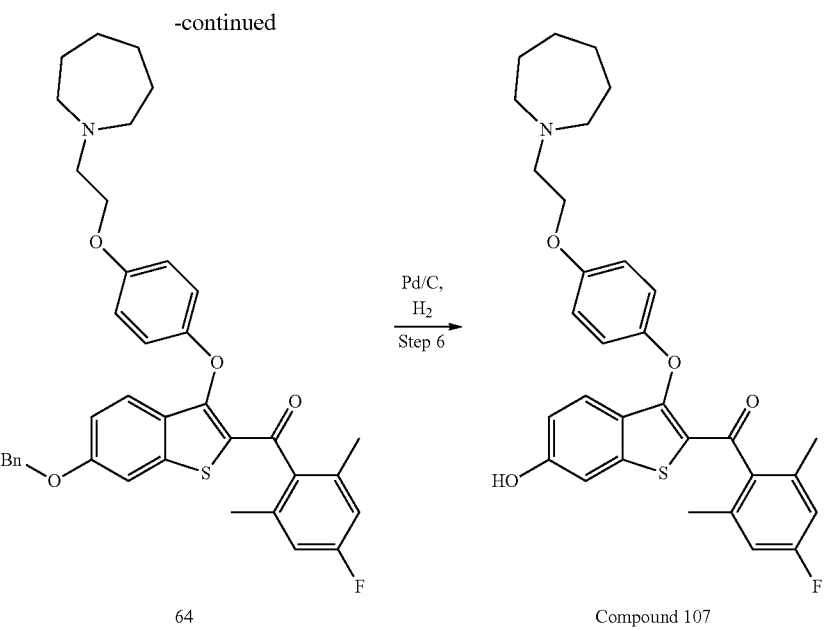

In Step 1, 500 milligrams of Compound 59 was reacted with 2-chloroacetyl chloride to afford 930 milligrams of crude Compound 60. In Step 2, 500 milligrams of crude Compound 60 was converted to 489 milligrams of Compound 61 after work-up and purification. The H-NMR was clean. In Step 3, 489 milligrams of Compound 61 was reduced by lithium aluminum hydride to afford 376 milligrams of Compound 62 after work-up and purification. The H-NMR was clean. In Step 4, 376 milligrams of Compound 62 was hydrogenated to afford 174 milligrams of Compound 63 after work-up and column purification. The H-NMR was clean. In Step 5, 174 milligrams of Compound 63 was mixed with Compound 53 in DMF in the presence of cesium carbonate to afford 190 milligrams of Compound 64 after work-up and purification. The H-NMR was clean. In Step 6, 90 milligrams of Compound 64 was hydrogenated with palladium on carbon in the presence of hydrogen gas to afford 20 milligrams of Compound 107 after work-up and purification. The H-NMR was clean except some residual solvent.

Synthesis of Compound 108 ((4-Fluoro-2,6-dimethylphenyl)(6-hydroxy-3-(4-(2-(pyrrolidin-1-yl)ethoxy)phenoxy)benzo[b]thiophen-2-yl)methanone)

Scheme 18

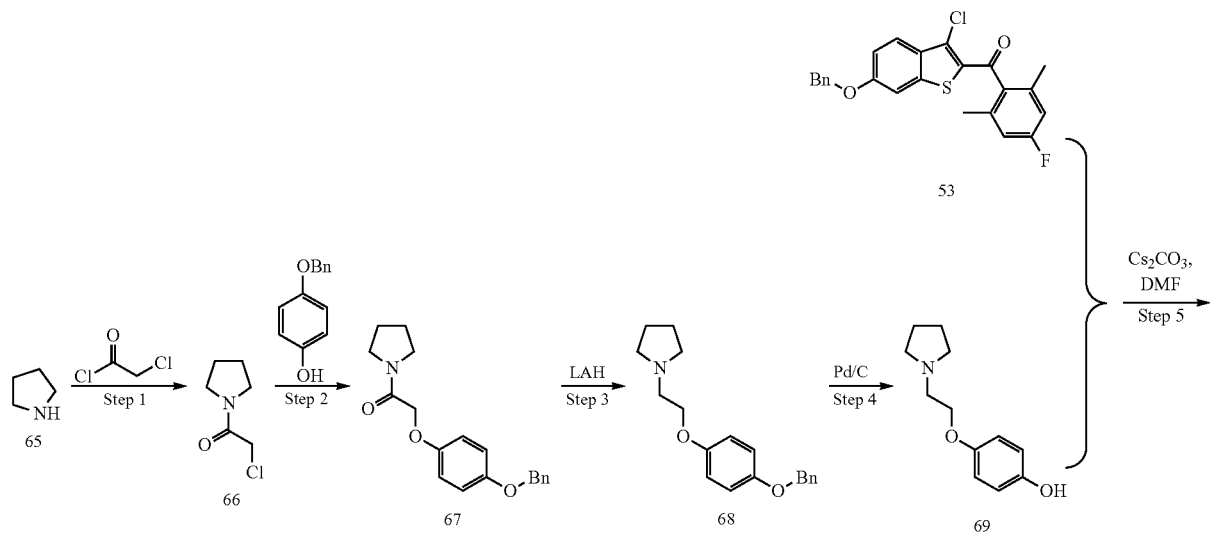

-continued

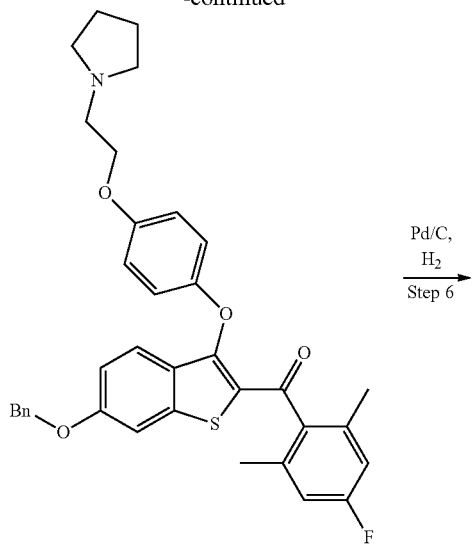

70

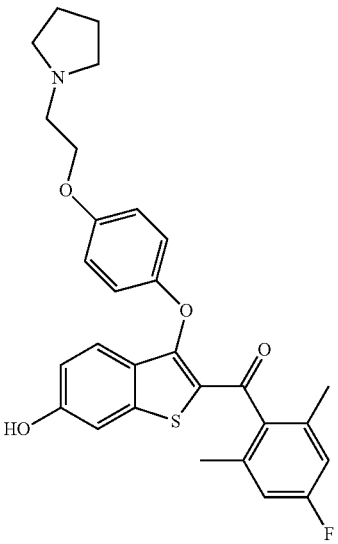

Compound 108

In Step 1, 500 milligrams of Compound 65 was reacted with 2-chloroacetyl chloride to afford 677 milligrams of Compound 66 after work-up and purification. In Step 2, 677 milligrams Compound 66 was converted to 987 milligrams of Compound 67 after work-up and purification. The H-NMR was clean. In Step 3, 987 milligrams of Compound 67 was reduced by lithium aluminum hydride to afford 600 milligrams of Compound 68 after work-up and purification. The H-NMR was clean. In Step 4, 600 milligrams of Compound 68 was hydrogenated to afford 359 milligrams of Compound 69 after work-up and column purification. The H-NMR was clean. In Step 5, 88 milligrams of Compound 69 was mixed with Compound 53 in DMF in the presence of cesium carbonate to afford 160 milligrams of Compound 70 after work-up and purification. The H-NMR was clean except for some residual DMF. In Step 6, 50 milligrams of Compound 70 was hydrogenated with palladium on carbon in the presence of hydrogen gas to afford 13 milligrams of Compound 108 after work-up and purification. The H-NMR was clean.

Synthesis of Compound 109 (4-Fluoro-2,6-dimethylphenyl)(6-hydroxy-3-(4-(2-(pentan-3-ylamino)ethyl)phenoxy)benzo[b]thiophen-2-yl)methanone Scheme 19

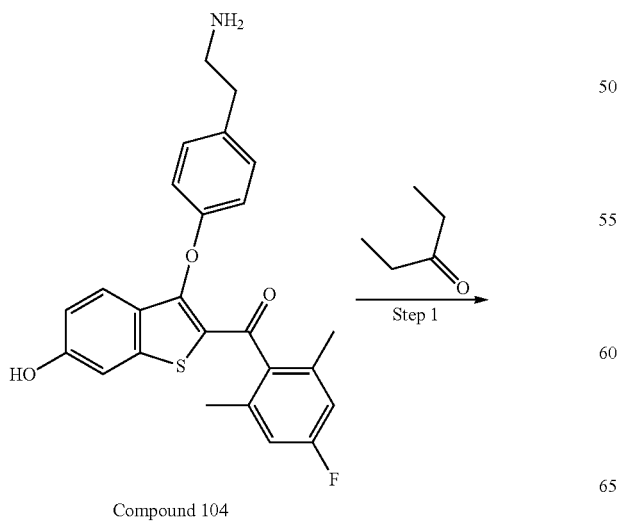

Compound 104

-continued

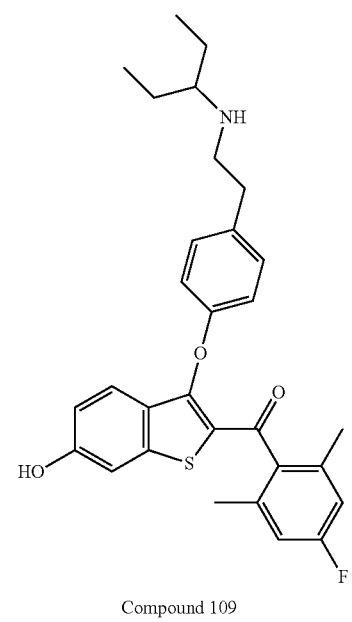

Compound 109

In Step 1, 50 milligrams of Compound 104 was subjected to reductive amination in the presence of pentan-3-one to afford Compound 109.

263
Synthesis of Compound 110 (3-(4-(2-(Cyclohexylamino)ethyl)phenoxy)-6-hydroxybenzo[b]thiophen-2-yl)(4-fluoro-2,6-dimethylphenyl)methanone

264
Synthesis of Compound 111 (3-(4-(2-(Sec-butylamino)ethyl)phenoxy)-6-hydroxybenzo[b]thiophen-2-yl)(4-fluoro-2,6-dimethylphenyl)methanone

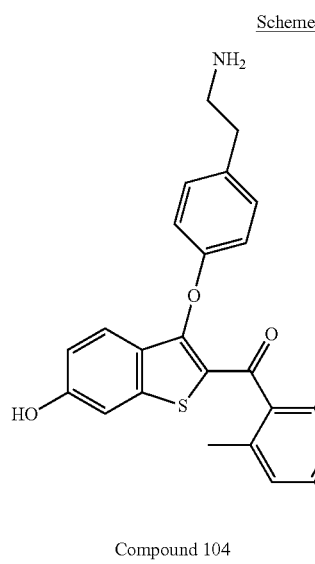

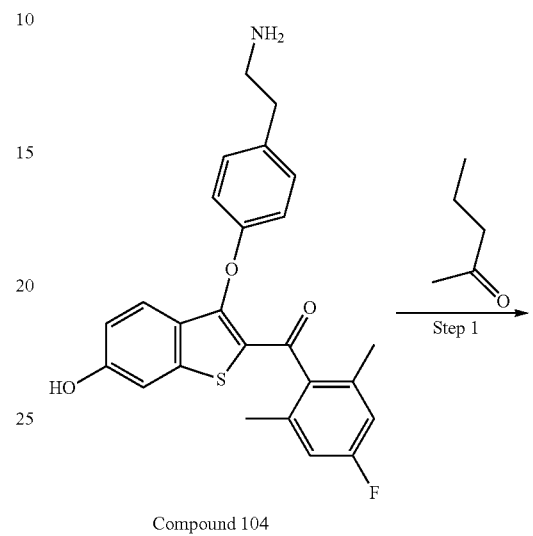

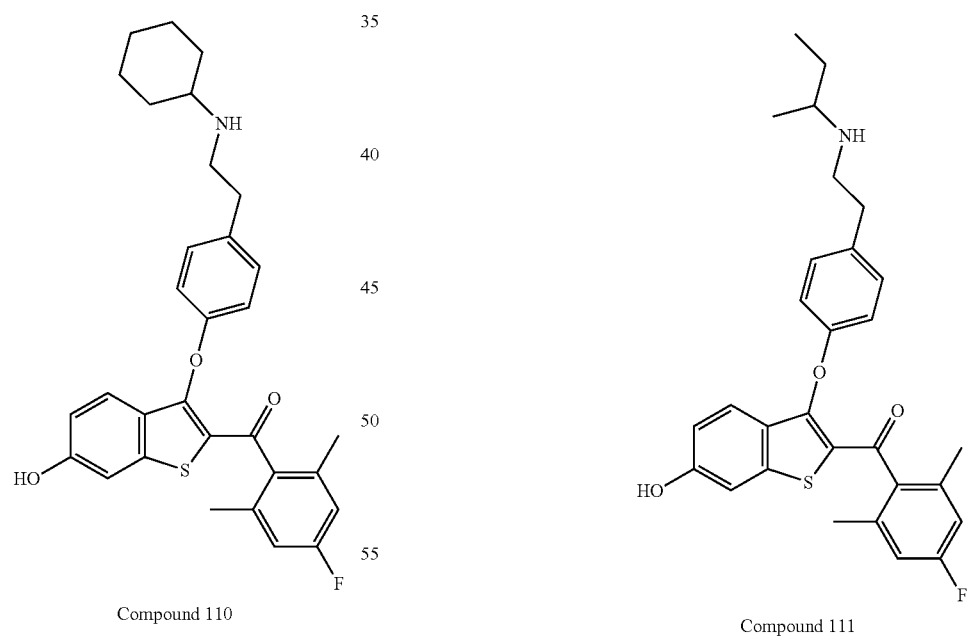

In Step 1, 50 milligrams of Compound 104 was subjected to reductive amination in the presence of cyclohexanone to afford 20 milligrams of Compound 110 after work-up and purification. The H-NMR was clean. The HPLC purity was 96.7%.

In Step 1, 50 mg of Compound 104 was subjected to reductive amination in the presence of pentan-2-one to afford 30 milligrams of Compound 111 after work-up and purification. The H-NMR was clean. The HPLC purity was 96%.

Synthesis of Compound 112 (3-(4-(2-(Diethylamino)ethyl)phenoxy)-6-hydroxybenzo[b]thiophen-2-yl)(4-fluoro-2,6-dimethylphenyl)methanone

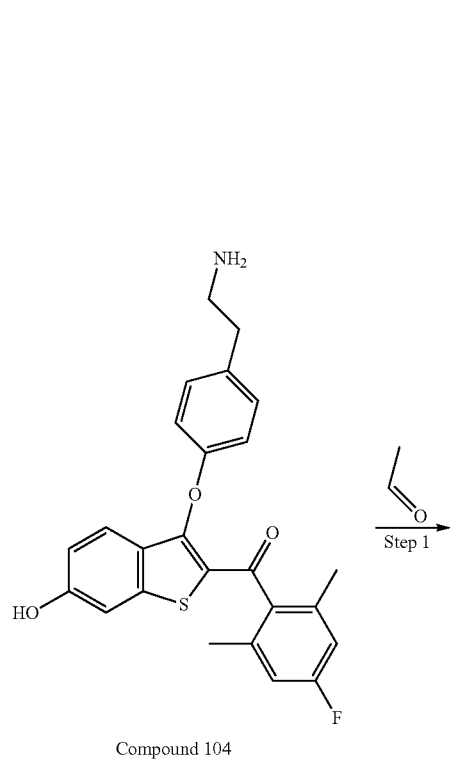

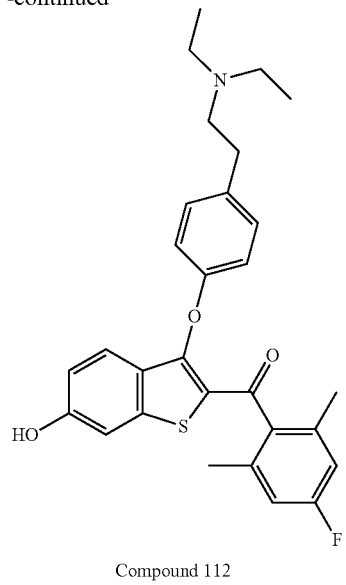

In Step 1, 50 mg of Compound 104 was subjected to reductive amination in the presence of acetaldehyde to afford 12 milligrams of Compound 112 after work-up and purification. The H-NMR was clean. The HPLC purity was 97.8%.

Synthesis of Compound 120 (4-Fluoro-2,6-dimethylphenyl)(3-(4-(2-(3-(fluoromethyl)azetidin-1-yl)ethoxy)phenyl)-6-hydroxybenzo[b]thiophen-2-yl)methanone

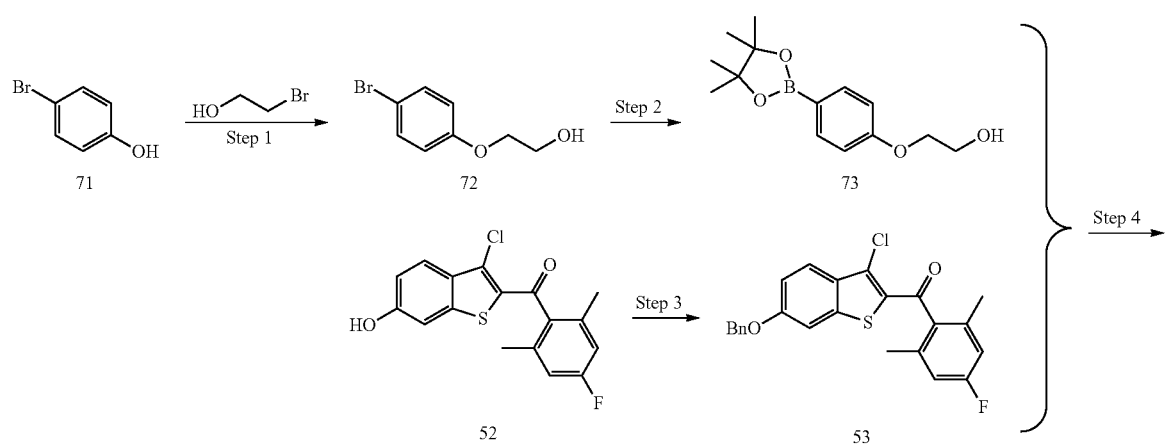

-continued

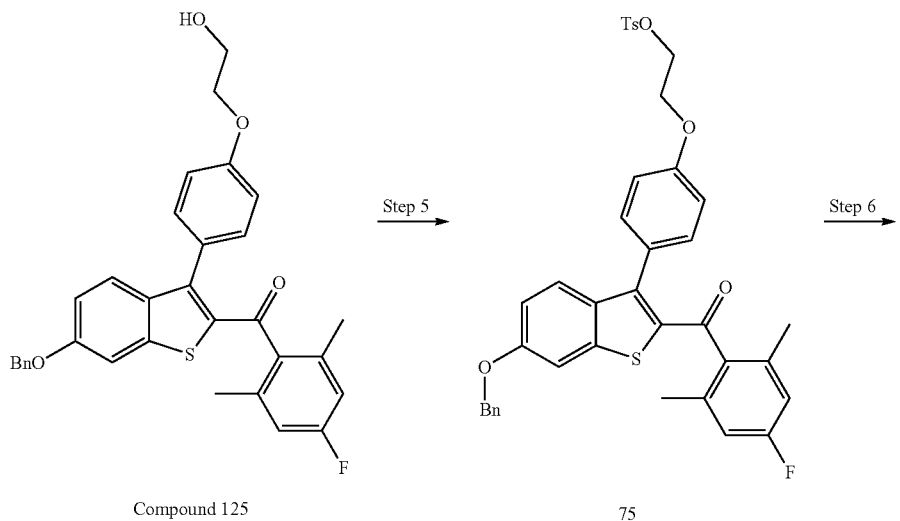

Compound 125

75

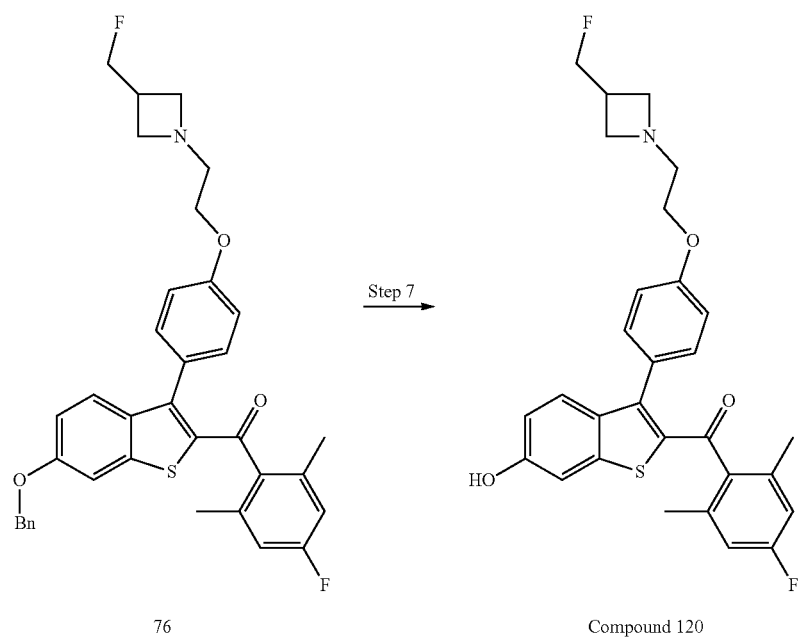

76

Compound 120

In Step 1, 500 mg 71 was alkylated with 2-bromoethanol in the presence of $K_2C_3$ in DMF at 80° C. to provide 500 mg of 72 after purification. In Step 2, 100 mg of 72 was borylated to afford 100 mg of 73 after purification. In Step 3, 240 mg of 52 was alkylated with benzyl bromide in the presence of sodium hydride in DMF to provide 250 mg of 53 after purification. In Step 4, 550 mg of 73 and 1.1 g of 53 was reacted in the presence of $Pd(PPh_3)_4$ and $K_2CO_3$ in toluene and water at 100° C. to provide 150 mg of Compound 12 after purification. In Step 5, 20 mg of Compound 125 was reacted with tosyl chloride and triethylamine in dichloromethane to provide 19 mg of 75 after purification. In Step 6, 17 mg of 75 was reacted with crude 3-(fluoromethyl)azetidine (prepared by deprotection of tert-butyl 3-(fluoromethyl)azetidine-1-carboxylate with trifluoroacetic acid in dichloromethane) in the presence of $K_2CO_3$ in acetonitrile to provide Compound 120.

269
Synthesis of Compound 121 1-(2-(4-(2-(4-Fluoro-2,6-dimethylbenzoyl)-6-hydroxybenzo[b]thiophen-3-yl)phenoxy)ethyl)azetidin-3-one
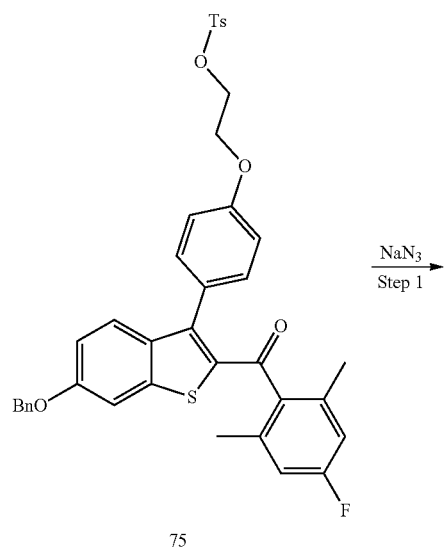
75
NaN₃
Step 1
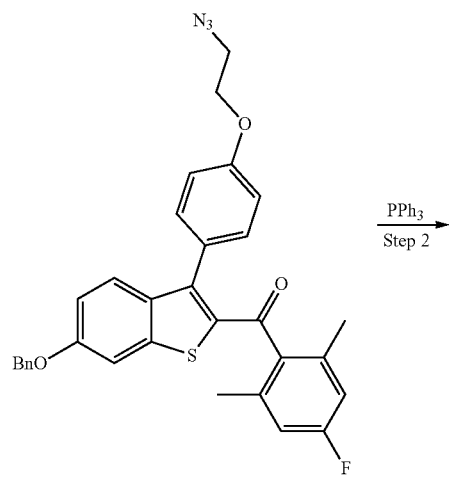
77
PPh₃
Step 2
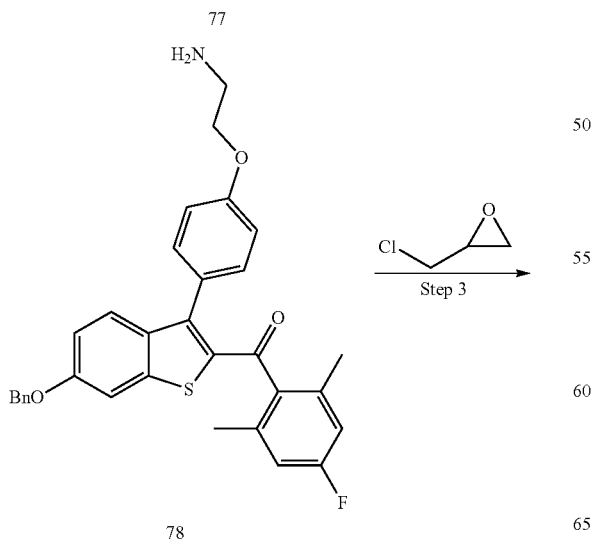
78
Cl—⟨epoxide⟩
Step 3
270
-continued
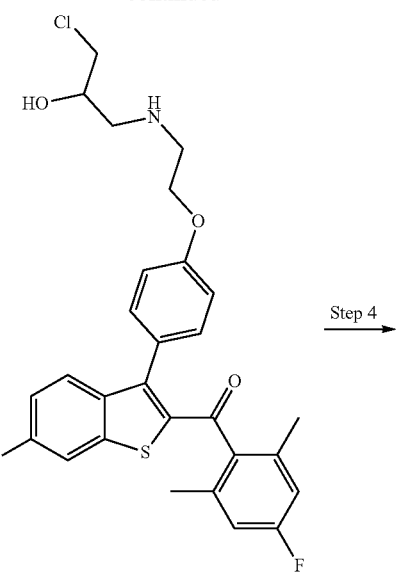
Step 4
79 HO—azetidine
Step 5
80
Step 6
81

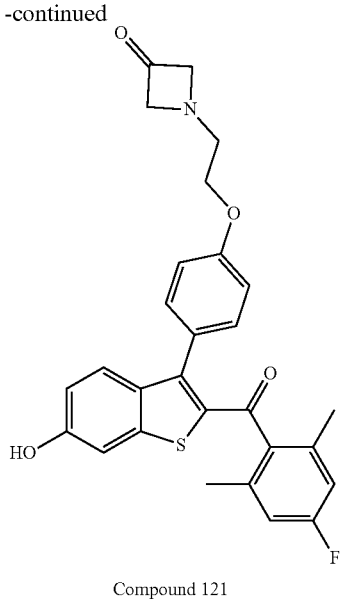

Compound 121

In Step 1, 500 mg of 75 was reacted with sodium azide in acetonitrile at 60° C. to provide 400 mg of 77 after purification. In Step 2, 270 mg of 77 was reacted with triphenylphosphine and water at 60° C. to provide 200 mg of 78 after purification. In Step 3, 78 was reacted with epichlorohydrin at room temperature over three days to provide a crude mixture in a 2.5 to 1 ratio of 79:78. In Step 4, the crude mixture in the previous step was heated to 60° C. for two days to provide 150 mg of 80 upon purification.

Example 3. Human ERα Reporter Assay

Figure 9:
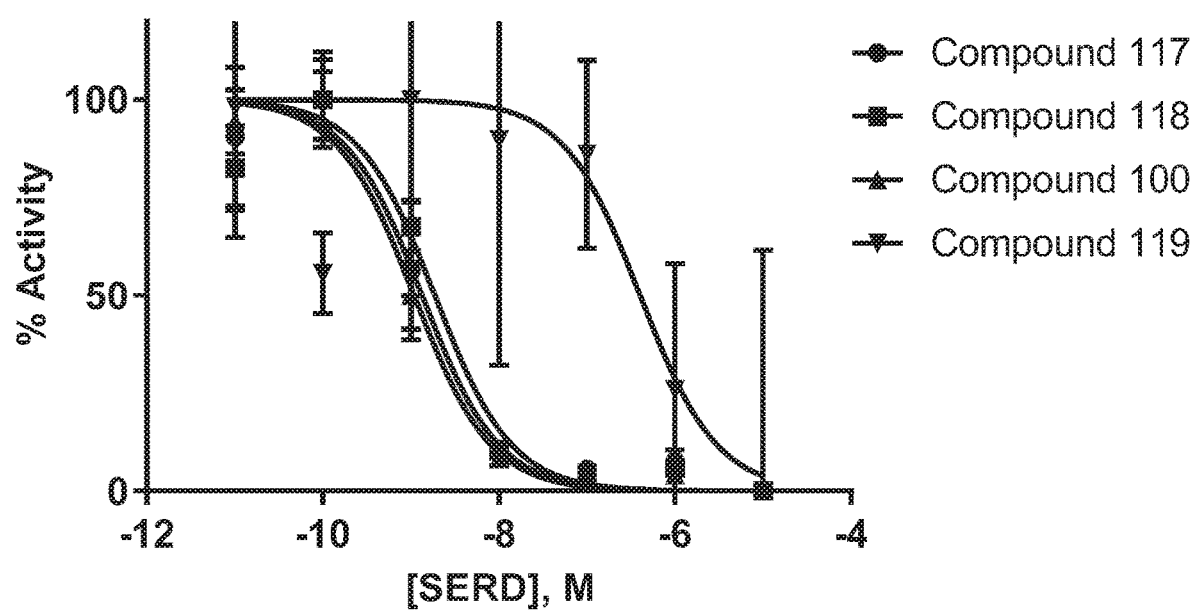
FIG. 9 is a graph of estrogen receptor activity measured in the Human Estrogen Receptor alpha Reporter Assay described in Example 3. The y-axis is estrogen receptor activity measured by percent. The x-axis is concentration of the SERD measured in Molar units and presented on logarithmic scale. The four compounds tested were Compound 100, Compound 117, Compound 118, and Compound 119. The $IC_{50}$ values corresponding to this dose response curves are provided in Table 3.
Figure 10:
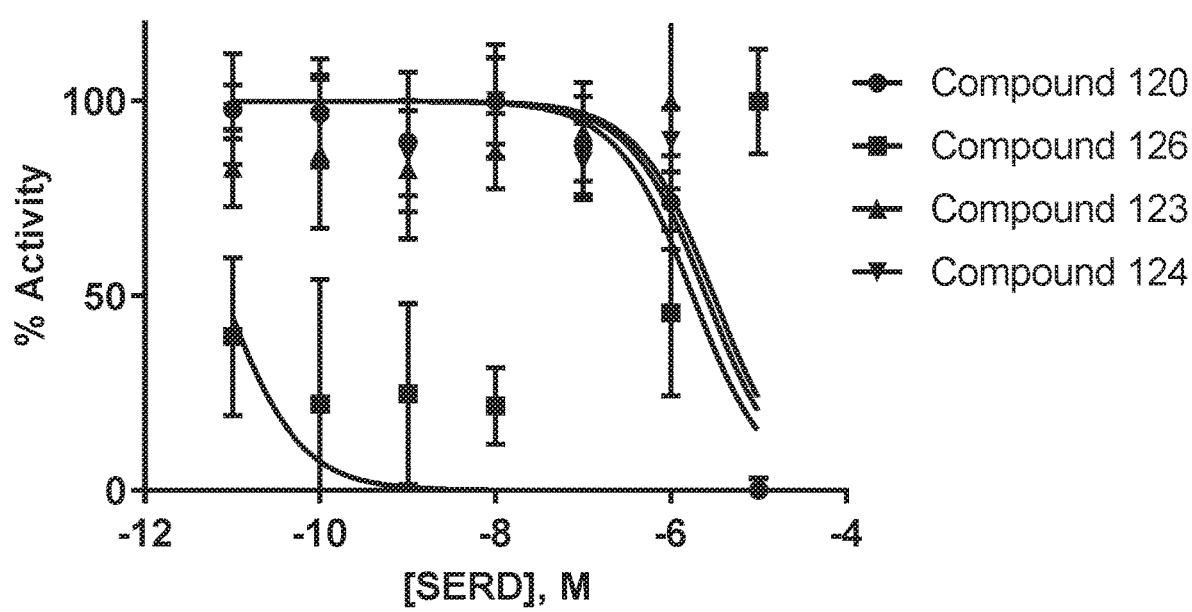
FIG. 10 is a graph of estrogen receptor activity measured in the Human Estrogen Receptor alpha Reporter Assay described in Example 3. The y-axis is estrogen receptor activity measured by percent. The x-axis is concentration of the SERD measured in Molar units and presented on logarithmic scale. The four compounds tested were Compound 120, Compound 123, Compound 124, and Compound 126. The IC$_{50}$ values corresponding to this dose response curves are provided in Table 3.
Figure 11:
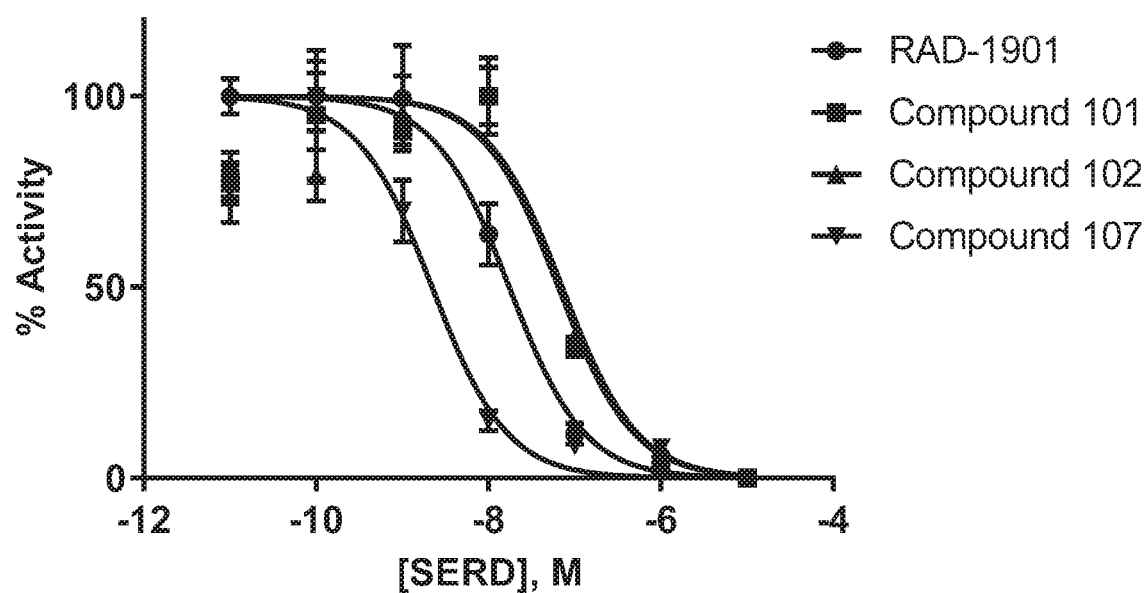
FIG. 11 is a graph of estrogen receptor activity measured in the Human Estrogen Receptor alpha Reporter Assay described in Example 3. The y-axis is estrogen receptor activity measured by percent. The x-axis is concentration of the SERD measured in Molar units and presented on logarithmic scale. The four compounds tested were Compound 101, Compound 102, Compound 107, and RAD-1901. The IC$_{50}$ values corresponding to this dose response curves are provided in Table 3.
Figure 12:
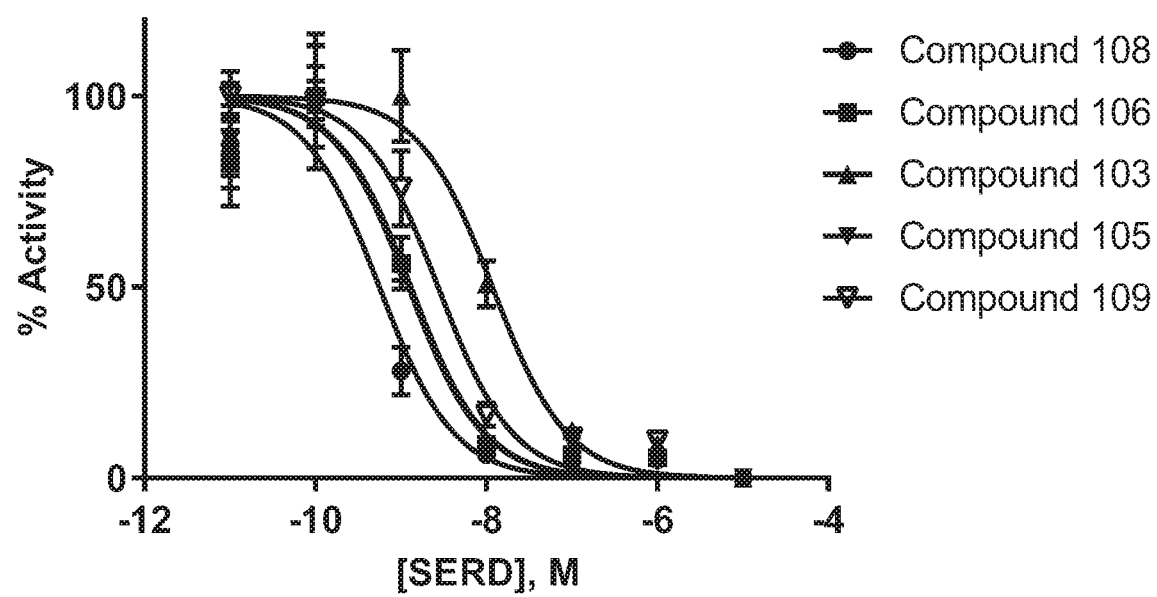
FIG. 12 is a graph of estrogen receptor activity measured in the Human Estrogen Receptor alpha Reporter Assay described in Example 3. The y-axis is estrogen receptor activity measured by percent. The x-axis is concentration of the SERD measured in Molar units and presented on logarithmic scale. The four compounds tested were Compound 103, Compound 105, Compound 106, Compound 108, and Compound 109. The IC$_{50}$ values corresponding to this dose response curves are provided in Table 3.
Figure 13:
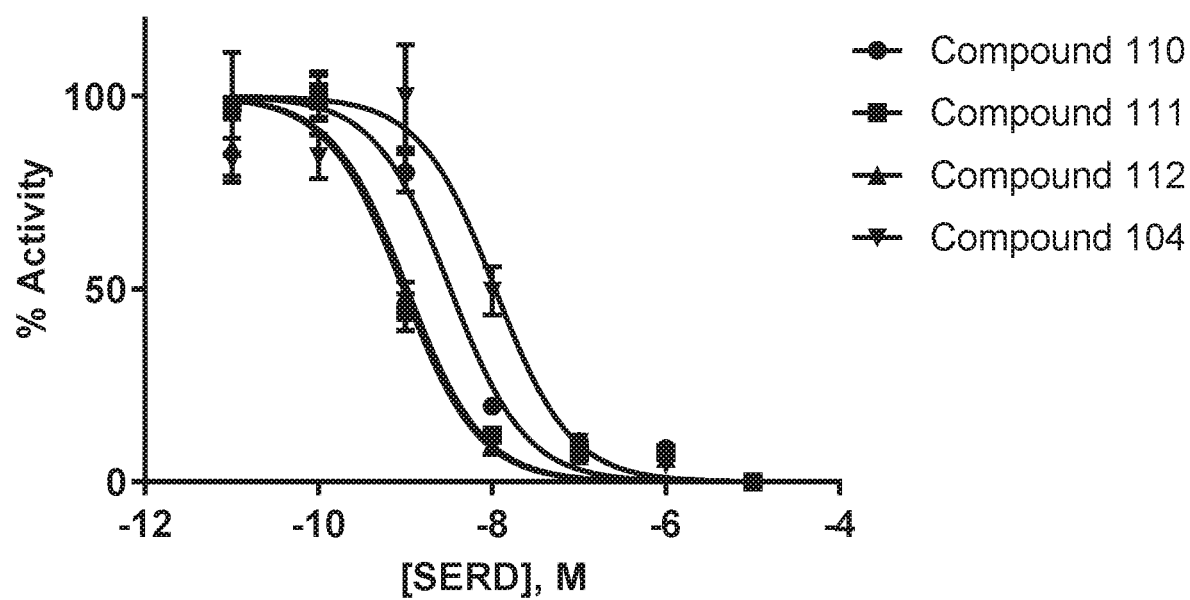
FIG. 13 is a graph of estrogen receptor activity measured in the Human Estrogen Receptor alpha Reporter Assay described in Example 3. The y-axis is estrogen receptor activity measured by percent. The x-axis is concentration of the SERD measured in Molar units and presented on logarithmic scale. The four compounds tested were Compound 104, Compound 110, Compound 111, and Compound 112. The IC$_{50}$ values corresponding to this dose response curves are provided in Table 3.
Figure 14:
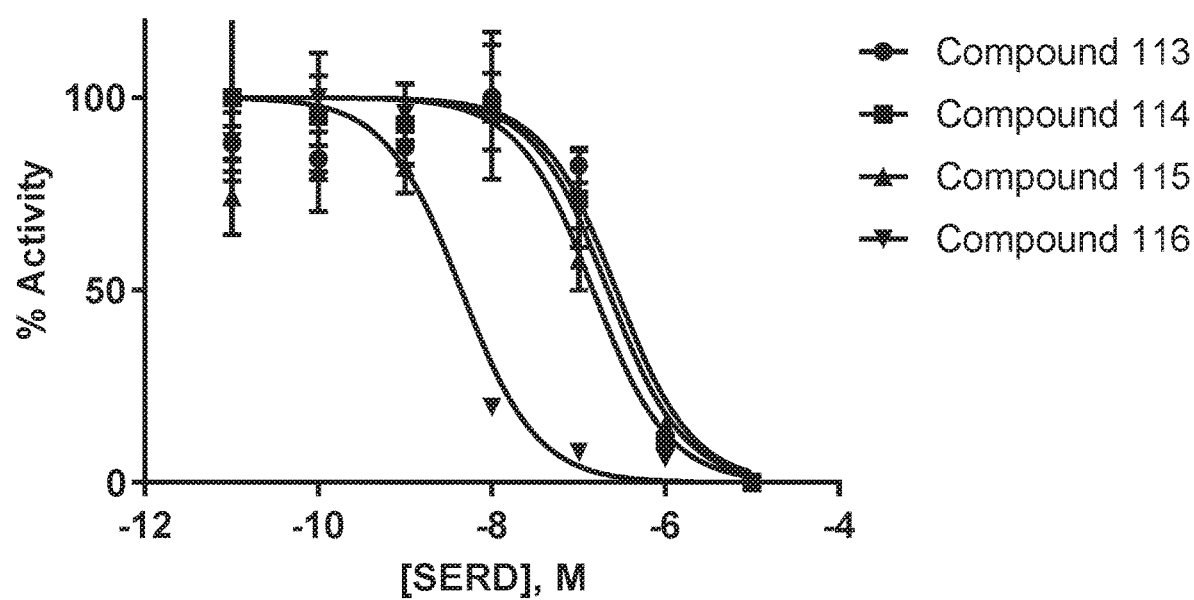
FIG. 14 is a graph of estrogen receptor activity measured in the Human Estrogen Receptor alpha Reporter Assay described in Example 3. The y-axis is estrogen receptor activity measured by percent. The x-axis is concentration of the SERD measured in Molar units and presented on logarithmic scale. The four compounds tested were Compound 113, Compound 114, Compound 115, and Compound 116. The IC$_{50}$ values corresponding to this dose response curves are provided in Table 3.
Figure 15:
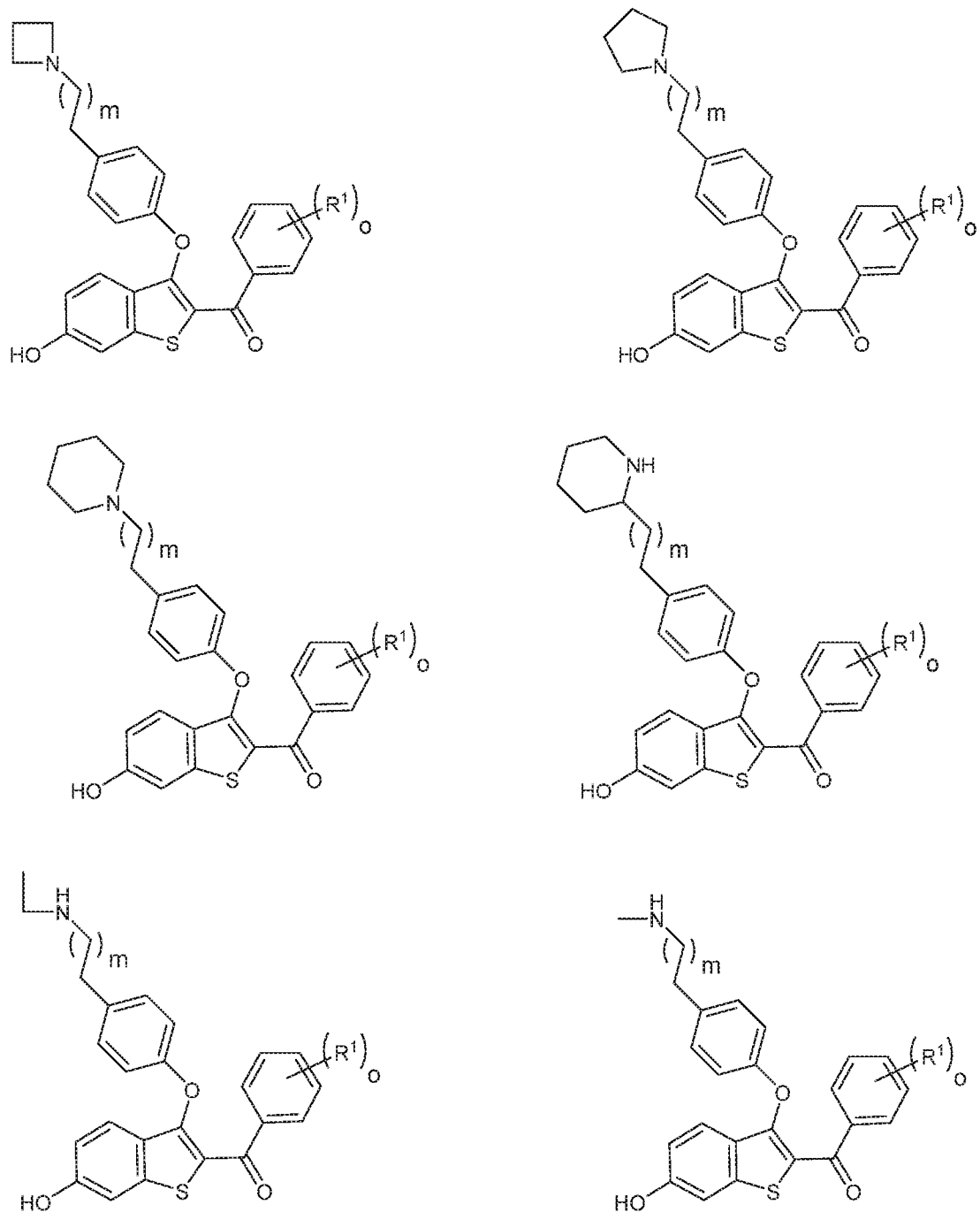
FIG. 15 depicts a few non-limiting subgenuses of Formula I.

All reagents used in this assay was supplied in the Human ERα Reporter Assay by Indigo Biosciences #IB00401. In an effort to screen selective estrogen receptor degraders (SERDs), the Human ERα Reporter Assay, supplied by Indigo Biosciences, was utilized to quantify antagonist functional activity against the human estrogen receptor. Reporter cells were thawed at 37° C. and added to pre-warmed to 37° C. cell recovery medium (CRM). Stock concentration of 17β-estradiol was serially diluted in CRM. Diluted 17β-estradiol was added to CRM containing reporter cells resulting in a working concentration of 1.6 nM (2×). Cells plus 17β-estradiol were dispensed in a kit-supplied white walled 96-well plate. Concentrated stocks of test compounds were diluted to 2× working concentrations in cell screening medium (CSM). 2× concentrated compounds were added to the plated cells in a dose-dependent manner resulting in a final concentration range of 1E-11 to 1E-5 M and a final 17β-estradiol concentration of 8E-10 M. Assay plates were incubated for 24 hours in a humidified 37° C. incubator. Culture medium was removed from the assay plates by inversion. Detection substrate and buffer was warmed to room temperature, mixed thoroughly, and immediately added to the assay plates. Assay plates were incubated for 15 minutes at room temperature protected from light. Luminescence was measured in a Synergy HTX luminescence plate reader. Data is processed utilizing GraphPad Prism 7 by graphing the relative light units measured at each compound concentration. This procedure was used to produce the graph in FIG. 1, FIG. 9, FIG. 10, FIG. 11, FIG. 12, FIG. 13, and FIG. 14.

Example 4. Estrogen Receptor (ER) Degradation Assay

Figure 2:
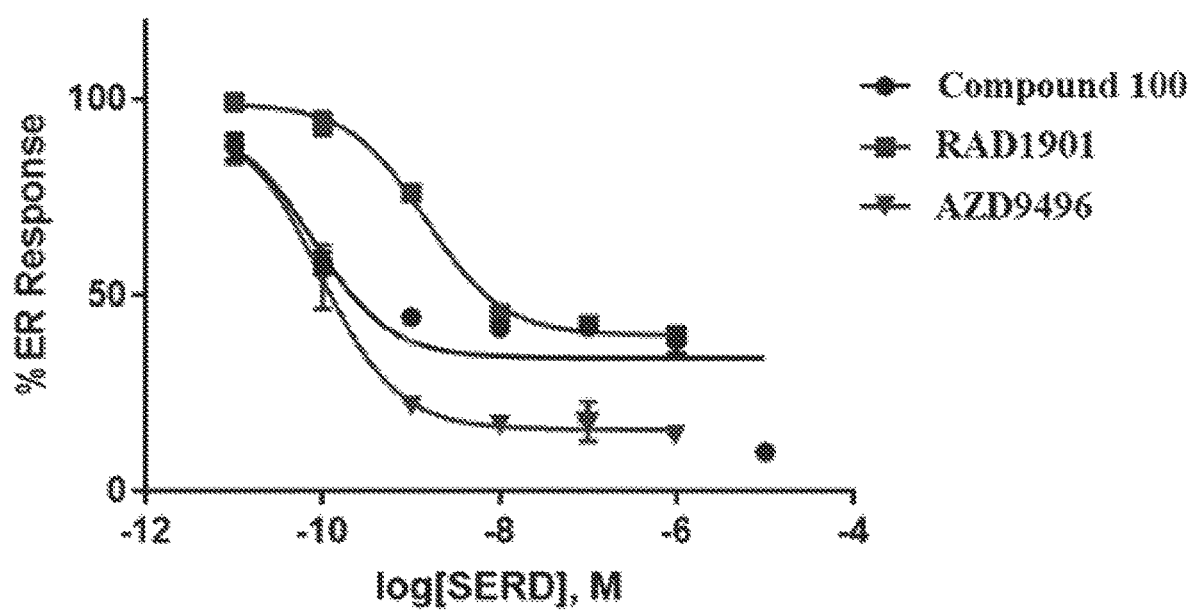
FIG. 2 is a graph of estrogen receptor activity measured in the Estrogen Receptor (ER) degradation assay described in Example 4. The y-axis is estrogen receptor response measured by percent. The x-axis is concentration of the SERD measured in Molar units and presented on logarithmic scale. The three compounds tested were Compound 100, RAD1901, and AZD9496.
Figure 3:
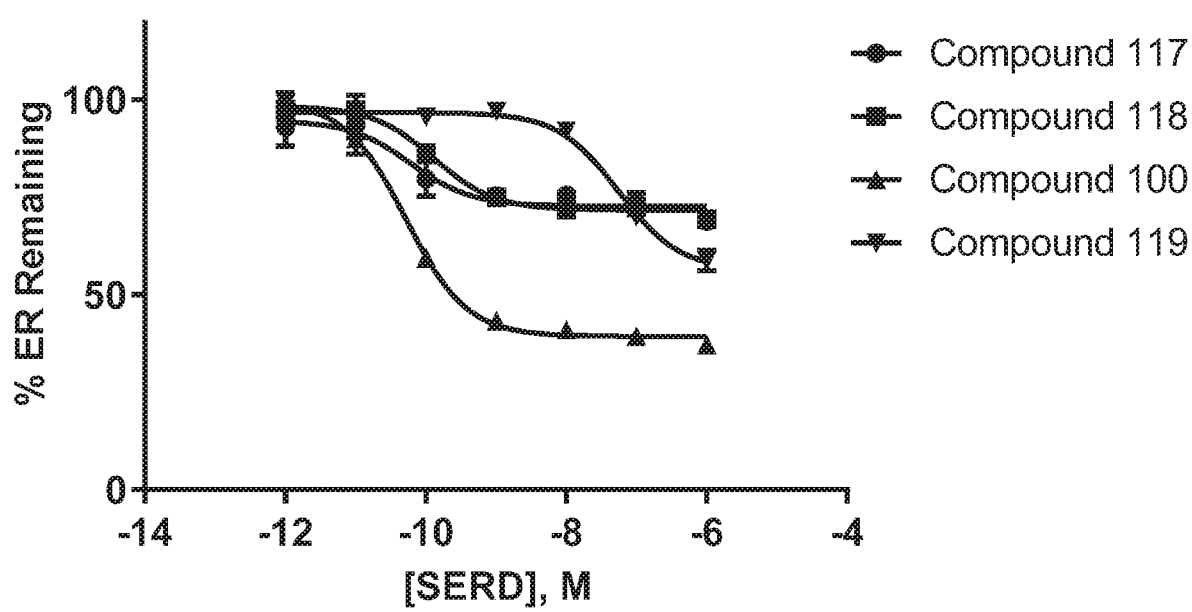
FIG. 3 is a graph of estrogen receptor remaining measured in the Estrogen Receptor (ER) degradation assay described in Example 4. The y-axis is estrogen receptor activity measured by percent. The x-axis is concentration of the SERD measured in Molar units and presented on logarithmic scale. The four compounds tested were Compound 100, Compound 117, Compound 118, and Compound 119. The $IC_{50}$ values corresponding to this dose response curves are provided in Table 3.
Figure 4:
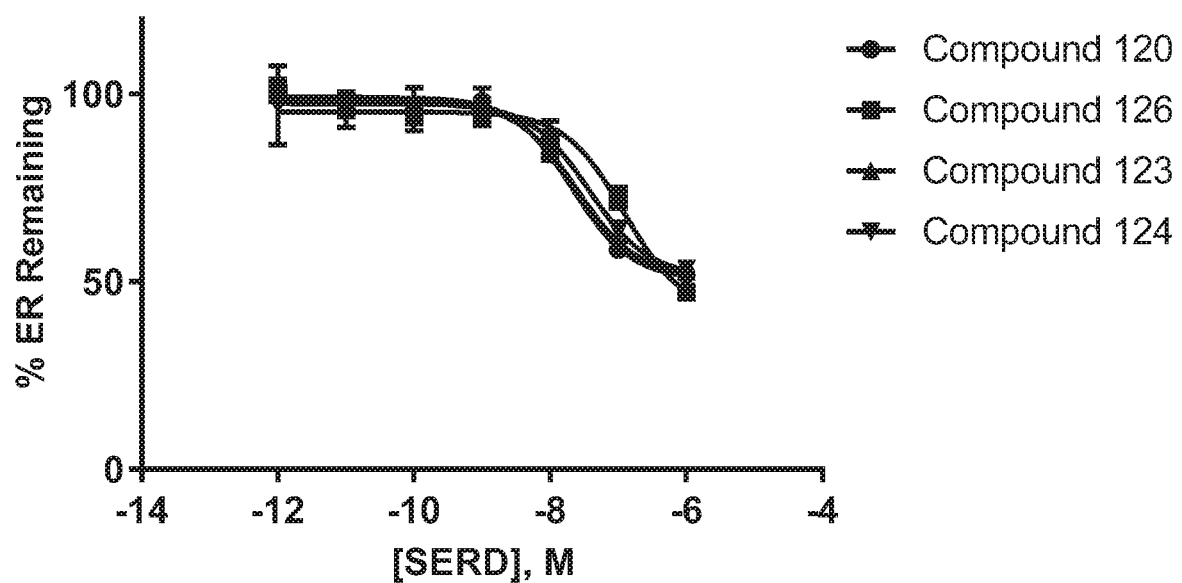
FIG. 4 is a graph of estrogen receptor remaining measured in the Estrogen Receptor (ER) degradation assay described in Example 4. The y-axis is estrogen receptor activity measured by percent. The x-axis is concentration of the SERD measured in Molar units and presented on logarithmic scale. The four compounds tested were Compound 120, Compound 123, Compound 124, and Compound 126. The $IC_{50}$ values corresponding to this dose response curves are provided in Table 3.
Figure 5:
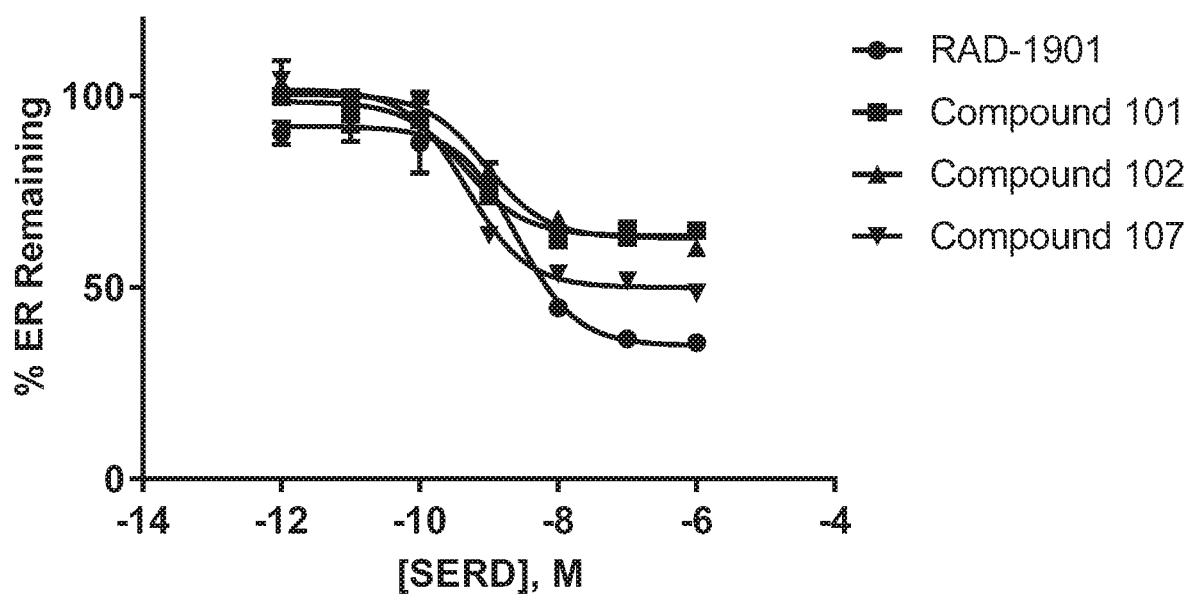
FIG. 5 is a graph of estrogen receptor remaining measured in the Estrogen Receptor (ER) degradation assay described in Example 4. The y-axis is estrogen receptor activity measured by percent. The x-axis is concentration of the SERD measured in Molar units and presented on logarithmic scale. The four compounds tested were Compound 101, Compound 102, Compound 107, and RAD-1901. The $IC_{50}$ values corresponding to this dose response curves are provided in Table 3.
Figure 6:
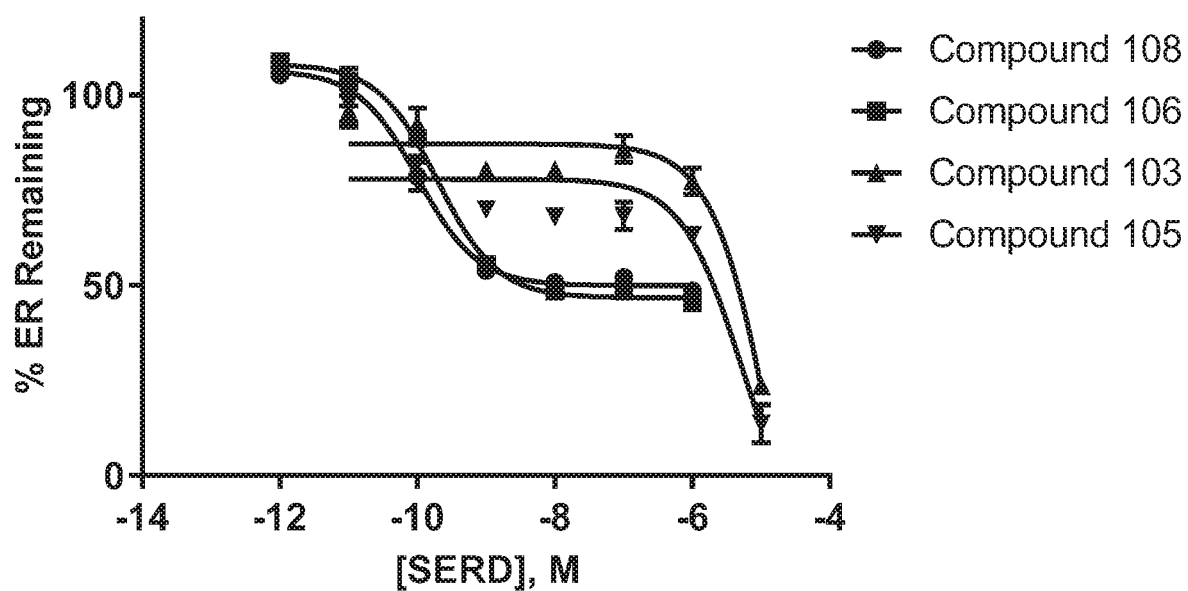
FIG. 6 is a graph of estrogen receptor remaining measured in the Estrogen Receptor (ER) degradation assay described in Example 4. The y-axis is estrogen receptor activity measured by percent. The x-axis is concentration of the SERD measured in Molar units and presented on logarithmic scale. The four compounds tested were Compound 103, Compound 105, Compound 106, and Compound 108. The $IC_{50}$ values corresponding to this dose response curves are provided in Table 3.
Figure 7:
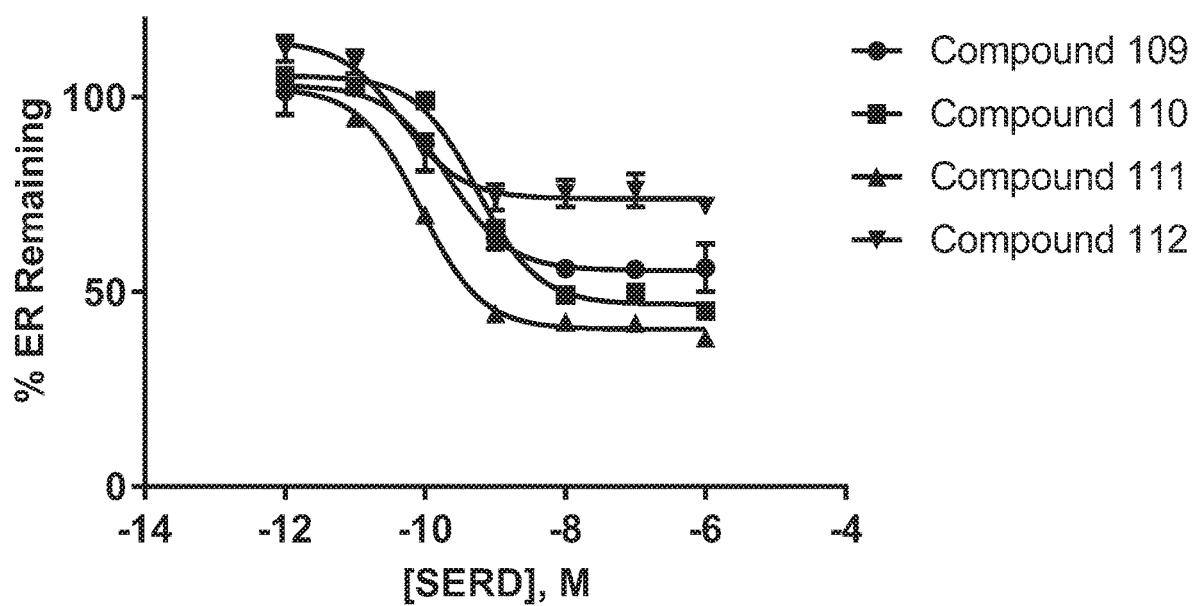
FIG. 7 is a graph of estrogen receptor remaining measured in the Estrogen Receptor (ER) degradation assay described in Example 4. The y-axis is estrogen receptor activity measured by percent. The x-axis is concentration of the SERD measured in Molar units and presented on logarithmic scale. The four compounds tested were Compound 109, Compound 110, Compound 111, and Compound 112. The $IC_{50}$ values corresponding to this dose response curves are provided in Table 3.
Figure 8:
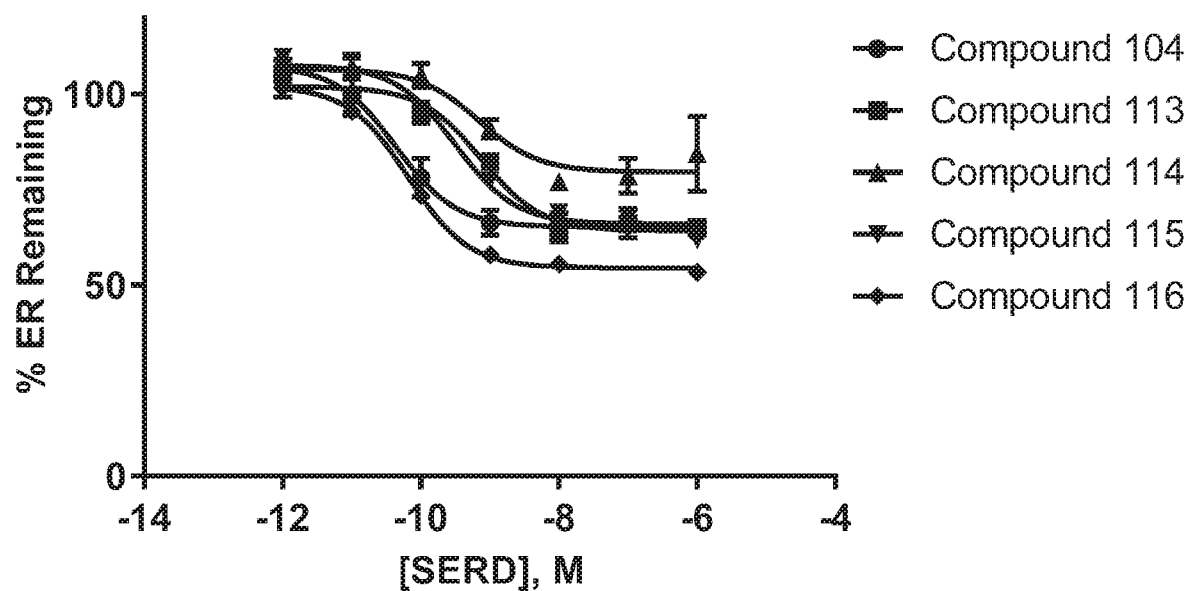
FIG. 8 is a graph of estrogen receptor remaining measured in the Estrogen Receptor (ER) degradation assay described in Example 4. The y-axis is estrogen receptor activity measured by percent. The x-axis is concentration of the SERD measured in Molar units and presented on logarithmic scale. The five compounds tested were Compound 104, Compound 113, Compound 114, Compound 115, and Compound 116. The $IC_{50}$ values corresponding to this dose response curves are provided in Table 3.

A screening strategy was implemented utilizing an In-Cell Western assay to measure their ability to degrade the estrogen receptor in vitro. MCF7 cells, which are estrogen receptor positive, were plated at a cell density of 3.5E-05 cells/mL into black walled clear bottom 96-well plates. Cells were incubated in phenol red free Dulbecco's Modified Eagle Media (DMEM) supplemented with 8% charcoal-stripped fetal bovine calf serum for 24 hours in a humidified 37° C. incubator. Concentrated stock compounds were diluted to 10× in complete media. Compounds were added to the plated cells in a dose-dependent manner ranging from 1E-12 to 1E-05 M and incubated for an additional 24 hours at 37° C. Culture medium was removed from the culture plates by gentle inversion. Cells were fixed in 4% paraformaldehyde in 1× phosphate buffered saline-calcium magnesium free (PBS-CMF) for 15 minutes at room temperature, washed 3 times for 5 minutes each in 1×PBS-CMF. Cells were permeabilized in immunofluorescence (IF) blocking buffer (Cell Signaling #12411) containing 0.3% Triton X100. Cells were washed 3 times for 5 minutes each in 1×PBS-CMF and incubated in estrogen receptor a (D6R2W) rabbit primary antibody (Cell Signaling #13258) diluted 1:300 in IF antibody dilution buffer (Cell Signaling #12378). Cells were washed 3 times for 5 minutes each in 1×PBS-CMF and stained with goat anti-rabbit (Biotium #CF770) secondary antibody diluted 1:2000 in IF antibody dilution buffer and normalizing stain CellTag 700 diluted 1:500 (Licor #926-41090). ER protein expression was assessed by the Licor Odyssey CLx imaging system using Image Studio v5.2. Data is processed utilizing GraphPad Prism 7 by subtracting background from the vehicle and setting the vehicle to 100% ER activity, followed by comparing treated samples to vehicle. This procedure was used to produce the graph in FIG. 2, FIG. 3, FIG. 4, FIG. 5, FIG. 6, FIG. 7, and FIG. 8.

Example 5. Data from Human ERα Reporter Assay and Estrogen Receptor (ER) Degradation Assay The procedures in Example 3 and Example 4 were used to produce the data provided in Table 3 below. In the below table for the Estrogen Receptor Degradation Assay and the Human ERα Reporter Assay:

*** denotes a <1 µM; $IC_{50}$;

** denotes a <50 µM $IC_{50}$; and

* denotes a >51 µM $IC_{50}$.

In the below table for the % Estrogen Receptor Remaining:

**** denotes 0-40% Estrogen Receptor remaining

*** denotes 41-70% Estrogen Receptor remaining

** denotes 71-90% Estrogen Receptor remaining

* denotes 91-100% Estrogen Receptor remaining

TABLE 3

| Comp. # | Structure | Estrogen Receptor Degradation Assay IC$_{50}$ | Human ERα Reporter Assay IC$_{50}$ | % Estrogen Receptor Remaining |
|---|---|---|---|---|
| 100 | 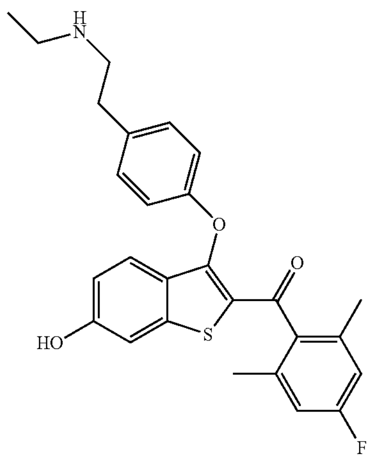 [SMILES: CCNCCc1ccc(Oc2c(C(=O)c3c(C)cc(F)cc3C)sc3cc(O)ccc23)cc1] | * | * | **** |
| 101 | 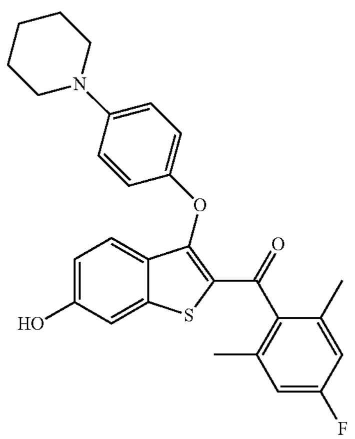 [SMILES: Cc1cc(F)cc(C)c1C(=O)c1sc2cc(O)ccc2c1Oc1ccc(N2CCCCC2)cc1] | * | * | *** |
| 102 | 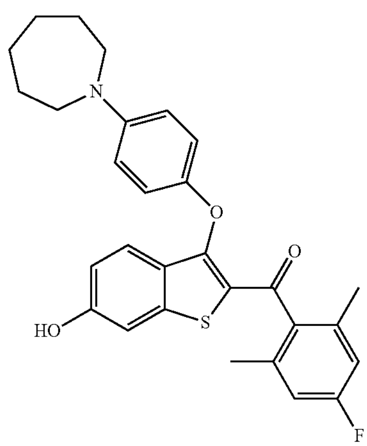 [SMILES: Cc1cc(F)cc(C)c1C(=O)c1sc2cc(O)ccc2c1Oc1ccc(N2CCCCCC2)cc1] | * | * | *** |

TABLE 3-continued

| Comp. # | Structure | Estrogen Receptor Degradation Assay IC$_{50}$ | Human ERα Reporter Assay IC$_{50}$ | % Estrogen Receptor Remaining |
|---|---|---|---|---|
| 103 | 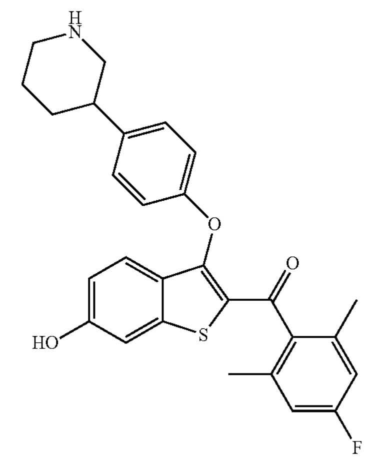 |  | * | **** |
| 104 | 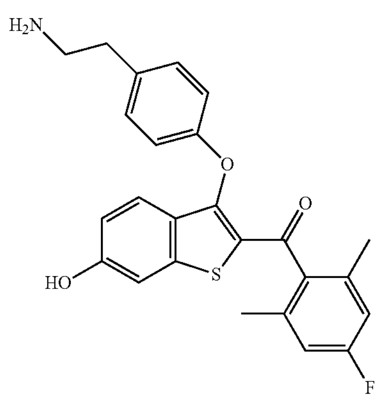 [SMILES: Cc1cc(F)cc(C)c1C(=O)c1sc2cc(O)ccc2c1Oc1ccc(CCN)cc1] | * | * | *** |
| 105 | 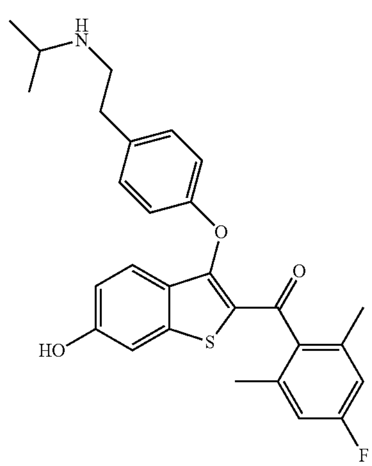 [SMILES: Cc1cc(F)cc(C)c1C(=O)c1sc2cc(O)ccc2c1Oc1ccc(CCNC(C)C)cc1] |  | * | **** |

TABLE 3-continued
| Comp. # | Structure | Estrogen Receptor Degradation Assay IC$_{50}$ | Human ERα Reporter Assay IC$_{50}$ | % Estrogen Receptor Remaining |
|---|---|---|---|---|
| 106 | 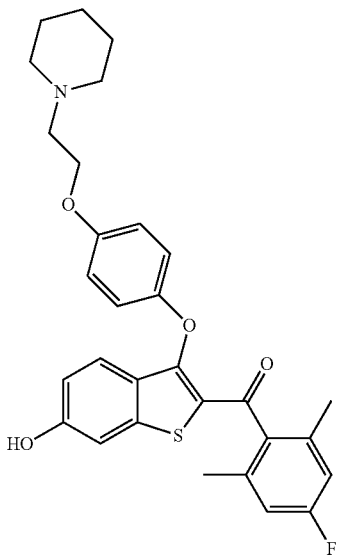 [SMILES: Cc1cc(F)cc(C)c1C(=O)c1sc2cc(O)ccc2c1Oc1ccc(OCCN2CCCCC2)cc1] | * | * | *** |
| 107 | 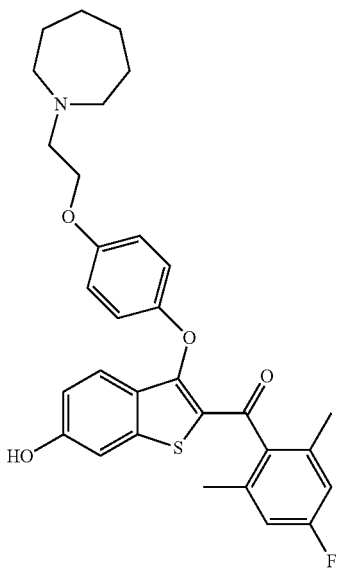 | * | * | *** |

TABLE 3-continued
| Comp. # | Structure | Estrogen Receptor Degradation Assay IC$_{50}$ | Human ERα Reporter Assay IC$_{50}$ | % Estrogen Receptor Remaining |
|---|---|---|---|---|
| 108 | 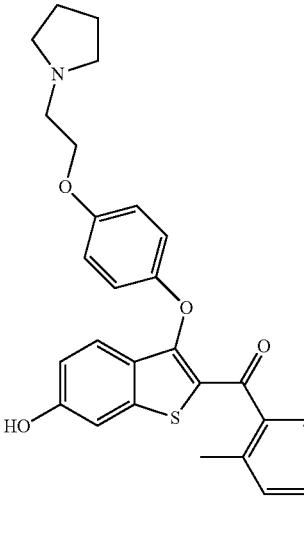 | * | * | *** |
| 109 | 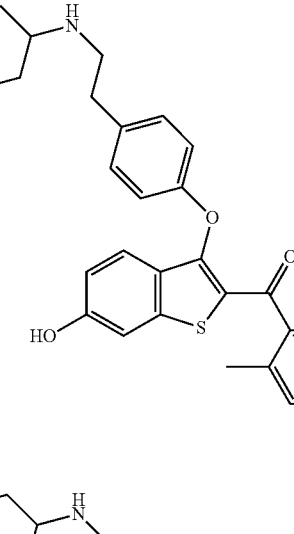 | * | * | *** |
| 110 | 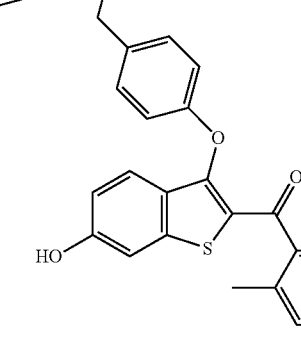 | * | * | *** |

TABLE 3-continued

| Comp. # | Structure | Estrogen Receptor Degradation Assay IC$_{50}$ | Human ERα Reporter Assay IC$_{50}$ | % Estrogen Receptor Remaining |
|---|---|---|---|---|
| 111 | 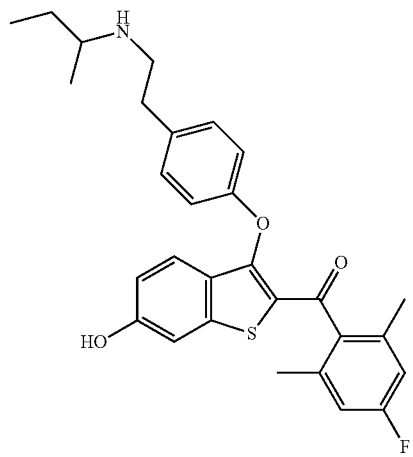 [SMILES: CCC(C)NCCc1ccc(Oc2c(C(=O)c3c(C)cc(F)cc3C)sc3cc(O)ccc23)cc1] | * | * | **** |
| 112 | 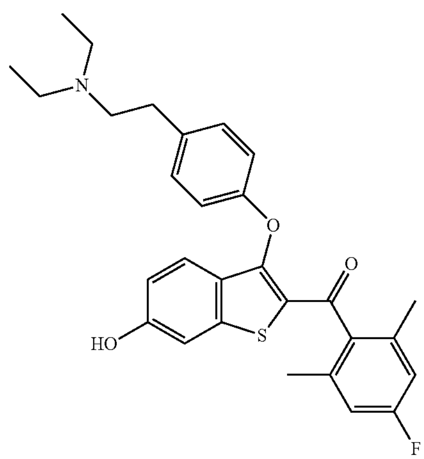 [SMILES: CCN(CC)CCc1ccc(Oc2c(C(=O)c3c(C)cc(F)cc3C)sc3cc(O)ccc23)cc1] | * | * | *** |
| 113 | 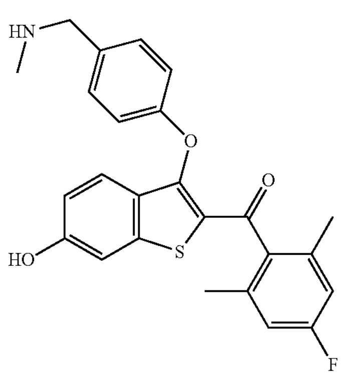 | * | * | *** |

TABLE 3-continued

| Comp. # | Structure | Estrogen Receptor Degradation Assay IC$_{50}$ | Human ERα Reporter Assay IC$_{50}$ | % Estrogen Receptor Remaining |
|---|---|---|---|---|
| 114 | 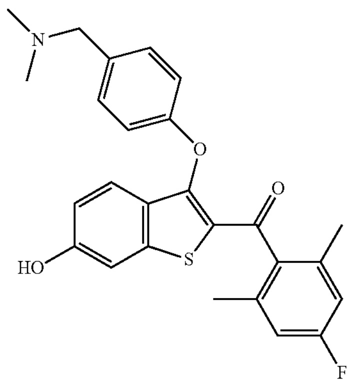 | * | * | ** |
| 115 | 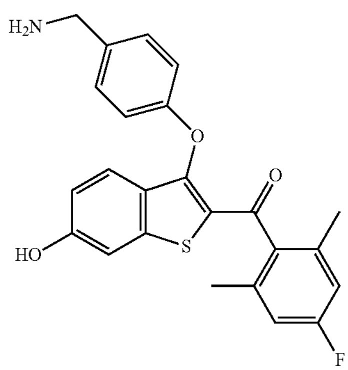 [SMILES: Cc1cc(F)cc(C)c1C(=O)c1sc2cc(O)ccc2c1Oc1ccc(CN)cc1] | * | * | *** |
| 116 | 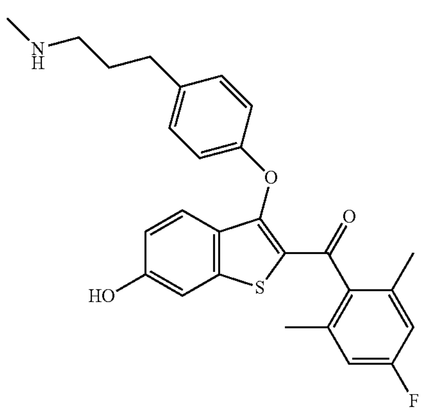 | * | * | *** |

TABLE 3-continued
| Comp. # | Structure | Estrogen Receptor Degradation Assay IC$_{50}$ | Human ERα Reporter Assay IC$_{50}$ | % Estrogen Receptor Remaining |
|---|---|---|---|---|
| 117 | 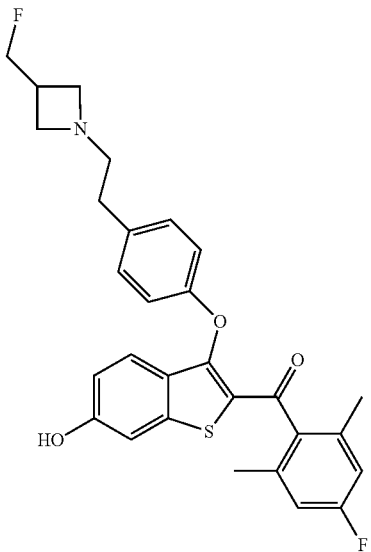 [SMILES: Cc1cc(F)cc(C)c1C(=O)c1sc2cc(O)ccc2c1Oc1ccc(CCN2CC(CF)C2)cc1] | * | * | *** |
| 118 | 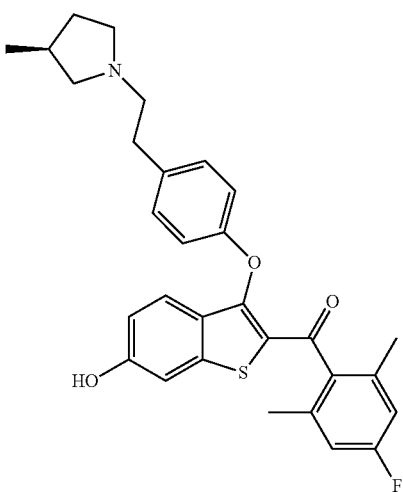 | * | * | *** |

TABLE 3-continued
| Comp. # | Structure | Estrogen Receptor Degradation Assay IC$_{50}$ | Human ERα Reporter Assay IC$_{50}$ | % Estrogen Receptor Remaining |
|---|---|---|---|---|
| 119 | 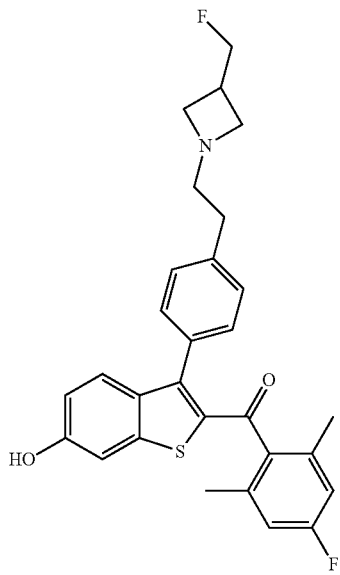 [SMILES: Cc1cc(F)cc(C)c1C(=O)c1sc2cc(O)ccc2c1-c1ccc(CCN2CC(CF)C2)cc1] | * | * | *** |
| 120 | 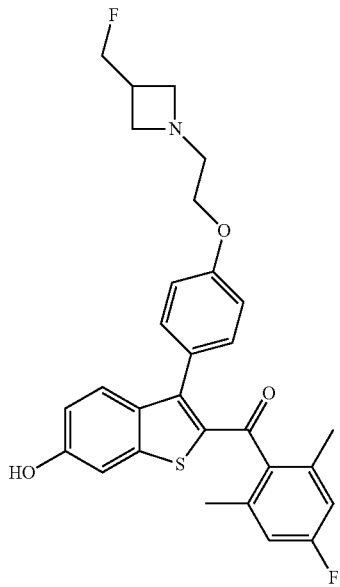 [SMILES: Cc1cc(F)cc(C)c1C(=O)c1sc2cc(O)ccc2c1-c1ccc(OCCN2CC(CF)C2)cc1] | * |  | *** |

TABLE 3-continued
| Comp. # | Structure | Estrogen Receptor Degradation Assay IC$_{50}$ | Human ERα Reporter Assay IC$_{50}$ | % Estrogen Receptor Remaining |
|---|---|---|---|---|
| 123 | 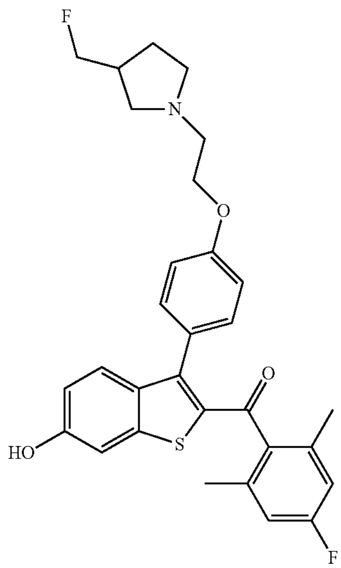 [SMILES: Cc1cc(F)cc(C)c1C(=O)c1sc2cc(O)ccc2c1-c1ccc(OCCN2CCC(CF)C2)cc1] | * |  | *** |
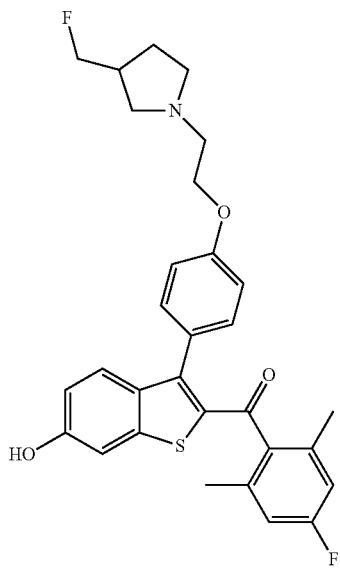
| 124 | | * |  | *** |
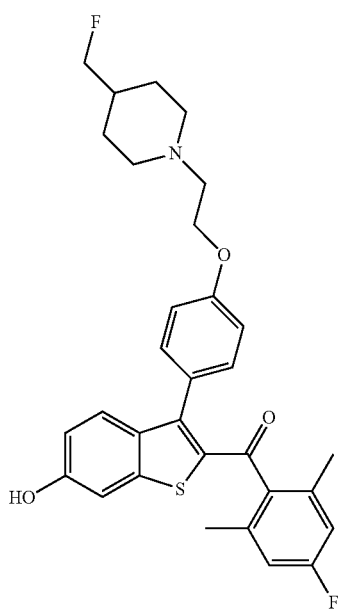 [SMILES: Cc1cc(F)cc(C)c1C(=O)c1sc2cc(O)ccc2c1-c1ccc(OCCN2CCC(CF)CC2)cc1]

TABLE 3-continued

| Comp. # | Structure | Estrogen Receptor Degradation Assay IC$_{50}$ | Human ERα Reporter Assay IC$_{50}$ | % Estrogen Receptor Remaining |
|---|---|---|---|---|
| 126 | (structure shown) | *** | *** | *** |
| RAD-1901 | (structure shown) | *** | *** | **** |

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

I claim:
1. A compound selected from:

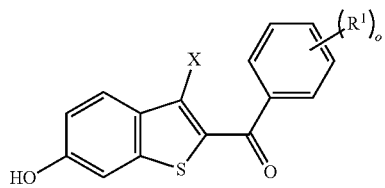

or a pharmaceutically acceptable salt thereof; wherein
X is

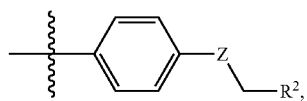

293

-continued

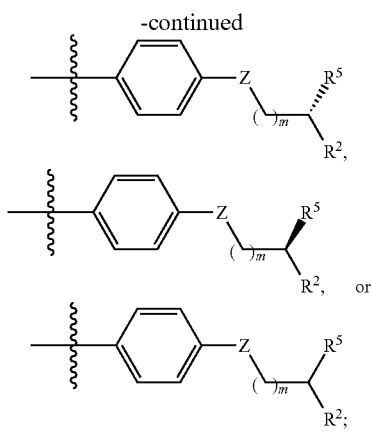

m is 0, 1, or 2;
o is 0, 1, 2, 3, 4, or 5;
Z is selected from —O—, —C(R$^3$)$_2$—, —CHR$^3$—, —CH$_2$—, —CHF—, —CF$_2$—, and —S—;
each R$^1$ is independently selected from C$_1$-C$_3$alkyl, halogen, and C$_1$-C$_3$haloalkyl;
R$^2$ is selected from:
  a) 4-6 membered heterocycle optionally substituted with one, two, or three groups independently selected from R$^4$;
  b) —NH$_2$, —NH(C$_1$-C$_3$alkyl or C$_2$-C$_3$haloalkyl), and —N((independently)C$_1$-C$_3$alkyl or C$_2$-C$_3$ haloalkyl)$_2$;
  c) monocyclic 7-8 membered heterocycle optionally substituted with one, two, or three groups independently selected from R$^4$; and
  d) 6-12 membered bicyclic or bridged heterocycle optionally substituted with one, two, or three groups independently selected from R$^4$;
R$^3$ is independently selected from —F, —Cl, —Br, —CH$_3$, —CH$_2$F, —CHF$_2$, and —CF$_3$; and
R$^4$ and R$^5$ are independently selected from halogen, C$_1$-C$_3$alkyl, and C$_1$-C$_3$haloalkyl.

2. The compound of claim 1, wherein Z is —O—.
3. The compound of claim 1, wherein o is 3.
4. The compound of claim 1, wherein o is 0, 1, or 2.
5. The compound of claim 1, wherein at least one R$^1$ is —F.
6. The compound of claim 1, wherein at least one R$^1$ is methyl.
7. The compound of claim 1, wherein R$^2$ is —N(CH$_2$CH$_3$)$_2$.
8. The compound of claim 1, wherein R$^2$ is selected from

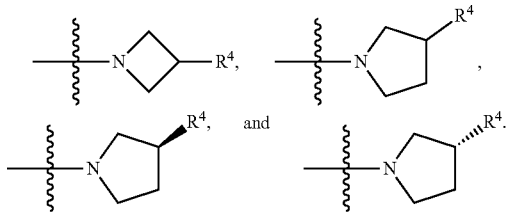

9. The compound of claim 1, wherein R$^3$ is —F.
10. The compound of claim 1, wherein R$^4$ is —F.
11. The compound of claim 1, wherein R$^4$ is C$_1$-C$_3$haloalkyl.

294

12. The compound of claim 1, wherein R$^5$ is halogen.
13. The compound of claim 1, wherein R$^5$ is C$_1$-C$_3$haloalkyl.
14. The compound of claim 1 selected from

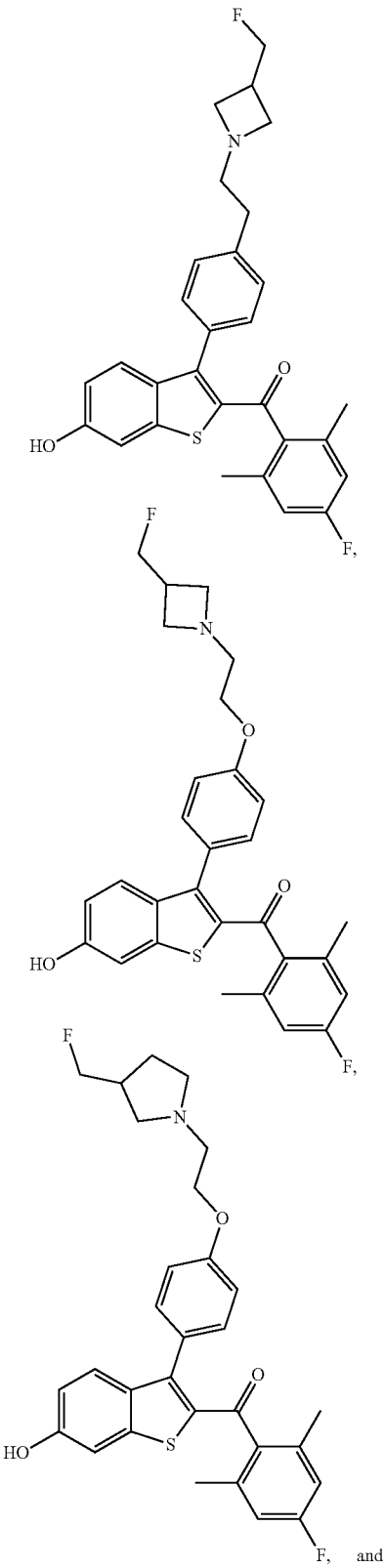

-continued

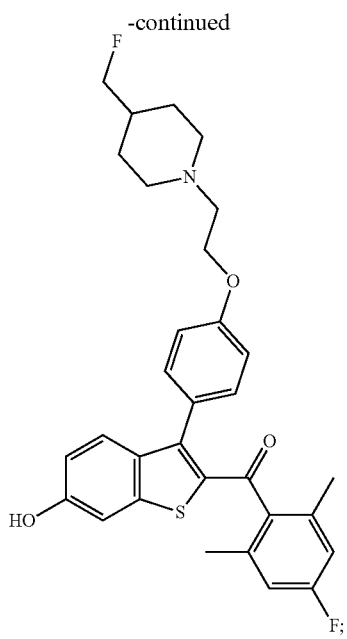

or a pharmaceutically acceptable salt thereof.

15. A pharmaceutical composition comprising a therapeutically effective amount of a compound of claim 1 or a pharmaceutically acceptable salt thereof, and a pharmaceutically acceptable carrier.

16. A method of treating a hormone-related cancer that is estrogen mediated comprising administering to a subject in need thereof a therapeutically effective amount of a compound of claim 1 or a pharmaceutically acceptable salt thereof.

17. The method of claim 16, wherein the subject is a human.

18. The method of claim 16, wherein the cancer is breast, endometrial or ovarian cancer.

19. The method of claim 17, wherein an effective amount of an additional therapeutic agent is administered.

* * * * *